(12) United States Patent
Sircar et al.

(10) Patent No.: US 7,361,760 B2
(45) Date of Patent: Apr. 22, 2008

(54) SUBSTITUTED NAPHTHYRIDINE DERIVATIVES AS INHIBITORS OF MACROPHAGE MIGRATION INHIBITORY FACTOR AND THEIR USE IN THE TREATMENT OF HUMAN DISEASES

(75) Inventors: Jagadish Sircar, San Diego, CA (US); Sunil Kumar K. C., San Diego, CA (US); Wenbin Ying, San Diego, CA (US); Timothy James Davis, San Diego, CA (US)

(73) Assignee: Avanir Pharmaceuticals, Aliso Viejo, CA (US)

( * ) Notice: Subject to any disclaimer, the term of this patent is extended or adjusted under 35 U.S.C. 154(b) by 0 days.

(21) Appl. No.: 11/687,601

(22) Filed: Mar. 16, 2007

(65) Prior Publication Data

US 2007/0191388 A1    Aug. 16, 2007

Related U.S. Application Data

(63) Continuation of application No. 10/920,031, filed on Aug. 17, 2004.

(60) Provisional application No. 60/497,443, filed on Aug. 22, 2003.

(51) Int. Cl.
   C07D 471/04        (2006.01)
   A61K 31/496        (2006.01)

(52) U.S. Cl. .................................. 544/362; 514/253.04

(58) Field of Classification Search ................. 544/362
   See application file for complete search history.

(56) References Cited

U.S. PATENT DOCUMENTS 4,284,768 A    8/1981   Santilli
4,299,814 A    11/1981  Brandt et al.

(Continued)

FOREIGN PATENT DOCUMENTS

AU    592753 A    1/1990
EP    0154454 A1  9/1985

OTHER PUBLICATIONS

Abe et al. 1993. "Induction of Vascular Endothelial Tubular Morphogenesis by Human Glioma Cells." *J. Clin. Invest.* 92:54.

(Continued)

*Primary Examiner*—Emily Bernhardt
(74) *Attorney, Agent, or Firm*—Knobbe Martens Olson & Bear LLP

(57) ABSTRACT

Inhibitors of MIF having a naphthyridine backbone are provided which have utility in the treatment of a variety of disorders, including the treatment of pathological conditions associated with MIF activity. The inhibitors of MIF have the following structures:

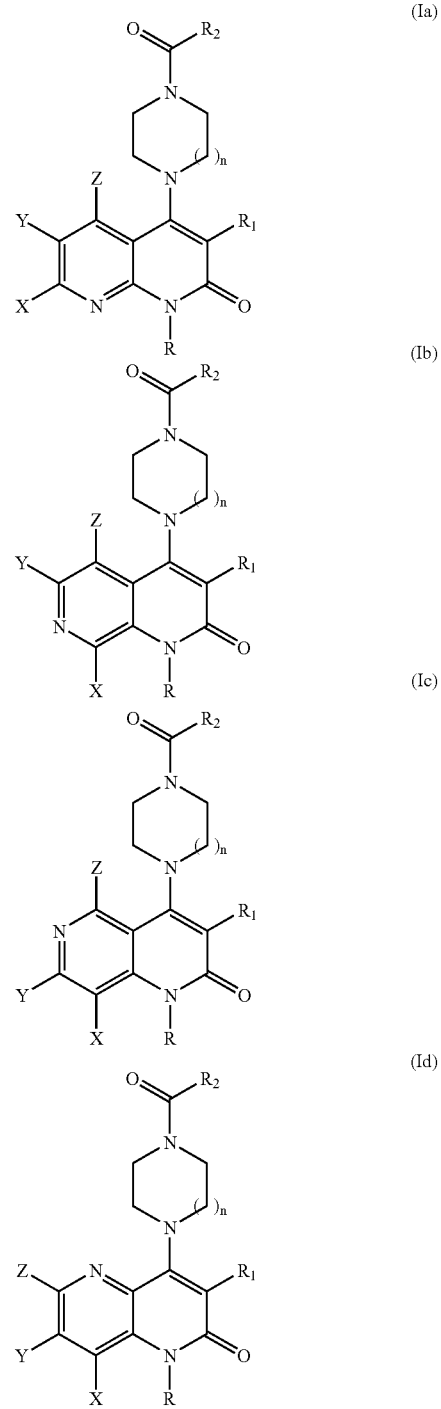

including stereoisomers, prodrugs and pharmaceutically acceptable salts thereof, wherein n, R, $R_1$, $R_2$, X, Y and Z are as defined herein. Compositions containing an inhibitor of MIF in combination with a pharmaceutically acceptable carrier are also provided, as well as methods for use of the same.

19 Claims, No Drawings

U.S. PATENT DOCUMENTS

| | | | |
|---|---|---|---|
| 4,683,202 | A | 7/1987 | Mullis |
| 4,708,937 | A | 11/1987 | Remold |
| 5,246,869 | A | 9/1993 | Potter et al. |
| 5,328,990 | A | 7/1994 | Wistow |
| 5,350,687 | A | 9/1994 | Odink et al. |
| 5,352,660 | A | 10/1994 | Pawson |
| 5,411,882 | A | 5/1995 | Odink et al. |
| 5,530,101 | A | 6/1996 | Queen et al. |
| 5,597,708 | A | 1/1997 | Holder et al. |
| 5,650,295 | A | 7/1997 | Li et al. |
| 5,656,596 | A | 8/1997 | Monard et al. |
| 5,656,737 | A | 8/1997 | Wistow |
| 5,683,887 | A | 11/1997 | Bucala et al. |
| 5,700,447 | A | 12/1997 | Bucala et al. |
| 5,702,920 | A | 12/1997 | Odink et al. |
| 5,733,524 | A | 3/1998 | Bucala et al. |
| 5,733,546 | A | 3/1998 | Bucala et al. |
| 5,733,933 | A | 3/1998 | Bucala et al. |
| 5,780,615 | A | 7/1998 | Bucala et al. |
| 5,801,200 | A | 9/1998 | Bucala et al. |
| 5,821,336 | A | 10/1998 | Odink et al. |
| 5,869,534 | A | 2/1999 | Bucala et al. |
| 5,883,224 | A | 3/1999 | Kirkpatrick et al. |
| 5,986,060 | A | 11/1999 | Li et al. |
| 6,028,081 | A | 2/2000 | Sada et al. |
| 6,030,615 | A | 2/2000 | Bucala et al. |
| 6,080,407 | A | 6/2000 | Bucala et al. |
| 6,214,343 | B1 | 4/2001 | Kink et al. |
| 6,238,874 | B1 | 5/2001 | Jarnagin et al. |
| 6,413,939 | B1 | 7/2002 | Bucala et al. |
| 6,420,188 | B1 | 7/2002 | Bucala et al. |
| 2003/0195194 | A1 | 10/2003 | Gaeta et al. |

FOREIGN PATENT DOCUMENTS

| | | |
|---|---|---|
| EP | 0263072 A2 | 4/1988 |
| EP | 0412050 A1 | 2/1991 |
| EP | 0900789 A2 | 3/1999 |
| WO | WO8002287 A1 | 10/1980 |
| WO | WO9420083 A1 | 9/1994 |
| WO | WO9426307 A1 | 11/1994 |
| WO | WO9729635 A1 | 8/1997 |
| WO | WO9739326 A2 | 10/1997 |
| WO | WO9740159 A1 | 10/1997 |
| WO | WO9817314 A1 | 4/1998 |
| WO | WO9929894 A1 | 6/1999 |
| WO | WO0132606 A1 | 5/2001 |
| WO | WO0207720 A1 | 1/2002 |
| WO | WO02094203 A1 | 11/2002 |
| WO | WO03104178 A1 | 12/2003 |
| WO | WO2004074218 A1 | 9/2004 |

OTHER PUBLICATIONS

Abe et al. 2001. "Regulation of the CTL Response by Macrophage Migration Inhibitory Factor." *J. Immunol.* 166:747-753.

Archer et al. 1983. "Electrophilic Aromatic Substitution. Part 34. Partial Rate Factors for Detritiation of Dithieno [1,2-*b*:4,3-*b*'] benzene, Dithieno[1,2-*b*:3,4-*b*'] benzene, and Dithieno [2,1-*b*:3,4-*b*']benzene." *J. Chem. Soc. Perkin Trans. II.* 813-819.

Aroca et al. 1991. "Specificity of dopachrome tautomerase and inhibition by carboxylated indoles." *Biochem. J.* 277:393-397.

Ausubel et al. 1987. *Current Protocols in Molecular Biology.* Ausubel et al.(ed.) John Wiley & Sons, Inc.

Bacher et al. 1998. "MIF Expression in the Rat Brain: Implications for Neuronal Function." *Mol. Med.* 4(4):217-230.

Banker et al. "Modern Pharmaceuticals", 3rd Ed. p. 596 (1996).

Baugh and Bucala. 2002. "Macrophage migration inhibitory factor." *Crit. Care Med.* 30(1 Suppl.):S27-S35.

Bernhagen et al. 1993. "MIF is a pituitary-derived cytokine that potentiates lethal endotoxaemia." *Nature* 365:756-759.

Bernhagen et al. 1994. "Macrophage migration inhibitory factor is a neuroendocrine mediator of endotoxaemia." *Trends Microbiol.* 2:198-201.

Bernhagen et al. 1995. "The emerging role of MIF in septic shock and infection." *Biotherapy* 8(2):123-7.

Bernhagen et al. 1998. "Regulation of the immune response by macrophage migration inhibitory factor: biological and structural features." *J. Mol. Med.* 76(3-4):151-161.

Bianchi et al. 1999. "Conformational Changes in Human Hepatitis C Virus NS3 Protease upon Binding of Product-Based Inhibitors." *Biochem.* 38(42): 13844-13852.

Blocki et al. 1992. "Rat liver protein linking chemical and immunological detoxification systems." *Nature* 360:269-270.

Blocki et al. 1993. "MIF proteins are theta-class glutathione S-transferase homologs." *Protein Science.* 2:2095-2102.

Bone et al. 1987. "A controlled clinical trial of high-dose methylprednisolone in the treatment of severe spesis and septic shock." N. Eng. J. Med. 317: 653-658.

Bucala. 1994. "MIF, a Previously Unrecognized Pituitary Hormone and Macrophage Cytokine, Is a Pivotal Mediator in Endotoxic Shock." *Circulatory Shock* 44(1):35-39.

Bucala. 1996. "MIF rediscovered: cytokine, pituitary hormone, and glucocorticoid-induced regulator of the immune response." *FASEB J.* 10(14):1607-1613.

Bucala. 1998. "Neuroimmunomodulation by Macrophage Migration Inhibitory Factor (MIF)." *Ann. N.Y. Acad. Sci.* 840:74-82.

Bucala. 2000. "A most interesting factor." *Nature* 408:146-147.

Calandra et al. 1996. "Macrophage Migration Inhibitory Factor: A Counter-Regulator of Glucocorticoid Action and Critical Mediator of Septic Shock." *J. Inflammation* 47:39-51.

Calandra et al. 1993. "Synthesis and Structure-Activity Relationships of 1-Acyl-4-((2-methyl-3-pyridyl)cyanomethyl)piperaines as PAF Antagonists." *J. Med. Chem.* 36:2984-2997.

Calandra et al. 1994. "The Macrophage Is an Important and Previously Unrecognized Source of Macrophage Migration Inhibitory Factor." *J. Exp. Med.* 179:1895-1902.

Calandra et al. 1995. "MIF as a glucocorticoid-induced modulator of cytokine production." *Nature* 377:68-71.

Calandra et al. 1997. "Macrophage Migration Inhibitory Factor (MIF): A Glucocorticoid Counter-Regulator within the Immune System." *Crit. Rev. Immunol.* 17(1):77-88.

Calandra et al. 2000. "Protection from septic shock by neutralization of macrophage migration inhibitory factor." *Nature Medicine* 6(2):164-170.

Carvajal et al. 1982. "Cell-Mediated Immunity Against Connective Tissue in Experimental Pulmonary Fibrosis." *Lung* 160(3): 131-40.

Chesney et al. 1999. "An Essential Role for Macrophage Migration Inhibitory Factor (MIF) in Angiogenesis and the Growth of a Murine Lymphoma." *Mol. Med.* 5: 181-191.

Coppola, et al.; Transformation in the 2-Quinolone Series, Journal of Heterocyclic Chemistry, Aug. 1981, vol. 18, No. 5. pp. 917-920.

Dandliker et al. 1970. "Fluorescence polarization in immunochemistry." *Immunochem.* 7:799-828.

Donnelly et al. 1997. "Macrophage migration inhibitory factor: a regulator of glucocorticoid activity with a critical role in inflammatory disease." *Mol. Med. Today* 3(11):502-507.

Donnelly et al. 1997. "Regulatory role for macrophage migration inhibitory factor in acute respiratory distress syndrome." *Nat. Med.* 3(3):320-323.

Durand et al. 1998. "Interaction of methyl green with an oligonucleotide in intramolecular duplex and triplex conformations." *Eur. Biophys. J.* 27(2):147-151.

Ferro et al. 1991. "Antigen induced inhibition of autoimmune response to rat male accessory glands: role of thymocytes on the efferent phase of the suppression." *Autoimmunity* 9(3):193-200.

Florkiewicz et al. 1991a. "Basic Fibroblast Growth Factor Gene Expression." Ann. N.Y. Acad. Sci. 638:109-126.

Florkiewicz et al. 1991b. "Multiple forms of bFGF: differential nuclear and cell surface localization." *Growth Factors* 4:265-275.

Galat et al. 1993. "Purification of macrophage migration inhibitory factor (MIF) from bovine brain cytosol." *Fed. Eur. Biochem. Soc.* 319:233-236.

Garner et al. 2003. "Macrophage Migration Inhibitory Factor (MIF) is a cardiac-derived myocardial depressant factor." *Amer. Jour. Physiol. Heart Circ Physiol.* 285(6):H2500-9. (E-pub Aug. 28, 2003).

Goto et al. 1993. "Synergistic Effects of Vascular Endothelial Growth Factor and Basic Fibroblast Growth Factor on the Proliferation and Cord Formation of Bovine Capillary Endothelial Cells Within Collagen Gels." *Lab. Invest.* 69:508-517.

Harrington et al. 1973. "Macrophage migration from an agarose droplet: development of a micromethod for assay of delayed hypersensitivity." *J. Immunol.* 110:752-759, 1973.

Haugland. 1999. *Handbook of Fluorescent Probes and Research Chemicals- Seventh Ed.*, Molecular Probes, Eugene, OR. Not included, substantially cumulative with Ninth Ed. below.

Haugland. 2002. *Handbook of Fluorescent Probes and Research Chemicals- Ninth Ed.*, Molecular Probes, Eugene, OR.

Hermanowski-Vosatka et al. 1999. "Enzymatically Inactive Macrophage Migration Inhibitory Factor Monocyte Chemotaxis and Random Migration." *Biochemistry* 38:12841-12849.

Huang et al. 2001. "Macrophage Migration Inhibitory Factor Is an Important Mediator in the Pathogenesis of Gastric Inflammation in Rats." *Gastroenterology* 121:619-630.

Huse et al. 1989. "Generation of a Large Combinatorial Library of the Immunoglobin Repertoire in Phage Lambda." *Science* 246:1275-1281.

Johnson et al. 1999. "A kinetic and stereochemical investigation of the role of lysine-32 in the phenylpyruvate tautomerase activity catalyzed by macrophage migration inhibitory factor." *Biochemistry* 38:16024-16033.

Kleifeld et al. 2000. "Spectroscopic Studies of Inhibited Alcohol Dehydrogenase from *Thermoanaerobacter brockii*: Proposed Structure for the Catalytic Intermediate State." *Biochem* 39(26):7702-7711.

Larsen et al. 1974. "Synthesis and Properties of 3-(3-Carboxyphenyl)pyruvic Acid and 3-(3-Carboxy-4-hydroxyphenyl)pyruvic Acid." *Acta. Chem. Scand. B.* 28:92-96.

Leech et al. 1998. "Involvement of macrophage migration inhibitory factor in the evolution of rat adjuvant arthritis." *Arthritis and Rheumatism* 41(5):910-917.

Lukes et al. 1954. "Synthese von α-methylfural." *Collection Czechoslov. Chem. Commun.* 19:609-610.

Lundblad et al. 1996. "Fluorescence Polarization Analysis of Protein-DNA and Protein-Protein Interactions." *Molec. Endocrinol.* 10:607-612.

Meanwell et al. 1993. "Inhibitors of Blood Platelet cAMP Phosphodiesterase. 4. Structural Variation of the Side-Chain Terminus of Water-Soluble 1,3-Dihydro-2*H*-imidazo[4,5-*b*]quinolin-2-one Derivatives." *J. Med. Chem.* 36:3251-3264.

Metz et al. 1997. "Role of Macrophage Migration Inhibitory Factor In Regulation of the Immune Response." *Advances in Immunology* 66:197-223.

Mitchell et al. 1999. "Sustained Mitogen-activated Protein Kinase (MAPK) and Cytoplasmic Phospholipase A2 Activation by Macrophage Migration Inhibitory Factor (MIF)." *J. Biol. Chem.* 274(25):18100-18106.

Monoclonal Anti-human MIF Antibody. Product information. R&D Systems. Minneapolis, MN, 2001.

Natanson et al. 1994. "Selected Treatment Strategies for Septic Shock Based on Proposed Mechanisms of Pathogenesis." *Annals of Internal Medicine* 120(9):771-783.

Nishihira, Jun. 1998. "Novel pathophysiological aspects of macrophage migration inhibitory factor (Review)." *Int. J. Mol. Med* 2(1):17-28.

Ogawa et al. 2000. "An anitbody for macrophage migration inhibitory factor suppresses tumour growth and inhibits tumour-associated angiogenesis." *Cytokine* 12(4):309-314.

Okamura et al. 1992. "Model system for tumor angiogenesis—involvement of transforming growth factor-α in tube formation of human microvascular endothelial cells induced by esophageal cancer cells." *Biochem. Biophys. Res. Comm.* 186:1471-1479.

Onodera et al. 2000. "Macrophage Migration Inhibitory Factor Up-regulates Expression of Matrix Metalloproteinases in Synovial Fibroblasts or Rheumatoid Arthritis." *J. Biol. Chem.* 275:444-450.

Pan et al. 2004. "Macrophage migration inhibitory factor deficiency impairs atherosclerosis in low-density lipoprotein receptor-deficient mice." *Circulation -Jour. Amer. Heart Assoc.* 3149-3153.

Perrin. 1926. "Polarisation de la lumiere de fluorescence vie moyenne des molecules dans l'etat excite." J. Phys. Rad. 1:390-401 (English Abstract included).

Petrovsky et al. 2002. "Macrophage Migration Inhibitory Factor: A Critical Neurohumoral Mediator." *Front Horm Res. Basel, Karger* 29:83-90.

Product Infomation. 1990. Cortone Acetate Tablets. Physicians' Desk Reference. Edward R. Barnhart, Publisher. USA p. 1341-1342.

Rice, et al. 1998. "Macrophage migration inhibitory factor (MIF): a critical upstream regulator of acute and chronic inflammatory responses." *Ann. Rep. Medicinal Chem.* 243-252.

Rosengren et al. 1996. "The Immunoregulatory Mediator Macrophage Migration Inhibitory Factor (MIF) Catalyzes a Tautomerization Reaction." *Mol. Med.* 2:143-149.

Rupreht et al., Murine monoclonal antibodies directed against human recombinant Macrophage Migration Inhibitory Factor, *Pflügers Arch.—Eur. J. Physiol.* (2000) 440 [Suppl.]:R78-R80.

Sakaue et al. 1999. "Regulation of Macrophage Migration Inhibitory Factor (MIF) Expression by Glucose and Insulin in Adipocytes In Vitro." *Mol. Med.* 5:361-371.

Sarver et al. 1999. "Thermodynamic and circular dichroism studies differentiate inhibitor interactions with the stromelysin $S_1$-$S_3$ and $S'_1$-$S'_3$ subsites." *Biochim Biophys Acta* 1434(2):304-316.

Scatchard et al. 1949. "The Attractions of Proteins for Small Molecules and Ions." Ann. N.Y. Acad. Sci. 51:660-672.

Scopes, R. K. 1987. *Protein Purification: Principles and Practice, Second Edition*, Springer-Verlag. N.Y.

Sprung et al. 1984. "The effects of high-dose corticosteroids in patients with septic shock." *N. Engl. J. Med.* 311: 1137-1143.

Swope et al. 1998. "Direct link between cytokine activity and catalytic site for macrophage migration inhibitory factor." *EMBO J.* 17(13):3534-3541.

Swope et al. 1999. "Macrophage Migration Inhibitory Factor: Cytokine, Hormone, or Enzyme?" *Rev. Physiol. Biochem. Pharmacol.* 139:1-32.

Takahashi et al. 1998. "Involvement of Macrophage Migration Inhibitory Factor (MIF) in the Mechanism of Tumor Cell Growth." *Mol. Med.* 4:707-714.

Takahashi et al. 1999 "Anitsense Macrophage Migration Inhibitory Factor (MIF) Prevents Anit-IgM Mediated Growth Arrest and Apoptosis of a Mature B Cell Line by Regulating Cell Cycle Progression." *Microbiol. Immunol.* 43(1)61-67.

Urry, D. W. 1969. "Optical Rotation and Biomolecular Conformation." *Spectroscopic Approaches to Biomolecular Conformation.* American Medical Association Press, Chicago, IL, pp. 33-121.

Waeber et al. 1999. "A Role for the Endocrine and Pro-inflammatory Mediator MIF in the Control of Insulin Secretion During Stress." *Diabetes Met. Res. Rev.* 15(1):47-54.

Ward et al. 1989. "Binding activities of a repertoire of single immunoglobulin variable domains secreted from *Escherichia coli*." *Nature* 341:544-546.

Warren et al. 1995. "Regulation by Vascular Endothelial Growth Factor of Human Colon Cancer Tumorgenesis in a Mouse Model of Experimental Liver Metastasis." *J. Clin. Invest.* 95:1789-1797.

Weir, D.M. 1986. *Handbook of Experimental Immunology, Cellular Immunology.* Backwell Scientific, Boston, MA.

Weiser et al. 1985. "Generation of human hybridomas producing migration inhibitory factor (MIF) and of murine hybridomas secreting monoclonal antibodies to human MIF." *Cellular Immunol.* 90:167-178.

Weiser et al. 1989. "Molecular cloning of a cDNA encoding a human macrophage migration inhibitory factor." *Proc. Natl. Acad. Sci. USA.* 86:7522-7526.

Weiser et al. 1991. "Human recombinant migration inhibitory factor activates human macrophages to kill *Leishmania donovani*." J. Immunol. 147:2006-2011.

Winder et al. 1993. "The mouse *brown* (b) locus protein has dopachrome tautomerase activity and is located in lysosomes in transfected fibroblasts." *J. Cell Sci.* 106:153-166.

Winter et al. 1993. "Humanized antibodies." *Immunol. Today* 14(6):243-246.

Wistow et al. 1993. "A macrophage migration inhibitory factor is expressed in the differentiating cells of the eye lens." *Proc. Natl. Acad. Sci. USA* 90:1272-1275.

Wolff, M. E. "Burger's Medicinal Chemistry, 5th Ed. Part 1", pp. 975-977 (1995).

Wu et al. 1994. "Resonance Energy Transfer: Methods and Applications." *Analytical Biochem.* 218:1-13.

Yang et al. 1998. "Reversal of Established Rat Crescentic Glomerulonephritis by Blockade of Macrophage Migration Inhibitory Factor (MIF): Potential Role of MIF in Regulating Glucocorticoid Production." *Mol. Med* 4(6):413-424.

Zuckerman et al. 1989. "Differential regulation of lipopolysaccharide-induced interleukin 1 and tumour necrosis factor synthesis: effects on endogenous and exogenous glucocorticoids and the role of the pituitary-adrenal axis." *Eur. J. Immunol.* 19:310-305.

SUBSTITUTED NAPHTHYRIDINE DERIVATIVES AS INHIBITORS OF MACROPHAGE MIGRATION INHIBITORY FACTOR AND THEIR USE IN THE TREATMENT OF HUMAN DISEASES

RELATED APPLICATION

This application is a continuation of U.S. patent application Ser. No. 10/920,031, filed Aug. 17, 2004, which claims priority under 35 U.S.C. §119(e) to U.S. Provisional Application No. 60/497,443, filed Aug. 22, 2003, the disclosures of which are hereby incorporated by reference in their entirety.

FIELD OF THE INVENTION

Inhibitors of macrophage migration inhibitory factor (MIF) having a naphthyridine backbone are provided which have utility in the treatment of a variety of disorders, including the treatment of pathological conditions associated with MIF activity.

BACKGROUND OF THE INVENTION

The lymphokine, macrophage migration inhibitory factor (MIF), has been identified as a mediator of the function of macrophages in host defense and its expression correlates with delayed hypersensitivity, immunoregulation, inflammation, and cellular immunity. See Metz and Bucala, *Adv. Immunol.* 66:197-223, 1997. Macrophage migration inhibitory factors (MIFs), which are between 12-13 kilodaltons (kDa) in size, have been identified in several mammalian and avian species; see, for example, Galat et al., *Fed. Eur. Biochem. Soc.* 319:233-236, 1993; Wistow et al., *Proc. Natl. Acad. Sci. USA* 90:1272-1275, 1993; Weiser et al., *Proc. Natl. Acad. Sci. USA* 86:7522-7526, 1989; Bernhagen et al., *Nature* 365:756-759, 1993; Blocki et al., *Protein Science* 2:2095-2102, 1993; and Blocki et al., *Nature* 360:269-270, 1992. Although MIF was first characterized as being able to block macrophage migration, MIF also appears to effect macrophage adherence; induce macrophage to express interleukin-1-beta, interleukin-6, and tumor necrosis factor alpha; up-regulate HLA-DR; increase nitric oxide synthase and nitric oxide concentrations; and activate macrophage to kill *Leishmania donovani* tumor cells and inhibit *Mycoplasma avium* growth, by a mechanism different from that effected by interferon-gamma. In addition to its potential role as an immunoevasive molecule, MIF can act as an immunoadjuvant when given with bovine serum albumin or HIV gp120 in incomplete Freunds or liposomes, eliciting antigen induced proliferation comparable to that of complete Freunds. Also, MIF has been described as a glucocorticoid counter regulator and angiogenic factor. As one of the few proteins that is induced and not inhibited by glucocorticoids, it serves to attenuate the immunosuppressive effects of glucocorticoids. As such, it is viewed as a powerful element that regulates the immunosuppressive effects of glucocorticoids. Hence, when its activities/gene expression are over-induced by the administration of excess exogenous glucocorticoids (for example when clinical indicated to suppress inflammation, immunity and the like), there is significant toxicity because MIF itself exacerbates the inflammatory/immune response. See Buccala et al., *Ann. Rep. Med. Chem.* 33:243-252, 1998.

While MIF is also thought to act on cells through a specific receptor that in turn activates an intracellular cascade that includes erk phosphorylation and MAP kinase and upregulation of matrix metalloproteases, c-jun, c-fos, and IL-1 mRNA (see Onodera et al., *J. Biol. Chem.* 275:444-450, 2000), it also possesses endogenous enzyme activity as exemplified by its ability to tautomerize the appropriate substrates (e.g., dopachrome). Further, it remains unclear whether this enzymatic activity mediates the biological response to MIF and the activities of this protein in vitro and in vivo. While site directed mutagenesis of MIF has generated mutants which possess full intrinsic activity, yet fail to possess enzyme activity (Hermanowski-Vosatka et al., *Biochemistry* 38:12841-12849, 1999), Swope et al. have described a direct link between cytokine activity and the catalytic site for MIF (Swope et al., *EMBO J.* 17(13):3534-3541, 1998). Accordingly, it is unclear that strategies to identify inhibitors of MIF activity through inhibition of dopachrome tautomerase alone yields inhibitors of MIF activity of clinical value. The ability to evaluate the inhibition of MIF to its cell surface receptor is also limited since no high affinity receptor is currently known.

The interest in developing MIF inhibitors derives from the observation that MIF is known for its cytokine activity concentrating macrophages at sites of infection, and cell-mediated immunity. Moreover, MIF is known as a mediator of macrophage adherence, phagocytosis, and tumoricidal activity. See Weiser et al., *J. Immunol.* 147:2006-2011, 1991. Hence, the inhibition of MIF results in the indirect inhibition of cytokines, growth factors, chemokines, and lymphokines that the macrophage can otherwise bring to a site of inflammation. Human MIF cDNA has been isolated from a T-cell line, and encodes a protein having a molecular mass of about 12.4 kDa with 115 amino acid residues that form a homotrimer as the active form (Weiser et al., *Proc. Natl. Acad. Sci. USA* 86:7522-7526, 1989). While MIF was originally observed in activated T-cells, it has now been reported in a variety of tissues including the liver, lung, eye lens, ovary, brain, heart, spleen, kidney, muscle, and others. See Takahashi et al., *Microbiol. Immunol.* 43(1):61-67, 1999. Another characteristic of MIF is its lack of a traditional leader sequence (i.e., a leaderless protein) to direct classical secretion through the ER/Golgi pathway.

A MIF inhibitor (and a method to identify MIF inhibitors) that act by neutralizing the cytokine activity of MIF presents significant advantages over other types of inhibitors. For example, the link between tautomerase activity alone and the inflammatory response is controversial. Furthermore, inhibitors that act intracellularly are often toxic by virtue of their action on related targets or the activities of the target inside cells. Small molecule inhibitors of the ligand receptor complex are difficult to identify let alone optimize and develop. The ideal inhibitor of a cytokine like MIF is one that alters MIF itself so that when released from the cell it is effectively neutralized. A small molecule with this activity is superior to antibodies because of the fundamental difference between proteins and chemicals as drugs. See, Metz and Bucala (supra); Swope and Lolis, *Rev. Physiol. Biochem. Pharmacol* 139:1-32, 1999; Waeber et al., *Diabetes M. Res. Rev.* 15(1):47-54, 1999; Nishihira, *Int. J. Mol. Med.* 2(1):17-28, 1998; Bucala, *Ann. N.Y. Acad. Sci.* 840:74-82, 1998; Bernhagen et al., *J. Mol. Med.* 76(3-4):151-161, 1998; Donnelly and Bucala, *Mol. Med. Today* 3(11):502-507, 1997; Bucala et al., *FASEB J.* 10(14):1607-1613, 1996.

SUMMARY OF THE INVENTION

As MIF has been identified in a variety of tissues and has been associated with numerous pathological events, there exists a need in the art to identify inhibitors of MIF. There is also a need for pharmaceutical compositions containing such inhibitors, as well as methods relating to the use thereof to treat, for example, immune related disorders or other MIF induced pathological events, such as tumor associated angiogenesis. The preferred embodiments can fulfill these needs, and provide other advantages as well.

In preferred embodiments, inhibitors of MIF are provided that have the following general structures (Ia), (Ib), (Ic), and (Id):

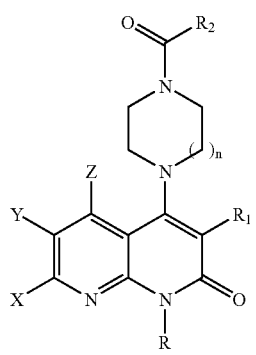
(Ia)

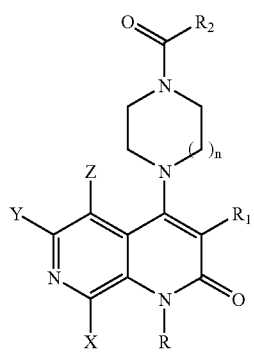
(Ib)

(Ic)

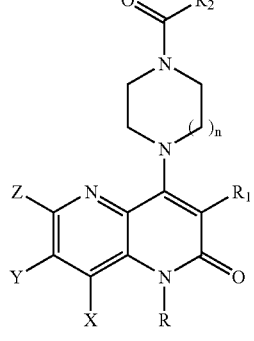
(Id)

including stereoisomers, prodrugs, and pharmaceutically acceptable salts thereof, wherein n, R, $R_1$, $R_2$, X, Y and Z are as defined below.

The MIF inhibitors of preferred embodiments have utility over a wide range of therapeutic applications, and can be employed to treat a variety of disorders, illnesses, or pathological conditions including, but not limited to, a variety of immune related responses, tumor growth (e.g., cancer, such as prostate cancer, breast cancer, lung cancer, liver cancer, skin cancer, brain cancer, bone cancer, colon cancer, testicular cancer, etc.), glomerulonephritis, inflammation, malarial anemia, septic shock, sepsis, tumor associated angiogenesis, vitreoretinopathy, psoriasis, graft versus host disease (tissue rejection), atopic dermatitis, rheumatoid arthritis, inflammatory bowel disease, inflammatory lung disease, otitis media, Crohn's disease, acute respiratory distress syndrome, delayed-type hypersensitivity, transplant rejection, immune-mediated and inflammatory elements of CNS disease (e.g., Alzheimer's, Parkinson's, multiple sclerosis, etc.), muscular dystrophy, diseases of hemostasis (e.g., coagulopathy, veno occlusive diseases, etc.), allergic neuritis, granuloma, diabetes, graft versus host disease, chronic renal damage, alopecia (hair loss), acute pancreatitis, joint disease, cardiac dysfunction (e.g., systolic cardiac dysfunction, diastolic cardiac dysfunction), myocardial infarction, congestive heart failure, cardiovascular disease (e.g., restenosis, atherosclerosis), joint disease, osteoarthritis, peritonitis, nephropathy and others. Such methods include administering an effective amount of one or more inhibitors of MIF as provided by the preferred embodiments, preferably in the form of a pharmaceutical composition, to an animal in need thereof. Pharmaceutical compositions are provided containing one or more inhibitors of MIF of preferred embodiments in combination with a pharmaceutically acceptable carrier and/or diluent.

Accordingly, in a first embodiment a compound for inhibiting macrophage migration inhibitory factor is provided, the compound having a structure selected from the group consisting of:

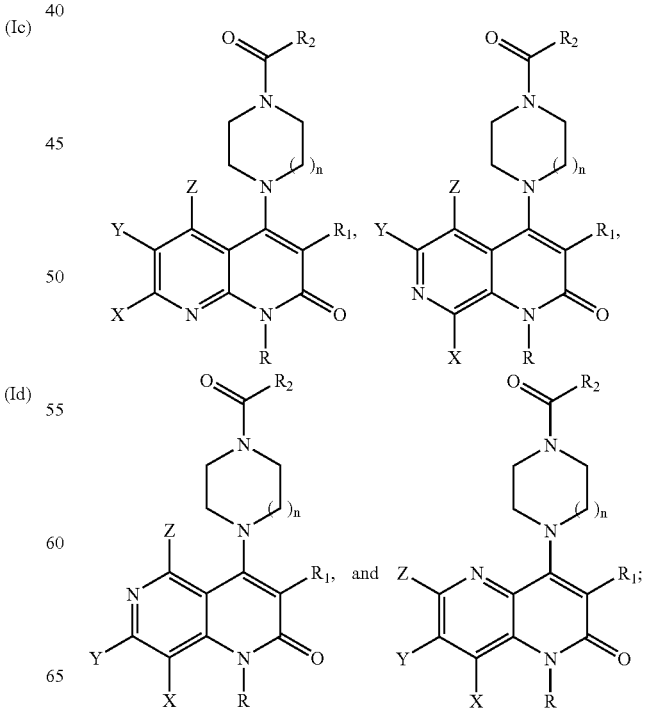

or a stereoisomer, a prodrug, or a pharmaceutically acceptable salt thereof, wherein R is selected from the group consisting of hydrogen, alkyl, substituted alkyl, alkenyl, substituted alkenyl, cycloalkyl, substituted cycloalkyl, aryl, substituted aryl, arylalkyl, substituted arylalkyl, acylalkyl, substituted acylalkyl, heterocycle, substituted heterocycle, —$(CH_2)_mC(=O)Ar$, and —$(CH_2)_mNR_4R_5$; $R_1$ is selected from the group consisting of —CN, —NO, —$NO_2$, —$C(=O)R_3$, —$C(=O)OH$, —$NHC(=O)R_3$, —$C(=O)OR_3$, —$C(=O)NR_4R_5$, —$NR_3C(=O)R_3$, —$SO_2NR_4R_5$, —$NR_3SO_2R_3$, —$NHSO_2R_3$, —$S(O)_mR_3$, —$(CH_2)_mNR_4R_5$, and —$(CH_2)_mC(=O)Ar$; $R_2$ is selected from the group consisting —$CH_2R_3$, —$NR_4R_5$, —$OR_3$, and —$R_3$; $R_3$ is independently selected from the group consisting of alkyl, substituted alkyl, alkenyl, substituted alkenyl, cycloalkyl, substituted cycloalkyl, aryl, substituted aryl, arylalkyl, substituted arylalkyl, acylalkyl, substituted acylalkyl, heterocycle, substituted heterocycle; $R_4$ and $R_5$ are independently selected from the group consisting of hydrogen, alkyl, substituted alkyl, alkenyl, substituted alkenyl, cycloalkyl, substituted cycloalkyl, aryl, substituted aryl, arylalkyl, substituted arylalkyl, acylalkyl, substituted acylalkyl, heterocycle, and substituted heterocycle, or $R_4$ and $R_5$ taken together comprise heterocycle or substituted heterocycle; X is selected from the group consisting of hydrogen, halogen, —F, —Cl, —CN, —NO, —$NO_2$, —$OCF_3$, —$CF_3$, —$NHSO_2R_3$, —$C(=O)R_3$, —$C(=O)OR_3$, —$C(=O)NR_4R_5$, —$NR_3C(=O)R_3$, —$NR_3SO_2R_3$, —$S(O)_mR_3$, —$R_3$, —$OR_3$, —$SR_3$, —$C(=O)OH$, —$NHC(=O)R_3$, and —$NR_4R_5$; Y is selected from the group consisting of hydrogen, halogen, —F, —Cl, —CN, —NO, —$NO_2$, —$OCF_3$, —$CF_3$, —$NHSO_2R_3$, —$C(=O)R_3$, —$C(=O)OR_3$, —$C(=O)NR_4R_5$, —$NR_3C(=O)R_3$, —$NR_3SO_2R_3$, —$S(O)_m R_5$, —$R_3$, —$OR_3$, —$SR_3$, —$C(=O)OH$, —$NHC(=O)R_3$, and —$NR_4R_5$; Z is selected from the group consisting of hydrogen, halogen, —F, —Cl, —CN, —NO, —$NO_2$, —$OCF_3$, —$CF_3$, —$NHSO_2R_3$, —$C(=O)R_3$, —$C(=O)OR_3$, —$C(=O)NR_4R_5$, —$NR_3C(=O)R_3$, —$NR_3SO_2R_3$, —$S(O)_mR_3$, —$R_3$, —$OR_3$, —$SR_3$, —$C(=O)OH$, —$NHC(=O)R_3$, and —$NR_4R_5$; Ar is selected from the group consisting of aryl and substituted aryl; m is independently 0, 1, 2, 3, or 4; and n is 0, 1, or 2.

In an aspect of the first embodiment, a compound having a structure:

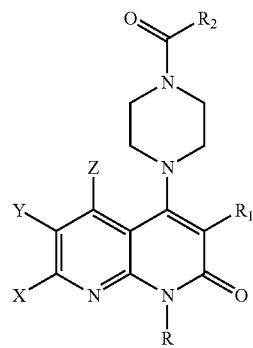

or a stereoisomer, a prodrug, or a pharmaceutically acceptable salt thereof, wherein R is selected from the group consisting of hydrogen, $C_1$-$C_{12}$ alkyl, $C_2$-$C_{12}$ alkenyl, $C_3$-$C_{12}$ cycloalkyl, $C_6$-$C_{12}$ aryl, $C_7$-$C_{12}$ arylalkyl, $C_7$-$C_{12}$ alkylaryl, $C_2$-$C_{12}$ acylalkyl, $C_3$-$C_{12}$ heterocyclealkyl, $C_3$-$C_{12}$ alkylheterocycle, and $C_2$-$C_{12}$ heterocycle, wherein R is substituted with one or more substitutents selected from the group consisting of hydrogen, —F, —Cl, —CN, —NO, —$NO_2$, —$C(=O)R_3$, —$C(=O)OR_3$, —$OC(=O)R_3$,—$C(=O)NR_3R_3$, —$NR_3C(=O)R_3$, —$SO_2NR_3R_3$, —$NR_3SO_2R_3$, —$OR_3$, —$SR_3$, —$NHSO_2R_3$, —$S(O)_mR_3$,—$C(=O)OH$, —$NHC(=O)R_3$, —$(CH_2)_mC(=O)Ar$, and —$(CH_2)_mNR_3R_3$; $R_1$ is selected from the group consisting of —CN, —NO, —$NO_2$, —$C(=O)R_3$, —$C(=O)OR_3$, —$OC(=O)R_3$, —$C(=O)NR_3R_3$, —$NR_3C(=O)R_3$, —$SO_2NR_3R_3$, —$NR_3SO_2R_3$, —$OR_3$, —$SR_3$, —$NHSO_2R_3$, —$S(O)_mR_3$, —$C(=O)OH$, —$NHC(=O)R_3$, —$(CH_2)_mC(=O)Ar$, and —$(CH_2)_mNR_3R_3$; $R_2$ is selected from the group consisting —$NR_4R_5$, —$OR_3$, and —$R_3$; $R_3$ is independently selected from the group consisting of $C_1$-$C_{12}$ alkyl, $C_2$-$C_{12}$ alkenyl, $C_3$-$C_{12}$ cycloalkyl, $C_6$-$C_{12}$ aryl, $C_7$-$C_{12}$ arylalkyl, $C_7$-$C_{12}$ alkylaryl, $C_2$-$C_{12}$ acylalkyl, $C_3$-$C_{12}$ heterocyclealkyl, $C_3$-$C_{12}$ alkylheterocycle, and $C_2$-$C_{12}$ heterocycle, wherein $R_3$ is substituted with one or more substitutents selected from the group consisting of hydrogen, —F, —Cl, —CN, —NO, —$NO_2$, —CN, —NO, —$NO_2$, $C_1$-$C_{12}$ alkoxy, and $C_1$-$C_{12}$ alkylthio; $R_4$ and $R_5$ are independently selected from the group consisting $C_1$-$C_{12}$ alkyl, $C_2$-$C_{12}$ alkenyl, $C_3$-$C_{12}$ cycloalkyl, $C_6$-$C_{12}$ aryl, $C_7$-$C_{12}$ arylalkyl, $C_7$-$C_{12}$ alkylaryl, $C_2$-$C_{12}$ acylalkyl, $C_3$-$C_{12}$ heterocyclealkyl, $C_3$-$C_{12}$ alkylheterocycle, and $C_2$-$C_{12}$ heterocycle substituted with one or more substitutents selected from the group consisting of hydrogen, —F, —Cl, —CN, —NO, —$NO_2$, —CN, —NO, —$NO_2$, $C_1$-$C_{12}$ alkoxy, and $C_1$-$C_{12}$ alkylthio, or $R_4$ and $R_5$ together comprise a $C_2$-$C_{12}$ heterocycle substituted with one or more substitutents selected from the group consisting of hydrogen, —F, —Cl, —CN, —NO, —$NO_2$, —CN, —NO, —$NO_2$, —$OCF_3$, —$CF_3$, $C_1$-$C_{12}$ alkoxy, and $C_1$-$C_{12}$ alkylthio; X is selected from the group consisting of hydrogen, —F, —Cl, —CN, —NO, —$NO_2$, —$OCF_3$, —$CF_3$, —$NHSO_2R_3$, —$C(=O)R_3$, —$C(=O)OR_3$, —$OC(=O)R_3$, —$C(=O)NR_3R_3$, —$NR_3C(=O)R_3$, —$SO_2NR_3R_3$, —$NR_3SO_2R_3$, —$OR_3$, —$S(O)_mR_3$, —$SR_3$, —$C(=O)OH$, —$NHC(=O)R_3$, —$(CH_2)_mC(=O)Ar$, and —$(CH_2)_mNR_3R_3$; Y is selected from the group consisting of hydrogen, —F, —Cl, —CN, —NO, —$NO_2$, —$OCF_3$, —$CF_3$, —$NHSO_2R_3$, —$C(=O)R_3$, —$C(=O)OR_3$, —$OC(=O)R_3$, —$C(=O)NR_3R_3$, —$NR_3C(=O)R_3$, —$SO_2NR_3R_3$, —$NR_3SO_2R_3$, —$OR_3$, —$S(O)_mR_3$, —$SR_3$, —$C(=O)OH$, —$NHC(=O)R_3$, —$(CH_2)_mC(=O)Ar$, and —$(CH_2)_m NR_3R_3$; Z is selected from the group consisting of hydrogen, —F, —Cl, —CN, —NO, —$NO_2$, —$OCF_3$, —$CF_3$, —$NHSO_2R_3$, —$C(=O)R_3$, —$C(=O)OR_3$, —$OC(=O)R_3$, —$C(=O)NR_3R_3$, —$NR_3C(=O)R_3$, —$SO_2NR_3R_3$, —$NR_3SO_2R_3$, —$OR_3$, —$S(O)_mR_3$, —$SR_3$, —$C(=O)OH$, —$NHC(=O)R_3$, —$(CH_2)_mC(=O)Ar$, and —$(CH_2)_m NR_3R_3$; Ar is independently selected from the group consisting of $C_6$-$C_{12}$ aryl substituted with one or more substitutents selected from the group consisting of hydrogen, —F, —Cl, —CN, —NO, —$NO_2$, —CN, —NO, —$NO_2$, $C_1$-$C_{12}$ alkyl, $C_1$-$C_{12}$ alkoxy, and $C_1$-$C_{12}$ alkylthio; and m is independently 0, 1, 2, 3, or 4.

In an aspect of the first embodiment, a compound having a structure:

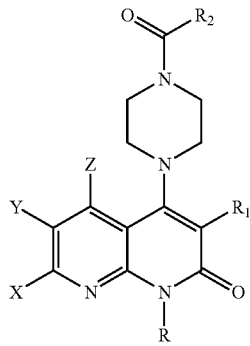

or a stereoisomer, a prodrug, or a pharmaceutically acceptable salt thereof, wherein R is selected from the group consisting of hydrogen, $C_1$-$C_{12}$ alkyl, $C_2$-$C_{12}$ alkenyl, $C_3$-$C_{12}$ cycloalkyl, $C_6$-$C_{12}$ aryl, $C_7$-$C_{12}$ arylalkyl, $C_7$-$C_{12}$ alkylaryl, $C_2$-$C_{12}$ acylalkyl, $C_3$-$C_{12}$ heterocyclealkyl, $C_3$-$C_{12}$ alkylheterocycle, and $C_2$-$C_{12}$ heterocycle, wherein R is substituted with one or more substitutents selected from the group consisting of hydrogen, —F, —Cl, —CN, —NO, —NO$_2$, —NHSO$_2$R$_3$, —C(=O)R$_3$, —C(=O)OR$_3$, —OC(=O)R$_3$, —C(=O)NR$_3$R$_3$, —NR$_3$C(=O)R$_3$, —SO$_2$NR$_3$R$_3$, —NR$_3$SO$_2$R$_3$, —OR$_3$, —SR$_3$, —S(O)$_m$R$_3$, —(CH$_2$)$_m$C(=O)Ar, and —(CH$_2$)$_m$NR$_3$R$_3$; R$_1$ is selected from the group consisting of —CN, —NO, —NO$_2$, —C(=O)R$_3$, —C(=O)OR$_3$, —OC(=O)R$_3$, —NHSO$_2$R$_3$, —C(=O)NR$_3$R$_3$, —NR$_3$C(=O)R$_3$, —SO$_2$NR$_3$R$_3$, —NR$_3$SO$_2$R$_3$, —OR$_3$, —SR$_3$, —S(O)$_m$R$_3$, —(CH$_2$)$_m$C(=O)Ar, and —(CH$_2$)$_m$NR$_3$R$_3$; R$_2$ is selected from the group consisting —NR$_4$R$_5$, —OR$_3$, and —R$_3$; R$_3$ is independently selected from the group consisting of $C_1$-$C_{12}$ alkyl, $C_2$-$C_{12}$ alkenyl, $C_3$-$C_{12}$ cycloalkyl, $C_6$-$C_{12}$ aryl, $C_7$-$C_{12}$ arylalkyl, $C_7$-$C_{12}$ alkylaryl, $C_2$-$C_{12}$ acylalkyl, $C_3$-$C_{12}$ heterocyclealkyl, $C_3$-$C_{12}$ alkylheterocycle, and $C_2$-$C_{12}$ heterocycle, wherein R$_3$ is substituted with one or more substitutents selected from the group consisting of hydrogen, —F, —Cl, —CN, —NO, —NO$_2$, —CN, —NO, —NO$_2$, $C_1$-$C_{12}$ alkoxy, and $C_1$-$C_{12}$ alkylthio; R$_4$ and R$_5$ are independently selected from the group consisting $C_1$-$C_{12}$ alkyl, $C_2$-$C_{12}$ alkenyl, $C_3$-$C_{12}$ cycloalkyl, $C_6$-$C_{12}$ aryl, $C_7$-$C_{12}$ arylalkyl, $C_7$-$C_{12}$ alkylaryl, $C_2$-$C_{12}$ acylalkyl, $C_3$-$C_{12}$ heterocyclealkyl, $C_3$-$C_{12}$ alkylheterocycle, and $C_2$-$C_{12}$ heterocycle substituted with one or more substitutents selected from the group consisting of hydrogen, —F, —Cl, —CN, —NO, —NO$_2$, —CN, —NO, —NO$_2$, $C_1$-$C_{12}$ alkoxy, and $C_1$-$C_{12}$ alkylthio, or R$_4$ and R$_5$ together comprise a $C_2$-$C_{12}$ heterocycle substituted with one or more substitutents selected from the group consisting of hydrogen, —F, —Cl, —CN, —NO, —NO$_2$, —CN, —NO, —NO$_2$, $C_1$-$C_{12}$ alkyl, $C_1$-$C_{12}$ alkoxy, $C_1$-$C_{12}$ alkylthio, and $C_1$-$C_{12}$ alkyl substituted with one or more substitutents selected from the group consisting of hydrogen, —F, and —Cl; X is selected from the group consisting of hydrogen, —F, —Cl, —OCF$_3$, —CF$_3$, $C_1$-$C_{12}$ alkyl, and $C_1$-$C_{12}$ alkyl substituted with one or more substitutents selected from the group consisting of hydrogen, —F, and —Cl; Y is selected from the group consisting of hydrogen, —F, —Cl, —OCF$_3$, —CF$_3$, $C_1$-$C_{12}$ alkyl, and $C_1$-$C_{12}$ alkyl substituted with one or more substitutents selected from the group consisting of hydrogen, —F, and —Cl; Z is selected from the group consisting of hydrogen, —F, —Cl, —OCF$_3$, —CF$_3$, $C_1$-$C_{12}$ alkyl, and $C_1$-$C_{12}$ alkyl substituted with one or more substitutents selected from the group consisting of hydrogen, —F, and —Cl; Ar is selected from the group consisting of $C_6$-$C_{12}$ aryl substituted with one or more substitutents selected from the group consisting of hydrogen, —F, —Cl, $C_1$-$C_{12}$ alkyl, and $C_1$-$C_{12}$ alkyl substituted with one or more substitutents selected from the group consisting of hydrogen, —F, and —Cl; and m is independently 0, 1, 2, 3, or 4.

In an aspect of the first embodiment, R$_1$ comprises —(CH$_2$)$_m$C(=O)Ar.

In an aspect of the first embodiment, R$_1$ comprises —C(=O)OCH$_2$CH$_3$.

In an aspect of the first embodiment, R$_1$ comprises —NH—C(=O)CH$_3$.

In an aspect of the first embodiment, R$_1$ comprises —CN.

In an aspect of the first embodiment, R$_1$ comprises —NO$_2$.

In an aspect of the first embodiment, R$_1$ comprises —NH$_2$.

In an aspect of the first embodiment, R$_2$ comprises

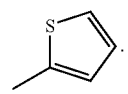

In an aspect of the first embodiment, R$_2$ comprises

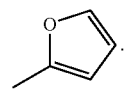

In an aspect of the first embodiment, R comprises —(CH$_2$)$_m$C(=O)Ar.

In an aspect of the first embodiment, X is selected from the group consisting of hydrogen, fluorine, and chlorine; wherein Y is selected from the group consisting of hydrogen, fluorine, and chlorine; and wherein Z is selected from the group consisting of hydrogen, fluorine, and chlorine.

In an aspect of the first embodiment, a compound having a structure:

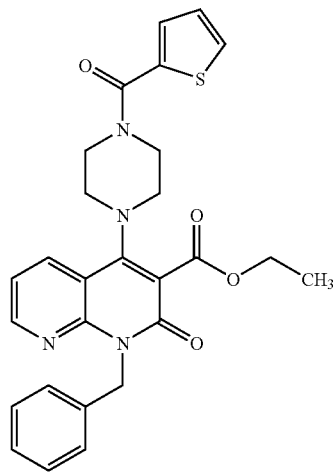

or a stereoisomer, a prodrug, or a pharmaceutically acceptable salt thereof is provided.

In an aspect of the first embodiment, a compound having a structure:

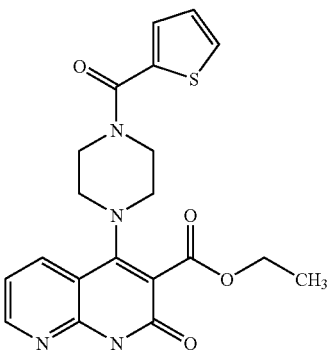

or a stereoisomer, a prodrug, or a pharmaceutically acceptable salt thereof is provided.

In an aspect of the first embodiment, a compound having a structure:

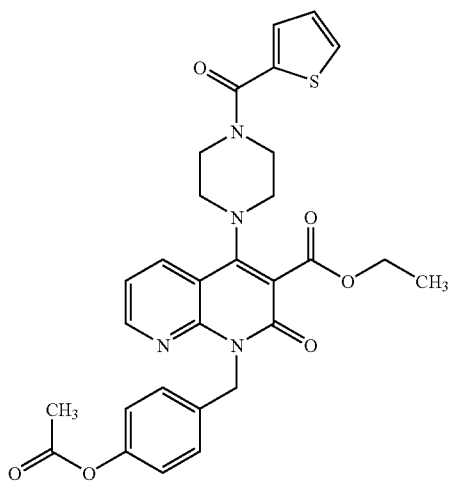

or a stereoisomer, a prod rug, or a pharmaceutically acceptable salt thereof is provided.

In an aspect of the first embodiment, a compound having a structure:

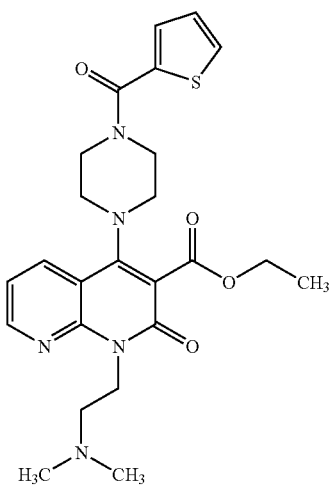

or a stereoisomer, a prodrug, or a pharmaceutically acceptable salt thereof is provided.

In an aspect of the first embodiment, a compound having a structure:

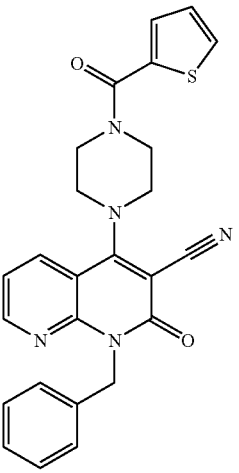

or a stereoisomer, a prodrug, or a pharmaceutically acceptable salt thereof is provided.

In an aspect of the first embodiment, a compound having a structure:

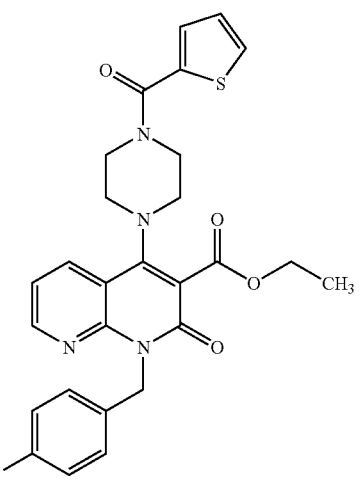

In an aspect of the first embodiment, a compound having a structure:

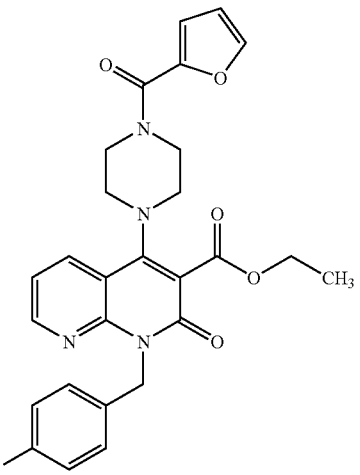

or a stereoisomer, a prodrug, or a pharmaceutically acceptable salt thereof is provided.- or a stereoisomer, a prodrug, or a pharmaceutically acceptable salt thereof is provided.

In an aspect of the first embodiment, a compound having a structure:

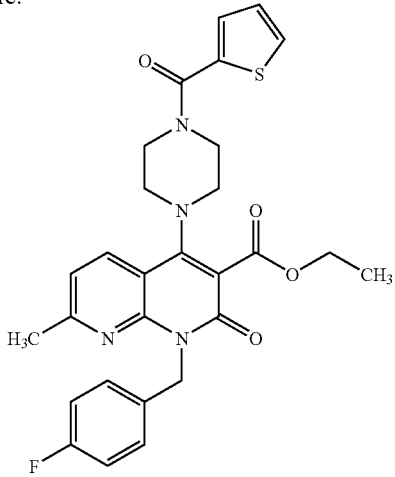

or a stereoisomer, a prodrug, or a pharmaceutically acceptable salt thereof.

In an aspect of the first embodiment, a compound having a structure:

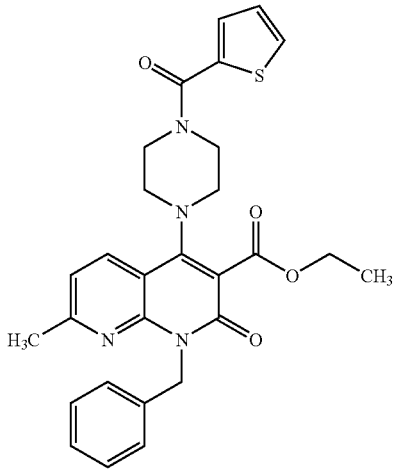

or a stereoisomer, a pro drug, or a pharmaceutically acceptable salt thereof is provided.

In an aspect of the first embodiment, a compound having a structure:

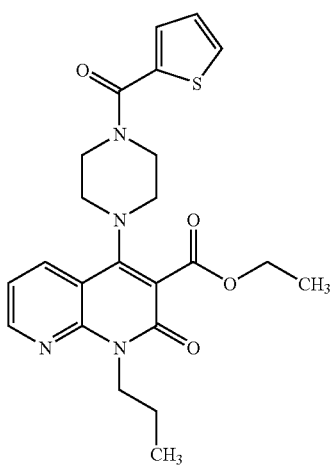

or a stereoisomer, a prodrug, or a pharmaceutically acceptable salt thereof is provided.

In an aspect of the first embodiment, a compound having a structure:

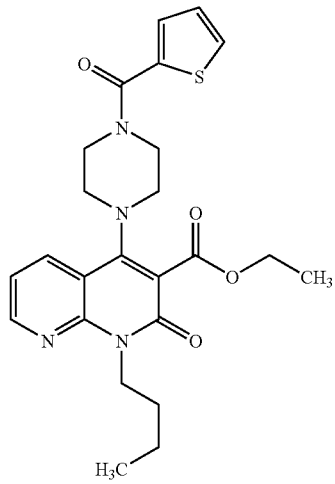

or a stereoisomer, a prodrug, or a pharmaceutically acceptable salt thereof is provided.

In an aspect of the first embodiment, a compound having a structure:

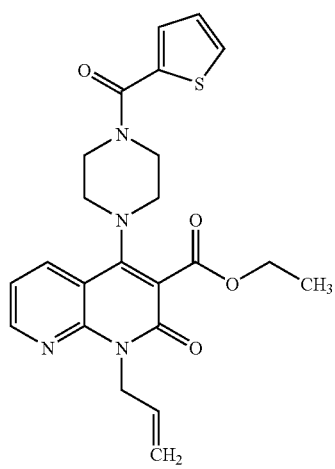

or a stereoisomer, a prodrug, or a pharmaceutically acceptable salt thereof is provided.

In an aspect of the first embodiment, a compound having a structure:

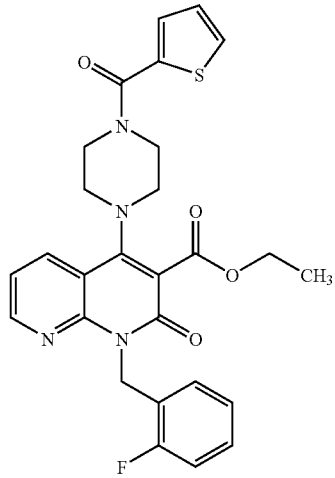

a stereoisomer, a prodrug, or a pharmaceutically acceptable salt thereof is provided.

In an aspect of the first embodiment, a compound having a structure:

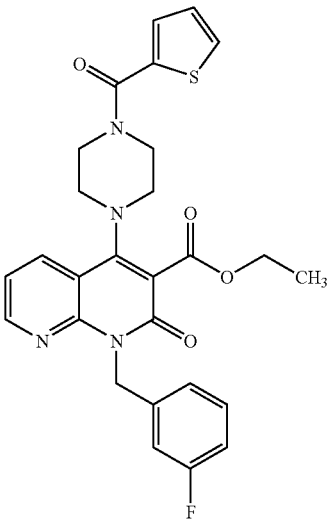

or a stereoisomer, a prodrug, or a pharmaceutically acceptable salt thereof is provided.

In an aspect of the first embodiment, a compound having a structure:

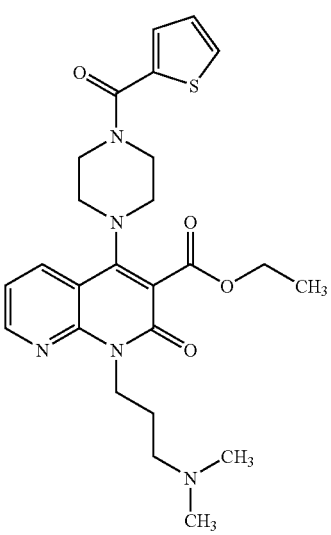

or a stereoisomer, a prodrug, or a pharmaceutically acceptable salt thereof is provided.

In an aspect of the first embodiment, a compound having a structure:

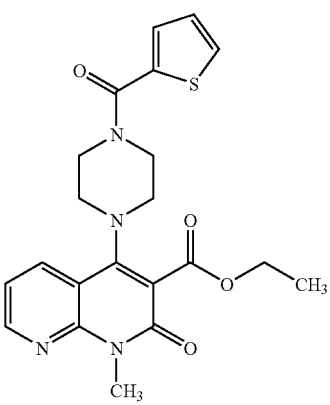

or a stereoisomer, a prodrug, or a pharmaceutically acceptable salt thereof is provided.

In an aspect of the first embodiment, a compound having a structure:

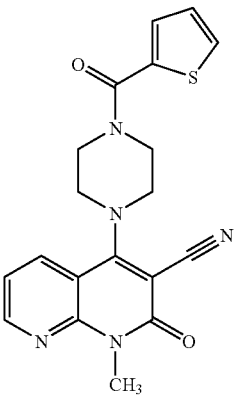

or a stereoisomer, a prodrug, or a pharmaceutically acceptable salt thereof is provided.

In an aspect of the first embodiment, a compound having a structure:

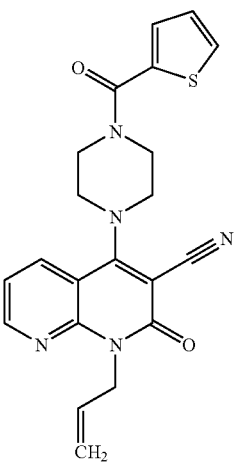

or a stereoisomer, a prodrug, or a pharmaceutically acceptable salt thereof is provided.

In an aspect of the first embodiment, a compound having a structure:

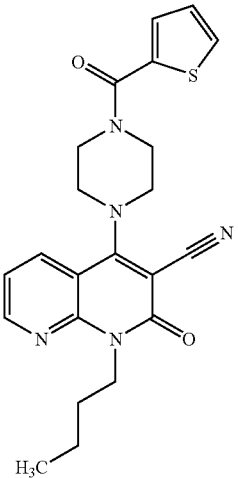

or a stereoisomer, a prodrug, or a pharmaceutically acceptable salt thereof is provided.

In an aspect of the first embodiment, a compound having a structure:

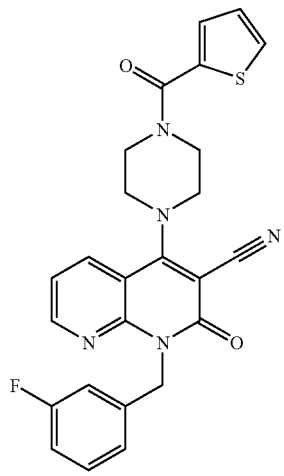

or a stereoisomer, a prodrug, or a pharmaceutically acceptable salt thereof is provided.

In an aspect of the first embodiment, a compound having a structure:

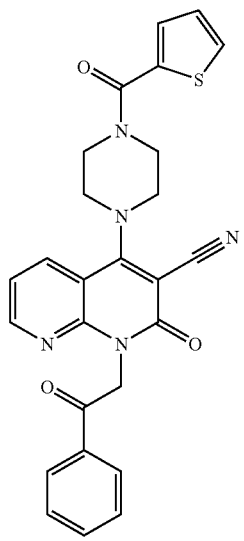

or a stereoisomer, a prodrug, or a pharmaceutically acceptable salt thereof is provided.

In an aspect of the first embodiment, a compound having a structure:

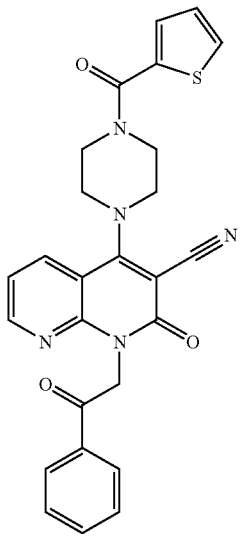

or a stereoisomer, a prodrug, or a pharmaceutically acceptable salt thereof is provided.

In an aspect of the first embodiment, a compound having a structure:

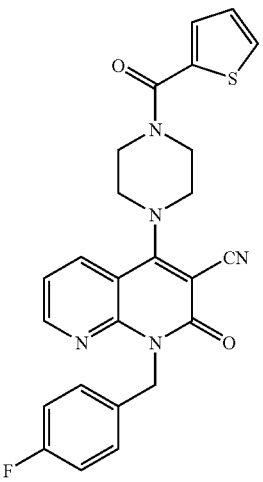

or a stereoisomer, a prodrug, or a pharmaceutically acceptable salt thereof is provided.

In an aspect of the first embodiment, a compound having a structure:

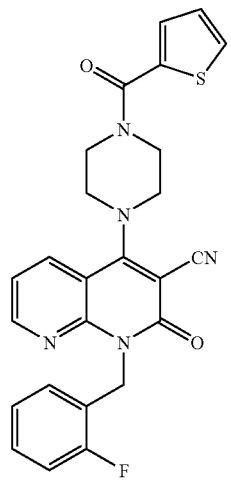

or a stereoisomer, a prodrug, or a pharmaceutically acceptable salt thereof is provided.

In an aspect of the first embodiment, a compound having a structure:

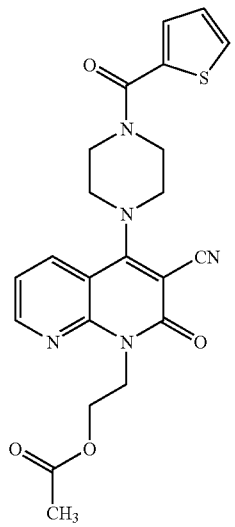

or a stereoisomer, a prodrug, or a pharmaceutically acceptable salt thereof is provided.

In an aspect of the first embodiment, a compound having a structure:

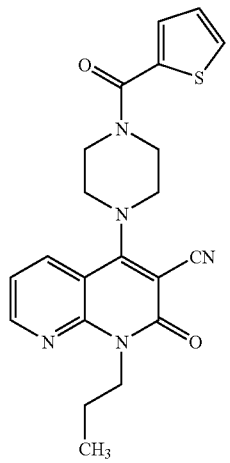

or a stereoisomer, a prodrug, or a pharmaceutically acceptable salt thereof is provided.

In an aspect of the first embodiment, a compound having a structure:

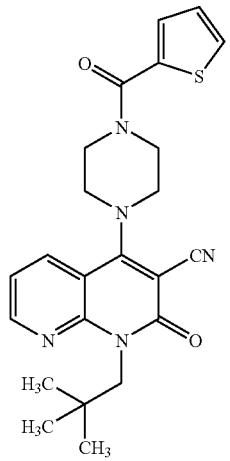

or a stereoisomer, a prodrug, or a pharmaceutically acceptable salt thereof is provided.

In an aspect of the first embodiment, a compound having a structure:

or a stereoisomer, a prodrug, or a pharmaceutically acceptable salt thereof is provided.

In an aspect of the first embodiment, a compound having a structure:

or a stereoisomer, a prodrug, or a pharmaceutically acceptable salt thereof is provided.

In an aspect of the first embodiment, a compound having a structure:

or a stereoisomer, a prodrug, or a pharmaceutically acceptable salt thereof is provided.

In an aspect of the first embodiment, a compound having a structure:

or a stereoisomer, a prodrug, or a pharmaceutically acceptable salt thereof is provided.

In an aspect of the first embodiment, a compound having a structure:

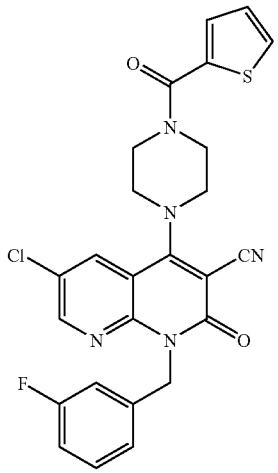

or a stereoisomer, a prodrug, or a pharmaceutically acceptable salt thereof is provided.

In an aspect of the first embodiment, a compound having a structure:

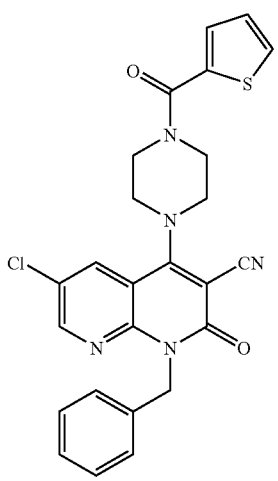

or a stereoisomer, a prodrug, or a pharmaceutically acceptable salt thereof is provided.

In an aspect of the first embodiment, a compound having a structure:

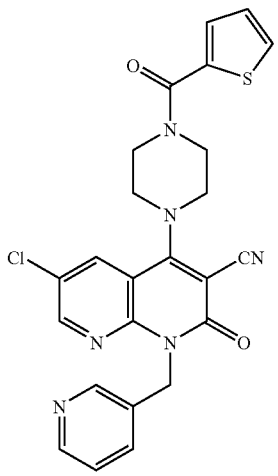

or a stereoisomer, a prodrug, or a pharmaceutically acceptable salt thereof is provided.

In an aspect of the first embodiment, a compound having a structure:

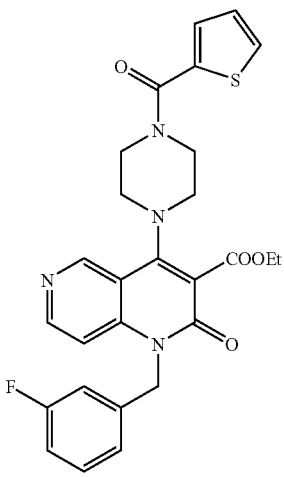

or a stereoisomer, a prodrug, or a pharmaceutically acceptable salt thereof is provided.

In an aspect of the first embodiment, the compound of the first embodiment in combination with a pharmaceutically acceptable carrier or diluent is provided.

In a second embodiment, a method for reducing MIF activity in a patient in need thereof is provided, comprising administering to the patient an effective amount of a compound, the compound having a structure selected from the group consisting of

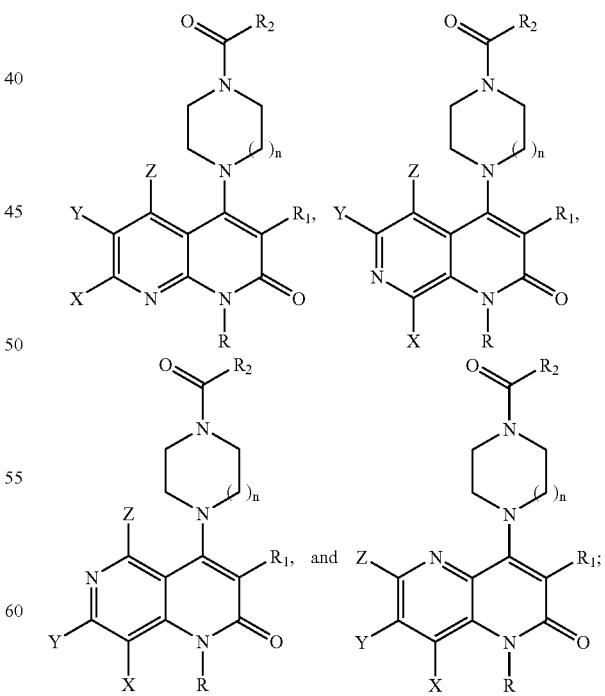

or a stereoisomer, a prodrug, or a pharmaceutically acceptable salt thereof, wherein R is selected from the group consisting of hydrogen, alkyl, substituted alkyl, alkenyl, substituted alkenyl, cycloalkyl, substituted cycloalkyl, aryl, substituted aryl, arylalkyl, substituted arylalkyl, acylalkyl, substituted acylalkyl, heterocycle, substituted heterocycle, —(CH$_2$)$_m$C(=O)Ar, and —(CH$_2$)$_m$NR$_4$R$_5$; R$_1$ is selected from the group consisting of —CN, —NO, —NO$_2$, —C(=O)R$_3$, —C(=O)OH, —NHC(=O)R$_3$, —C(=O)OR$_3$, —C(=O)NR$_4$R$_5$, —NR$_3$C(=O)R$_3$, —SO$_2$NR$_4$R$_5$, —NR$_3$SO$_2$R$_3$, —NHSO$_2$R$_3$, —S(O)$_m$R$_3$, —(CH$_2$)$_m$NR$_4$R$_5$, and —(CH$_2$)$_m$C(=O)Ar; R$_2$ is selected from the group consisting —CH$_2$R$_3$, —NR$_4$R$_5$, —OR$_3$, and —R$_3$; R$_3$ is independently selected from the group consisting of alkyl, substituted alkyl, alkenyl, substituted alkenyl, cycloalkyl, substituted cycloalkyl, aryl, substituted aryl, arylalkyl, substituted arylalkyl, acylalkyl, substituted acylalkyl, heterocycle, substituted heterocycle; R$_4$ and R$_5$ are independently selected from the group consisting of hydrogen, alkyl, substituted alkyl, alkenyl, substituted alkenyl, cycloalkyl, substituted cycloalkyl, aryl, substituted aryl, arylalkyl, substituted arylalkyl, acylalkyl, substituted acylalkyl, heterocycle, and substituted heterocycle, or R$_4$ and R$_5$ taken together comprise heterocycle or substituted heterocycle; X is selected from the group consisting of hydrogen, halogen, —F, —Cl, —CN, —NO, —NO$_2$, —OCF$_3$, —CF$_3$, —NHSO$_2$R$_3$, —C(=O)R$_3$, —C(=O)OR$_3$, —C(=O)NR$_4$R$_5$, —NR$_3$C(=O)R$_3$, —NR$_3$SO$_2$R$_3$, —S(O)$_m$R$_3$, —R$_3$, —OR$_3$, —SR$_3$, —C(=O)OH, —NHC(=O)R$_3$, and —NR$_4$R$_5$; Y is selected from the group consisting of hydrogen, halogen, —F, —Cl, —CN, —NO, —NO$_2$, —OCF$_3$, —CF$_3$, —NHSO$_2$R$_3$, —C(=O)R$_3$, —C(=O)OR$_3$, —C(=O)NR$_4$R$_5$, —NR$_3$C(=O)R$_3$, —NR$_3$SO$_2$R$_3$, —S(O)$_m$ R$_3$, —R$_3$, —OR$_3$, —SR$_3$, —C(=O)OH, —NHC(=O)R$_3$, and —NR$_4$R$_5$; Z is selected from the group consisting of hydrogen, halogen, —F, —Cl, —CN, —NO, —NO$_2$, —OCF$_3$, —CF$_3$, —NHSO$_2$R$_3$, —C(=O)R$_3$, —C(=O)OR$_3$, —C(=O)NR$_4$R$_5$, —NR$_3$C(=O)R$_3$, —NR$_3$SO$_2$R$_3$, —S(O)$_m$R$_3$, —R$_3$, —OR$_3$, —SR$_3$, —C(=O)OH, —NHC(=O)R$_3$, and —NR$_4$R$_5$; Ar is selected from the group consisting of aryl and substituted aryl; m is independently 0, 1, 2, 3, or 4; and n is 0, 1, or 2.

In an aspect of the first embodiment, a method for treating inflammation in a warm-blooded animal is provided, comprising administering to the animal an effective amount of the compound of the first embodiment.

In an aspect of the first embodiment, a method for treating septic shock in a warm-blooded animal is provided, comprising administering to the animal an effective amount of the compound of the first embodiment.

In an aspect of the first embodiment, a method for treating arthritis in a warm-blooded animal is provided, comprising administering to the animal an effective amount of the compound of the first embodiment.

In an aspect of the first embodiment, a method for treating cancer in a warm-blooded animal is provided, comprising administering to the animal an effective amount of the compound of the first embodiment.

In an aspect of the first embodiment, a method for treating acute respiratory distress syndrome in a warm-blooded anima is provided, comprising administering to the animal an effective amount of the compound of the first embodiment.

In an aspect of the first embodiment, a method for treating an inflammatory disease in a warm-blooded animal is provided, comprising administering to the animal an effective amount of the compound of the first embodiment. The inflammatory disease can be selected from the group consisting of rheumatoid arthritis, osteoarthritis, inflammatory bowel disease, and asthma.

In an aspect of the first embodiment, a method for treating a cardiac disease in a warm-blooded animal is provided, comprising administering to the animal an effective amount of the compound of the first embodiment. The cardiac disease can be selected from the group consisting of cardiac dysfunction, myocardial infarction, congestive heart failure, restenosis, and atherosclerosis.

In an aspect of the first embodiment, a method for treating an autoimmune disorder in a warm-blooded animal is provided, comprising administering to the animal an effective amount of the compound of the first embodiment. The autoimmune disorder can be selected from the group consisting of diabetes, asthma, and multiple sclerosis.

In an aspect of the first embodiment, a method for suppressing an immune response in a warm-blooded animal is provided, comprising administering to the animal an effective amount of the compound of the first embodiment.

In an aspect of the first embodiment, a method for decreasing angiogenesis in a warm-blooded animal is provided, comprising administering to the animal an effective amount of the compound of the first embodiment.

In an aspect of the first embodiment, a method for treating a disease associated with excess glucocorticoid levels in a warm-blooded animal is provided, comprising administering to the animal an effective amount of the compound of the first embodiment. The disease can be Cushing's disease.

In a third embodiment, a process for preparing a compound is provided, the process comprising the steps of reacting POCl$_3$ with a compound of Formula (3):

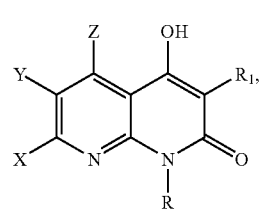

Formula (3)

wherein R is selected from the group consisting of hydrogen, alkyl, substituted alkyl, alkenyl, substituted alkenyl, cycloalkyl, substituted cycloalkyl, aryl, substituted aryl, arylalkyl, substituted arylalkyl, acylalkyl, substituted acylalkyl, heterocycle, substituted heterocycle, —(CH$_2$)$_m$C(=O)Ar, and —(CH$_2$)$_m$NR$_4$R$_5$; R$_1$ is selected from the group consisting of —CN, —NO, —NO$_2$, —C(=O)R$_3$, —C(=O)OH, —NHC(=O)R$_3$, —C(=O)OR$_3$, —C(=O)NR$_4$R$_5$, —NR$_3$C(=O)R$_3$, —SO$_2$NR$_4$R$_5$, —NR$_3$SO$_2$R$_3$, —NHSO$_2$R$_3$, —S(O)$_m$R$_3$, —(CH$_2$)$_m$NR$_4$R$_5$, and —(CH$_2$)$_m$C(=O)Ar; R$_3$ is independently selected from the group consisting of alkyl, substituted alkyl, alkenyl, substituted alkenyl, cycloalkyl, substituted cycloalkyl, aryl, substituted aryl, arylalkyl, substituted arylalkyl, acylalkyl, substituted acylalkyl, heterocycle, substituted heterocycle; R$_4$ and R$_5$ are independently selected from the group consisting of hydrogen, alkyl, substituted alkyl, alkenyl, substituted alkenyl, cycloalkyl, substituted cycloalkyl, aryl, substituted aryl, arylalkyl, substituted arylalkyl, acylalkyl, substituted acylalkyl, heterocycle, and substituted heterocycle, or R$_4$ and R$_5$ taken together comprise heterocycle or substituted heterocycle; X is selected from the group consisting of hydrogen, halogen, —F, —Cl, —CN, —NO, —NO$_2$, —OCF$_3$, —CF$_3$, —NHSO$_2$R$_3$, —C(=O)R$_3$, —C(=O)OR$_3$, —C(=O)NR$_4$R$_5$, —NR$_3$C(=O)R$_3$, —NR$_3$SO$_2$R$_3$, —S(O)$_m$R$_3$, —R$_3$, —OR$_3$, —SR$_3$, —C(=O)OH, —NHC(=O)R$_3$, and —NR$_4$R$_5$; Y is selected from the group consisting of hydrogen, halogen, —F, —Cl, —CN, —NO, —NO$_2$, —OCF$_3$, —CF$_3$, —NHSO$_2$R$_3$, —C(=O)R$_3$, —C(=O)OR₃, —C(=O)NR₄R₅, —NR₃C(=O)R₃, —NR₃SO₂R₃, —S(O)ₘR₃, —R₃, —OR₃, —SR₃, —C(=O)OH, —NHC(=O)R₃, and —NR₄R₅; Z is selected from the group consisting of hydrogen, halogen, —F, —Cl, —CN, —NO, —NO₂, —OCF₃, —CF₃, —NHSO₂R₃, —C(=O)R₃, —C(=O)OR₃, —C(=O)NR₄R₅, —NR₃C(=O)R₃, —NR₃SO₂R₃, —S(O)ₘR₃, —R₃, —OR₃, —SR₃, —C(=O)OH, —NHC(=O)R₃, and —NR₄R₅; Ar is selected from the group consisting of aryl and substituted aryl; and m is independently 0, 1, 2, 3, or 4; thereby yielding a compound of Formula (4):

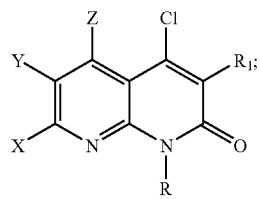

Formula (4)

reacting the compound of Formula (4) with piperazine, thereby yielding a compound of Formula (5):

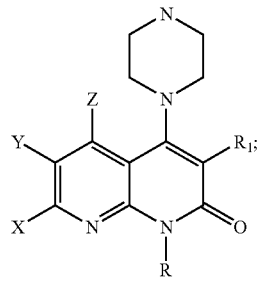

Formula (5)

reacting the compound of Formula (5) with a compound having the formula R₂—C(=O)Cl, wherein R₂ is selected from the group consisting —CH₂R₃, —NR₄R₅, —OR₃, and —R₃, thereby yielding a compound of Formula (6):

Formula (6)

wherein the compound of Formula (6) is suitable for use as a MIF inhibitor.

In an aspect of the third embodiment, R₁ comprises —(CH₂)ₘC(=O)Ar.

In an aspect of the third embodiment, R₁ comprises —C(=O)OCH₂CH₃.

In an aspect of the third embodiment, R₁ comprises —NH—C(=O)CH₃.

In an aspect of the third embodiment, R₁ comprises —CN.

In an aspect of the third embodiment, R₁ comprises —NO₂.

In an aspect of the third embodiment, R₁ comprises —NH₂.

In an aspect of the third embodiment, R₂ comprises

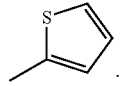

In an aspect of the third embodiment, R₂ comprises

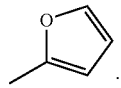

In an aspect of the third embodiment, R comprises —(CH₂)ₘC(=O)Ar.

In an aspect of the third embodiment, X is selected from the group consisting of hydrogen, fluorine, and chlorine; wherein Y is selected from the group consisting of hydrogen, fluorine, and chlorine; and wherein Z is selected from the group consisting of hydrogen, fluorine, and chlorine.

In a fourth embodiment, a process for preparing a compound is provided, the process comprising the steps of reacting a compound of Formula (13):

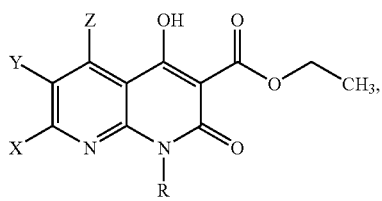

Formula (13)

wherein R is selected from the group consisting of hydrogen, alkyl, substituted alkyl, alkenyl, substituted alkenyl, cycloalkyl, substituted cycloalkyl, aryl, substituted aryl, arylalkyl, substituted arylalkyl, acylalkyl, substituted acylalkyl, heterocycle, substituted heterocycle, —(CH₂)ₘC(=O)Ar, and —(CH₂)ₘNR₄R₅; R₄ and R₅ are independently selected from the group consisting of hydrogen, alkyl, substituted alkyl, alkenyl, substituted alkenyl, cycloalkyl, substituted cycloalkyl, aryl, substituted aryl, arylalkyl, substituted arylalkyl, acylalkyl, substituted acylalkyl, heterocycle, and substituted heterocycle, or R₄ and R₅ taken together comprise heterocycle or substituted heterocycle; X is selected from the group consisting of hydrogen, halogen, —F, —Cl, —CN, —NO, —NO₂, —OCF₃, —CF₃, —NHSO₂R₃, —C(=O)R₃, —C(=O)OR₃, —C(=O)NR₄R₅, —NR₃C(=O)R₃, —NR₃SO₂R₃, —S(O)ₘR₃, —R₃, —OR₃, —SR₃, —C(=O)OH, —NHC(=O)R₃, and —NR₄R₅; Y is selected from the group consisting of hydrogen, halogen, —F, —Cl, —CN, —NO, —NO₂, —OCF₃, —CF₃, —NHSO₂R₃, —C(=O)R₃, —C(=O)OR₃, —C(=O)NR₄R₅, —NR₃C(=O)R₃, —NR₃SO₂R₃, —S(O)ₘR₃, —R₃, —OR₃, —SR₃, —C(=O)OH, —NHC(=O)R₃, and —NR₄R₅; Z is selected from the group consisting of hydrogen, halogen, —F, —Cl, —CN, —NO, —NO₂, —OCF₃, —CF₃, —NHSO₂R₃, —C(=O)R₃, —C(=O)OR₃, —C(=O)NR₄R₅, —NR₃C(=O)R₃, —NR₃SO₂R₃, —S(O)ₘR₃, —R₃, —OR₃, —SR₃, —C(=O)OH, —NHC(=O)R₃, and —NR₄R₅; R₃ is independently selected from the group consisting of alkyl, substituted alkyl, alkenyl, substituted alkenyl, cycloalkyl, substituted cycloalkyl, aryl, substituted aryl, arylalkyl, substituted arylalkyl, acylalkyl, substituted acylalkyl, hetero cycle, substituted hetero cycle; Ar is selected from the group consisting of aryl and substituted aryl; and m is independently 0, 1, 2, 3, or 4, with cyclohexylamine, thereby yielding a compound of Formula (14):

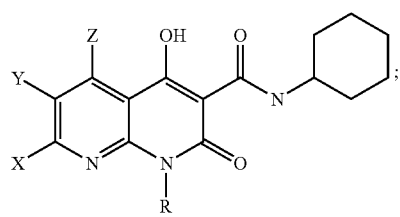

Formula (14)

reacting the compound of Formula (14) with POCl₃, thereby yielding a compound of Formula (15):

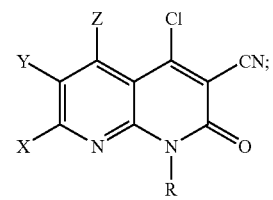

Formula (15)

reacting the compound of Formula (15) with piperazine, thereby yielding a compound of Formula (16):

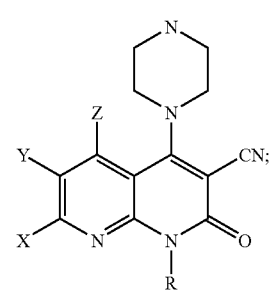

Formula (16)

reacting the compound of Formula (16) with a compound having the formula R₂—C(=O)Cl, wherein R₂ is selected from the group consisting —CH₂R₃, —NR₄R₅, —OR₃, and —R₃, thereby yielding a compound of Formula (17):

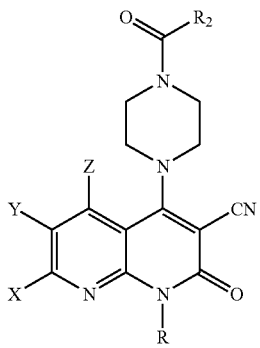

Formula (17)

wherein the compound of Formula (17) is suitable for use as a MIF inhibitor.

In an aspect of the fourth embodiment, R₂ comprises

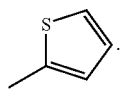

In an aspect of the fourth embodiment, R₂ comprises

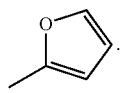

In an aspect of the fourth embodiment, R comprises —(CH₂)ₘC(=O)Ar.

In an aspect of the fourth embodiment, X is selected from the group consisting of hydrogen, fluorine, and chlorine; wherein Y is selected from the group consisting of hydrogen, fluorine, and chlorine; and wherein Z is selected from the group consisting of hydrogen, fluorine, and chlorine.

In a fifth embodiment, a process for preparing a compound is provided, the process comprising the steps of reacting a compound of Formula (23):

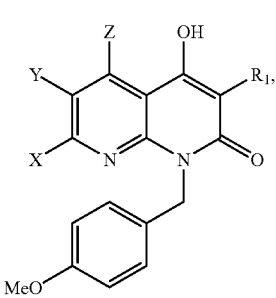

Formula (23)

wherein R₁ is selected from the group consisting of —CN, —NO, —NO₂, —C(=O)R₃, —C(=O)OH, —NHC(=O)

$R_3$, —C(=O)OR$_3$, —C(=O)NR$_4$R$_5$, —NR$_3$C(=O)R$_3$, —SO$_2$NR$_4$R$_5$, —NR$_3$SO$_2$R$_3$, —NHSO$_2$R$_3$, —S(O)$_m$R$_3$, —(CH$_2$)$_m$NR$_4$R$_5$, and —(CH$_2$)$_m$C(=O)Ar; R$_3$ is independently selected from the group consisting of alkyl, substituted alkyl, alkenyl, substituted alkenyl, cycloalkyl, substituted cycloalkyl, aryl, substituted aryl, arylalkyl, substituted arylalkyl, acylalkyl, substituted acylalkyl, heterocycle, substituted heterocycle; R$_4$ and R$_5$ are independently selected from the group consisting of hydrogen, alkyl, substituted alkyl, alkenyl, substituted alkenyl, cycloalkyl, substituted cycloalkyl, aryl, substituted aryl, arylalkyl, substituted arylalkyl, acylalkyl, substituted acylalkyl, heterocycle, and substituted heterocycle, or R$_4$ and R$_5$ taken together comprise heterocycle or substituted heterocycle; X is selected from the group consisting of hydrogen, halogen, —F, —Cl, —CN, —NO, —NO$_2$, —OCF$_3$, —CF$_3$, —NHSO$_2$R$_3$, —C(=O)R$_3$, —C(=O)OR$_3$, —C(=O)NR$_4$R$_5$, —NR$_3$C(=O)R$_3$, —NR$_3$SO$_2$R$_3$, —S(O)$_m$R$_3$, —R$_3$, —OR$_3$, —SR$_3$, —C(=O)OH, —NHC(=O)R$_3$, and —NR$_4$R$_5$; Y is selected from the group consisting of hydrogen, halogen, —F, —Cl, —CN, —NO, —NO$_2$, —OCF$_3$, —CF$_3$, —NHSO$_2$R$_3$, —C(=O)R$_3$, —C(=O)OR$_3$, —C(=O)NR$_4$R$_5$, —NR$_3$C(=O)R$_3$, —NR$_3$SO$_2$R$_3$, —S(O)$_m$R$_3$, —R$_3$, —OR$_3$, —SR$_3$, —C(=O)OH, —NHC(=O)R$_3$, and —NR$_4$R$_5$; Z is selected from the group consisting of hydrogen, halogen, —F, —Cl, —CN, —NO, —NO$_2$, —OCF$_3$, —CF$_3$, —NHSO$_2$R$_3$, —C(=O)R$_3$, —C(=O)OR$_3$, —C(=O)NR$_4$R$_5$, —NR$_3$C(=O)R$_3$, —NR$_3$SO$_2$R$_3$, —S(O)$_m$R$_3$, —R$_3$, —OR$_3$, —SR$_3$, —C(=O)OH, —NHC(=O)R$_3$, and —NR$_4$R$_5$; Ar is independently selected from the group consisting of aryl and substituted aryl; and m is independently 0, 1, 2, 3, or 4, with POCl$_3$ and trifluoroacetic acid, thereby yielding a compound of Formula (24):

Formula (24)

reacting the compound of Formula (24) with a compound of formula:

wherein R$_2$ is selected from the group consisting —CH$_2$R$_3$, —NR$_4$R$_5$, —OR$_3$, and —R$_3$ thereby yielding a compound of Formula (25):

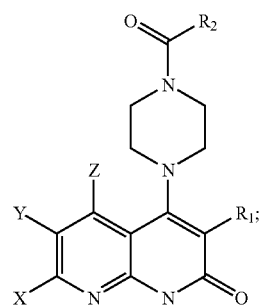

Formula (25)

reacting the compound of Formula (25) with a compound having the formula RX' wherein X' comprises halogen and wherein R is selected from the group consisting of hydrogen, alkyl, substituted alkyl, alkenyl, substituted alkenyl, cycloalkyl, substituted cycloalkyl, aryl, substituted aryl, arylalkyl, substituted arylalkyl, acylalkyl, substituted acylalkyl, heterocycle, substituted heterocycle, —(CH$_2$)$_m$C(=O)Ar, and —(CH$_2$)$_m$NR$_4$R$_5$, thereby yielding a compound of Formula (26):

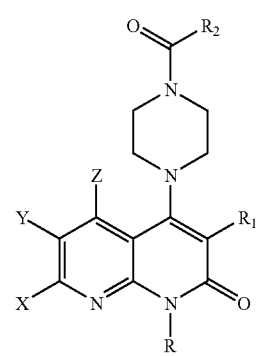

Formula (26)

wherein the compound of Formula (26) is suitable for use as a MIF inhibitor.

In an aspect of the fifth embodiment, R$_1$ comprises —(CH$_2$)$_m$C(=O)Ar.

In an aspect of the fifth embodiment, R$_1$ comprises —C(=O)OCH$_2$CH$_3$.

In an aspect of the fifth embodiment, R$_1$ comprises —NH—C(=O)CH$_3$.

In an aspect of the fifth embodiment, R$_1$ comprises —CN.

In an aspect of the fifth embodiment, R$_1$ comprises —NO$_2$.

In an aspect of the fifth embodiment, R$_1$ comprises —NH$_2$.

In an aspect of the fifth embodiment, R$_2$ comprises

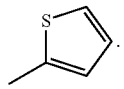.

In an aspect of the fifth embodiment, R$_2$ comprises

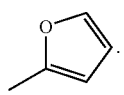.

In an aspect of the fifth embodiment, R comprises —(CH$_2$)$_m$C(=O)Ar.

In an aspect of the fifth embodiment, X is selected from the group consisting of hydrogen, fluorine, and chlorine; wherein Y is selected from the group consisting of hydrogen, fluorine, and chlorine; and wherein Z is selected from the group consisting of hydrogen, fluorine, and chlorine.

In an aspect of the fifth embodiment, R comprises benzyl.

In a sixth embodiment, a process for preparing a compound is provided, the process comprising the steps of reacting a compound of Formula (3a):

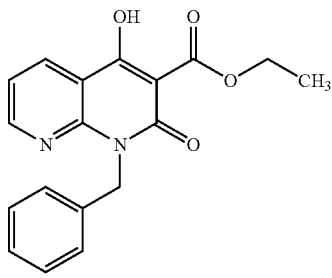

Formula (3a)

with POCl$_3$, thereby yielding a compound of Formula (4a):

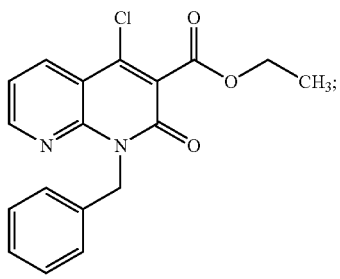

Formula (4a)

reacting the compound of Formula (4a) with piperazine, thereby yielding a compound of Formula (5a):

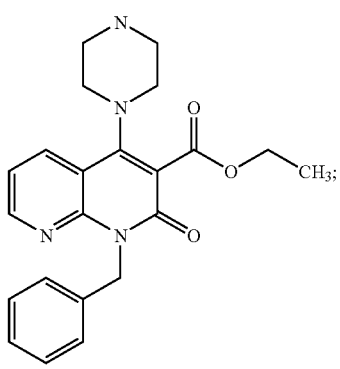

Formula (5a)

reacting the compound of Formula (5a) with a compound having the formula R$_2$—C(=O)Cl, wherein R$_2$ is selected from the group consisting —CH$_2$R$_3$, —NR$_4$R$_5$, —OR$_3$, and —R$_3$, wherein R$_3$ is selected from the group consisting of alkyl, substituted alkyl, alkenyl, substituted alkenyl, cycloalkyl, substituted cycloalkyl, aryl, substituted aryl, arylalkyl, substituted arylalkyl, acylalkyl, substituted acylalkyl, heterocycle, substituted heterocycle, and wherein R$_4$ and R$_5$ are independently selected from the group consisting of hydrogen, alkyl, substituted alkyl, alkenyl, substituted alkenyl, cycloalkyl, substituted cycloalkyl, aryl, substituted aryl, arylalkyl, substituted arylalkyl, acylalkyl, substituted acylalkyl, heterocycle, and substituted heterocycle, or R$_4$ and R$_5$ taken together comprise heterocycle or substituted heterocycle, thereby yielding a compound of Formula (6a):

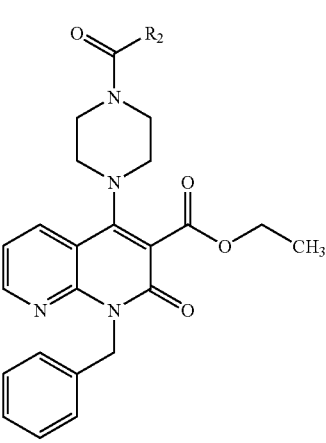

Formula (6a)

wherein the compound of Formula (6a) is suitable for use as a MIF inhibitor.

In an aspect of the sixth embodiment, R$_2$ comprises

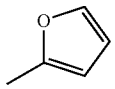

or

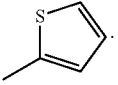

In a seventh embodiment, a process for preparing a compound is provided, the process comprising the steps of reacting a compound of Formula (13a):

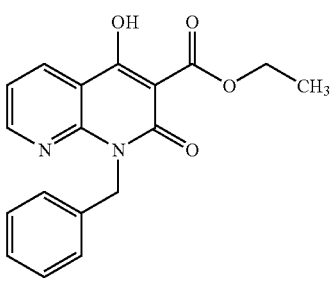

Formula (13a)

with cyclohexylamine, thereby yielding a compound of Formula (14):

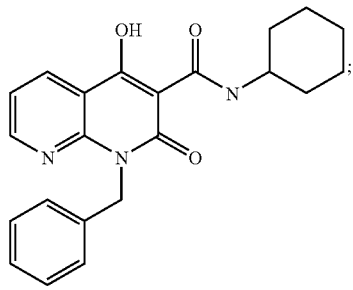

Formula (14a)

reacting the compound of Formula (14a) with POCl$_3$, thereby yielding a compound of Formula (15a):

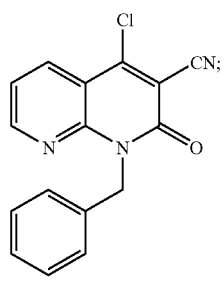

Formula (15a)

reacting the compound of Formula (15a) with piperazine, thereby yielding a compound of Formula (16a):

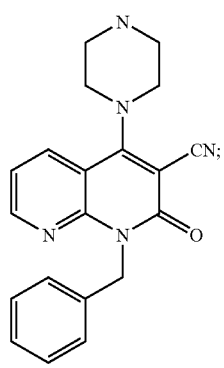

Formula (16a)

reacting the compound of Formula (16a) with a compound having the formula R$_2$—C(=O)Cl, wherein R$_2$ is selected from the group consisting —CH$_2$R$_3$, —NR$_4$R$_5$, —OR$_3$, and —R$_3$, wherein R$_3$ is selected from the group consisting of R$_3$ alkyl, substituted alkyl, alkenyl, substituted alkenyl, cycloalkyl, substituted cycloalkyl, aryl, substituted aryl, arylalkyl, substituted arylalkyl, acylalkyl, substituted acylalkyl, heterocycle, substituted heterocycle; R$_4$ and R$_5$ are independently selected from the group consisting of hydrogen, alkyl, substituted alkyl, alkenyl, substituted alkenyl, cycloalkyl, substituted cycloalkyl, aryl, substituted aryl, arylalkyl, substituted arylalkyl, acylalkyl, substituted acylalkyl, heterocycle, and substituted heterocycle, or R$_4$ and R$_5$ taken together comprise heterocycle or substituted heterocycle, thereby yielding a compound of Formula (17a):

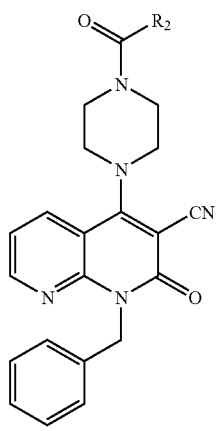

Formula (17a)

wherein the compound of Formula (17a) is suitable for use as a MIF inhibitor.

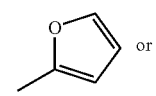 or

In an aspect of the seventh embodiment, R$_2$ comprises

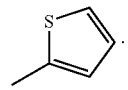.

or

In an eighth embodiment, a process for preparing a compound is provided, the process comprising the steps of reacting a compound of Formula (23a):

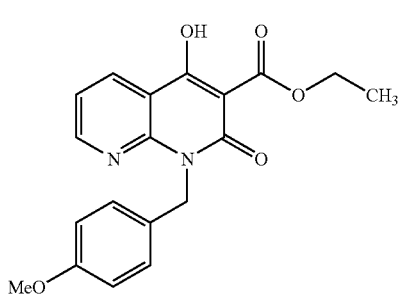

Formula (23a)

with POCl$_3$ and trifluoroacetic acid, thereby yielding a compound of Formula (24a):

Formula (24a):

[structure: 4-chloro-2-oxo-1,8-naphthyridine-3-carboxylic acid ethyl ester]

reacting the compound of Formula (24a) with a compound of formula

[structure: piperazine with N-C(=O)R₂]

wherein $R_2$ is selected from the group consisting —$CH_2R_3$, —$NR_4R_5$, —$OR_3$, and —$R_3$ wherein $R_3$ is selected from the group consisting of alkyl, substituted alkyl, alkenyl, substituted alkenyl, cycloalkyl, substituted cycloalkyl, aryl, substituted aryl, arylalkyl, substituted arylalkyl, acylalkyl, substituted acylalkyl, heterocycle, substituted heterocycle; $R_4$ and $R_5$ are independently selected from the group consisting of hydrogen, alkyl, substituted alkyl, alkenyl, substituted alkenyl, cycloalkyl, substituted cycloalkyl, aryl, substituted aryl, arylalkyl, substituted arylalkyl, acylalkyl, substituted acylalkyl, heterocycle, and substituted heterocycle, or $R_4$ and $R_5$ taken together comprise heterocycle or substituted heterocycle, thereby yielding a compound of Formula (25a):

Formula (25a):

[structure]

reacting the compound of Formula (25a) with a compound having the formula RX wherein X comprises halogen and wherein R is selected from the group consisting of hydrogen, alkyl, substituted alkyl, alkenyl, substituted alkenyl, cycloalkyl, substituted cycloalkyl, aryl, substituted aryl, arylalkyl, substituted arylalkyl, acylalkyl, substituted acylalkyl, heterocycle, substituted heterocycle, —$(CH_2)_mC(=O)$Ar, and —$(CH_2)_mNR_4R_5$, wherein Ar is selected from the group consisting of aryl and substituted aryl; and m is independently 0, 1, 2, 3, or 4, thereby yielding a compound of Formula (26a):

Formula (26a):

[structure]

wherein the compound of Formula (26a) is suitable for use as a MIF inhibitor.

In an aspect of the eighth embodiment, $R_2$ comprises

[structure: 2-thienyl]

In an aspect of the eighth embodiment, $R_2$ comprises

[structure: 2-furyl]

In an aspect of the eighth embodiment, R comprises —$(CH_2)_mC(=O)$Ar.

In an aspect of the eighth embodiment, R comprises benzyl.

These and other embodiments and aspects thereof will be apparent upon reference to the following detailed description. To this end, various references are set forth herein which describe in more detail certain procedures, compounds and/or compositions, and are hereby incorporated by reference in their entirety.

DETAILED DESCRIPTION OF THE PREFERRED EMBODIMENT

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

As an aid to understanding the preferred embodiments, certain definitions are provided herein.

The term "MIF activity," as used herein is a broad term and is used in its ordinary sense, including, without limitation, to refer to an activity or effect mediated at least in part by macrophage migration inhibitory factor. Accordingly, MIF activity includes, but is not limited to, inhibition of macrophage migration, tautomerase activity (e.g., using phenylpyruvate or dopachrome), endotoxin induced shock, inflammation, glucocorticoid counter regulation, induction of thymidine incorporation into 3T3 fibroblasts, induction of erk phosphorylation and MAP kinase activity.

The term "export," as used herein is a broad term and is used in its ordinary sense, including, without limitation, to refer to a metabolically active process, which may or may not be energy-dependent, of transporting a translated cellular product to the cell membrane or the extracellular space by a mechanism other than standard leader sequence directed secretion via a canonical leader sequence. Further, "export," unlike secretion that is leader sequence-dependent, is resistant to brefeldin A (i.e., the exported protein is not transported via the ER/Golgi; brefeldin A is expected to have no direct effect on trafficking of an exported protein) and other similar compounds. As used herein, "export" can also be referred to as "non-classical secretion."

The term "leaderless protein," as used herein is a broad term and is used in its ordinary sense, including, without limitation, to refer to a protein or polypeptide that lacks a canonical leader sequence, and is exported from inside a cell to the extracellular environment. Leaderless proteins in the extracellular environment refer to proteins located in the extracellular space, or associated with the outer surface of the cell membrane. Within the context of preferred embodiments, leaderless proteins include naturally occurring proteins, such as macrophage migration inhibitory factor and fragments thereof as well as proteins that are engineered to lack a leader sequence and are exported, or proteins that are engineered to include a fusion of a leaderless protein, or fraction thereof, with another protein.

The term "inhibitor," as used herein is a broad term and is used in its ordinary sense, including, without limitation, to refer to a molecule (e.g., natural or synthetic compound) that can alter the conformation of MIF and/or compete with a monoclonal antibody to MIF and decrease at least one activity of MIF or its export from a cell as compared to activity or export in the absence of the inhibitor. In other words, an "inhibitor" alters conformation and/or activity and/or export if there is a statistically significant change in the amount of MIF measured, MIF activity or in MIF protein detected extracellularly and/or intracellularly in an assay performed with an inhibitor, compared to the assay performed without the inhibitor.

The term "binding agent" as used herein is a broad term and is used in its ordinary sense, including, without limitation, to refer to any molecule that binds MIF, including inhibitors.

In general, MIF inhibitors inhibit the physiological function of MIF, and thus are useful in the treatment of diseases where MIF is pathogenic.

In certain of the preferred embodiments, inhibitors of MIF are provided that have the following structures (Ia), (Ib), (Ic), and (Id):

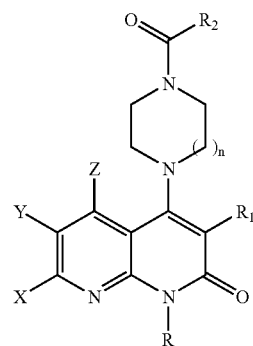

(Ia)

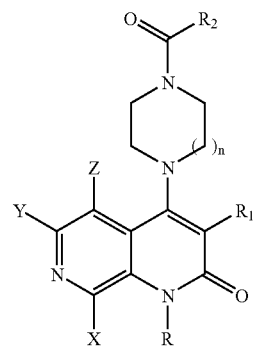

(Ib)

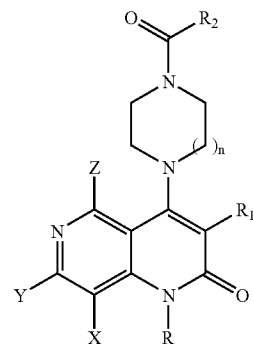

(Ic)

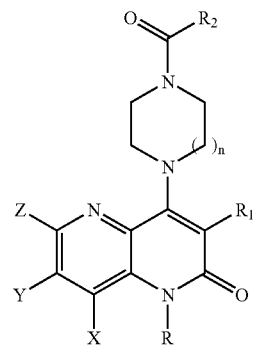

(Id)

or a stereoisomer, a prodrug, or a pharmaceutically acceptable salt thereof, wherein R is selected from the group consisting of hydrogen, alkyl, substituted alkyl, alkenyl, substituted alkenyl, cycloalkyl, substituted cycloalkyl, aryl, substituted aryl, arylalkyl, substituted arylalkyl, acylalkyl, substituted acylalkyl, heterocycle, substituted heterocycle, —(CH$_2$)$_m$C(=O)Ar, and —(CH$_2$)$_m$NR$_4$R$_5$; R$_1$ is selected from the group consisting of —CN, —NO, —NO$_2$, —C(=O)R$_3$, —C(=O)OH, —NHC(=O)R$_3$, —C(=O)OR$_3$, —C(=O)NR$_4$R$_5$—NR$_3$C(=O)R$_3$, —SO$_2$NR$_4$R$_5$, —NR$_3$SO$_2$R$_3$, —NHSO$_2$R$_3$, —S(O)$_m$R$_3$, —(CH$_2$)$_m$NR$_4$R$_5$, and —(CH$_2$)$_m$C(=O)Ar; R$_2$ is selected from the group consisting —CH$_2$R$_3$, —NR$_4$R$_5$, —OR$_3$, and —R$_3$; each R$_3$ is independently selected from the group consisting of alkyl, substituted alkyl, alkenyl, substituted alkenyl, cycloalkyl, substituted cycloalkyl, aryl, substituted aryl, arylalkyl, substituted arylalkyl, acylalkyl, substituted acylalkyl, heterocycle, substituted heterocycle; R$_4$ and R$_5$ are independently selected from the group consisting of hydrogen, alkyl, substituted alkyl, alkenyl, substituted alkenyl, cycloalkyl, substituted cycloalkyl, aryl, substituted aryl, arylalkyl, substituted arylalkyl, acylalkyl, substituted acylalkyl, heterocycle, and substituted heterocycle, or R$_4$ and R$_5$ taken together comprise heterocycle or substituted heterocycle; X is selected from the group consisting of hydrogen, halogen, —F, —Cl, —CN, —NO, —NO$_2$, —OCF$_3$, —CF$_3$, —NHSO$_2$R$_3$, —C(=O)R$_3$, —C(=O)OR$_3$, —C(=O)NR$_4$R$_5$, —NR$_3$C(=O)R$_3$, —NR$_3$SO$_2$R$_3$, —S(O)$_m$R$_3$, —R$_3$, —OR$_3$, —SR$_3$, —C(=O)OH, —NHC(=O)R$_3$, and —NR$_4$R$_5$; Y is selected from the group consisting of hydrogen, halogen, —F, —Cl, —CN, —NO, —NO$_2$, —OCF$_3$, —CF$_3$, —NHSO$_2$R$_3$, —C(=O)R$_3$, —C(=O)OR$_3$, —C(=O)NR$_4$R$_5$, —NR$_3$C(=O)R$_3$, —NR$_3$SO$_2$R$_3$, —S(O)$_m$ R$_3$, —R$_3$, —OR$_3$, —SR$_3$, —C(=O)OH, —NHC(=O)R$_3$, and —NR$_4$R$_5$; Z is selected from the group consisting of hydrogen, halogen, —F, —Cl, —CN, —OCF$_3$, —CF$_3$, —NHSO$_2$R$_3$, —NO, —NO$_2$, —C(=O)R$_3$, —C(=O)OR$_3$, —C(=O)NR$_4$R$_5$, —NR$_3$C(=O)R$_3$, —NR$_3$SO$_2$R$_3$, —S(O)$_m$ R$_3$, —R$_3$, —OR$_3$, —SR$_3$, —C(=O)OH, —NHC(=O)R$_3$, and —NR$_4$R$_5$; each Ar is independently selected from the group consisting of aryl and substituted aryl; each m is independently 0, 1, 2, 3, or 4; and n is 0, 1, or 2.

In a preferred embodiment, methods are provided for reducing MIF activity in a patient in need thereof by administering to the patient an effective amount of a compound having the following structure (Ia), (Ib), (Ic), or (Id):

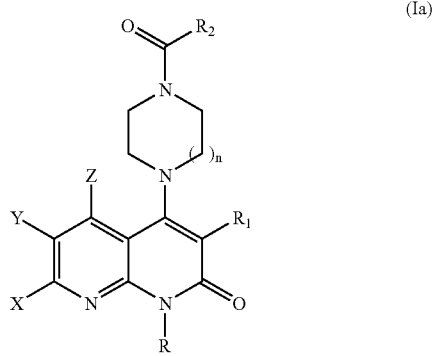

(Ia)

(Ib)

(Ic)

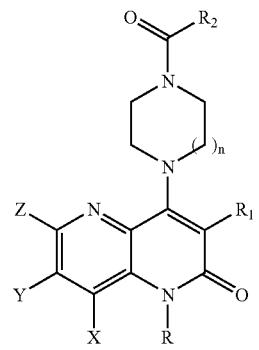

(Id)

or a stereoisomer, a prodrug, or a pharmaceutically acceptable salt thereof, wherein R is selected from the group consisting of hydrogen, alkyl, substituted alkyl, alkenyl, substituted alkenyl, cycloalkyl, substituted cycloalkyl, aryl, substituted aryl, arylalkyl, substituted arylalkyl, acylalkyl, substituted acylalkyl, heterocycle, substituted heterocycle, —(CH$_2$)$_m$C(=O)Ar, and —(CH$_2$)$_m$NR$_4$R$_5$; R$_1$ is selected from the group consisting of —CN, —NO, —NO$_2$, —C(=O)R$_3$, —C(=O)OH, —NHC(=O)R$_3$, —C(=O)OR$_3$, —C(=O)NR$_4$R$_5$, —NR$_3$C(=O)R$_3$, —SO$_2$NR$_4$R$_5$, —NR$_3$SO$_2$R$_3$, —NHSO$_2$R$_3$, —S(O)$_m$R$_3$, —(CH$_2$)$_m$NR$_4$R$_5$, and —(CH$_2$)$_m$C(=O)Ar; R$_2$ is selected from the group consisting —CH$_2$R$_3$, —NR$_4$R$_5$, —OR$_3$, and —R$_3$; each R$_3$ is independently selected from the group consisting of alkyl, substituted alkyl, alkenyl, substituted alkenyl, cycloalkyl, substituted cycloalkyl, aryl, substituted aryl, arylalkyl, substituted arylalkyl, acylalkyl, substituted acylalkyl, heterocycle, and substituted heterocycle, or R₄ and R₅ taken together comprise heterocycle or substituted heterocycle; X is selected from the group consisting of hydrogen, halogen, —F, —Cl, —CN, —NO, —NO₂, —OCF₃, —CF₃, —NHSO₂R₃, —C(=O)R₃, —C(=O)OR₃, —C(=O)NR₄R₅, —NR₃C(=O)R₃, —NR₃SO₂R₃, —S(O)ₘR₃, —OR₃, —SR₃, —C(=O)OH, —NHC(=O)R₃, and —NR₄R₅; Y is selected from the group consisting of hydrogen, halogen, —F, —Cl, —CN, —NO, —NO₂, —OCF₃, —CF₃, —NHSO₂R₃, —C(=O)R₃, —C(=O)OR₃, —C(=O)NR₄R₅, —NR₃C(=O)R₃, —NR₃SO₂R₃, —S(O)ₘ R₃, —R₃, —OR₃, —SR₃, —C(=O)OH, —NHC(=O)R₃, and —NR₄R₅; Z is selected from the group consisting of hydrogen, halogen, —F, —Cl, —CN, —OCF₃, —CF₃, —NHSO₂R₃, —NO, —NO₂, —C(=O)R₃, —C(=O)OR₃, —C(=O)NR₄R₅, —NR₃C(=O)R₃, —NR₃SO₂R₃, —S(O)ₘ R₃, —R₃, —OR₃, —SR₃, —C(=O)OH, —NHC(=O)R₃, and —NR₄R₅; each Ar is independently selected from the group consisting of aryl and substituted aryl; each m is independently 0, 1, 2, 3, or 4; and n is 0, 1, or 2.

As used herein, the above terms have the following meanings. The term "alkyl," as used herein is a broad term and is used in its ordinary sense, including, without limitation, to refer to a straight chain or branched, acyclic or cyclic, unsaturated or saturated aliphatic hydrocarbon containing from 1 to 2, 3, 4, 5, 6, 7, 8, 9, 10, 11, 12, 13, 14, 15, 16, 17, 18, 19, 20, or more carbon atoms, while the term "lower alkyl" has the same meaning as alkyl but contains from 1 to 2, 3, 4, 5, 6 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl," respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like.

The term "cycloalkyl," as used herein is a broad term and is used in its ordinary sense, including, without limitation, to refer to alkyls that include mono-, di-, or poly-homocyclic rings. Cycloalkyls are also referred to as "cyclic alkyls" or "homocyclic rings." Representative saturated cyclic alkyls include cyclopropyl, cyclobutyl, cyclopentyl, cyclohexyl, —CH₂cyclopropyl, —CH₂cyclobutyl, —CH₂cyclopentyl, —CH₂cyclohexyl, and the like; while unsaturated cyclic alkyls include cyclopentenyl and cyclohexenyl, and the like. Cyclic alkyls include decalin, adamantane, and the like.

The term "aryl," as used herein is a broad term and is used in its ordinary sense, including, without limitation, to refer to an aromatic carbocyclic moiety such as phenyl or naphthyl. Preferably, the aryl group contains from 6 to 7, 8, 9, 10, 11, 12, 13, 14, 15, 16, 17, 18, 19, 20, or more carbon atoms.

The term "arylalkyl," as used herein is a broad term and is used in its ordinary sense, including, without limitation, to refer to an alkyl having at least one alkyl hydrogen atom replaced with an aryl moiety, such as benzyl, —CH₂(1 or 2-naphthyl), —(CH₂)₂phenyl, —(CH₂)₃phenyl, —CH(phenyl)₂, and the like.

The term "heteroaryl" as used herein is a broad term and is used in its ordinary sense, including, without limitation, to refer to an aromatic heterocycle ring of 5 or 6 to 10 members and having at least one heteroatom (or 2, 3, or 4 or more heteroatoms) selected from nitrogen, oxygen and sulfur, and containing at least one carbon atom, including both mono and bicyclic ring systems. Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

The term "heteroarylalkyl" as used herein is a broad term and is used in its ordinary sense, including, without limitation, to refer to an alkyl having at least one alkyl hydrogen atom replaced with a heteroaryl moiety, such as —CH₂pyridinyl, —CH₂pyrimidinyl, and the like.

The terms "heterocycle" and "heterocycle ring," as used herein, are broad terms and are used in their ordinary sense, including, without limitation, to refer to a 5, 6, or 7 membered monocyclic heterocyclic ring, or a 7, 8, 9, 10, 11, 12, 13, to 14 or more membered polycyclic heterocyclic ring. The ring can be saturated, unsaturated, aromatic, or nonaromatic, and contains 1, 2, 3, or 4 or more heteroatoms independently selected from nitrogen, oxygen, and sulfur. The nitrogen and sulfur heteroatoms can be optionally oxidized, and the nitrogen heteroatom can be optionally quaternized, including bicyclic rings in which any of the above heterocycles are fused to a benzene ring as well as tricyclic (and higher) heterocyclic rings. The heterocycle can be attached via any heteroatom or carbon atom of the ring or rings. Heterocycles include heteroaryls as defined above. Thus, in addition to the aromatic heteroaryls listed above, heterocycles also include (but are not limited to) morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like. Also included are heterocycles of the following structures:

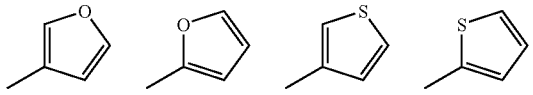

The term "heterocyclealkyl," as used herein is a broad term and is used in its ordinary sense, including, without limitation, to refer to an alkyl having at least one alkyl hydrogen atom replaced with a heterocycle, such as —CH₂morpholinyl, and the like.

The term "substituted," as used herein is a broad term and is used in its ordinary sense, including, without limitation, to refer to any of the above groups (e.g., alkyl, aryl, arylalkyl, heteroaryl, heteroarylalkyl, heterocycle or heterocyclealkyl) wherein at least one hydrogen atom is replaced with a substitutent. In the case of a keto substitutent, for example —C(=O)—, two hydrogen atoms are replaced. When substituted, "substitutents" within the context of preferred embodiment, include halogen, hydroxy, cyano, nitro, amino, alkylamino, dialkylamino, alkyl, alkoxy, alkylthio, haloalkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl, substituted heterocyclealkyl, —NR$_a$R$_b$, —NR$_a$C(=O)R$_b$, —NR$_a$C(=O)NR$_b$R$_c$, —NR$_a$C(=O)OR$_b$, —NR$_a$SO$_2$R$_b$, —OR$_a$, —C(=O)R$_a$, —C(=O)OR$_a$, —C(=O)NR$_a$R$_b$, —OC(=O)NR$_a$R$_b$, —SH, —SR$_a$, —SOR$_a$, —S(=O)$_2$R$_a$, —OS(=O)$_2$R$_a$, —S(=O)$_2$OR$_a$, wherein R$_a$, R$_b$, and R$_c$ are the same or different and independently selected from hydrogen, alkyl, haloalkyl, substituted alkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl or substituted heterocyclealkyl.

The term "halogen," as used herein is a broad term and is used in its ordinary sense, including, without limitation, to refer to fluoro, chloro, bromo, and iodo.

The term "haloalkyl," as used herein is a broad term and is used in its ordinary sense, including, without limitation, to refer to an alkyl having at least one hydrogen atom replaced with halogen, such as trifluoromethyl and the like.

The term "alkoxy," as used herein is a broad term and is used in its ordinary sense, including, without limitation, to refer to an alkyl moiety attached through an oxygen bridge (i.e., —O-alkyl) such as methoxy, ethoxy, and the like.

The term "thioalkyl" as used herein is a broad term and is used in its ordinary sense, including, without limitation, to refer to an alkyl moiety attached through a sulfur bridge (i.e., —S-alkyl) such as methylthio, ethylthio, and the like.

The term "alkylsulfonyl" as used herein is a broad term and is used in its ordinary sense, including, without limitation, to refer to an alkyl moiety attached through a sulfonyl bridge (i.e., —SO$_2$-alkyl) such as methylsulfonyl, ethylsulfonyl, and the like.

The terms "alkylamino" and "dialkyl amino" as used herein, are broad terms and are used in their ordinary sense, including, without limitation, to refer to one alkyl moiety or two alkyl moieties, respectively, attached through a nitrogen bridge (i.e., —N-alkyl) such as methylamino, ethylamino, dimethylamino, diethylamino, and the like.

The term "hydroxyalkyl" as used herein is a broad term and is used in its ordinary sense, including, without limitation, to refer to an alkyl substituted with at least one hydroxyl group.

The term "mono- or di(cycloalkyl)methyl," as used herein is a broad term and is used in its ordinary sense, including, without limitation, to refer to a methyl group substituted with one or two cycloalkyl groups, such as cyclopropylmethyl, dicyclopropylmethyl, and the like.

The terms "alkylcarbonylalkyl" or "acylalkyl" as used herein are broad terms and are used in their ordinary sense, including, without limitation, to refer to an alkyl substituted with a —C(=O)alkyl group.

The term "alkylcarbonyloxyalkyl" as used herein is a broad term and is used in its ordinary sense, including, without limitation, to refer to an alkyl substituted with a —C(=O)O-alkyl group or a —OC(=O)alkyl group.

The term "alkyloxyalkyl" as used herein is a broad term and is used in its ordinary sense, including, without limitation, to refer to an alkyl substituted with an —O-alkyl group.

The term "arylcarbonylaryl," as used herein is a broad term and is used in its ordinary sense, including, without limitation, to refer to an aryl substituted with a —C(=O) aryl group.

The term "arylcarbonyloxyaryl" as used herein is a broad term and is used in its ordinary sense, including, without limitation, to refer to an aryl substituted with a —C(=O) O-aryl group or a —OC(=O)aryl group.

The term "aryloxyaryl" as used herein is a broad term and is used in its ordinary sense, including, without limitation, to refer to an alkyl substituted with an —O-aryl group.

The term "alkylcarbonylaryl," as used herein is a broad term and is used in its ordinary sense, including, without limitation, to refer to an alkyl substituted with a —C(=O) aryl group.

The term "alkylcarbonyloxyaryl" as used herein is a broad term and is used in its ordinary sense, including, without limitation, to refer to an alkyl substituted with a —C(=O) O-aryl group or a —OC(=O)aryl group.

The term "alkyloxyaryl" as used herein is a broad term and is used in its ordinary sense, including, without limitation, to refer to an alkyl substituted with an —O-aryl group.

The term "arylcarbonylalkyl," as used herein is a broad term and is used in its ordinary sense, including, without limitation, to refer to an aryl substituted with a —C(=O) alkyl group.

The term "arylcarbonyloxyalkyl" as used herein is a broad term and is used in its ordinary sense, including, without limitation, to refer to an aryl substituted with a —C(=O) O-alkyl group or a —OC(=O)alkyl group.

The term "aryloxyalkyl" as used herein is a broad term and is used in its ordinary sense, including, without limitation, to refer to an aryl substituted with an —O-alkyl group.

The term "alkylthioalkyl" as used herein is a broad term and is used in its ordinary sense, including, without limitation, to refer to an alkyl substituted with a —S-alkyl group.

The term "mono- or di(alkyl)amino" as used herein is a broad term and is used in its ordinary sense, including, without limitation, to refer to an amino substituted with one alkyl or with two alkyls, respectively.

The term "mono- or di(alkyl)aminoalkyl" as used herein is a broad term and is used in its ordinary sense, including, without limitation, to refer to an alkyl substituted with a mono- or di(alkyl)amino.

The cyclic systems referred to herein include fused ring, bridged ring, and spiro ring moieties, in addition to isolated monocyclic moieties.

The following numbering schemes are used in the context of preferred embodiments:

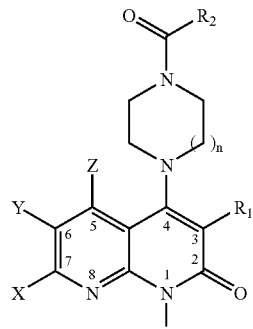

(Ia)

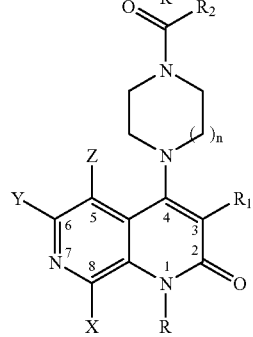

(Ib)

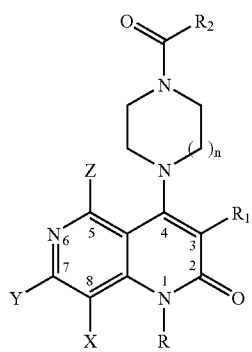

(Ic)

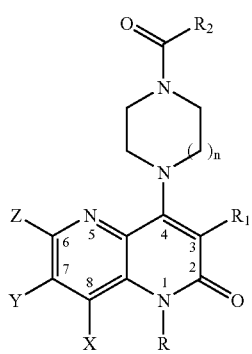

(Id)

As depicted above, the nitrogen atom of the naphthyridine ring can occupy the 5, 6, 7, or 8 ring position. Chemical structures for representative compounds of the preferred embodiments are provided below. In these structures, the following symbol is employed to represent a pyridine ring wherein the nitrogen atom can occupy either the 5, 6, 7, or 8 ring position:

In certain of the chemical structures provided below, the pyridine ring so depicted includes as a substitutent a methyl group or a chlorine atom. Where such a substitutent is present, if the nitrogen atom of the pyridine ring occupies the 5 ring position, then the substitutent occupies either the 6, 7, or 8 ring position. If the nitrogen atom of the pyridine ring occupies the 6 ring position, then the substitutent occupies either the 5, 7, or 8 ring position. If the nitrogen atom of the pyridine ring occupies the 7 ring position, then the substitutent occupies either the 5, 6, or 8 ring position. If the nitrogen atom of the pyridine ring occupies the 8 ring position, then the substitutent occupies either the 5, 6, or 7 ring position. In particularly preferred embodiments, the nitrogen atom of the pyridine ring occupies the 8 ring position, and a substitutent, if present, occupies the 6 ring position.

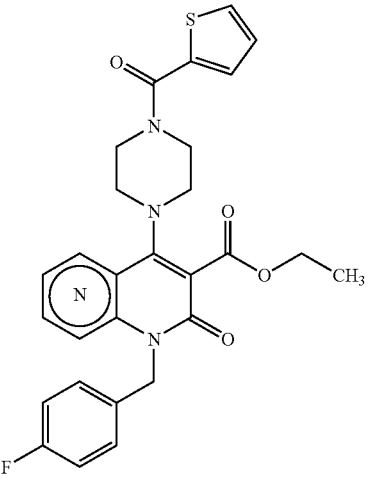

101

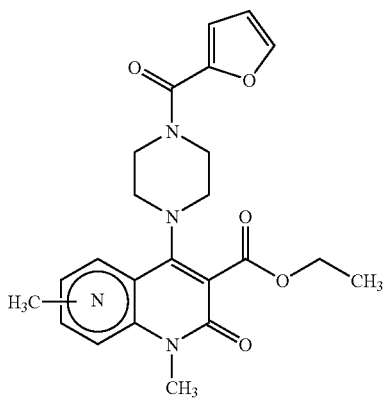

102

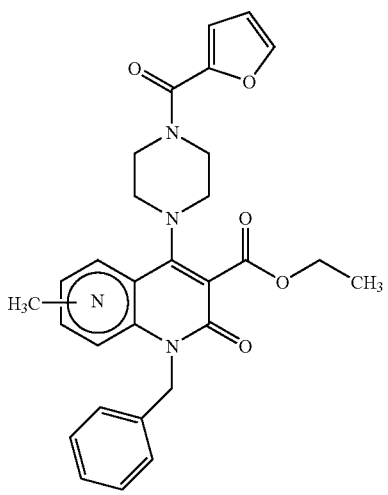

103

-continued
104
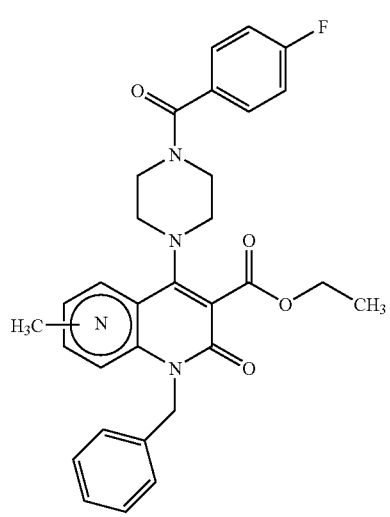
105
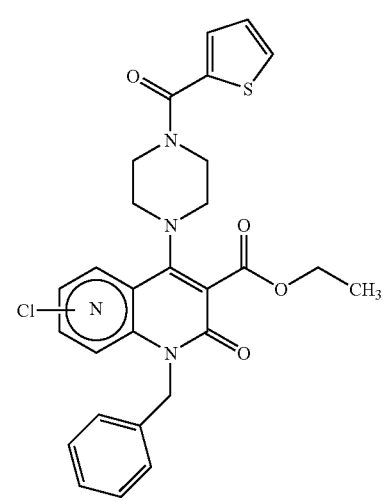
106
-continued
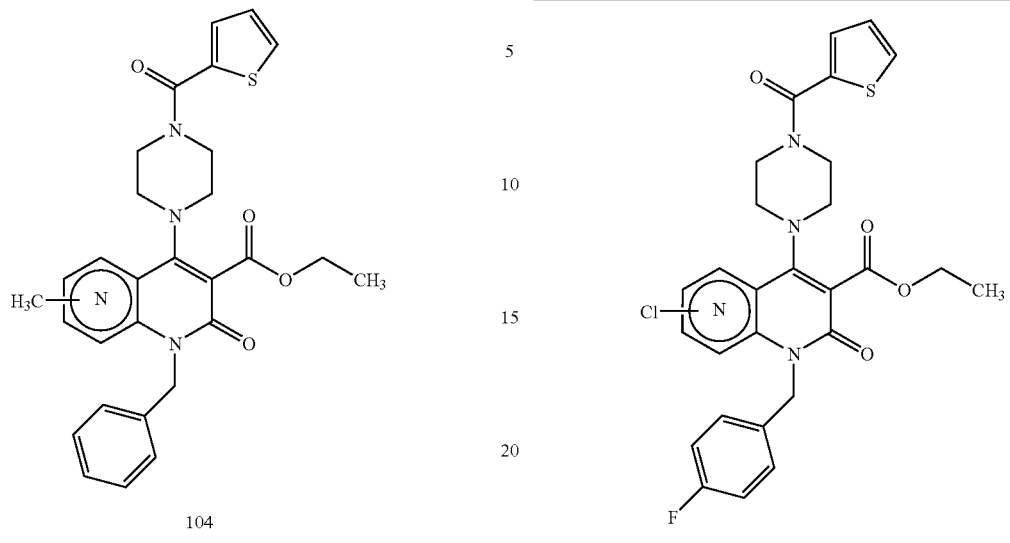
107
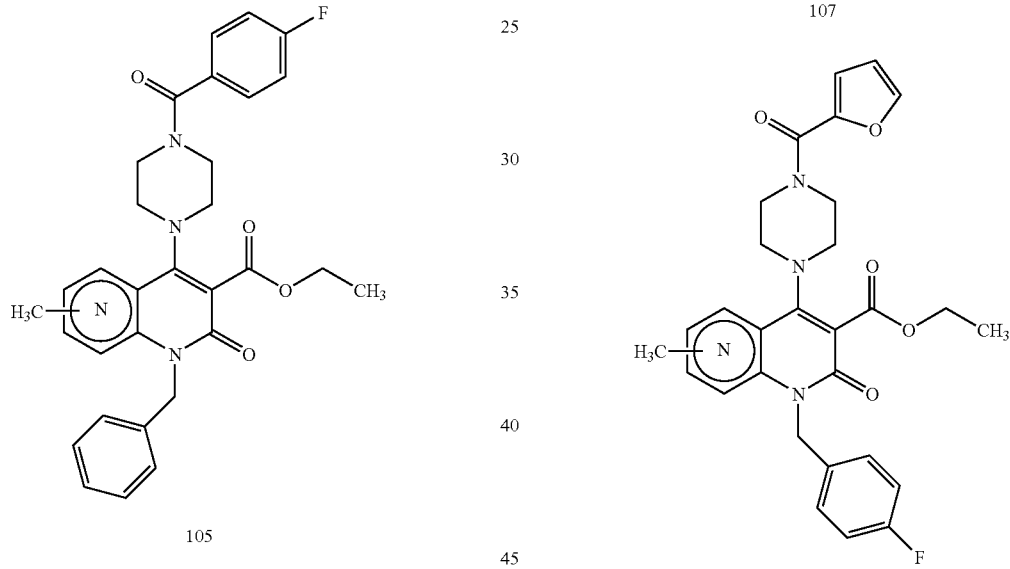
108
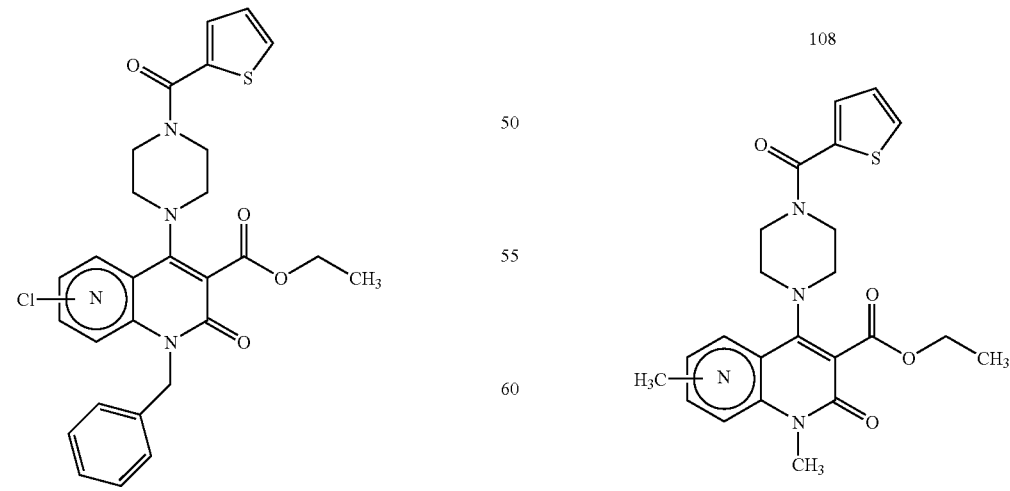
109

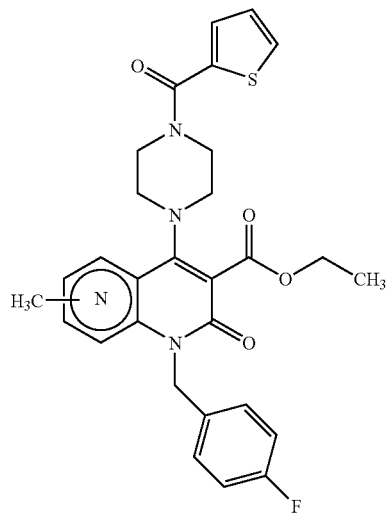
110
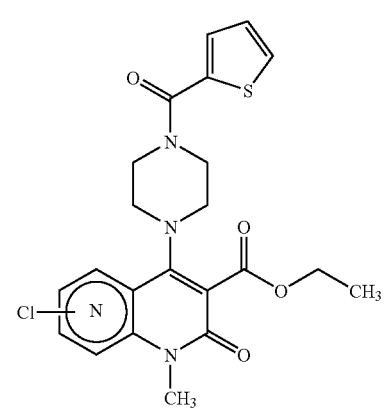
111
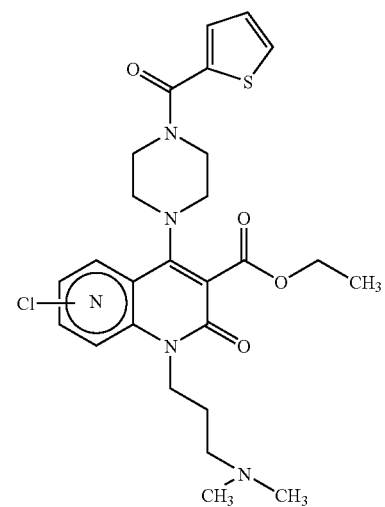
112
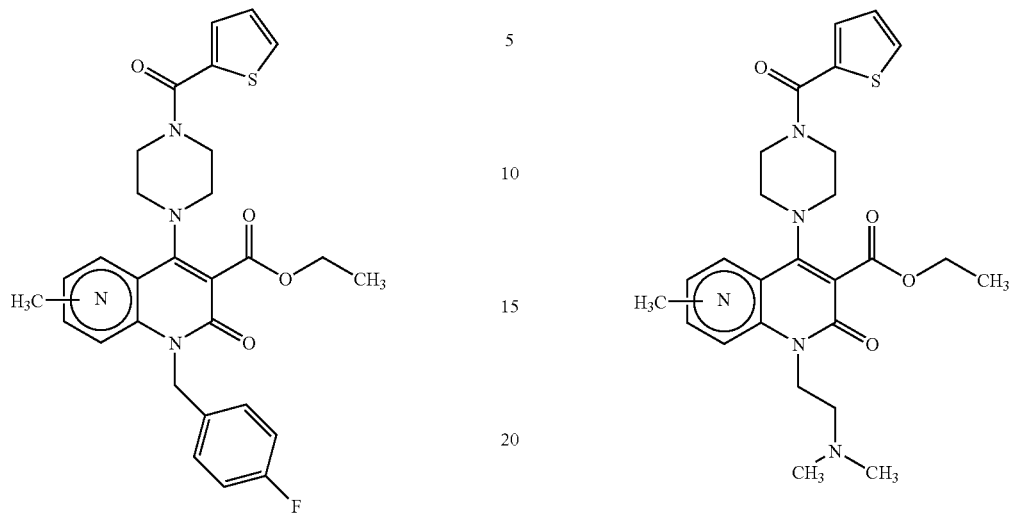
113
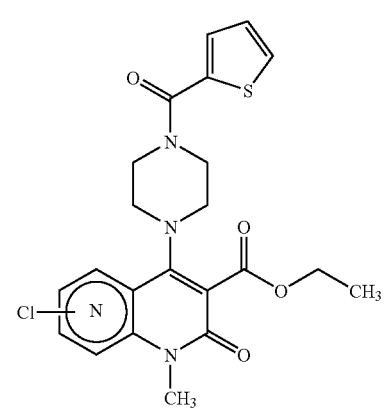
114
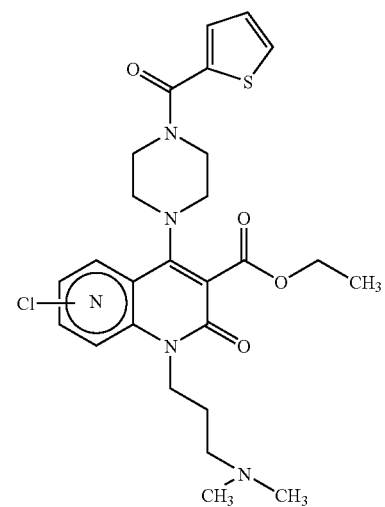
115

-continued
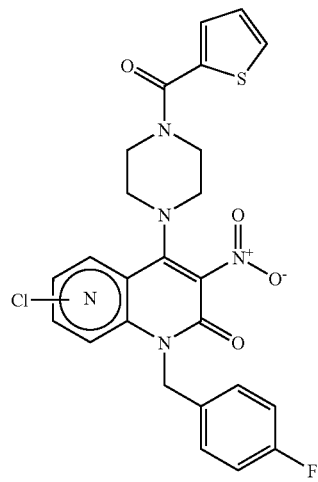
116
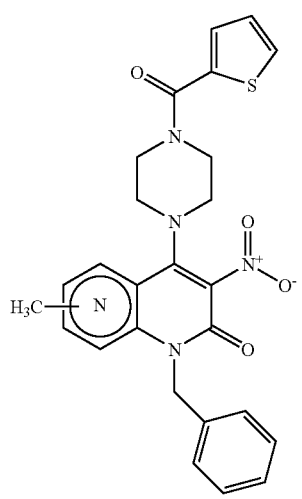
117
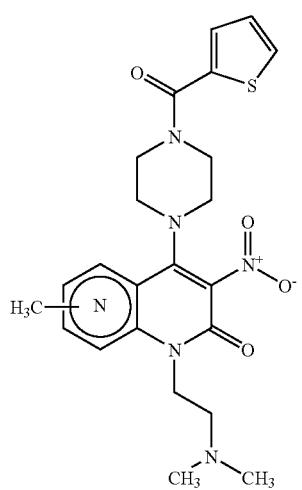
118
-continued
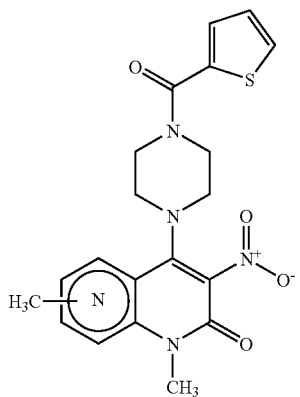
119
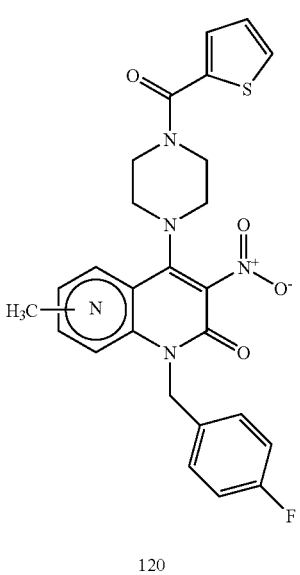
120
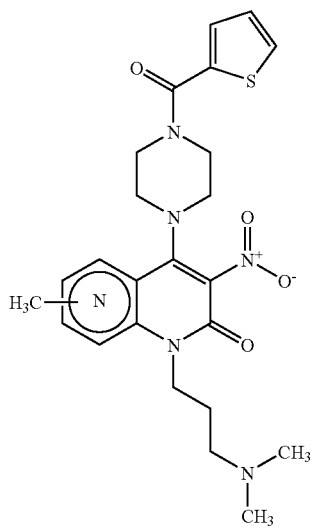
121

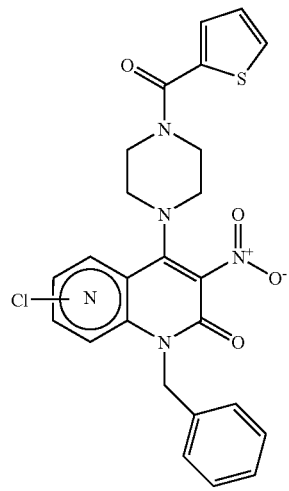
122
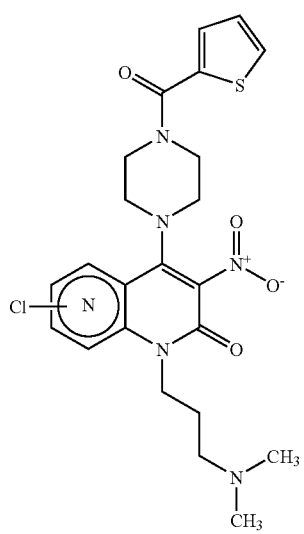
123
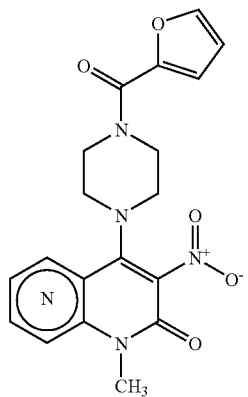
124
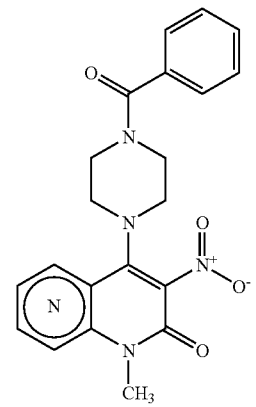
125
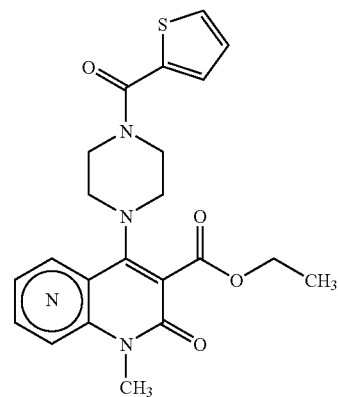
126
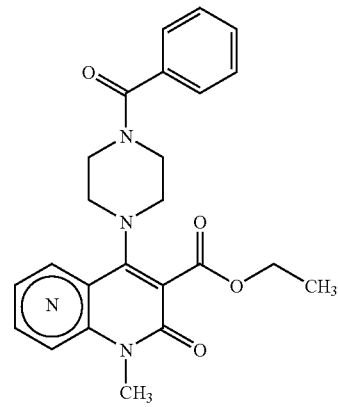
127

-continued
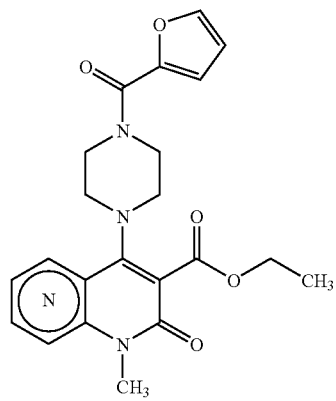
128
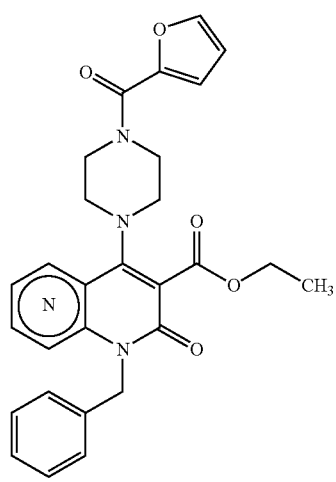
129
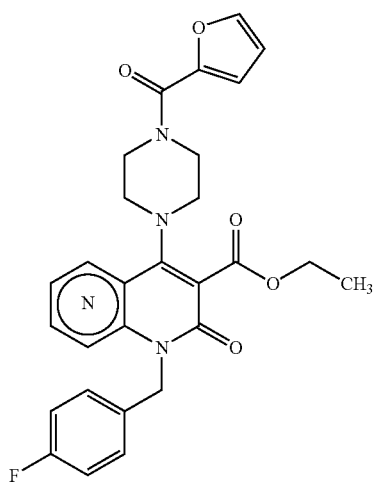
130
-continued
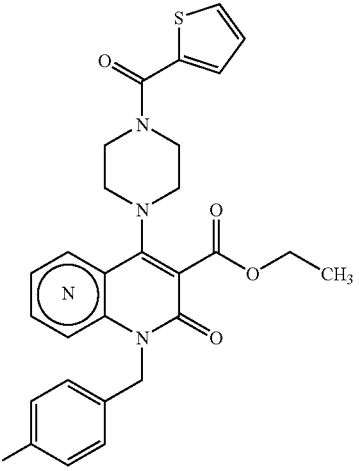
131
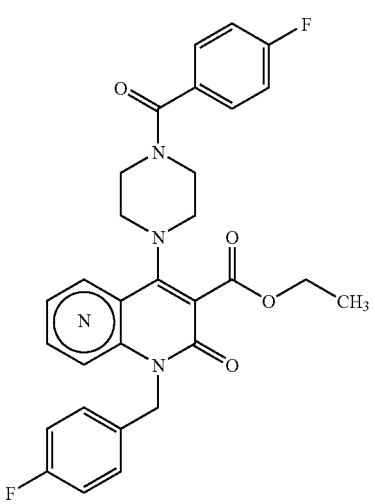
132
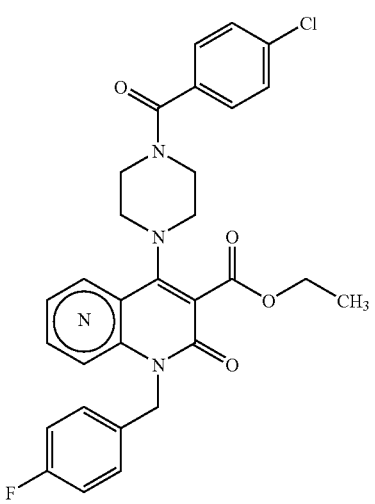
133

-continued
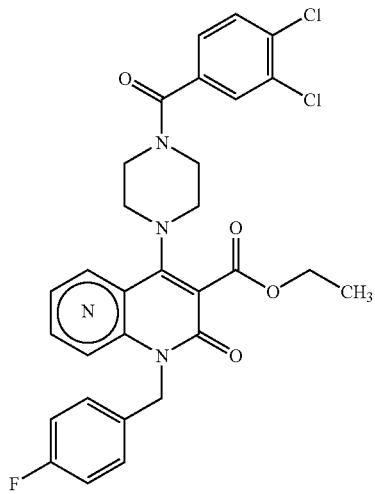
134
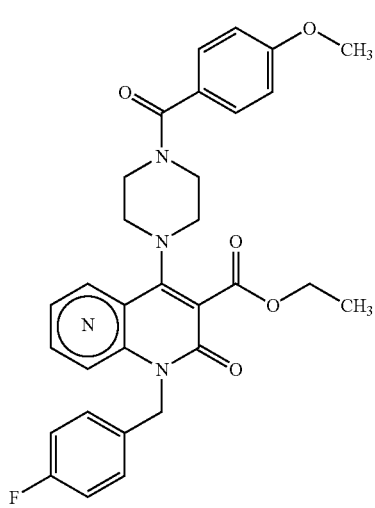
135
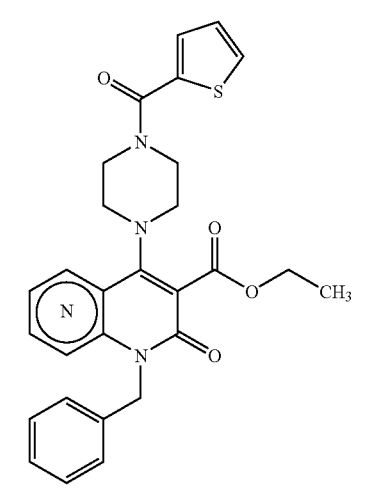
136
-continued
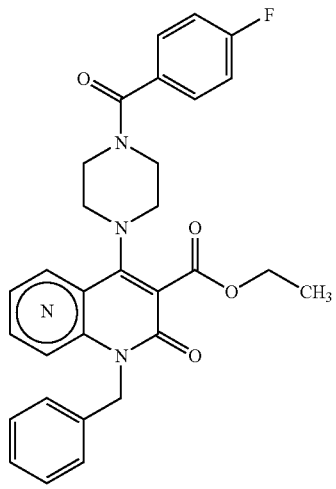
137
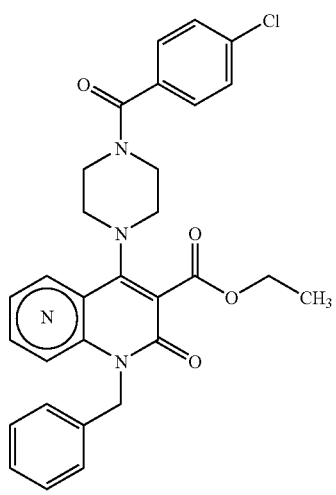
138
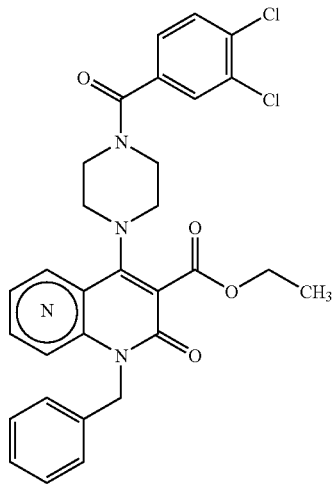
139

-continued
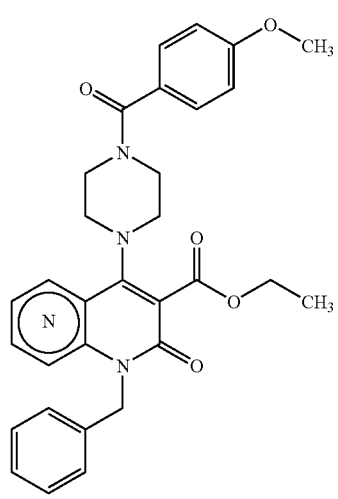
140
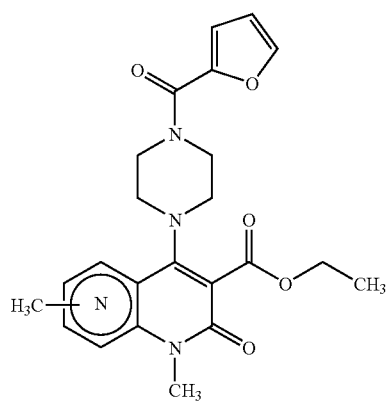
141
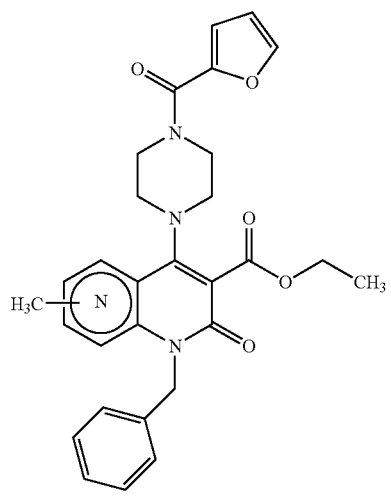
142
-continued
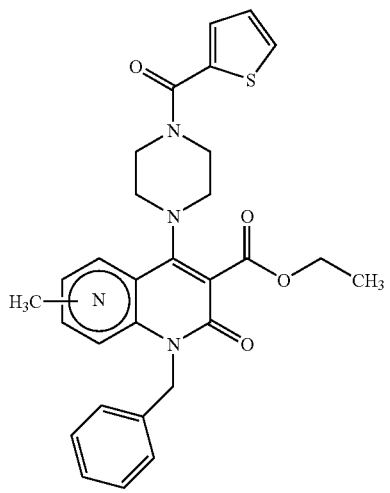
143
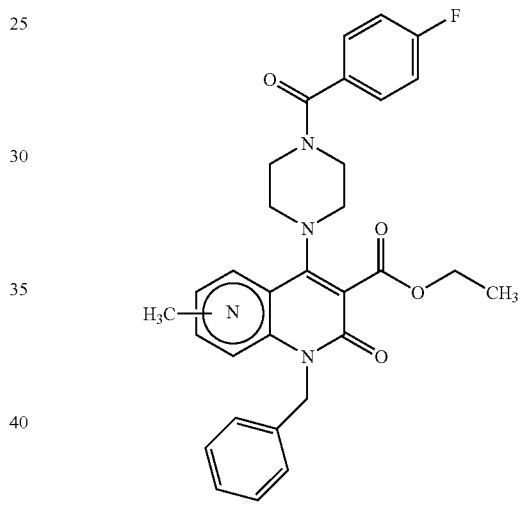
144
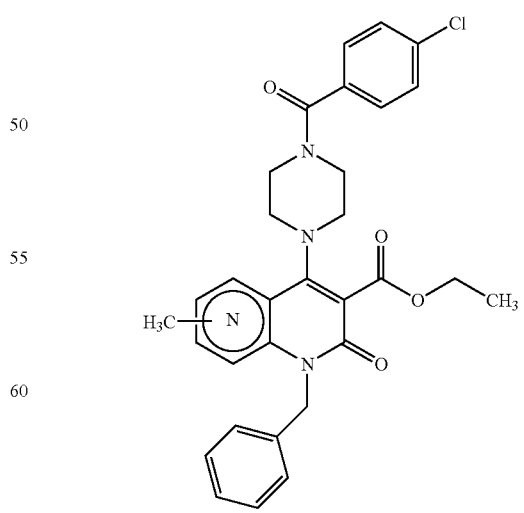
145

-continued
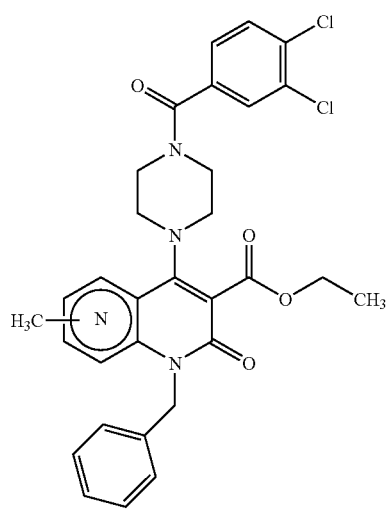
146
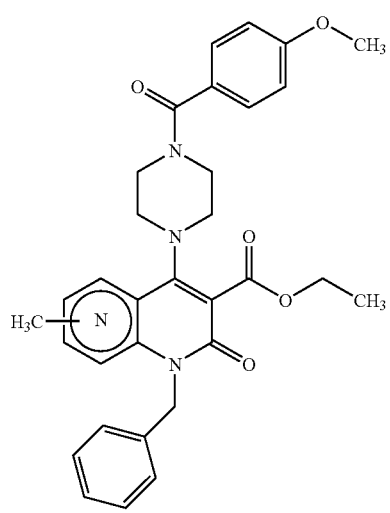
147
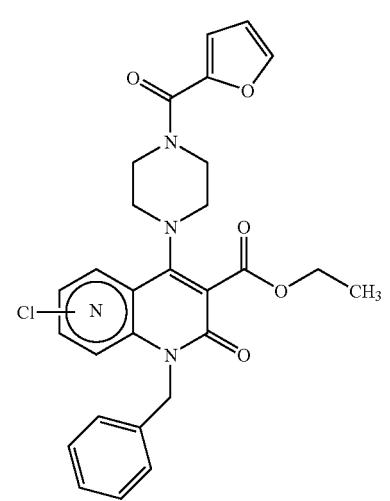
148
-continued
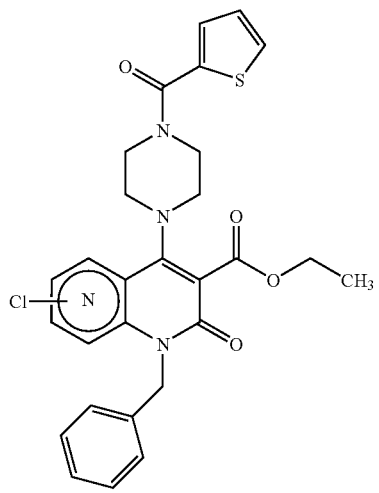
149
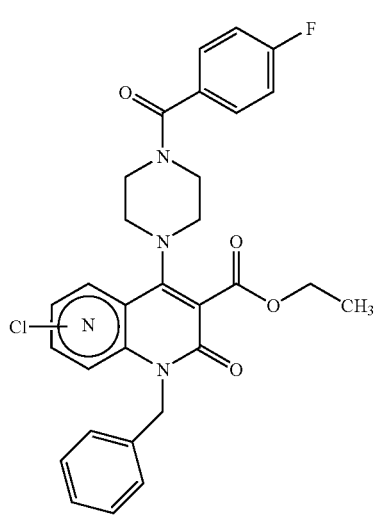
150
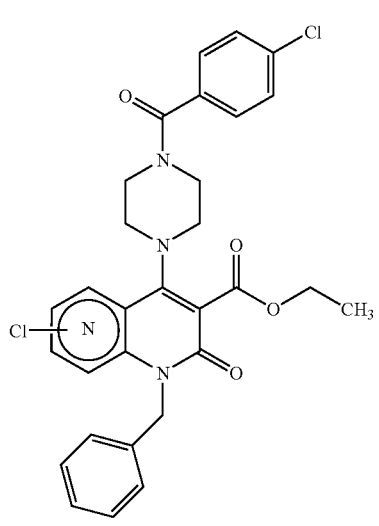
151

-continued
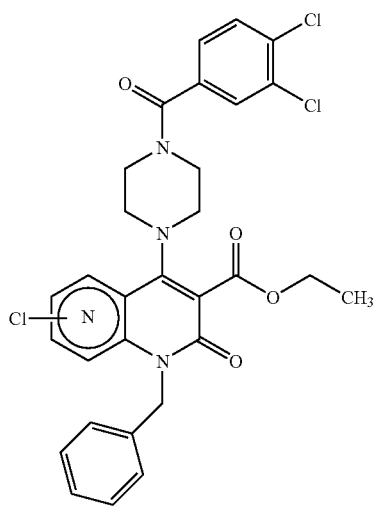
152
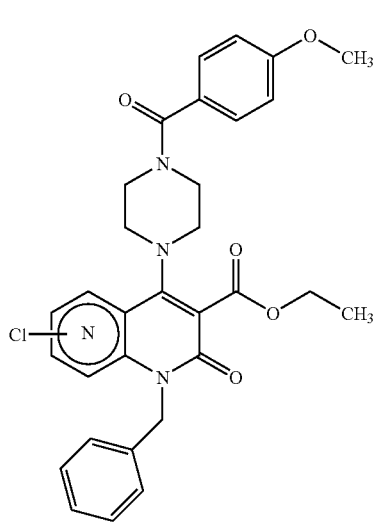
153
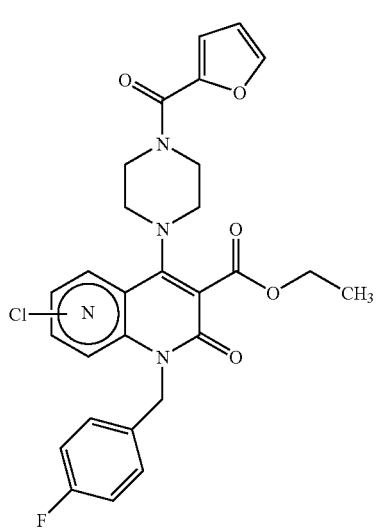
154
-continued
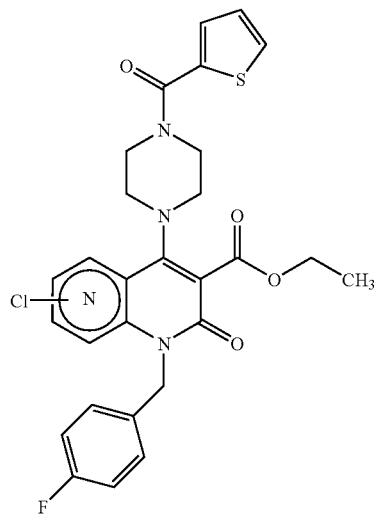
155
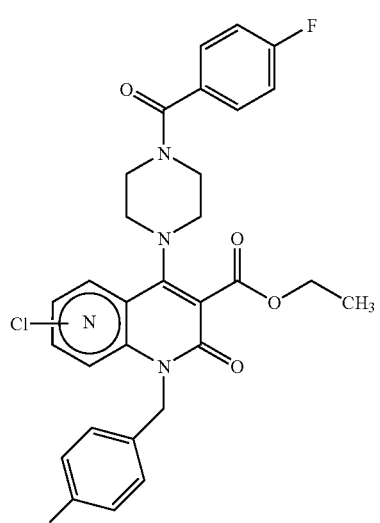
156
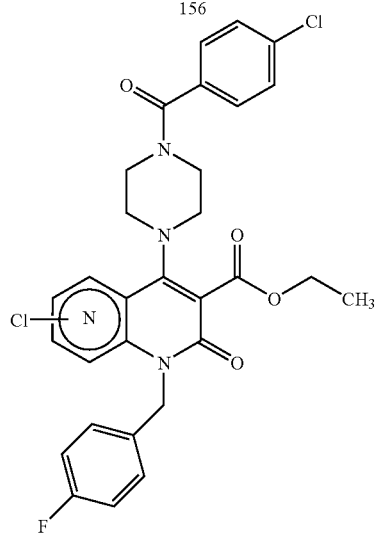
157

-continued
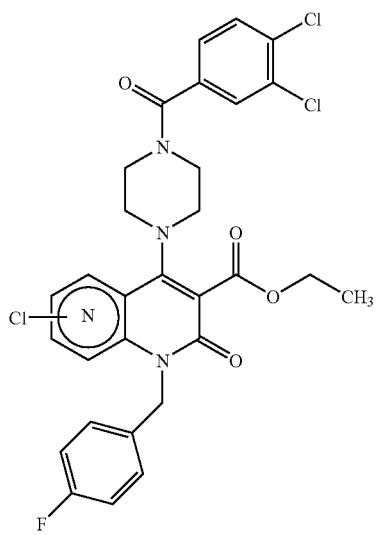
158
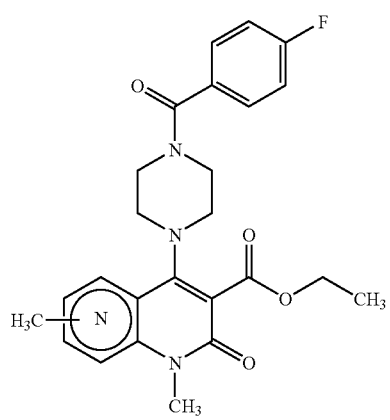
159
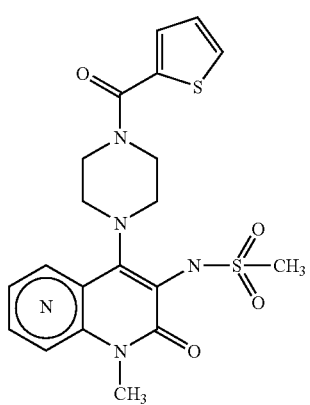
160
-continued
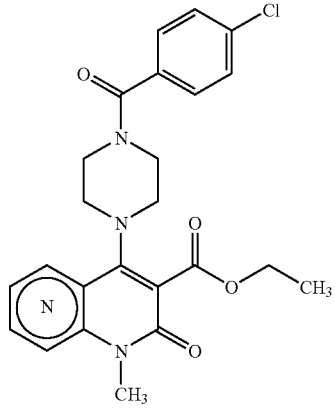
161
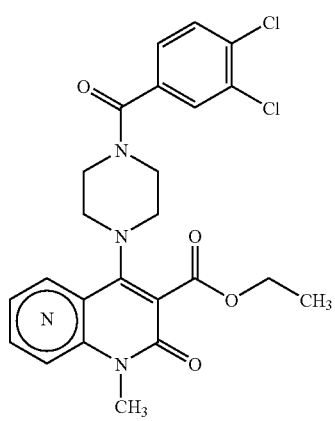
162
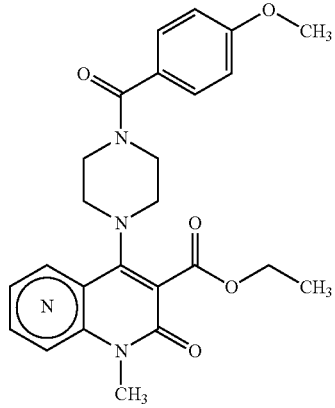
163

-continued
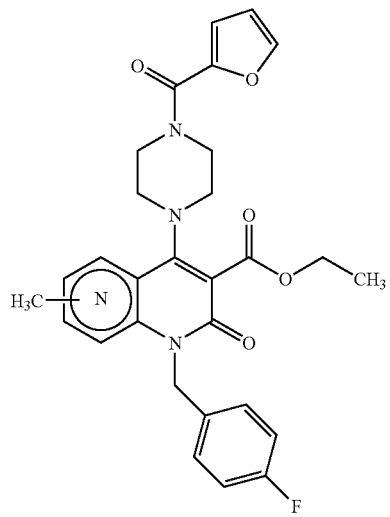
164
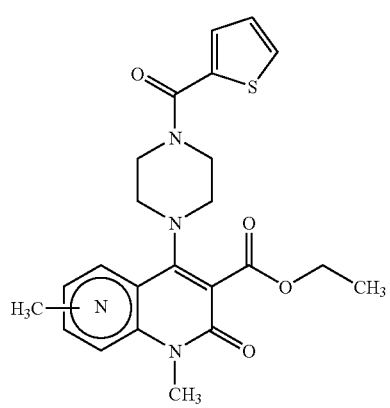
165
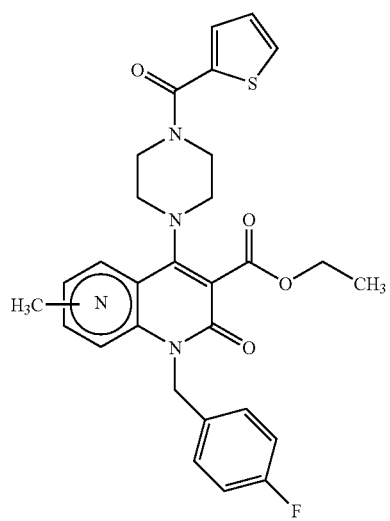
166
-continued
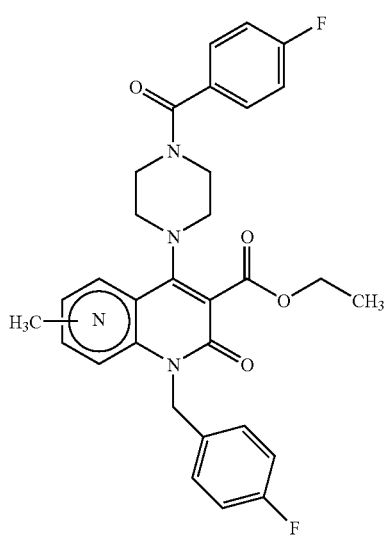
167
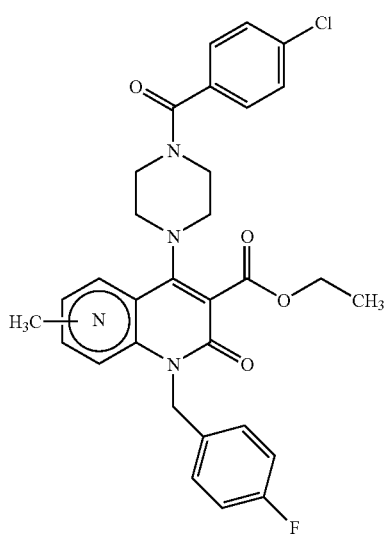
168

-continued
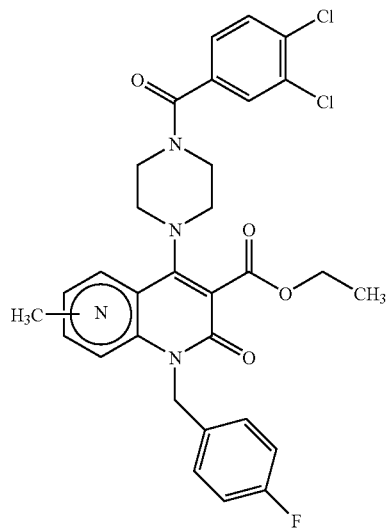
169
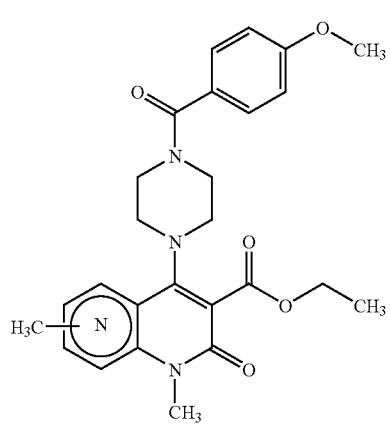
170
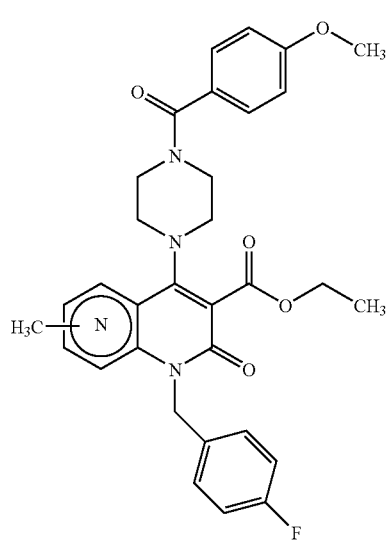
171
-continued
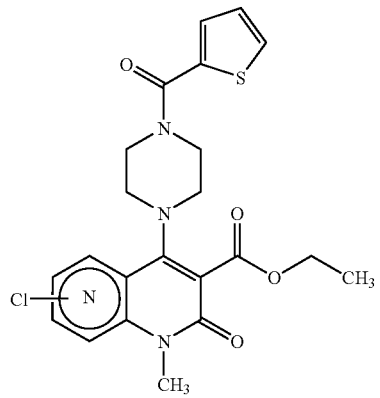
172
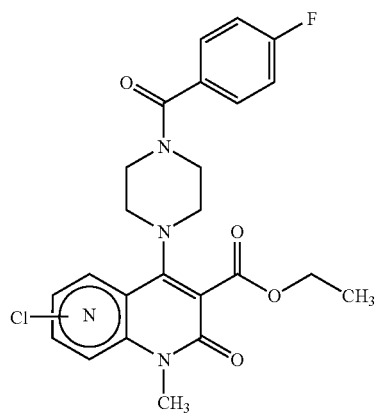
173
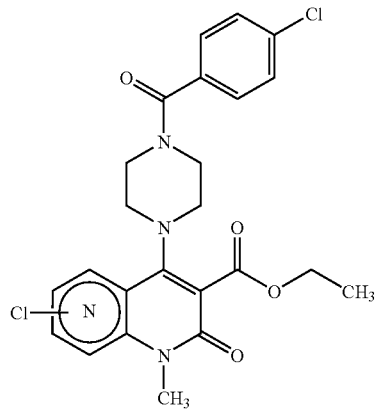
174

-continued
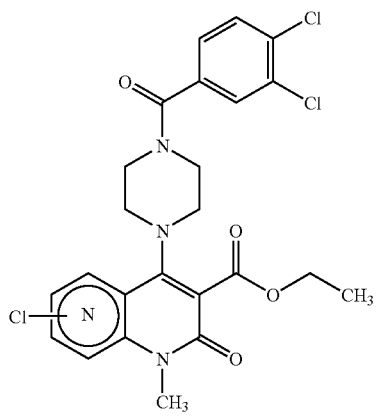
175
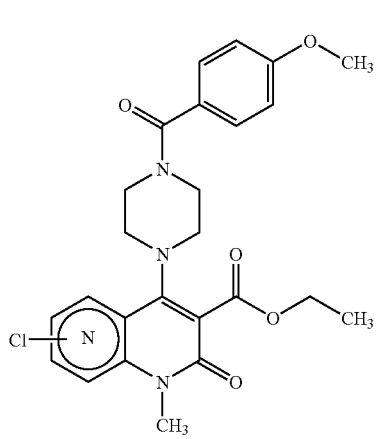
176
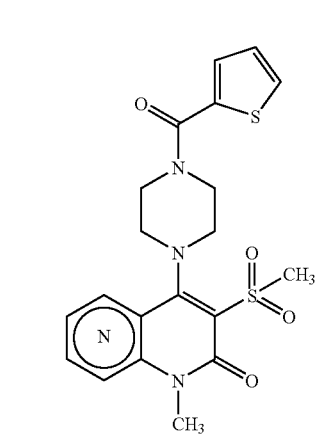
177
-continued
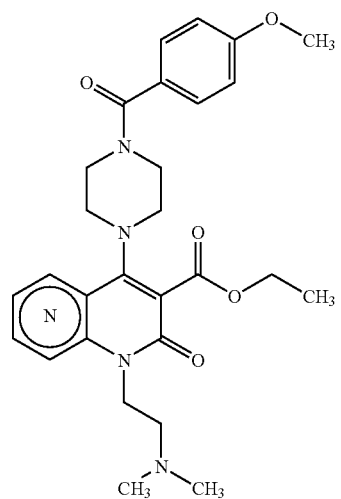
178
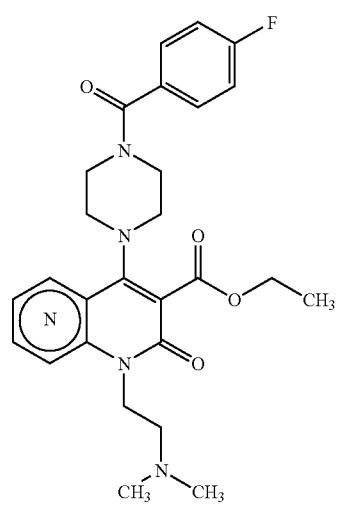
179
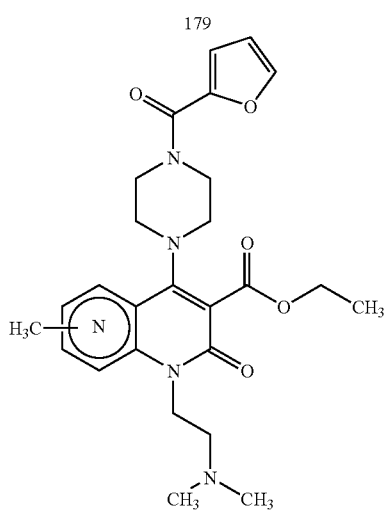
180

-continued
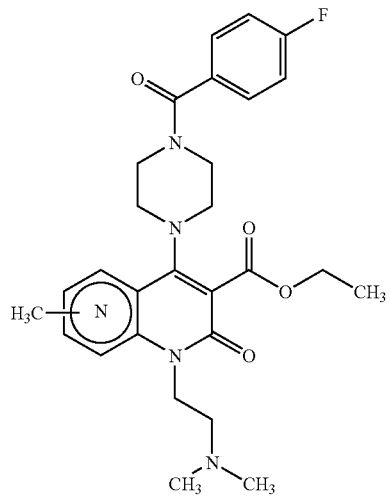
181
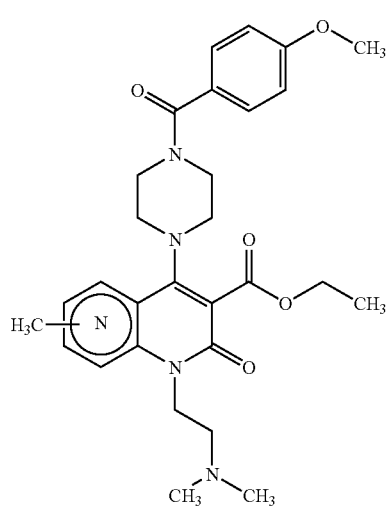
182
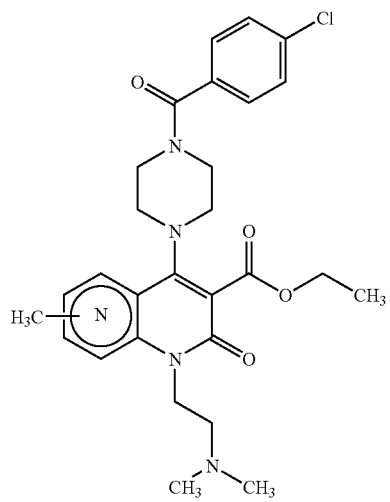
183
-continued
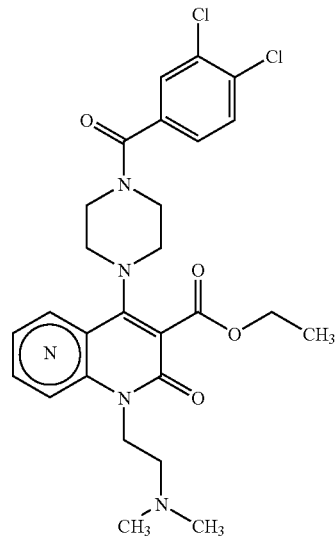
184
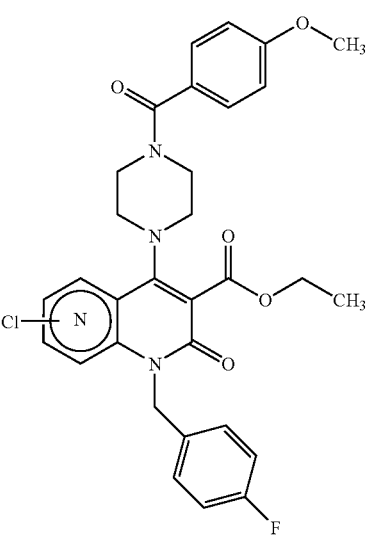
185
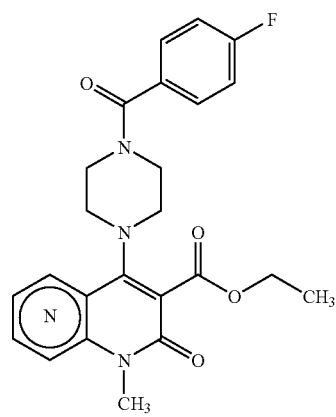
186

187
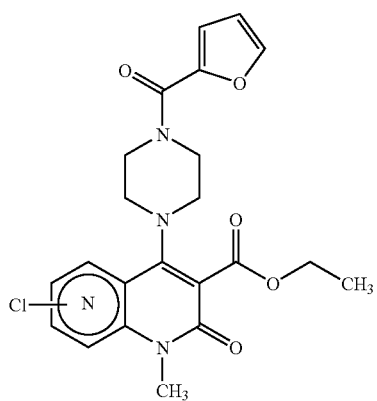
188
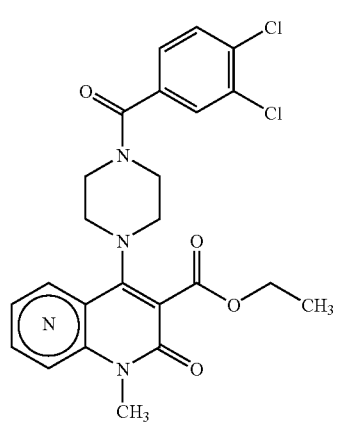
189
190
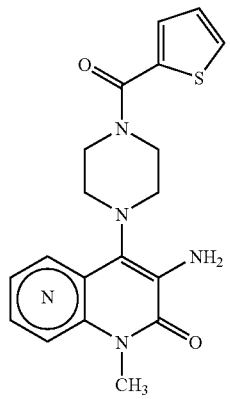
191
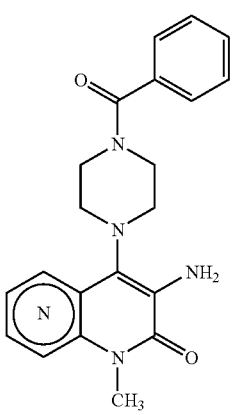
192
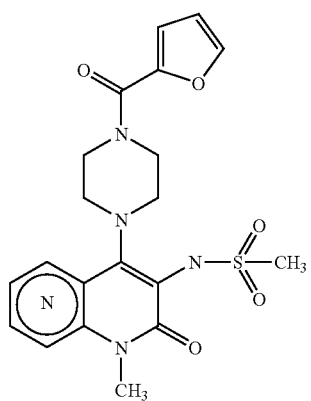
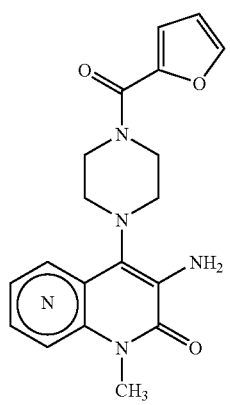

192
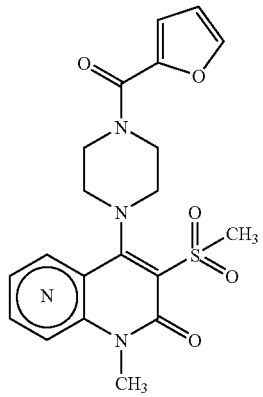
193
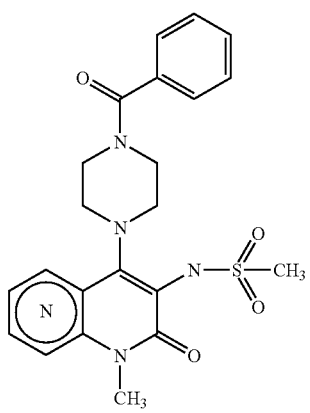
194
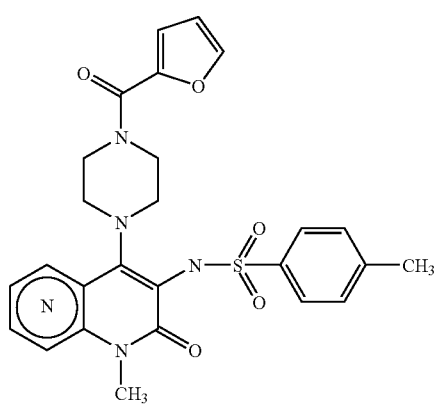
195
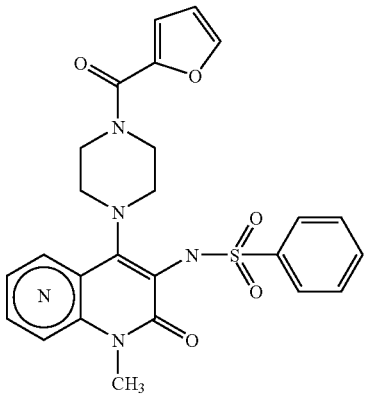
196
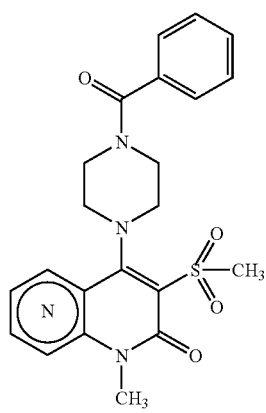
197
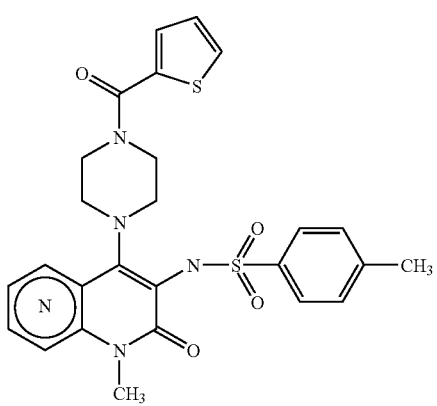
198

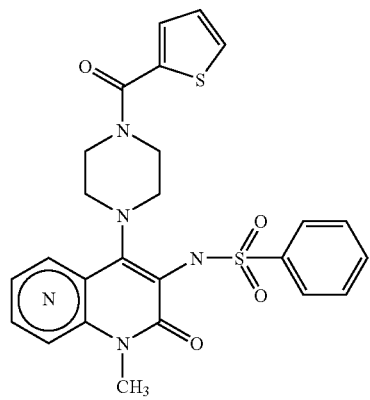
199
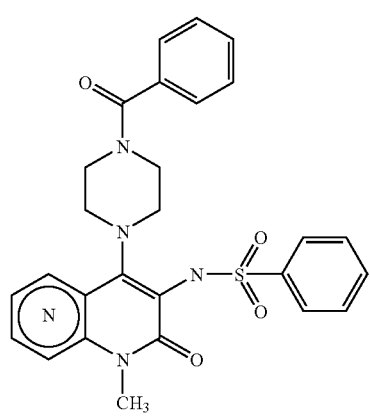
200
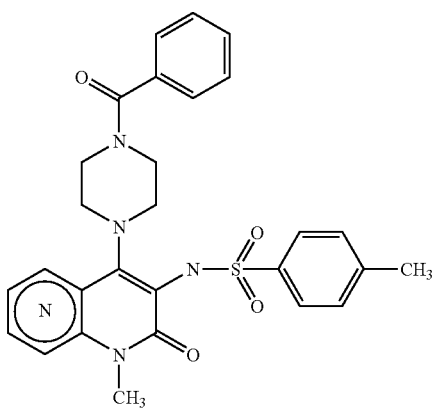
201
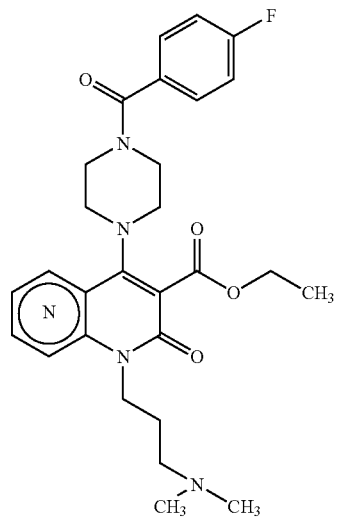
202
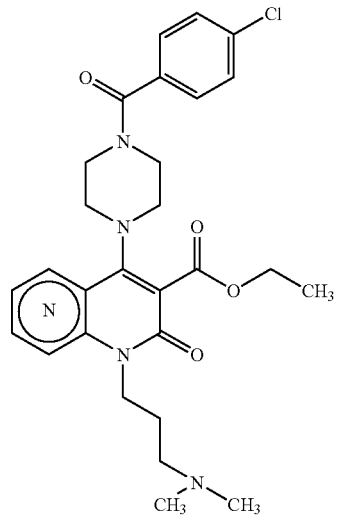
203
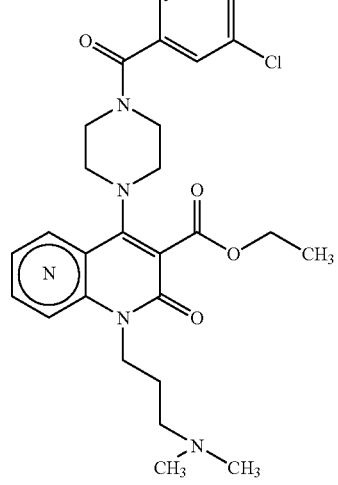
204

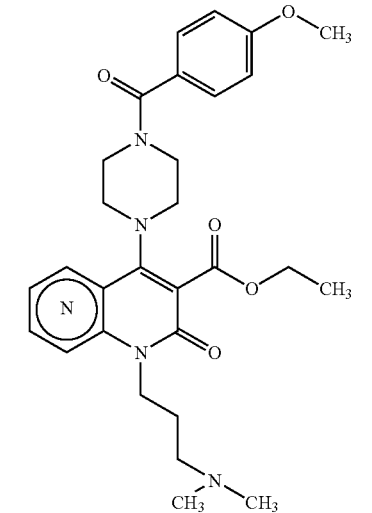
205
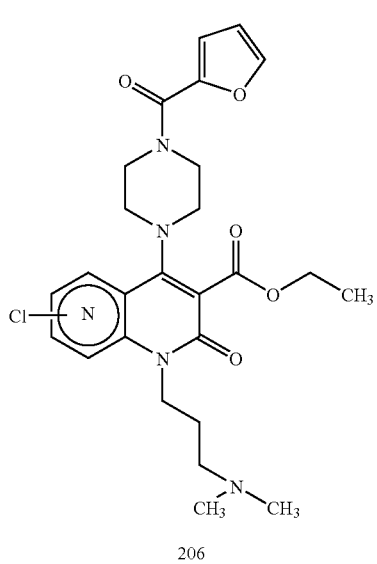
206
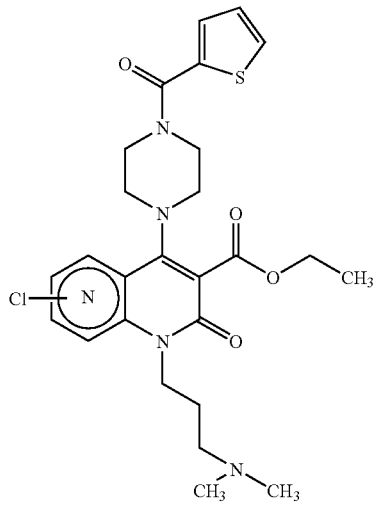
207
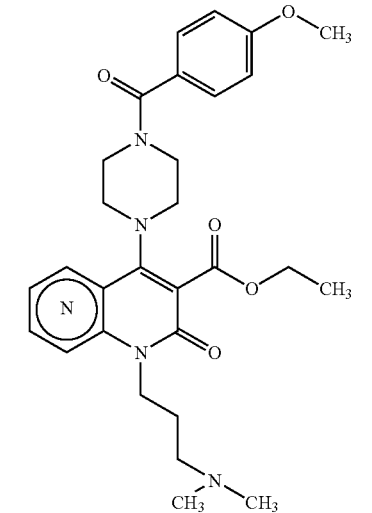
208
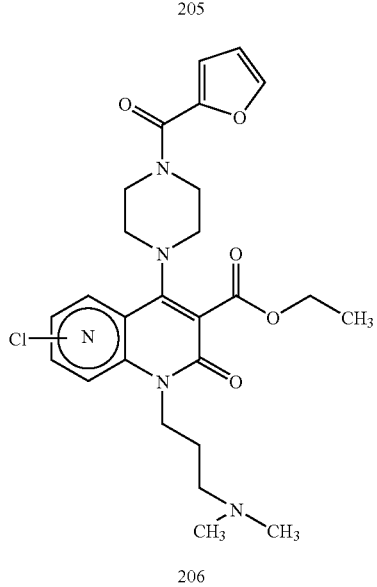
209
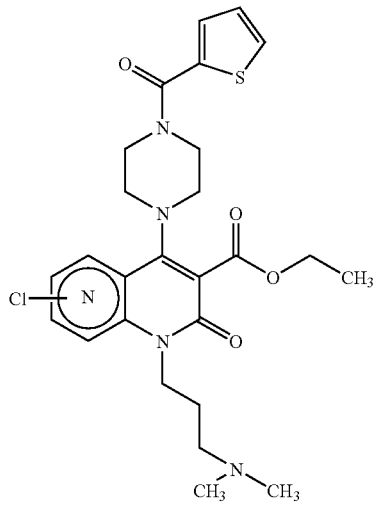
210

-continued
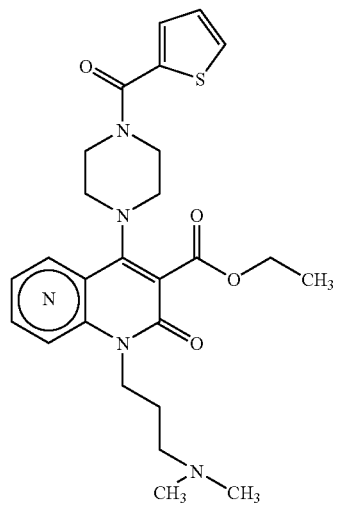
211
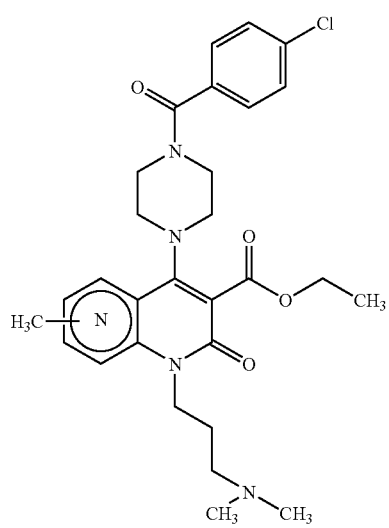
212
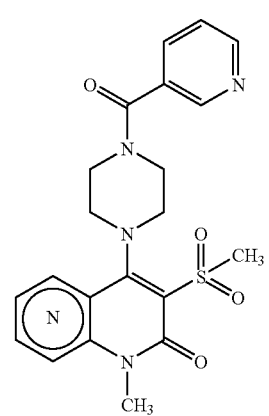
213
-continued
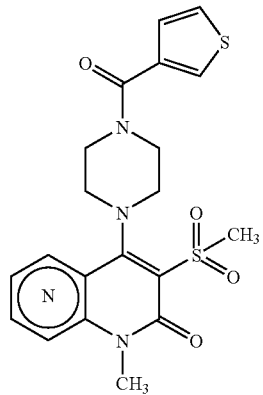
214
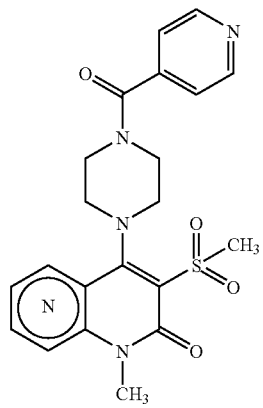
215
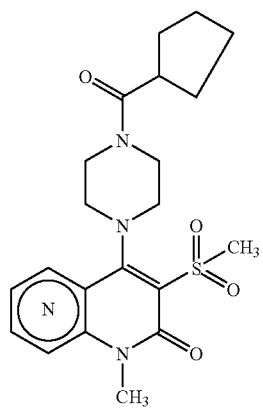
216

-continued
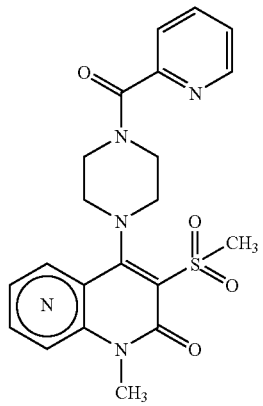
217
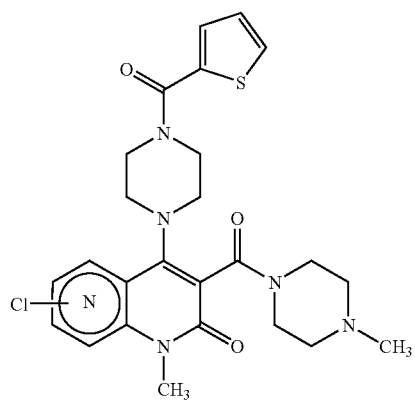
218
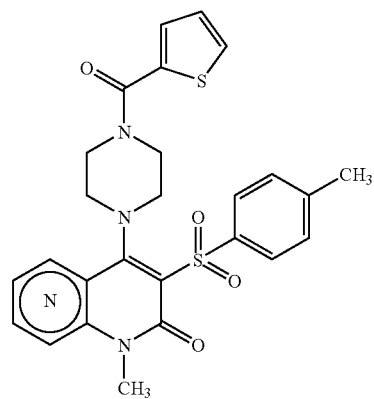
219
-continued
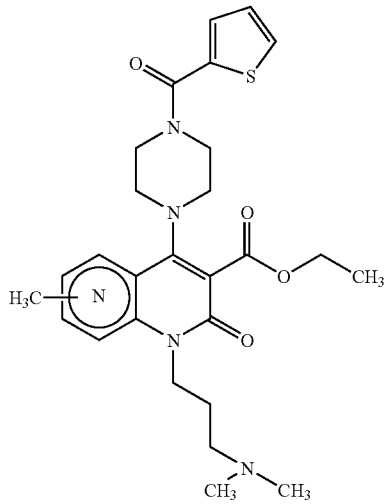
220
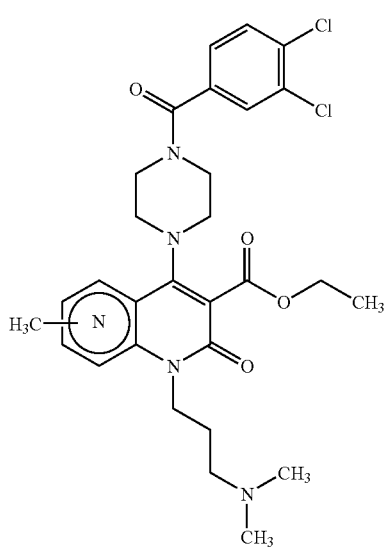
221
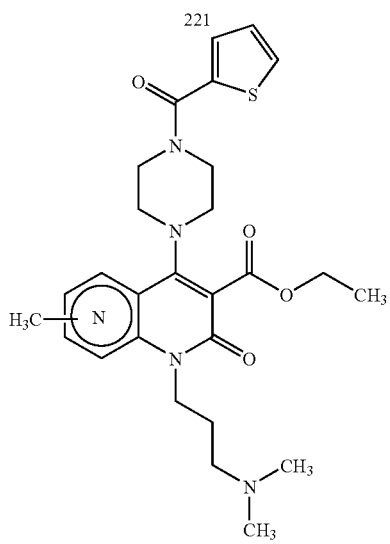
222

-continued
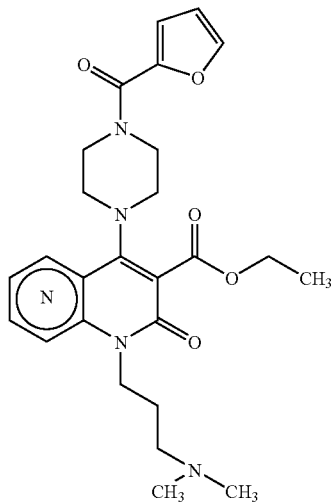
223
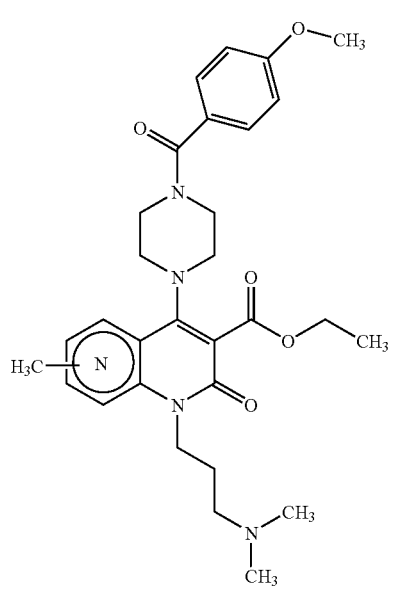
224
-continued
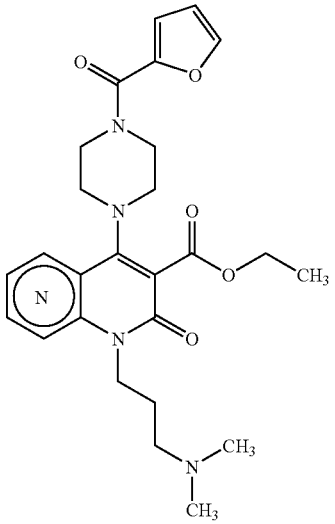
225
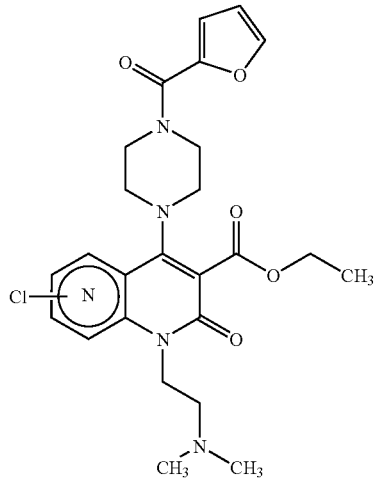
226

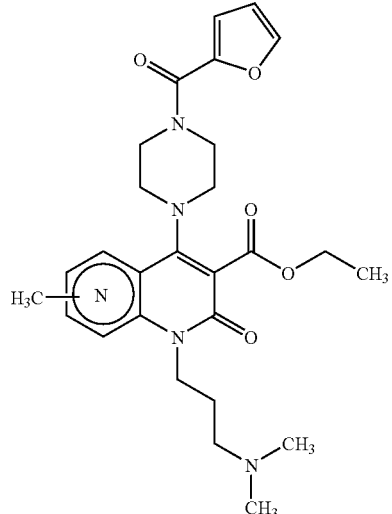
227
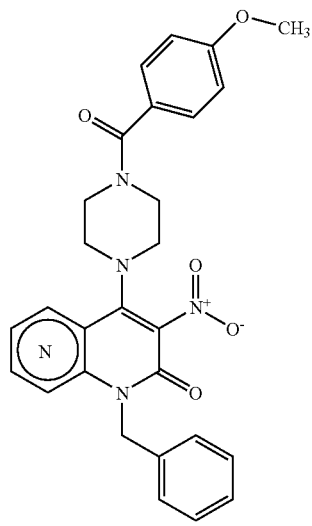
229
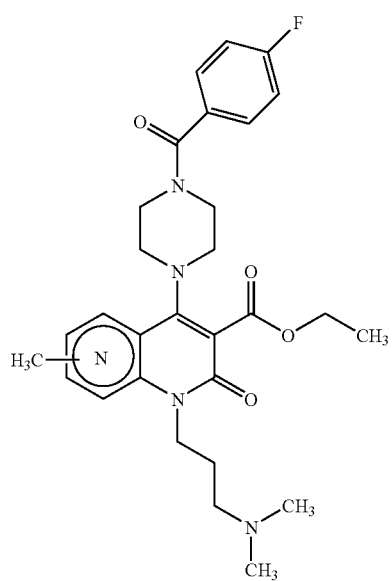
228
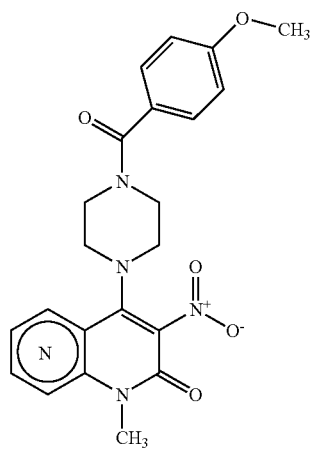
230

-continued
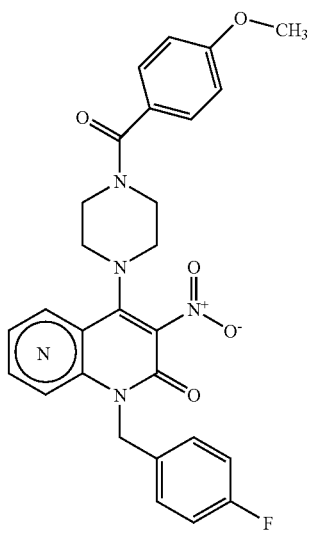
231
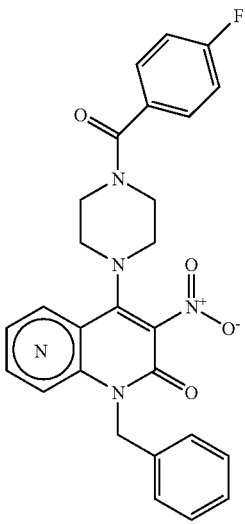
233
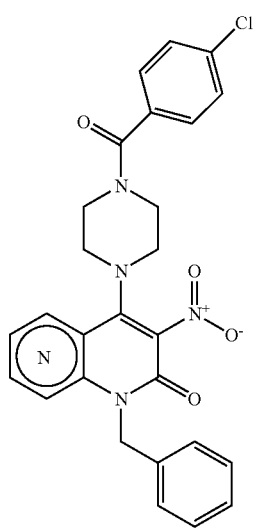
232
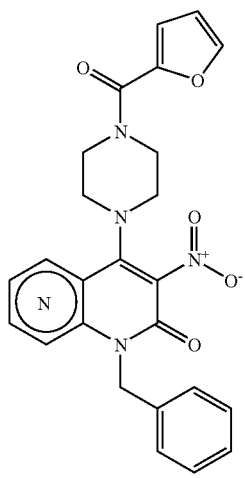
234

-continued
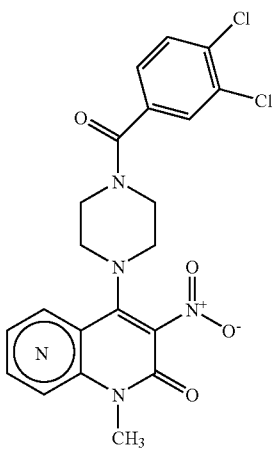
235
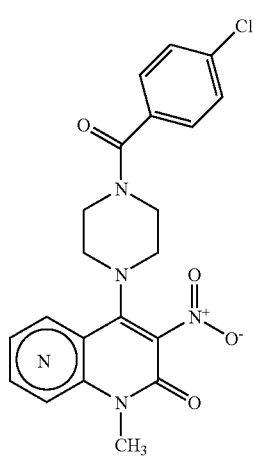
236
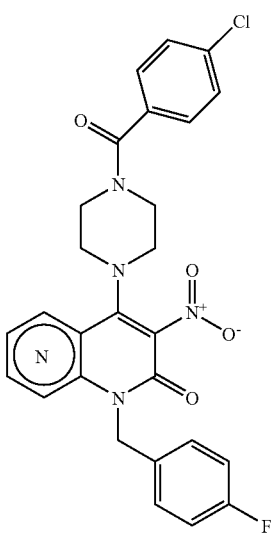
237
-continued
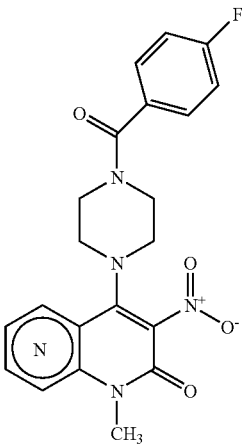
238
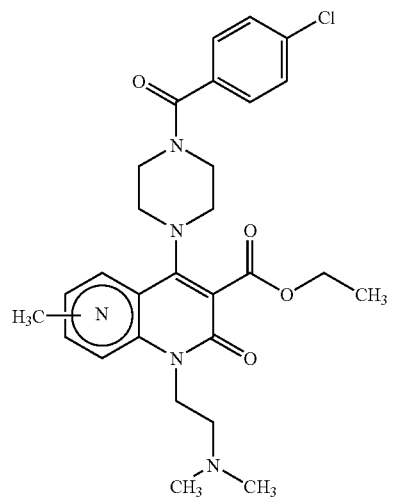
239
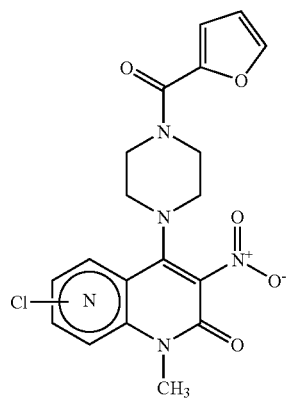
240

-continued
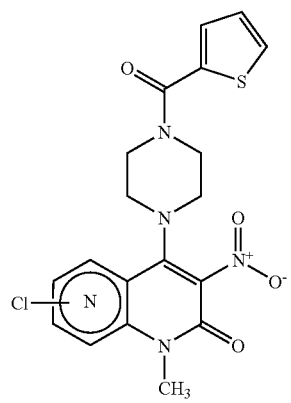
241
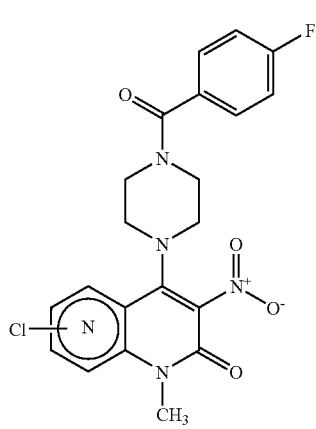
242
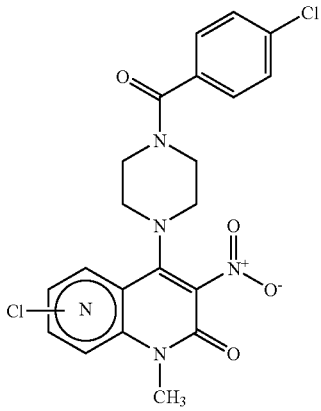
243
-continued
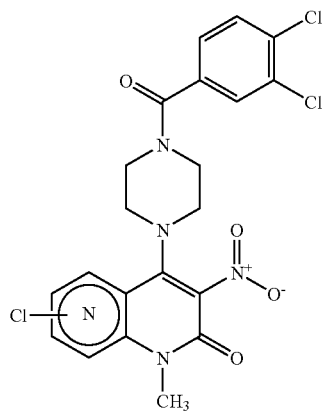
244
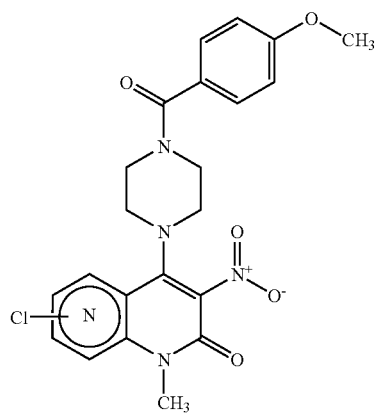
245
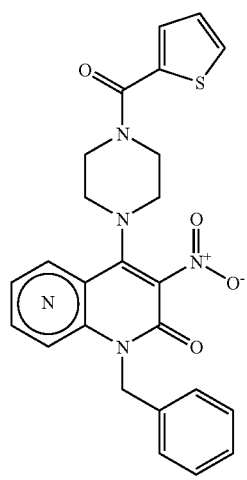
246

-continued
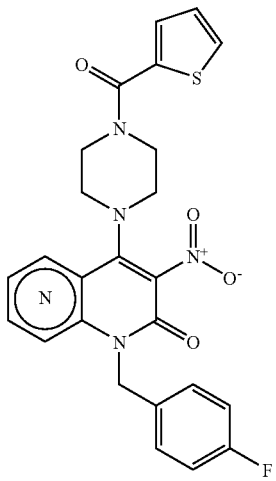
247
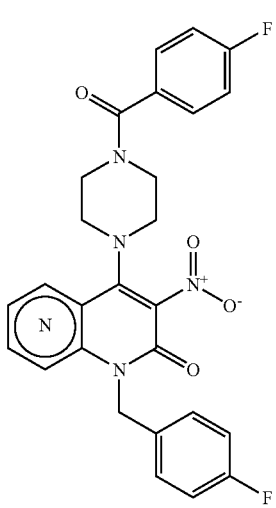
248
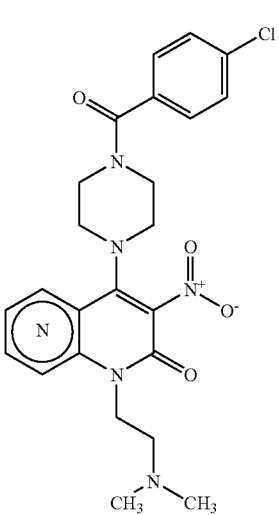
249
-continued
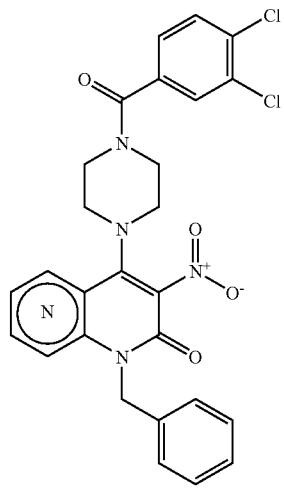
250
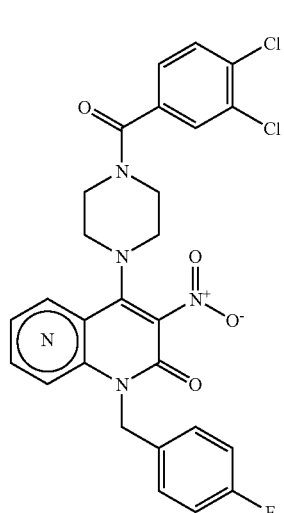
251
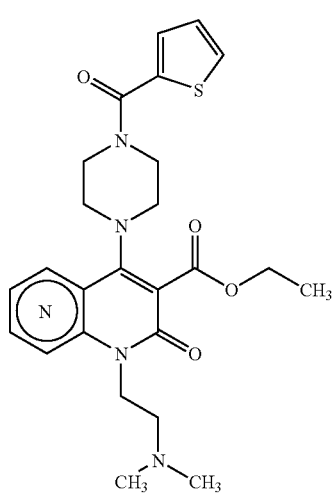
252

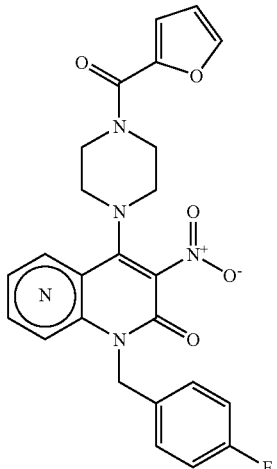
253
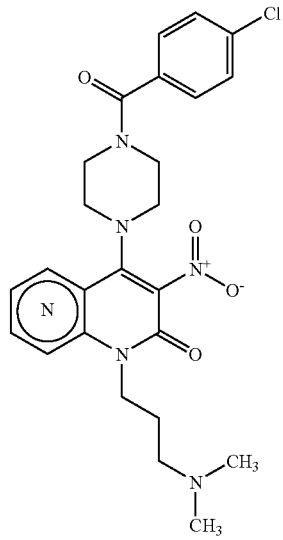
255
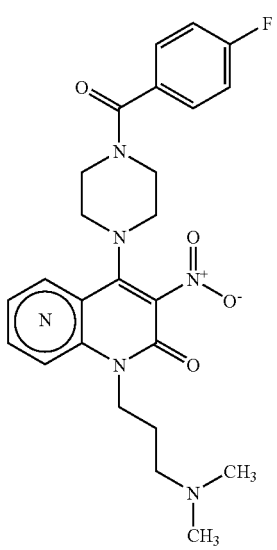
254
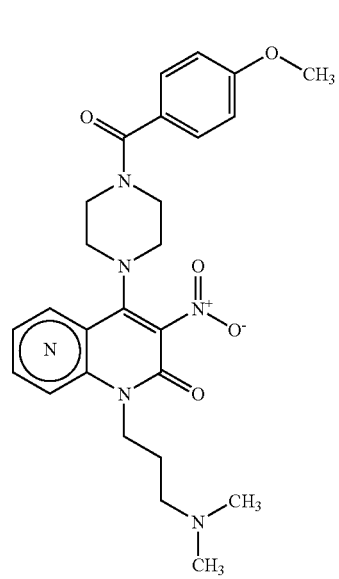
256

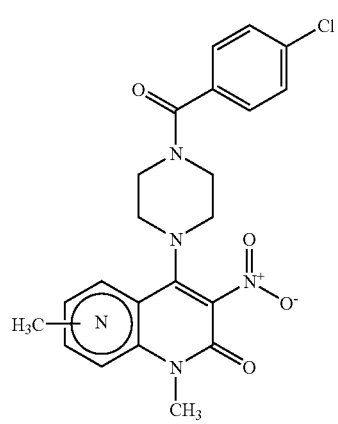
257
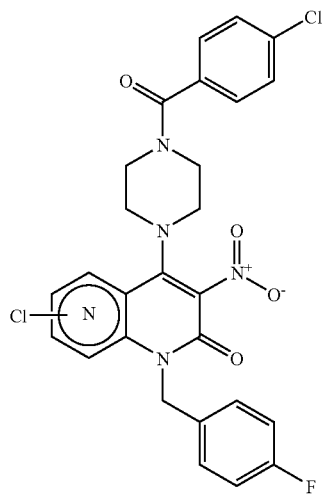
260
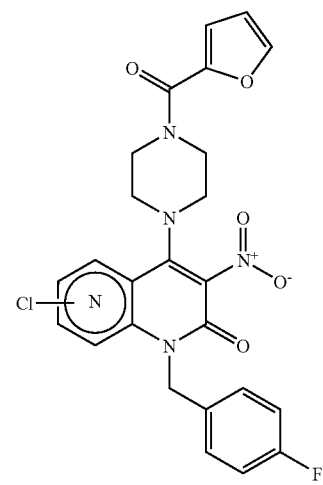
258
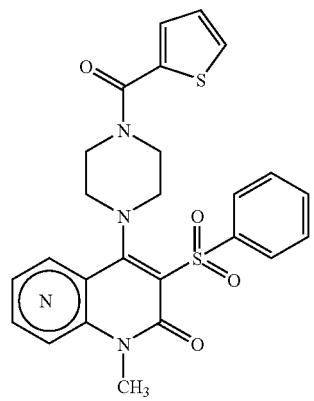
261
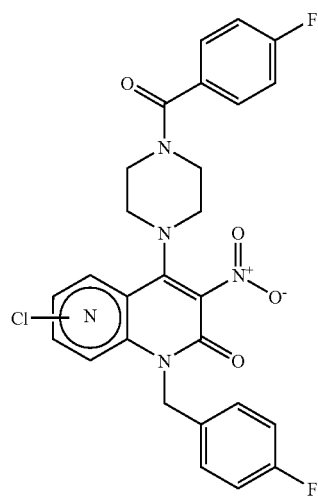
259
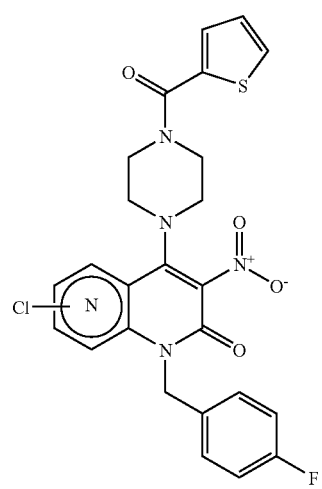
262

-continued
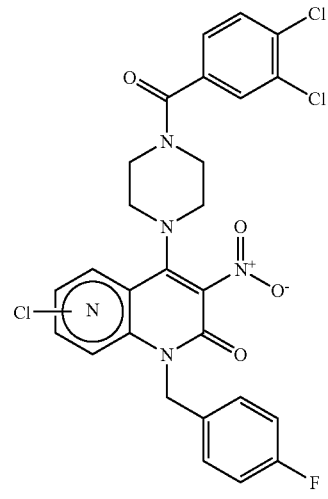
263
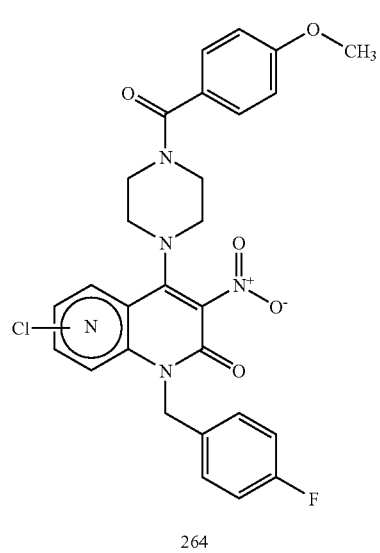
264
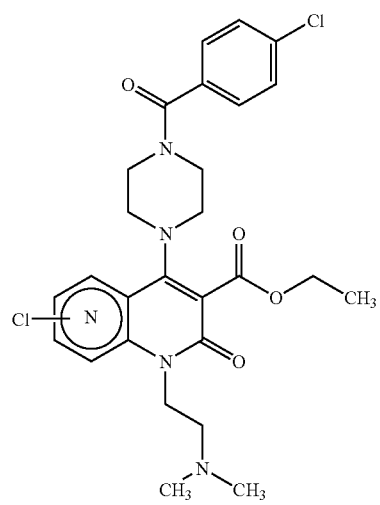
265
-continued
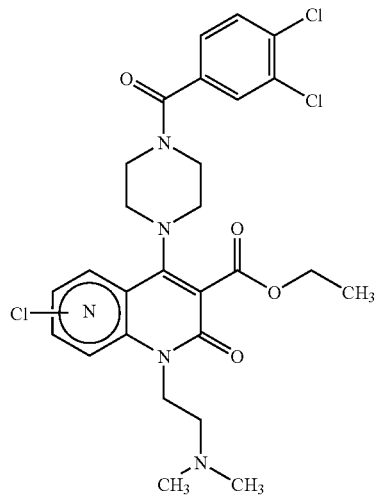
266
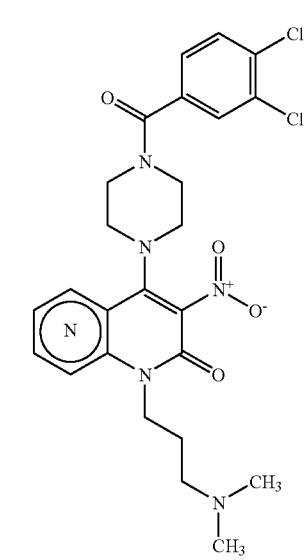
267
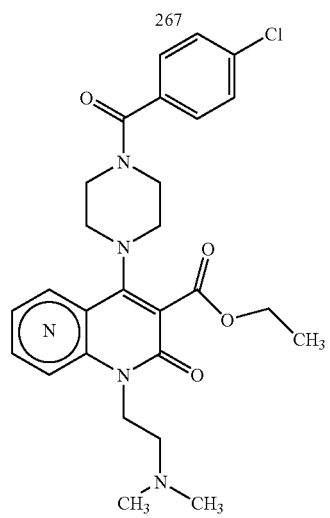
268

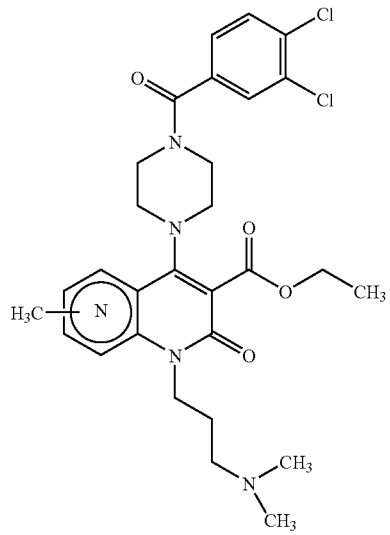
269
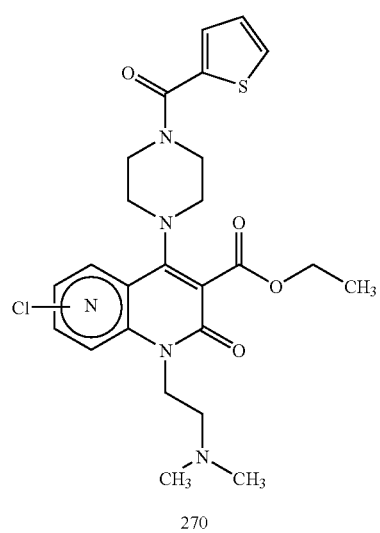
270
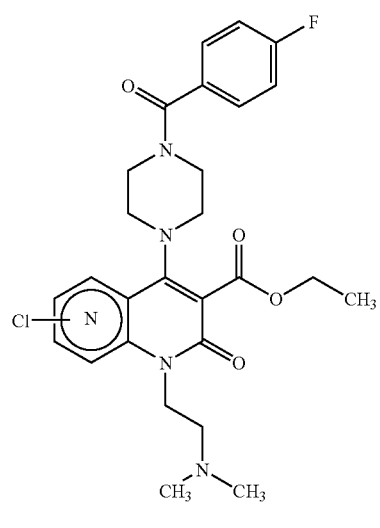
271
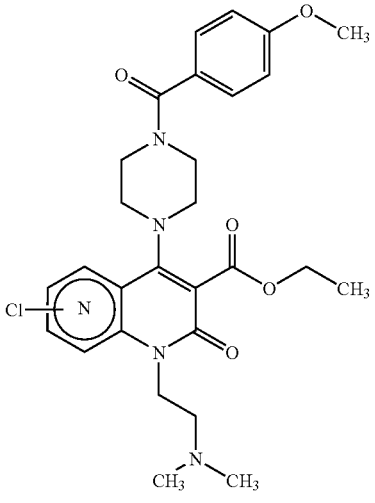
272
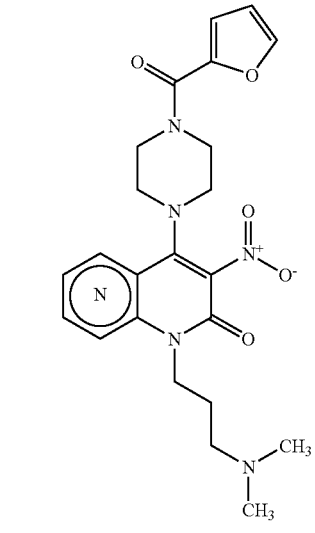
273
274

-continued
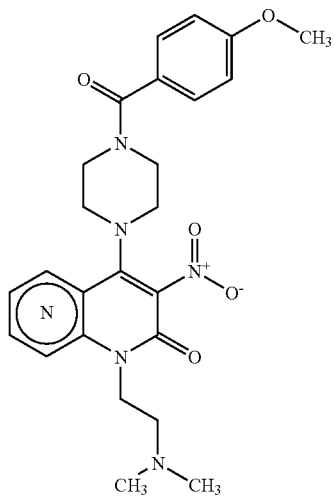
275
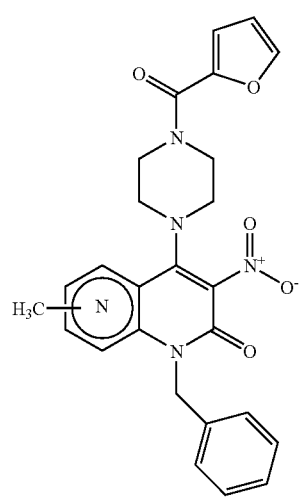
276
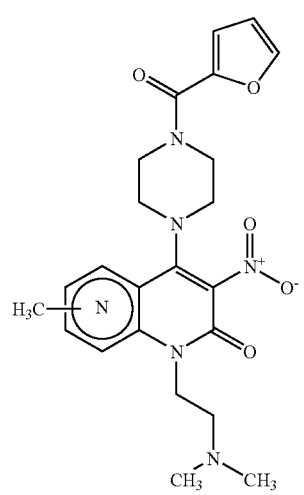
277
-continued
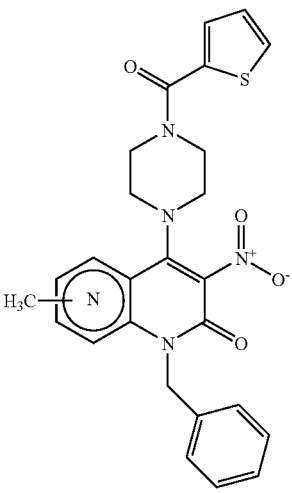
278
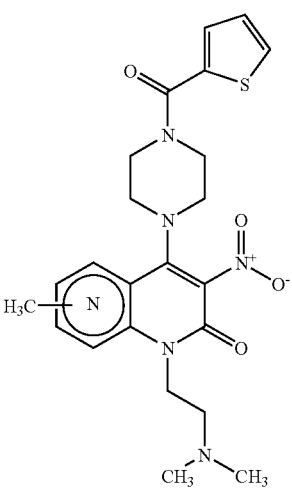
279
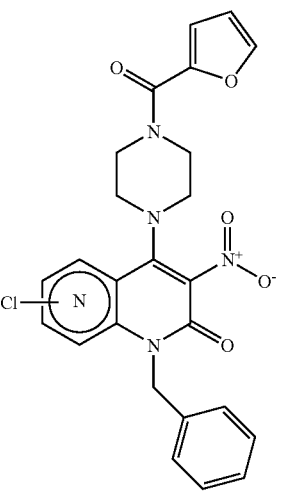
280

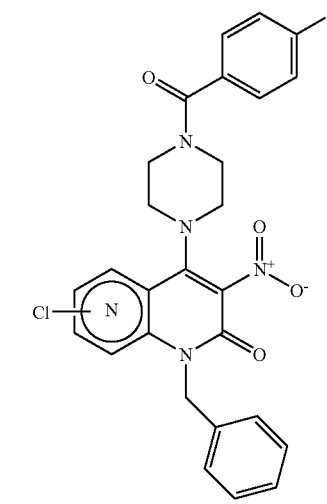
281
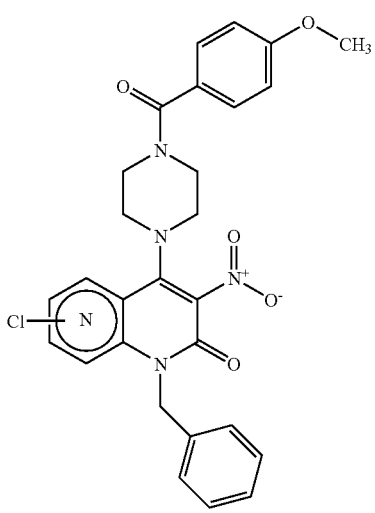
282
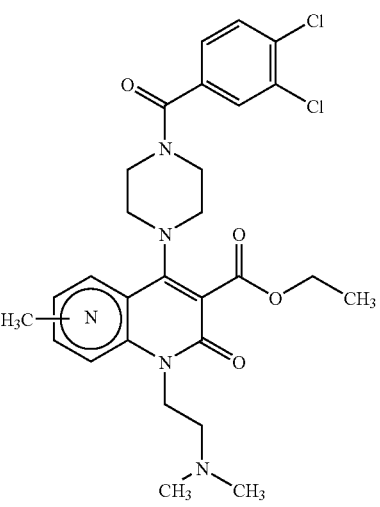
283
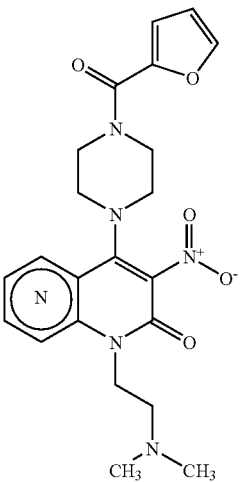
284
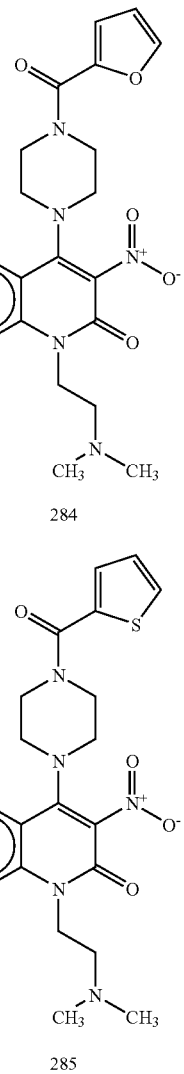
285
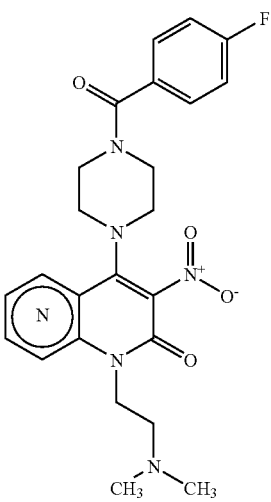
286

-continued
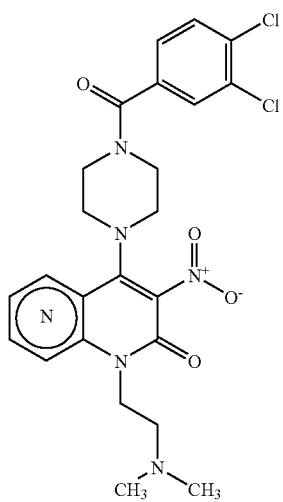
287
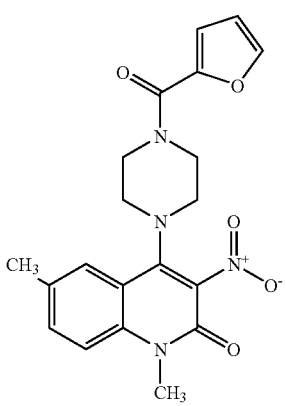
288
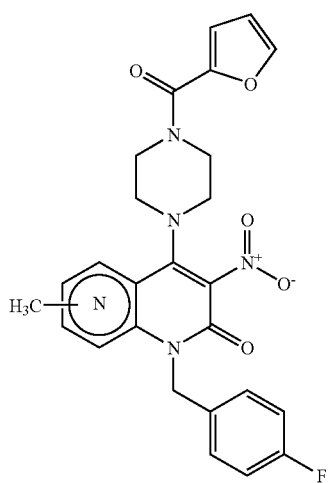
289
-continued
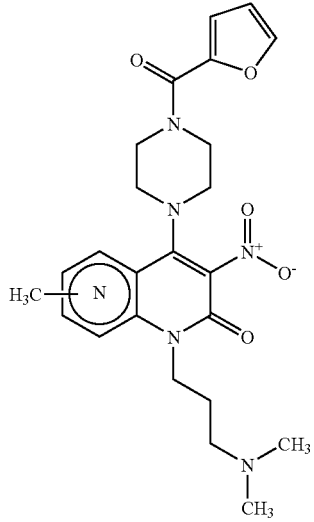
290
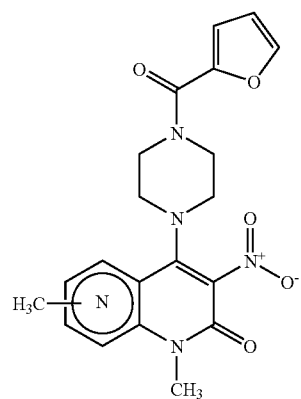
291
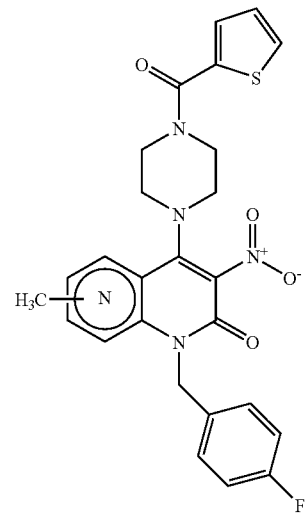
292

-continued
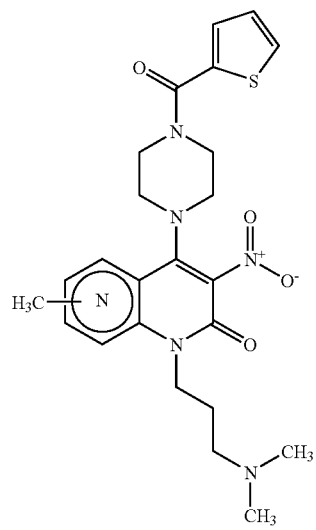
293
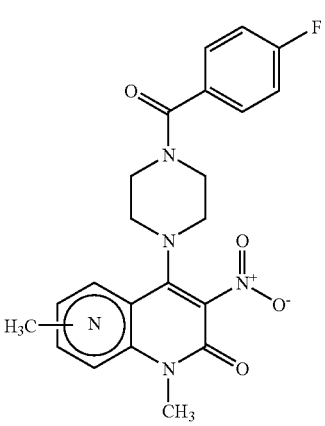
294
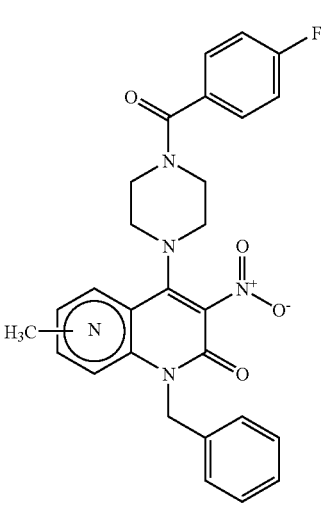
295
-continued
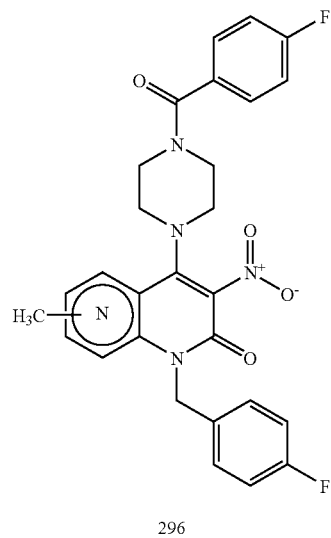
296
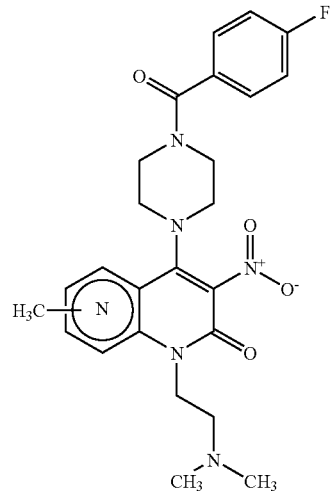
297
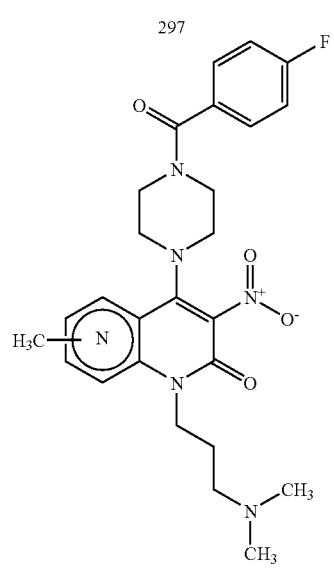
298

-continued
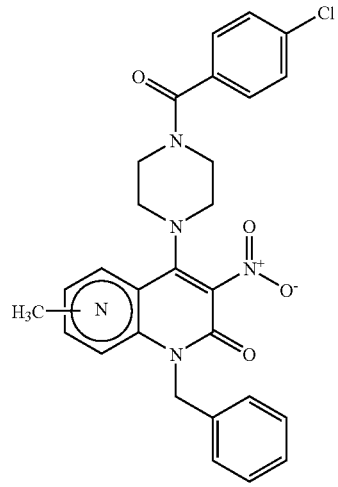
299
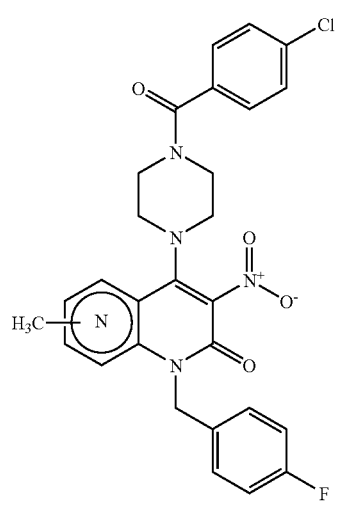
300
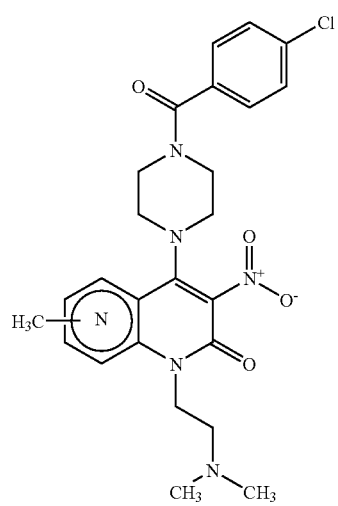
301
-continued
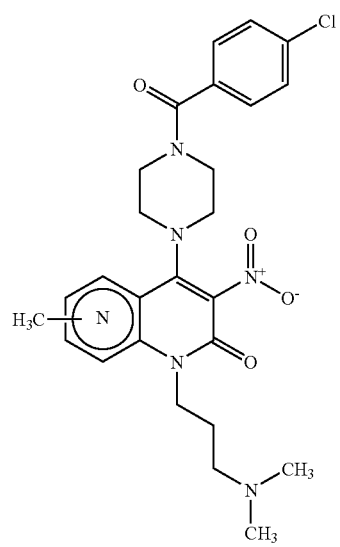
302
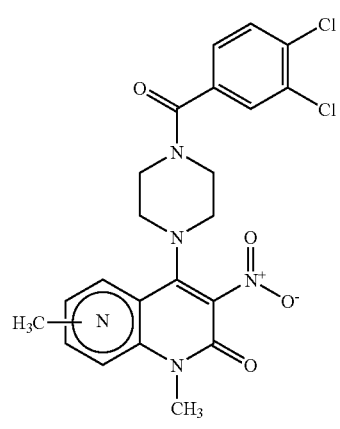
303
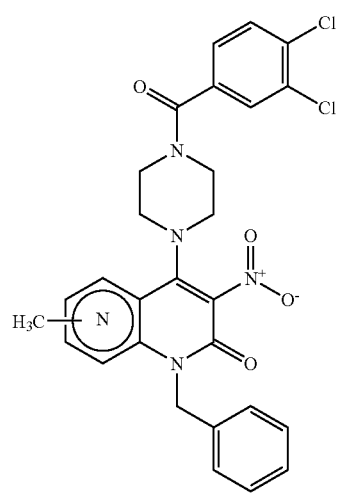
304

-continued
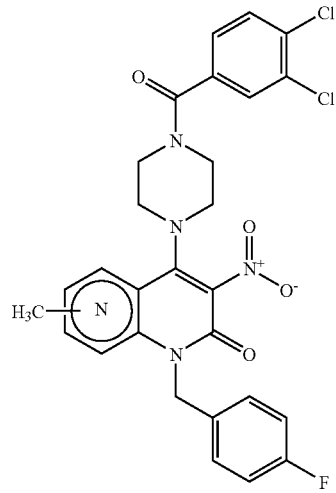
305
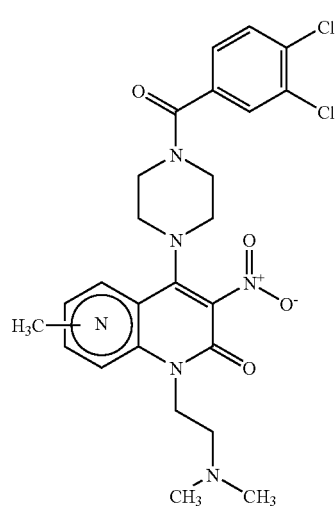
306
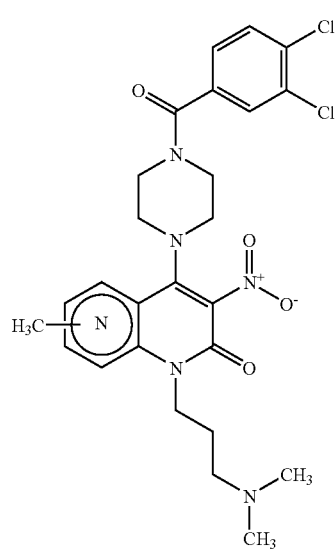
307
-continued
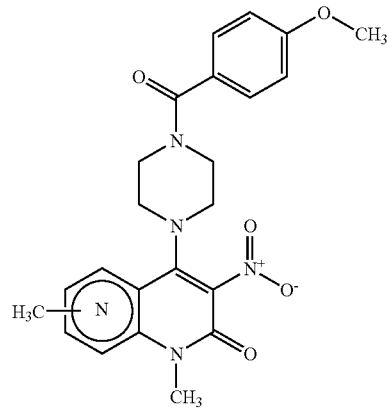
308
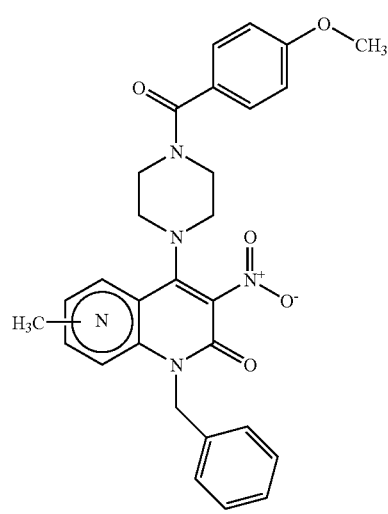
309
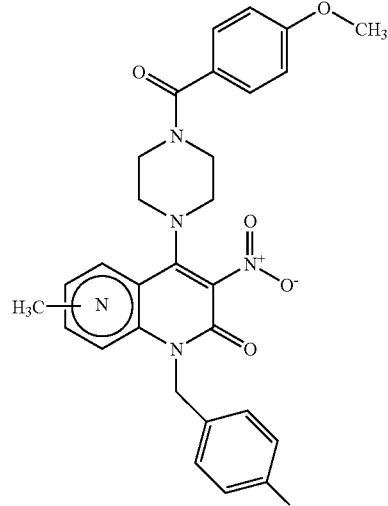
310

-continued
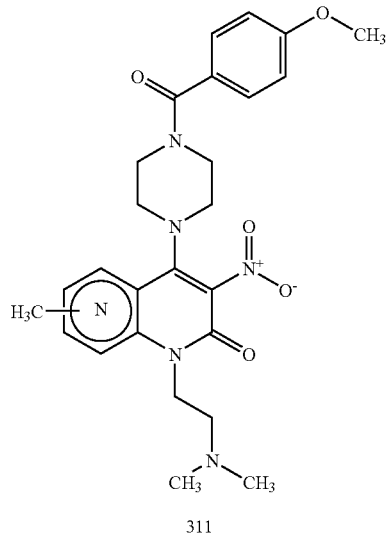
311
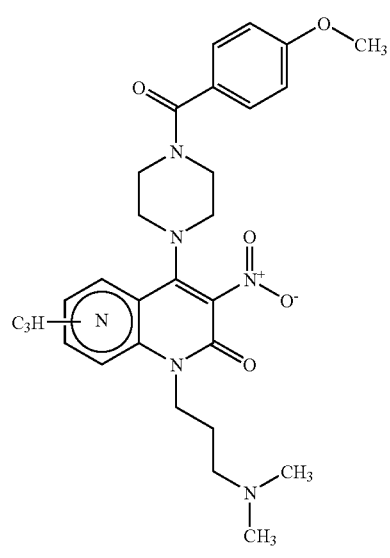
312
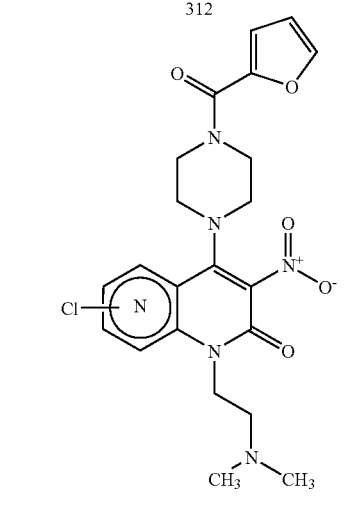
313
-continued
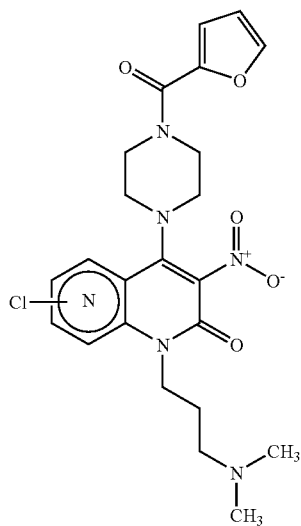
314
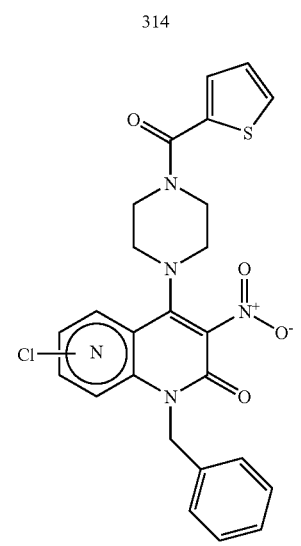
315
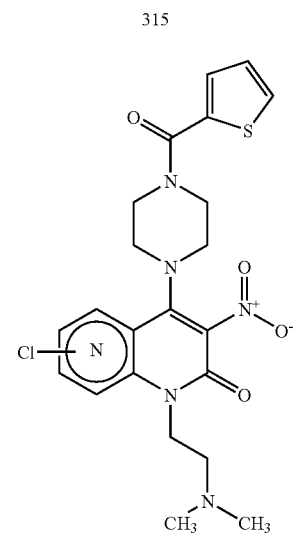
316

-continued
121
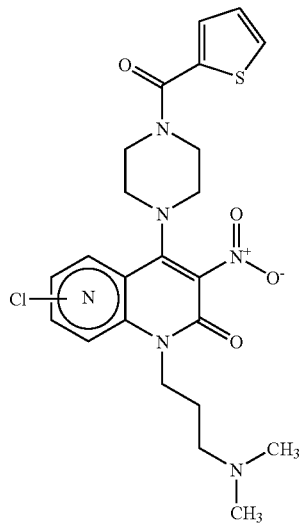
317
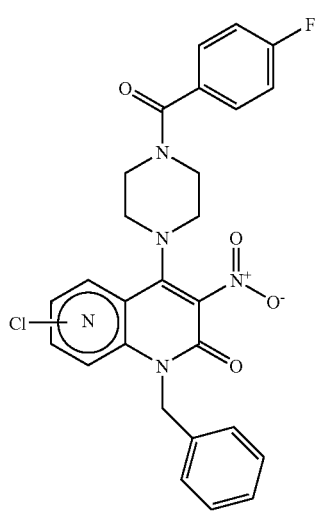
318
-continued
122
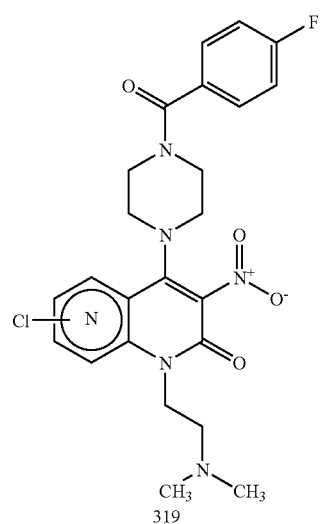
319
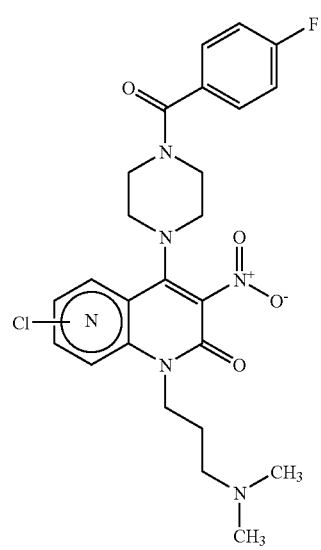
320

-continued
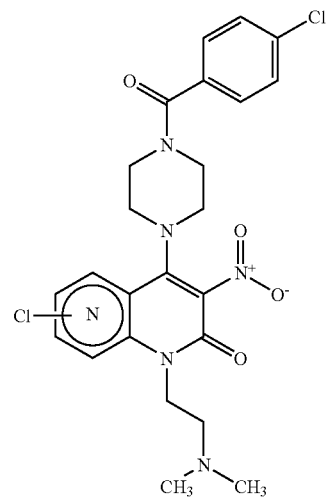
321
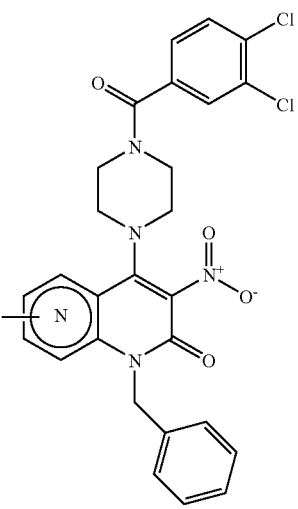
323
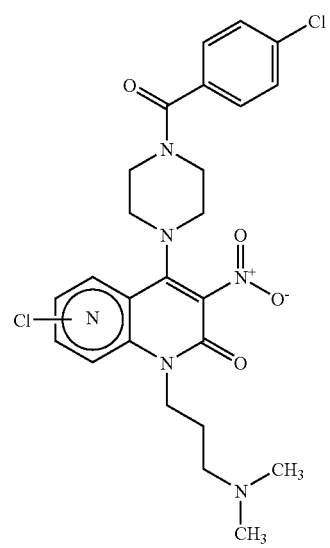
322
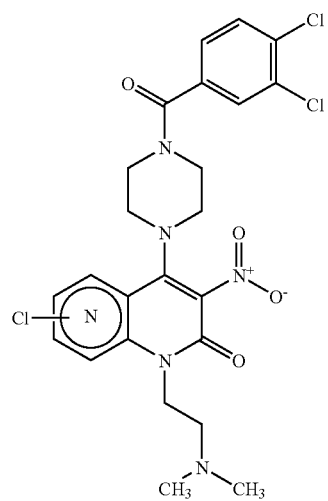
324

-continued
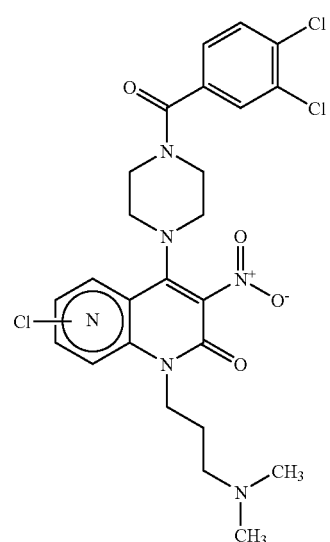
325
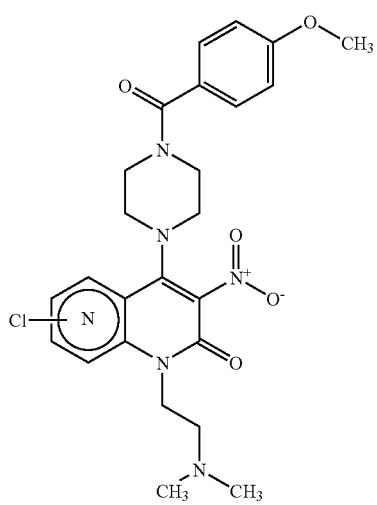
326
-continued
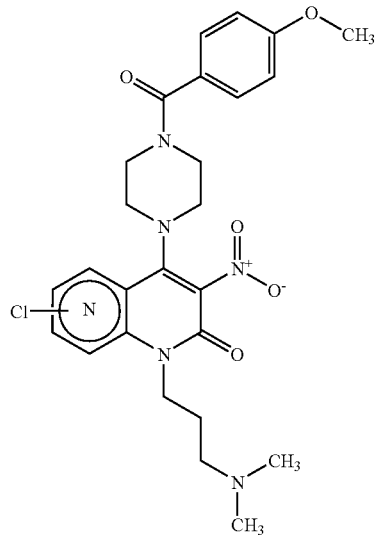
327
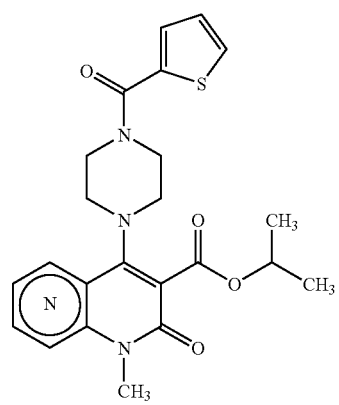
328
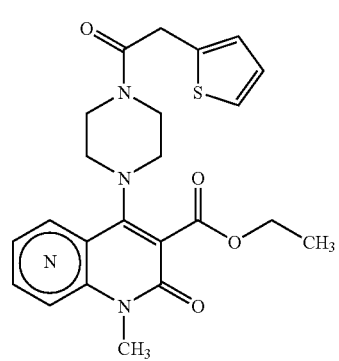
329

-continued
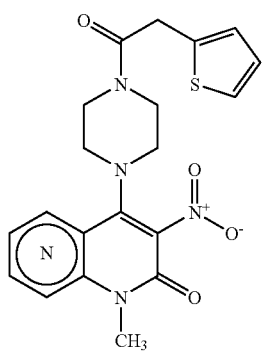
330
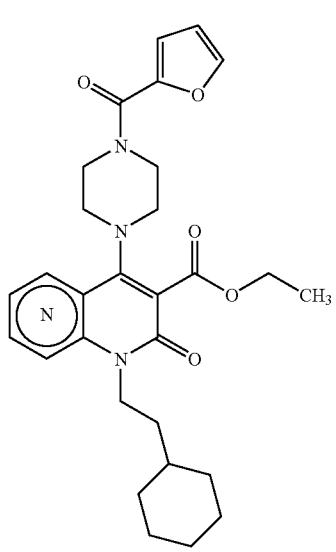
331
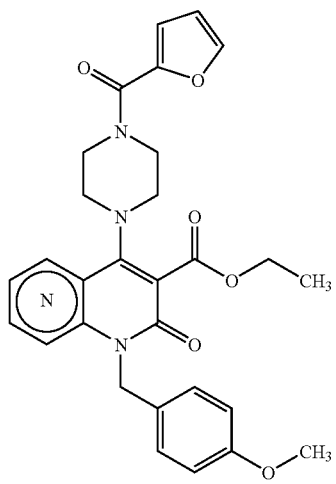
332
-continued
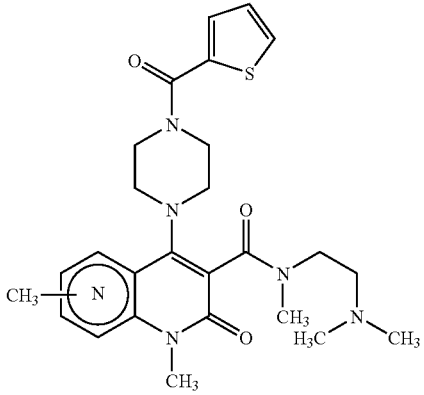
333
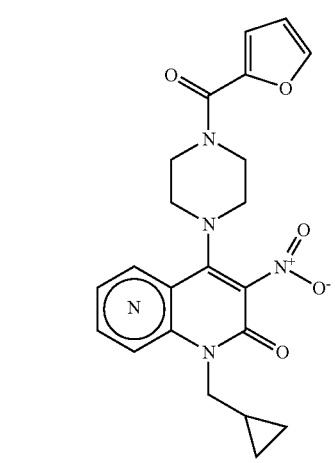
334
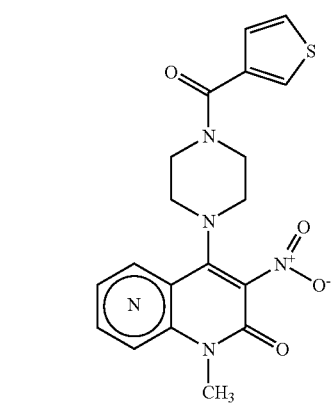
335

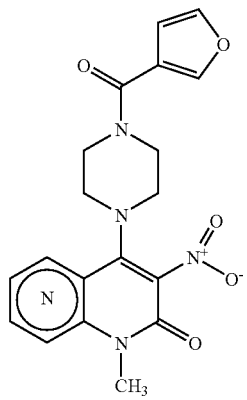
336
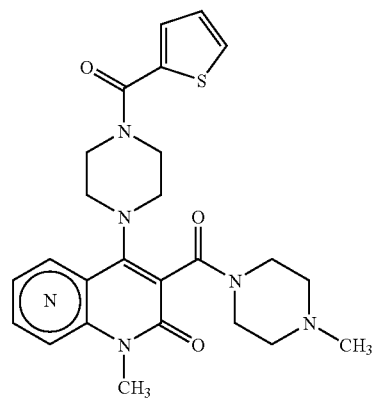
337
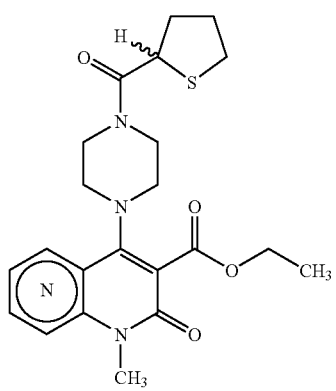
338
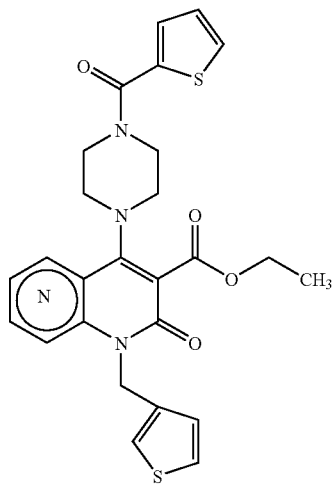
339
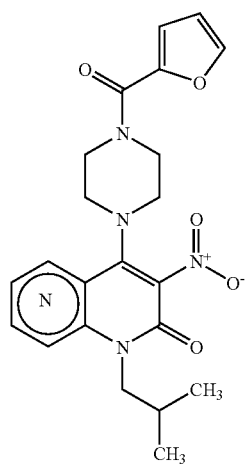
340
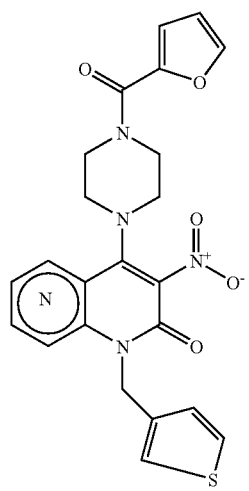
341

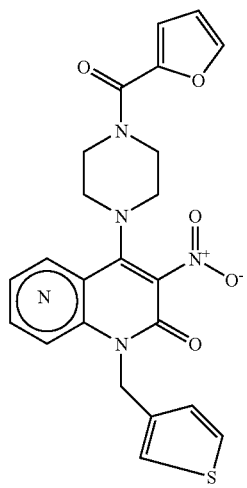
342
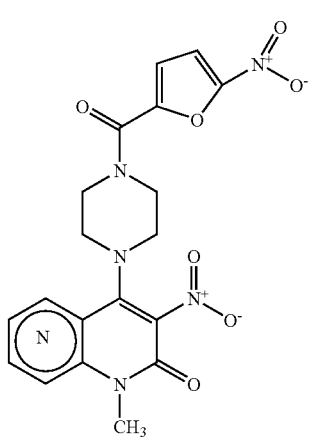
343
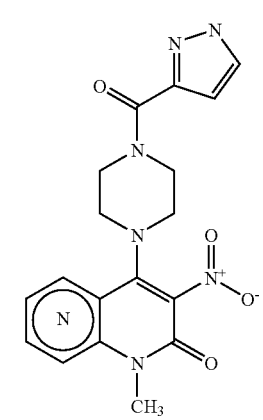
344
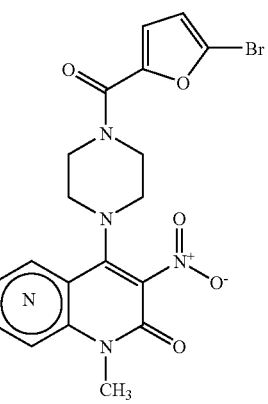
345
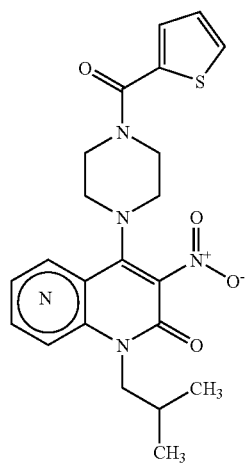
346
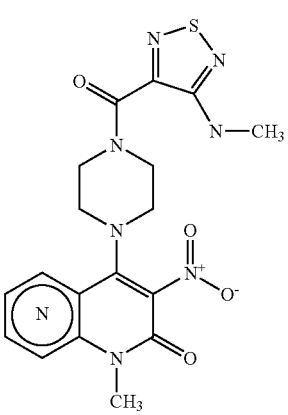
347

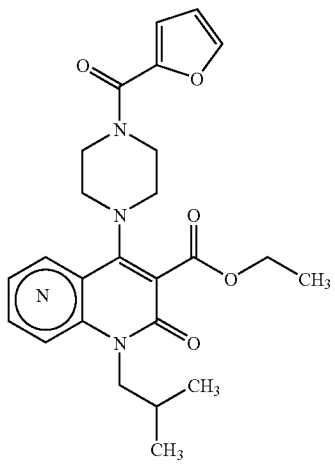
348
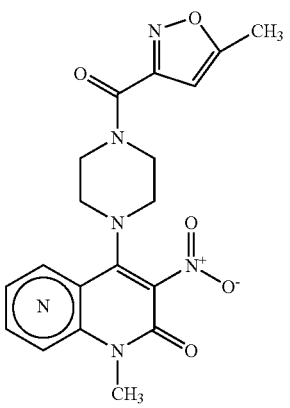
349
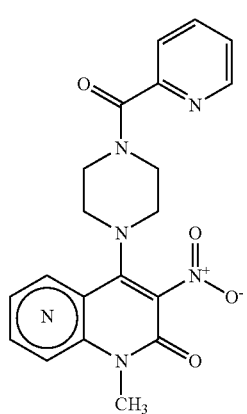
350
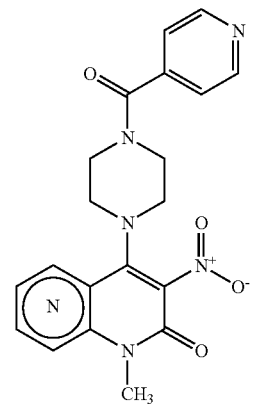
351
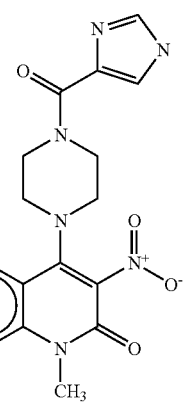
352
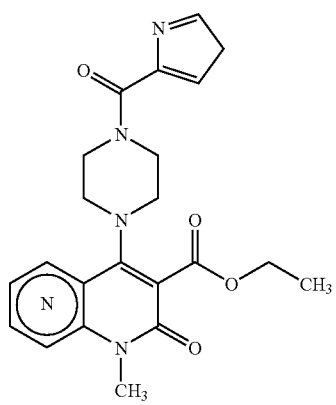
353

-continued
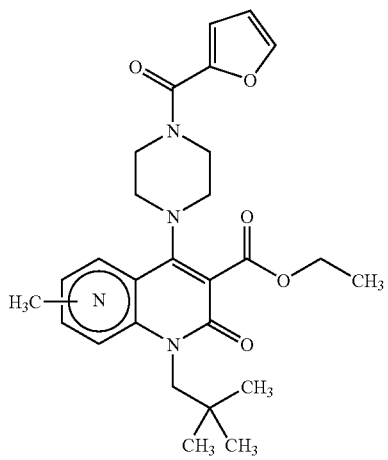
354
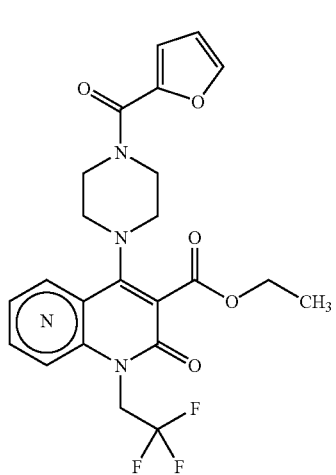
355
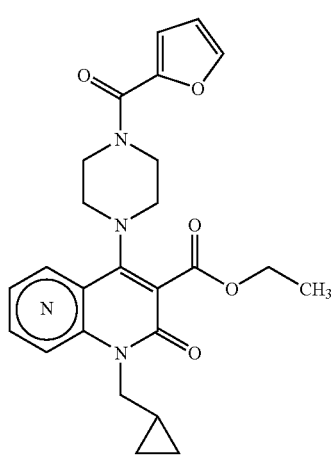
356
-continued
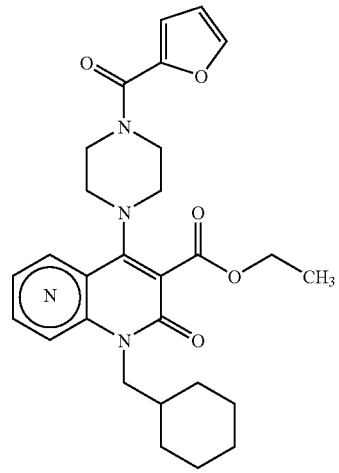
357
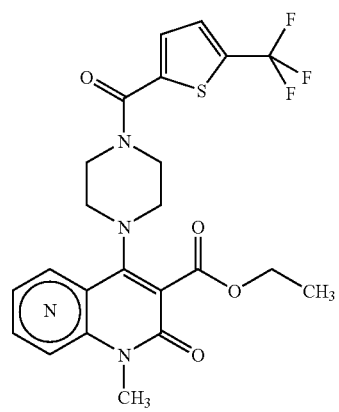
358
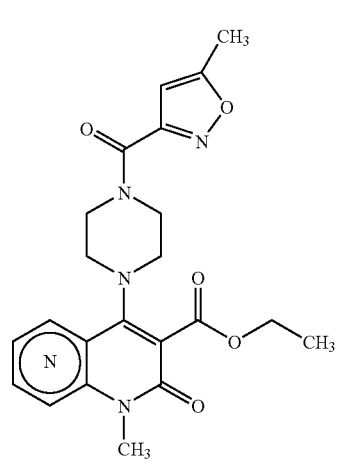
359

-continued
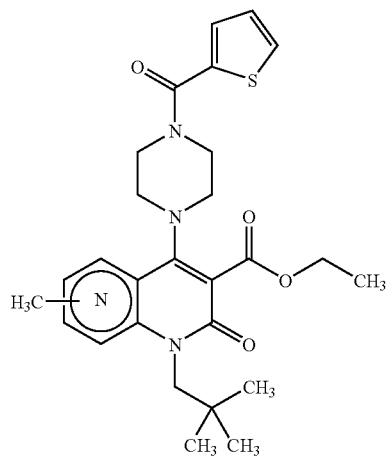
360
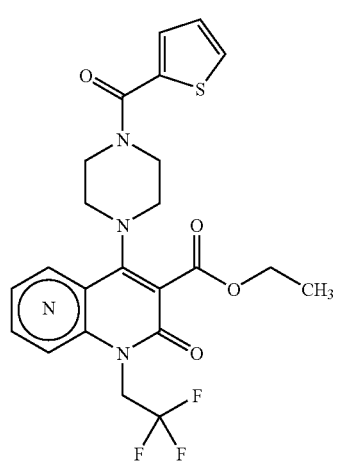
361
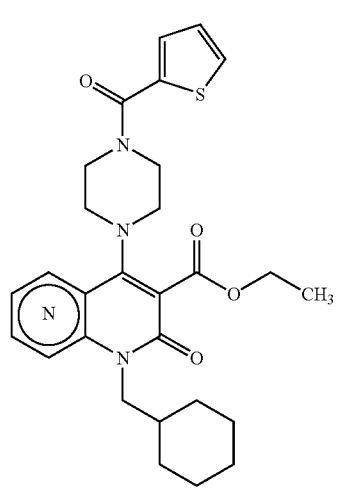
362
-continued
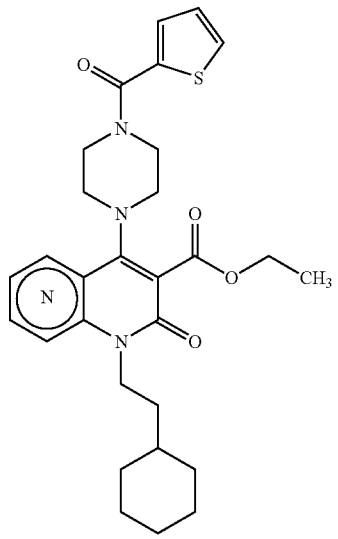
363
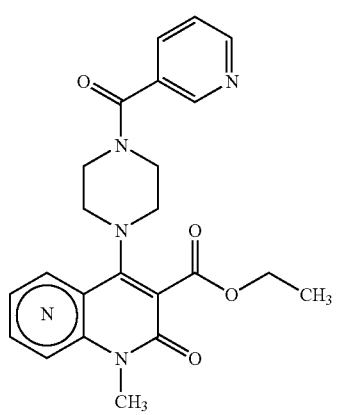
364
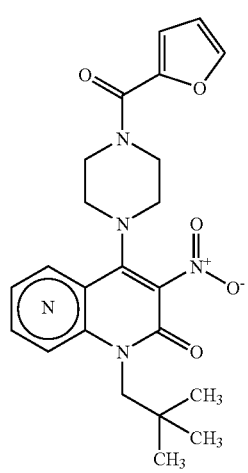
365

-continued
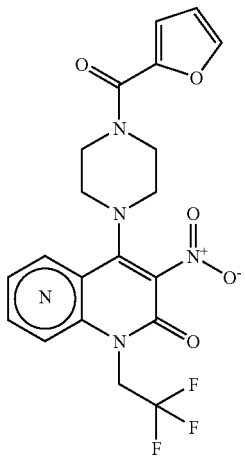
366
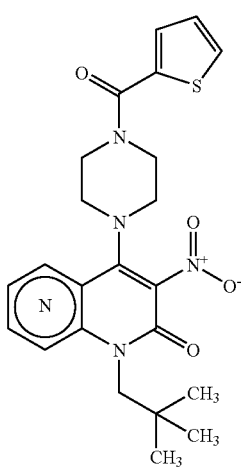
367
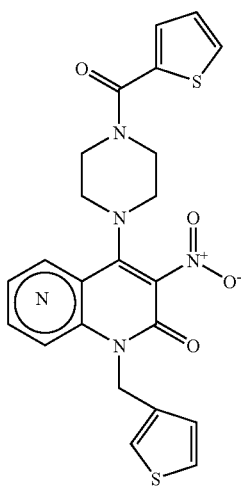
368
-continued
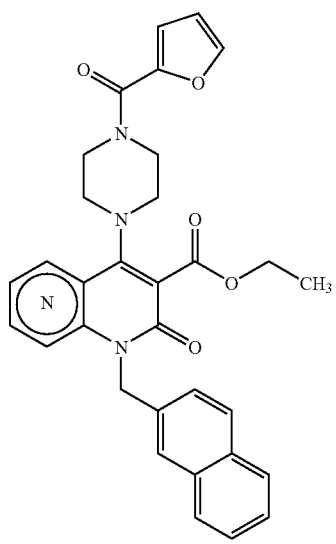
369
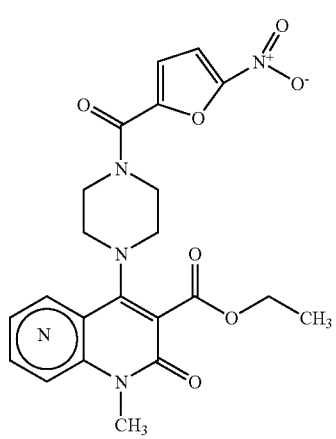
370
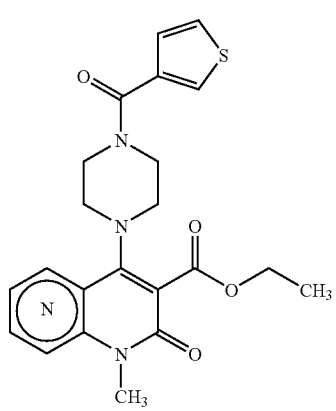
371

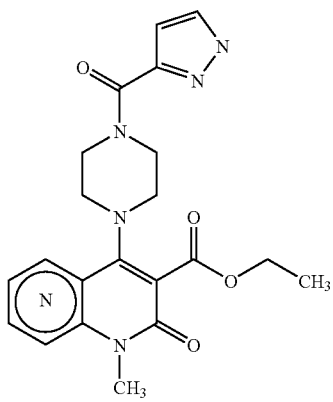
372
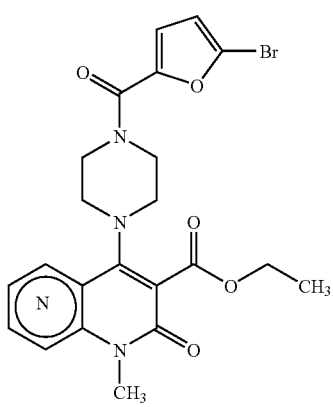
373
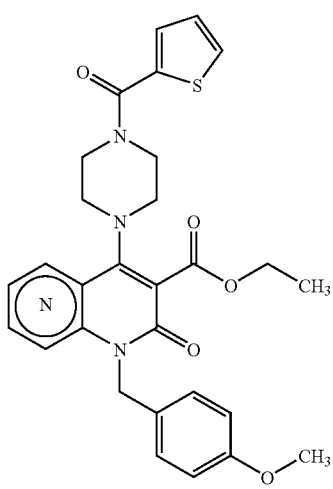
374
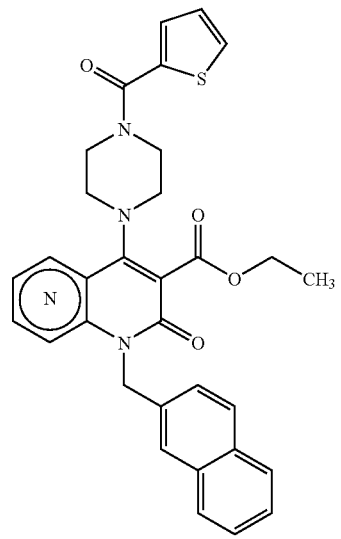
375
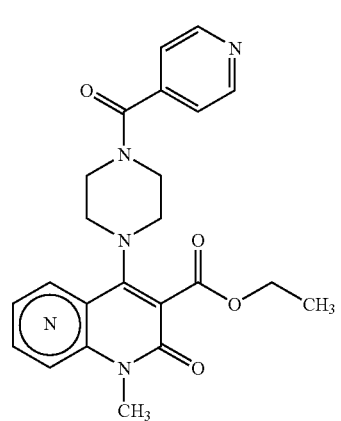
376
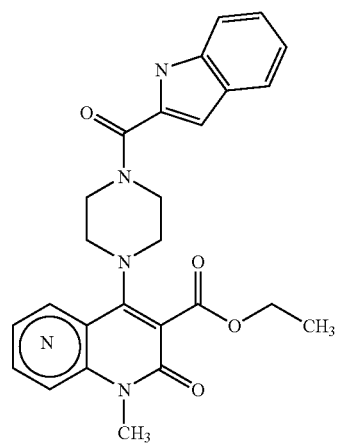
377

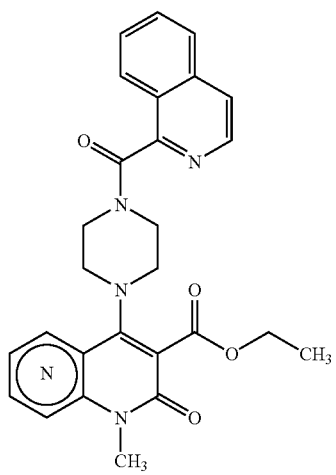
378
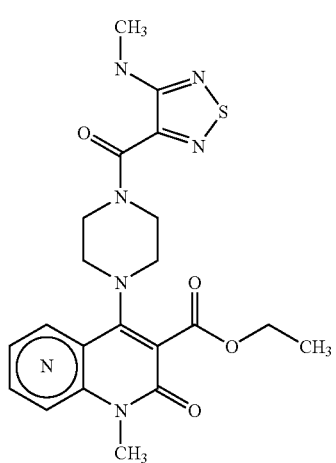
379
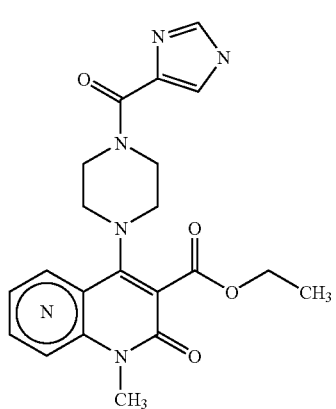
380
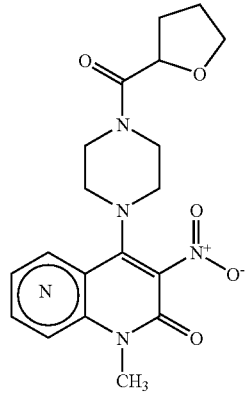
381
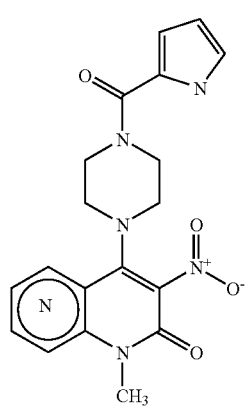
382
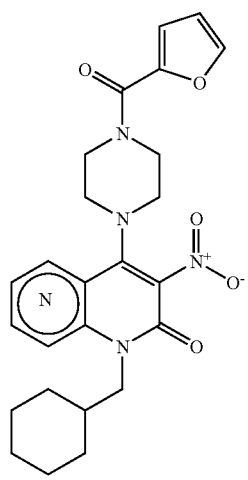
383

-continued
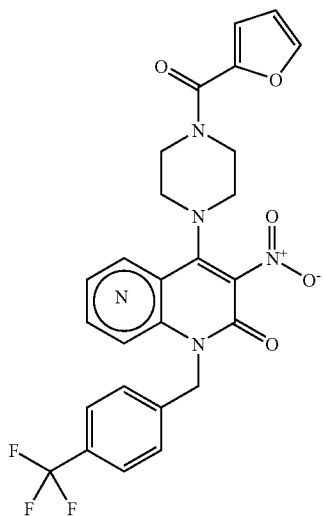
384
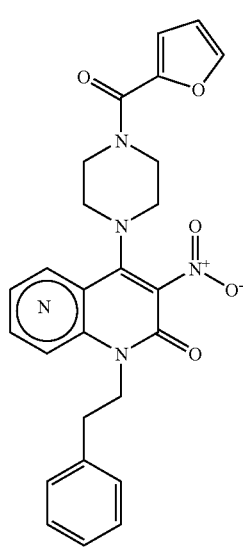
385
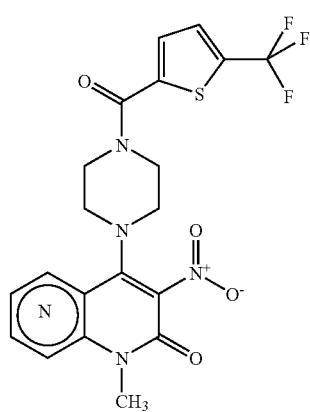
386
-continued
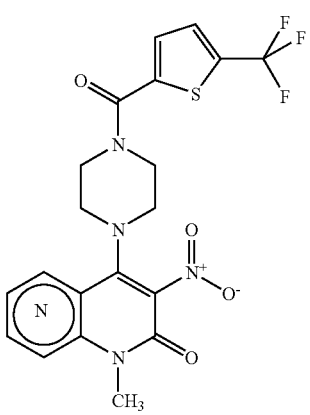
387
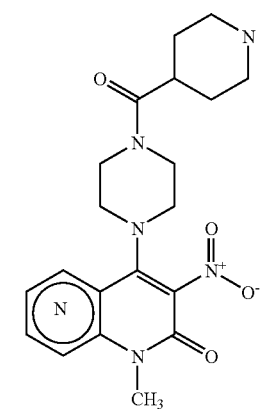
388
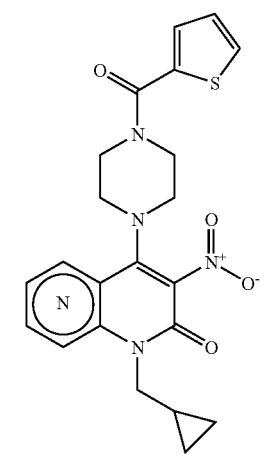
389

-continued
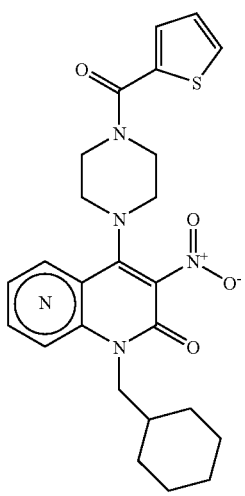
390
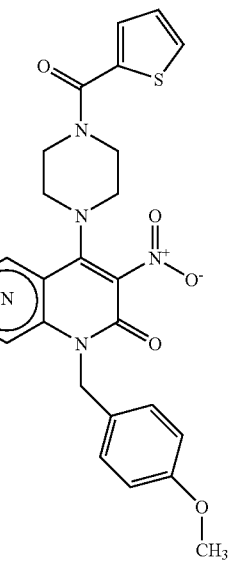
392
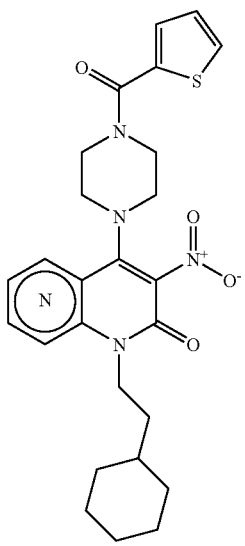
391
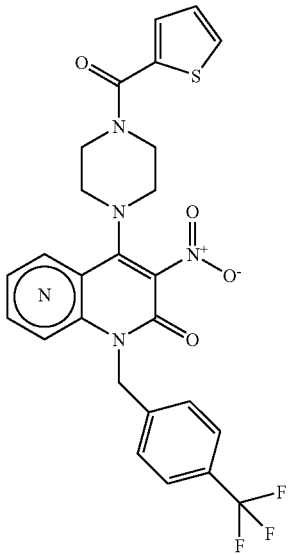
393

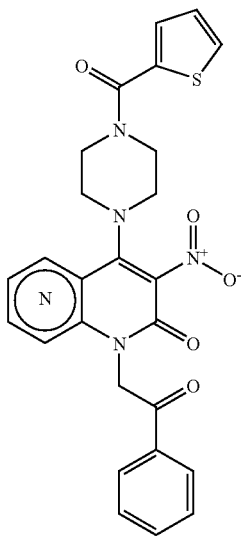
394
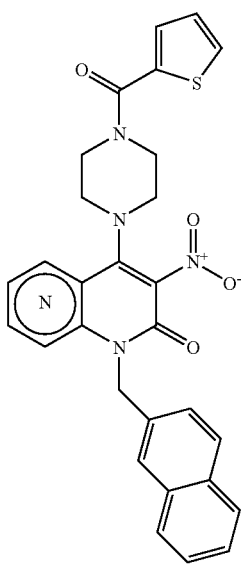
395
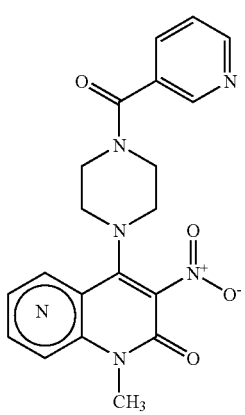
396
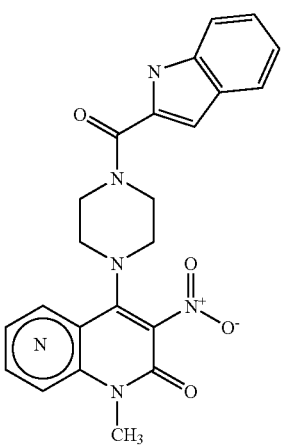
397
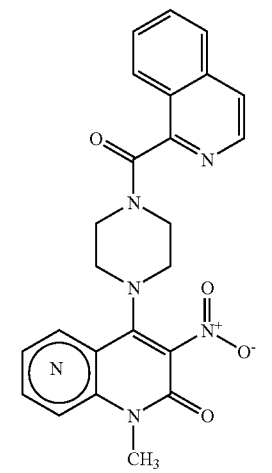
398
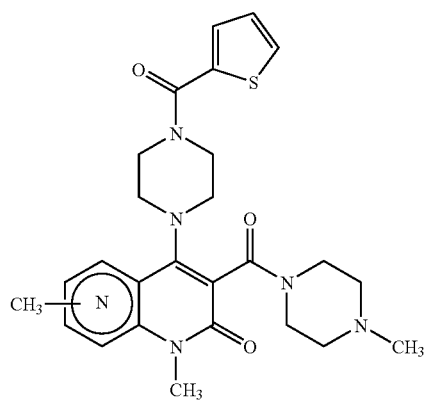
399

-continued
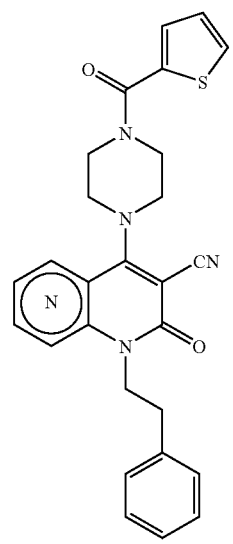
400
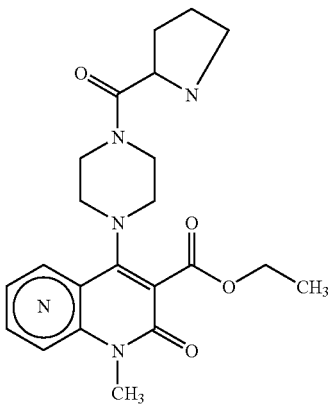
401
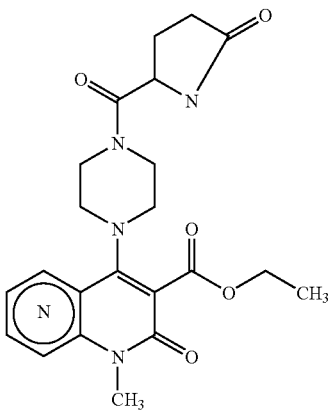
402
-continued
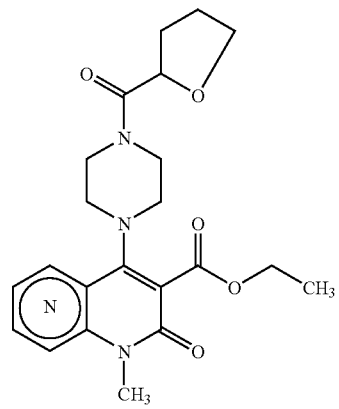
403
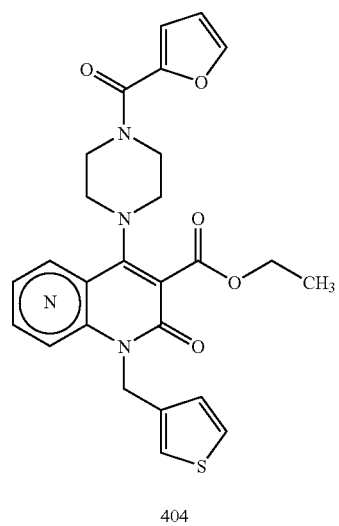
404
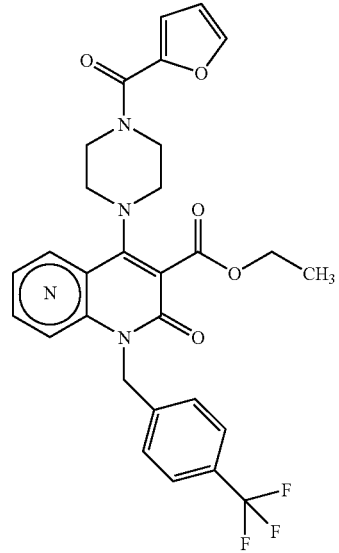
405

-continued
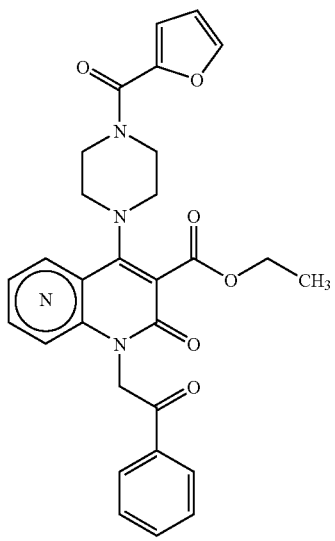
406
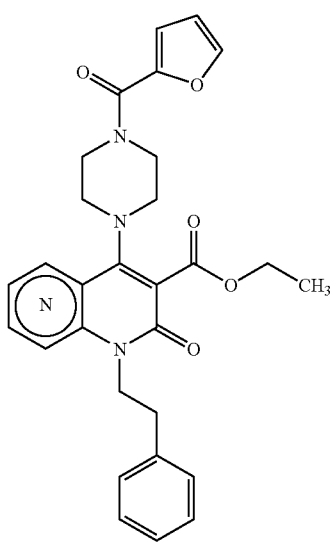
407
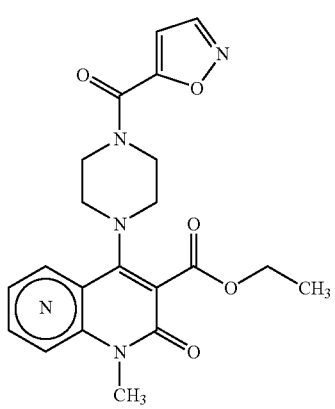
408
-continued
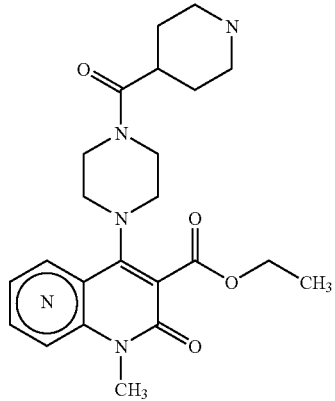
409
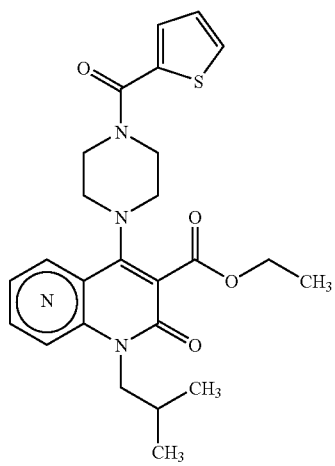
410
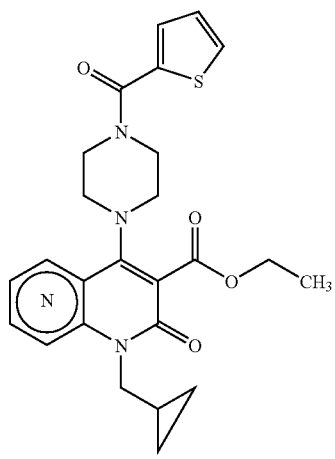
411

-continued
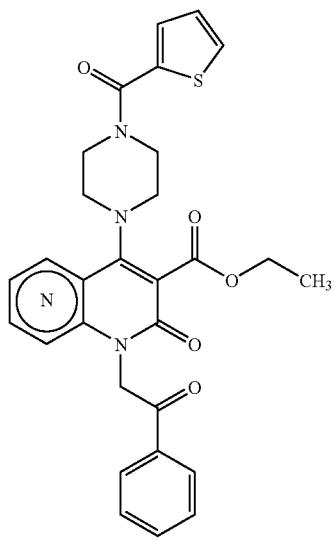
412
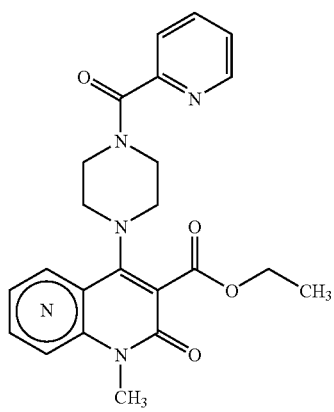
413
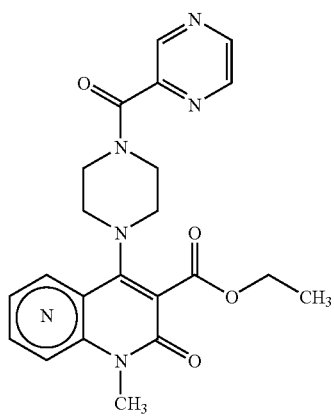
414
-continued
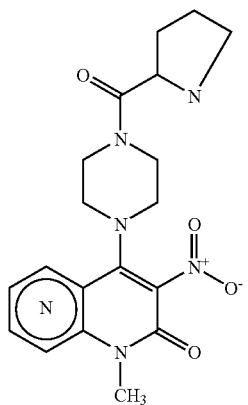
415
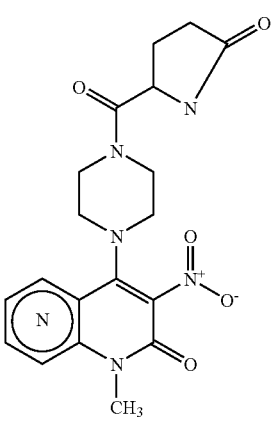
416
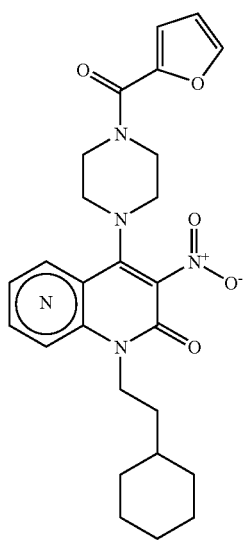
417

-continued
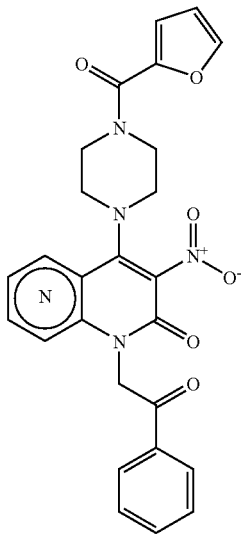
418
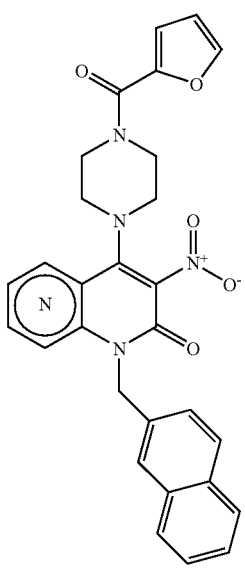
419
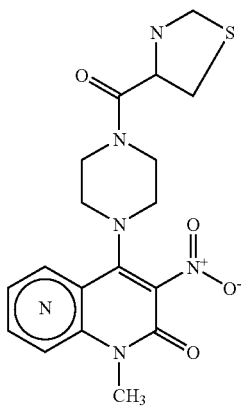
420
-continued
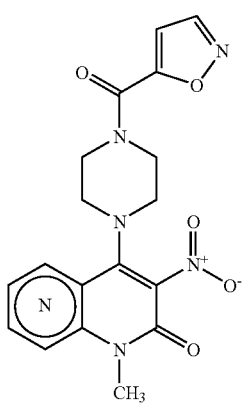
421
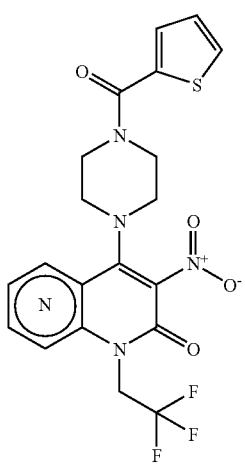
422
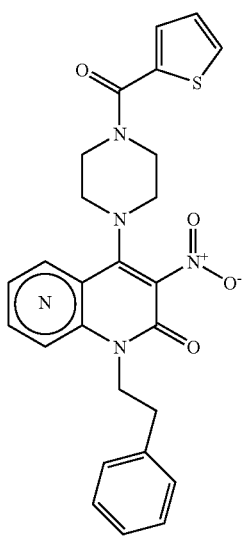
423

-continued
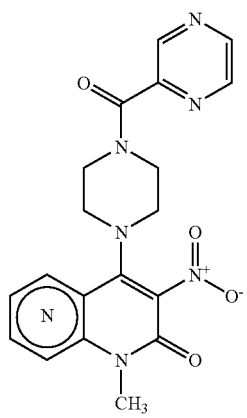
424
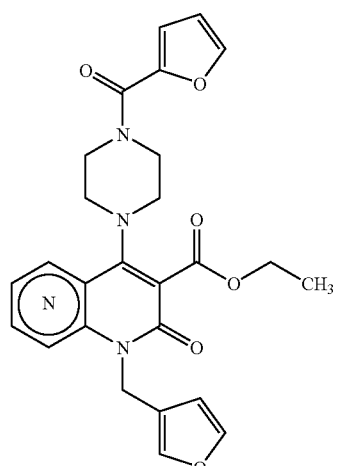
425
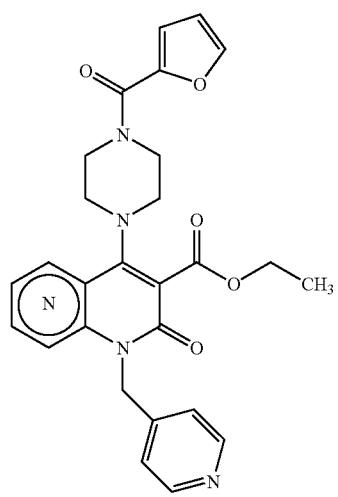
426
-continued
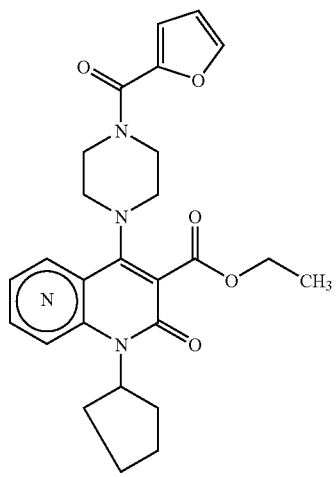
427
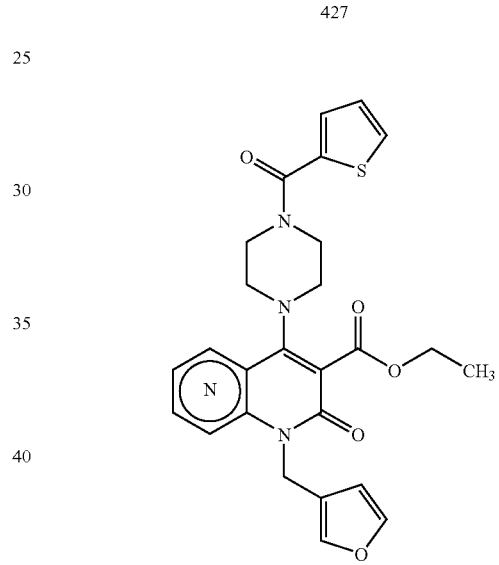
428
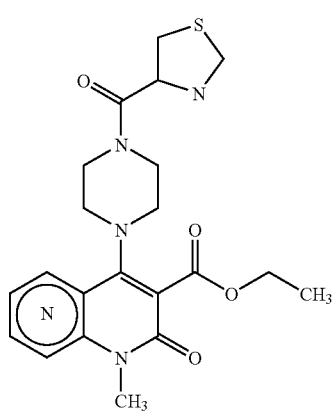
429

-continued
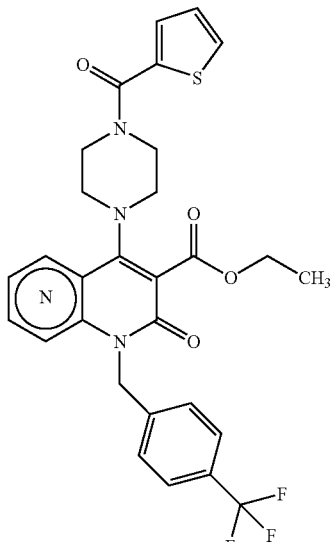
430
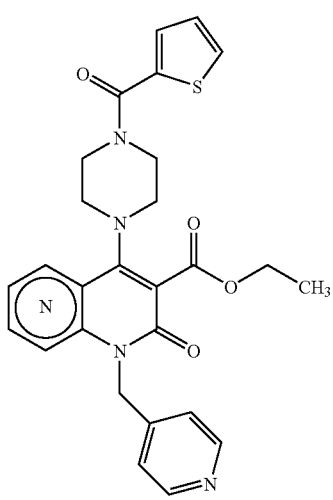
431
-continued
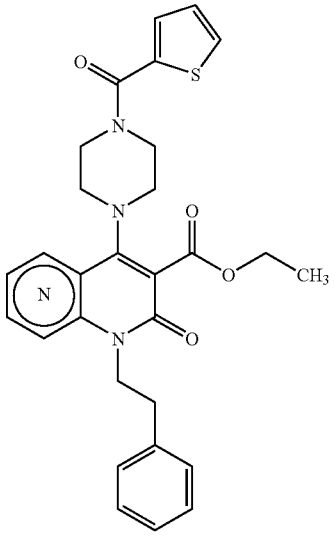
432
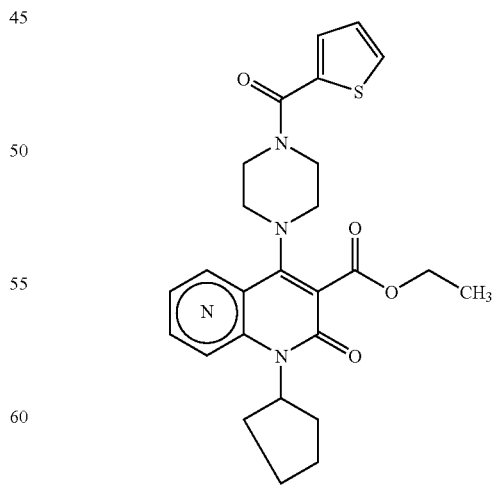
433

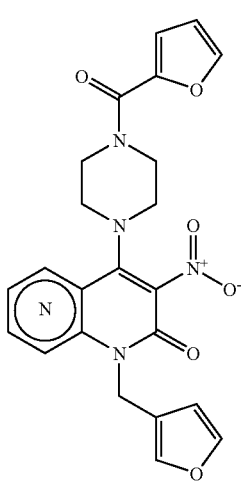
434
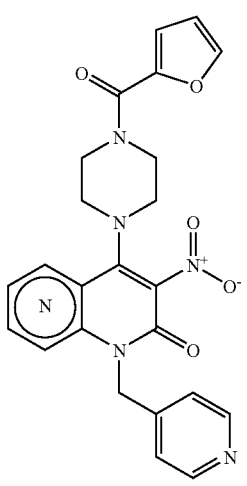
435
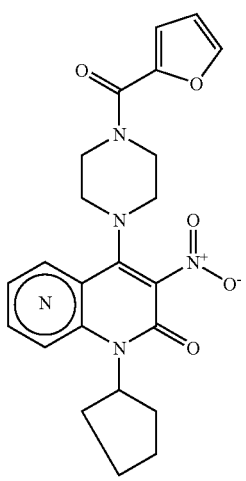
436
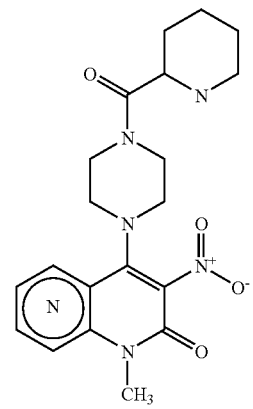
437
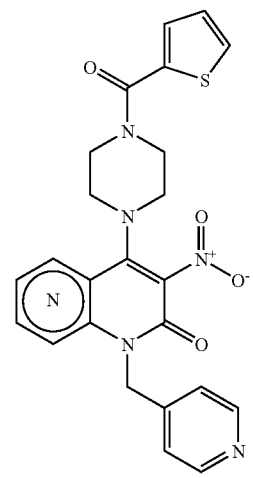
438
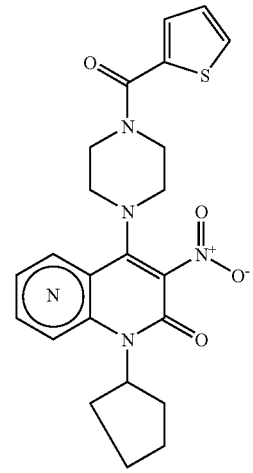
439

-continued
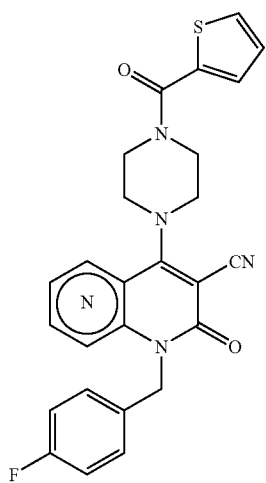
440
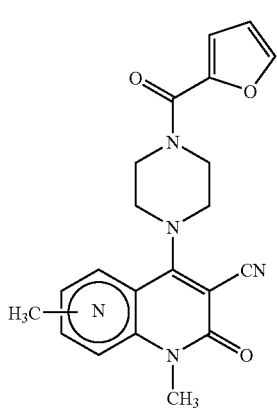
441
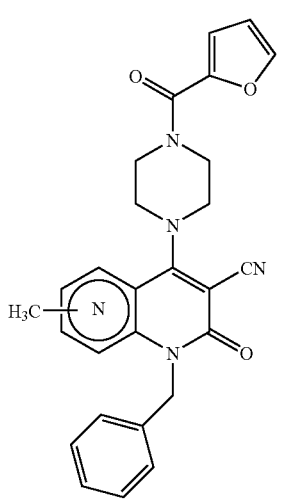
442
-continued
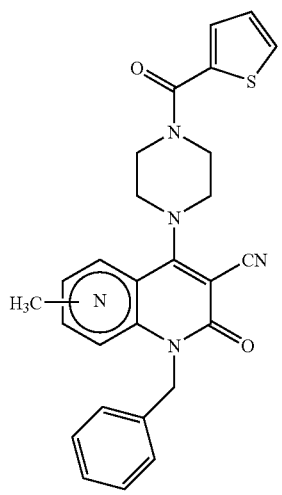
443
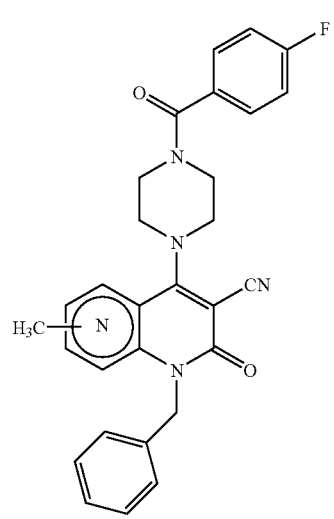
444
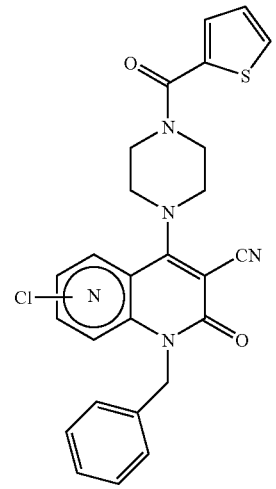
445

-continued
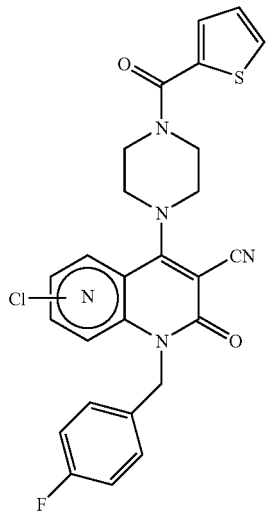
446
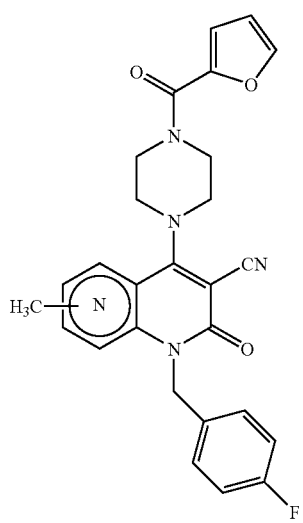
447
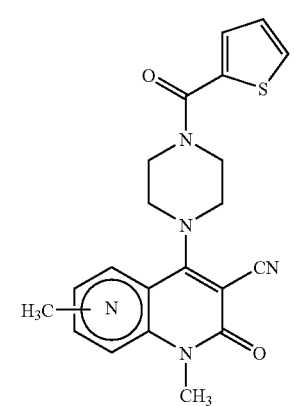
448
-continued
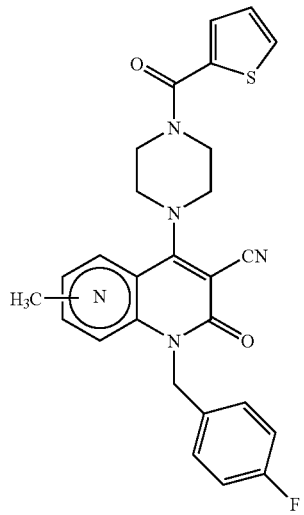
449
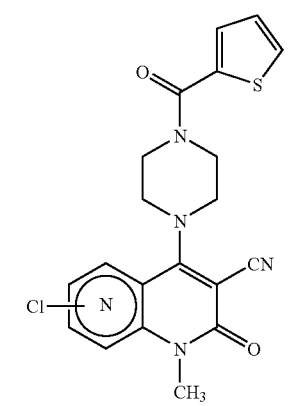
450
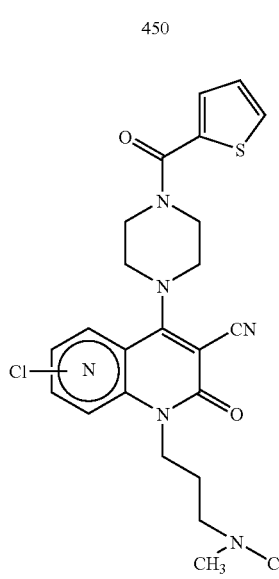
451

-continued
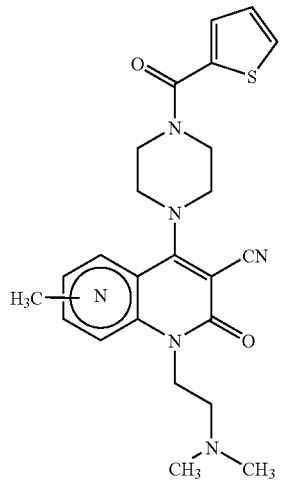
452
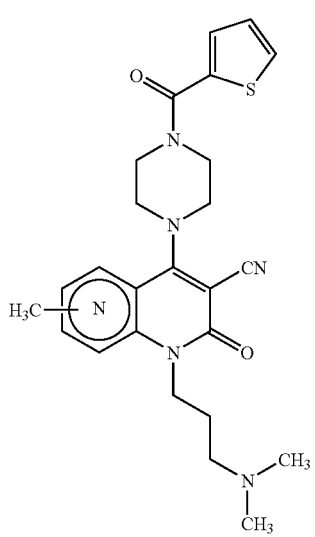
453
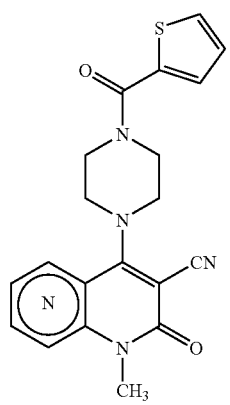
454
-continued
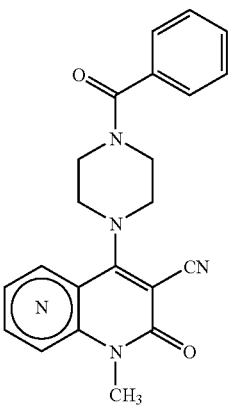
455
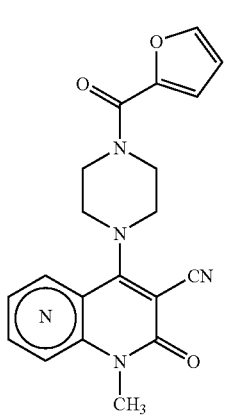
456
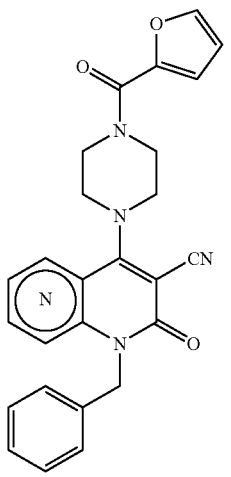
457

-continued
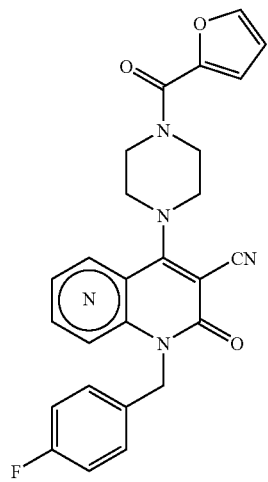
458
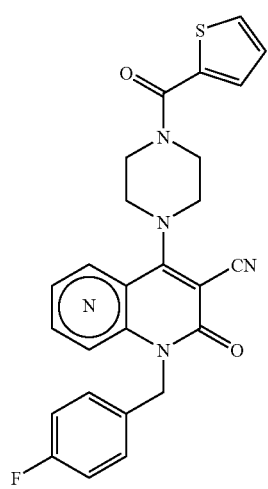
459
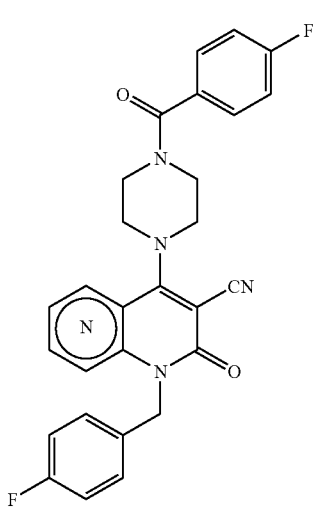
460
-continued
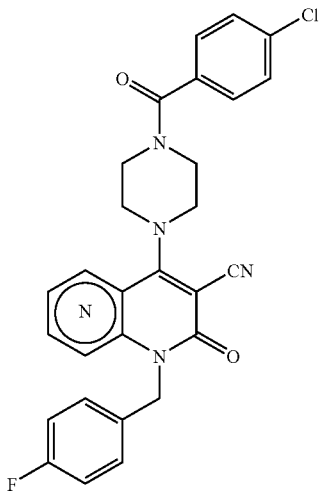
461
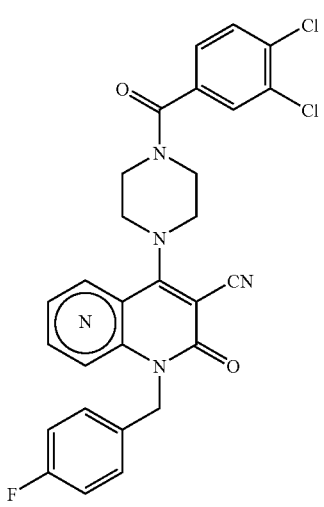
462
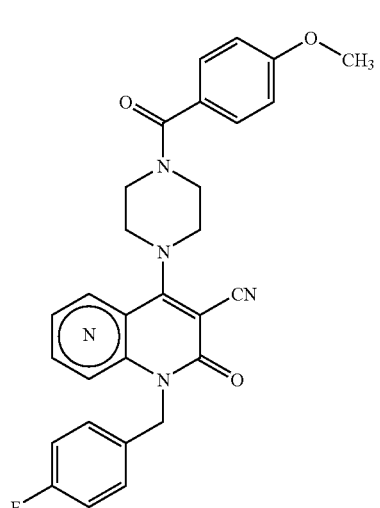
463

-continued
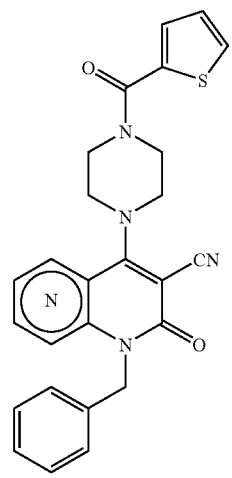
464
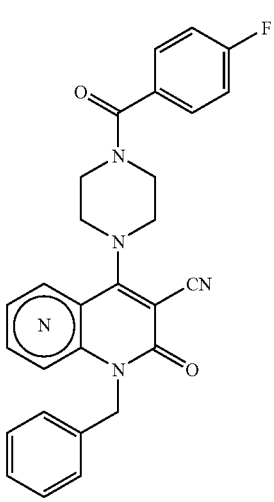
465
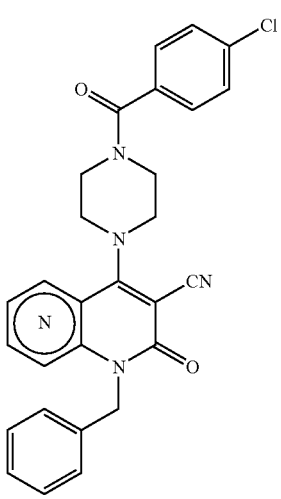
466
-continued
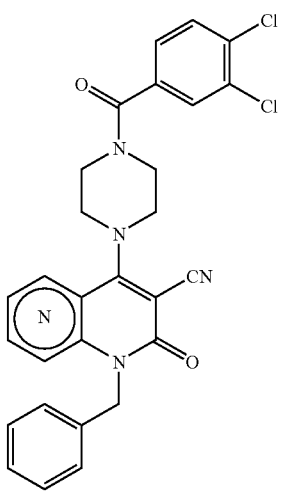
467
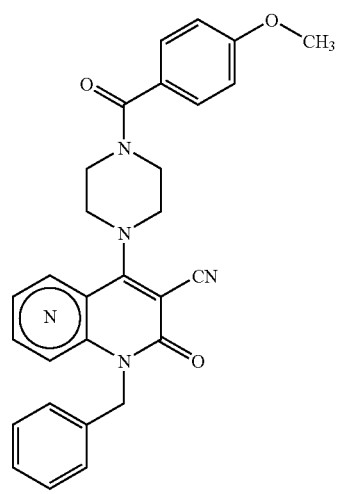
468
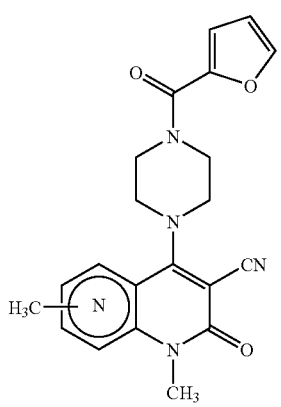
469

-continued
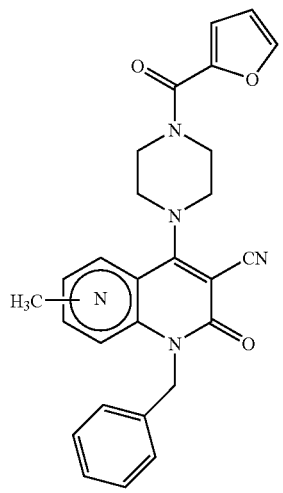
470
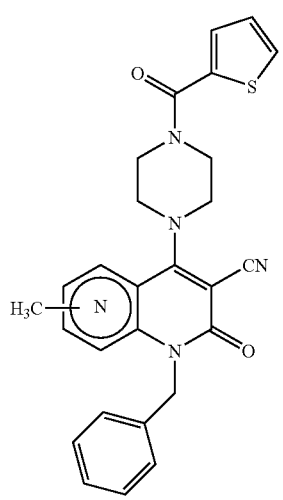
471
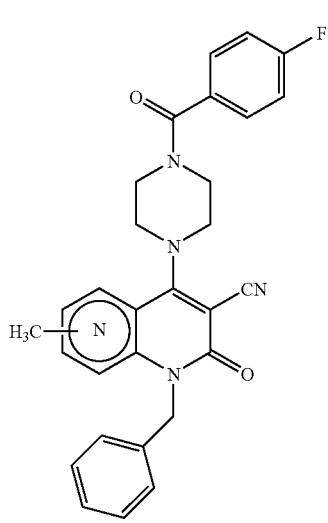
472
-continued
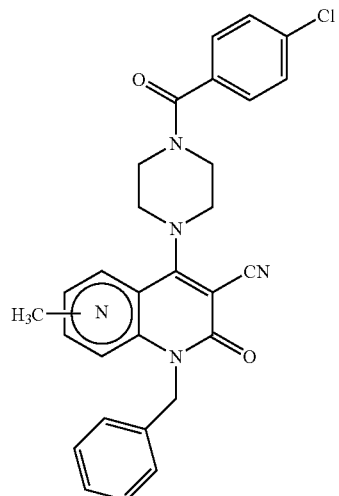
473
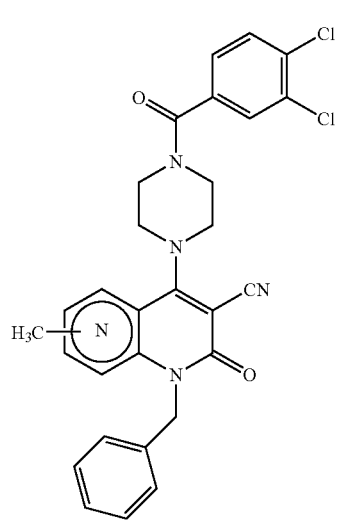
474
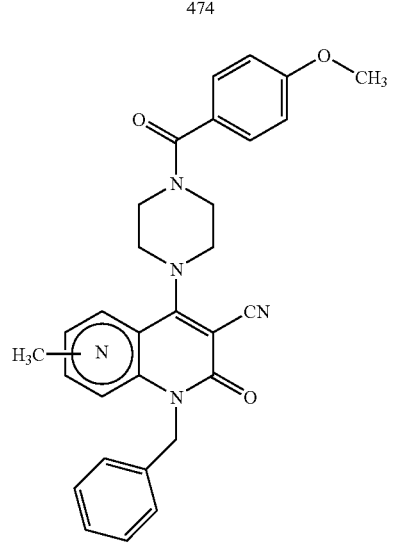
475

-continued
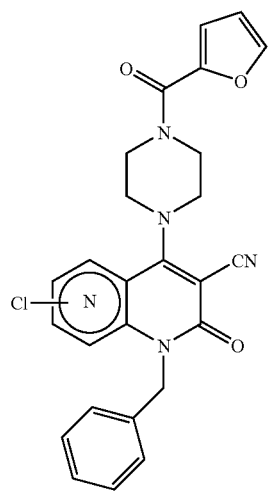
476
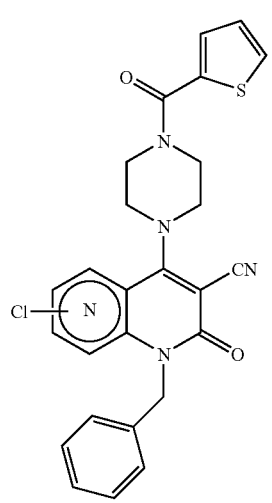
477
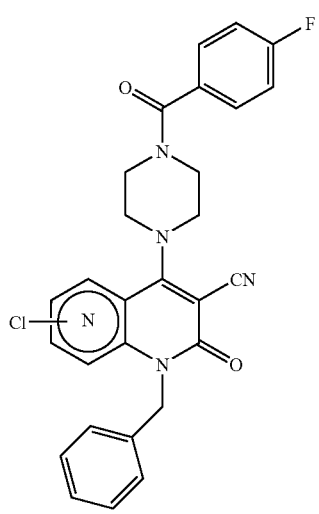
478
-continued
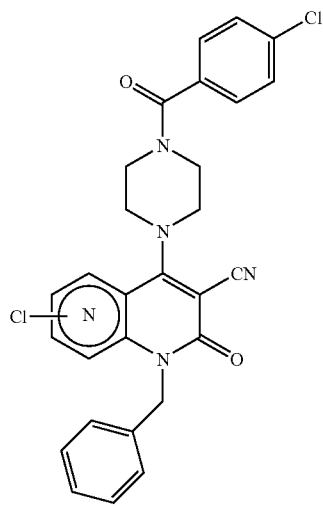
479
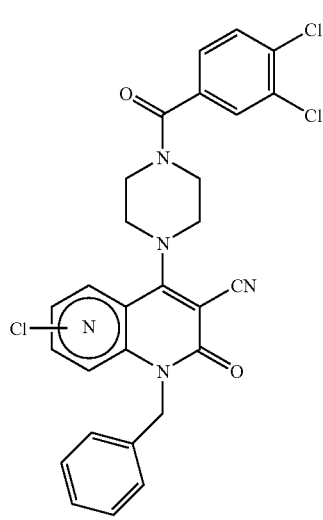
480
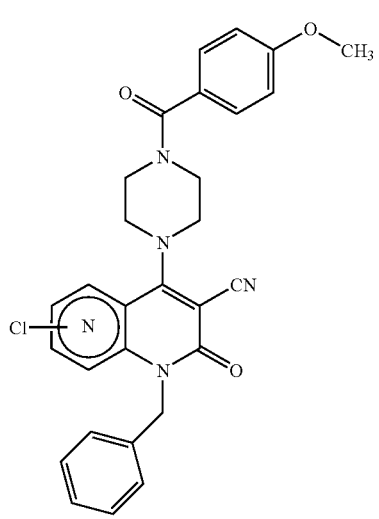
481

-continued
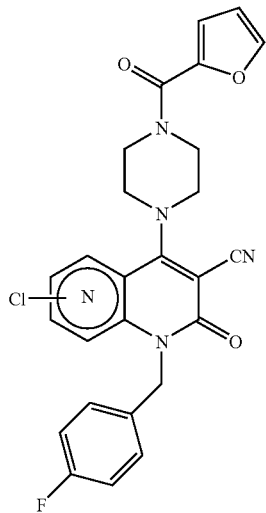
482
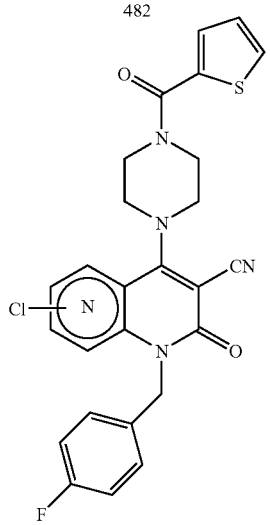
483
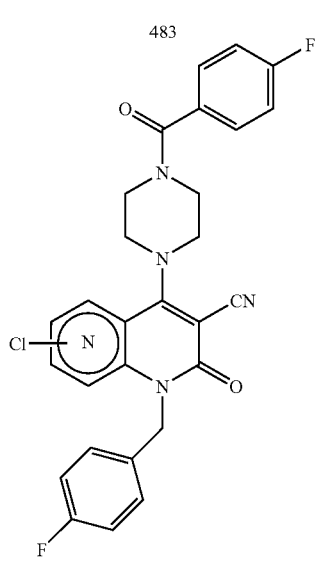
484
-continued
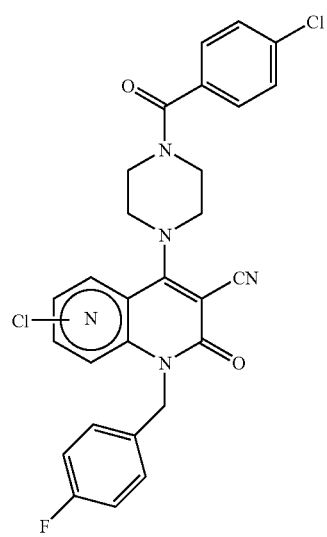
485
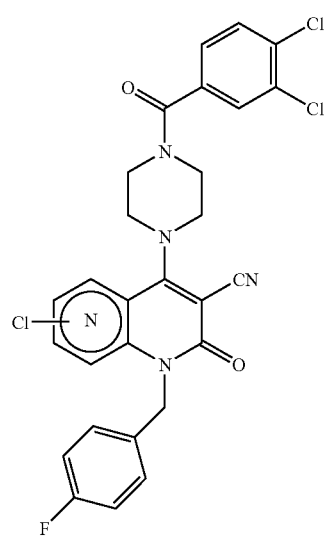
486
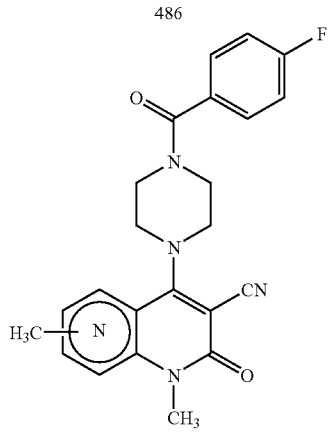
487

-continued
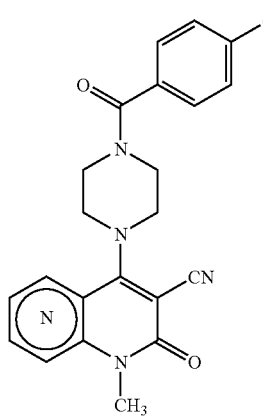
488
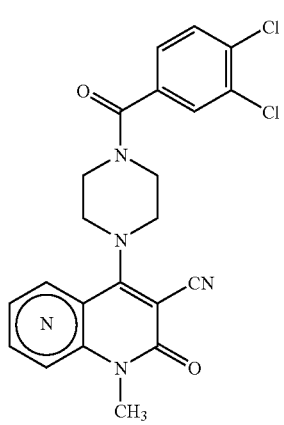
489
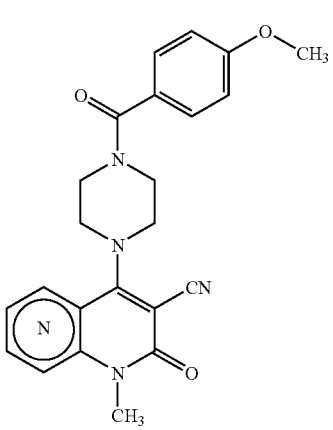
490
-continued
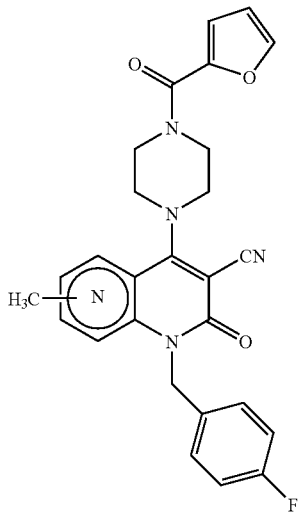
491
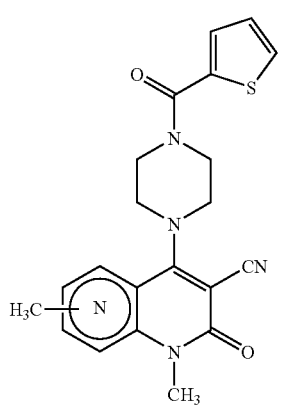
492
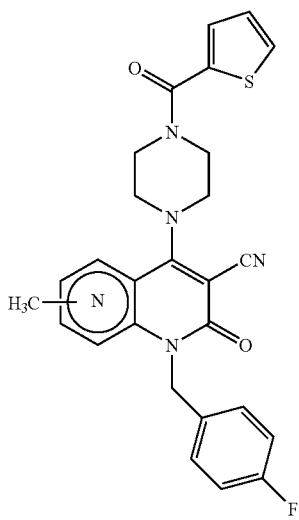
493

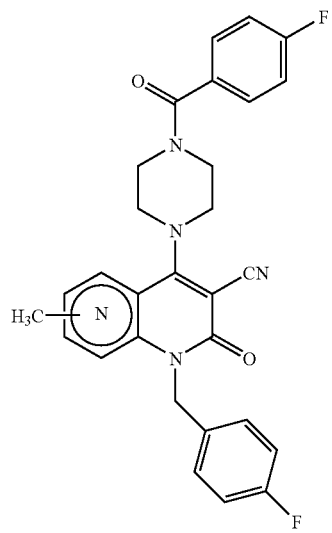
494
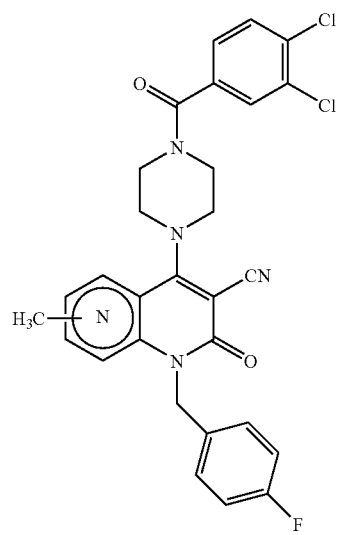
496
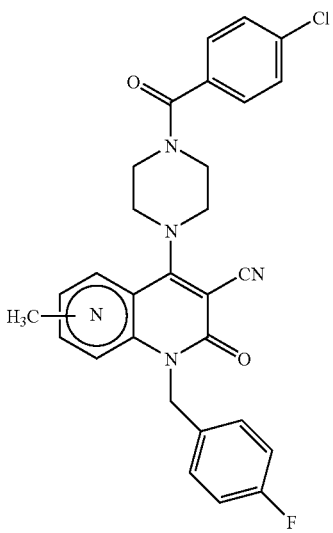
495
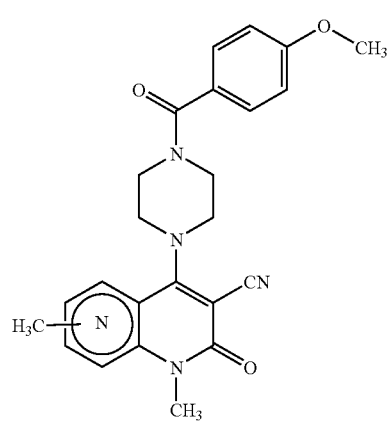
497

-continued
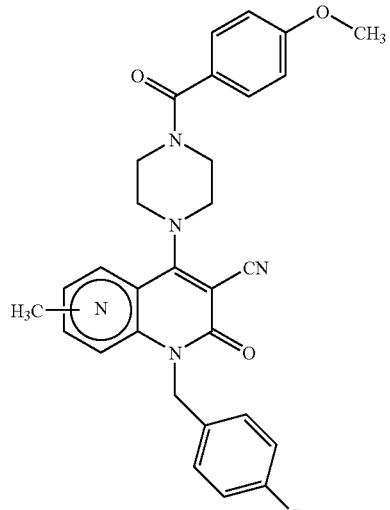
498
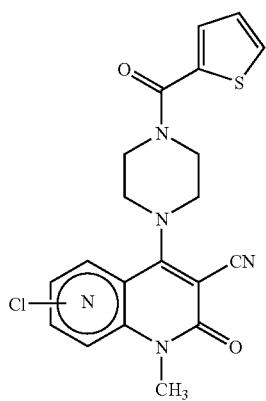
499
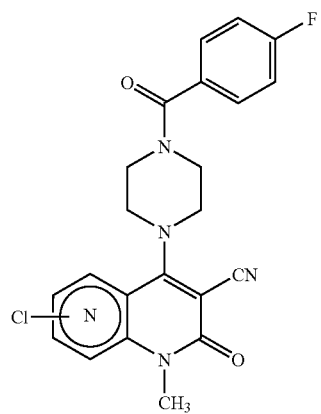
500
-continued
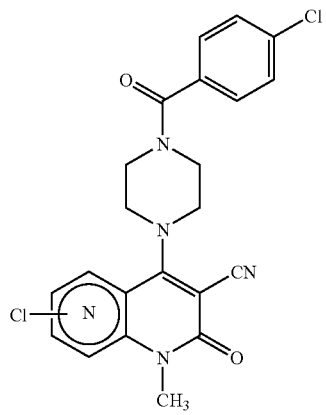
501
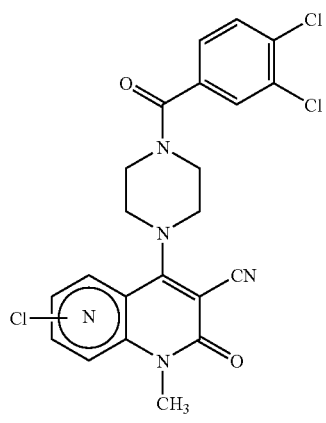
502
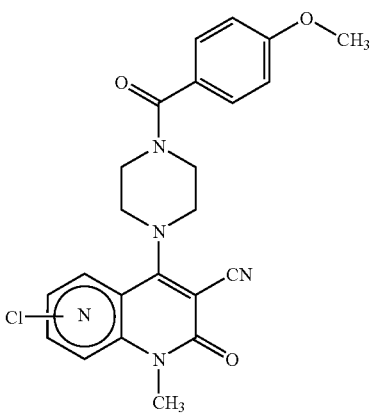
503

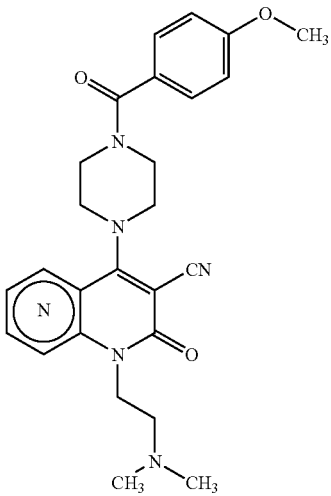
504
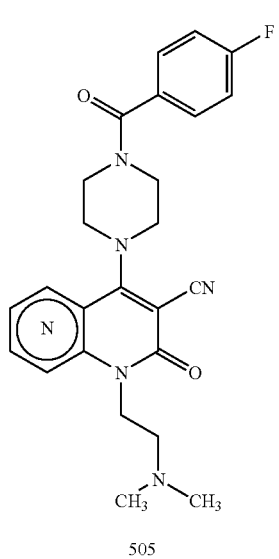
505
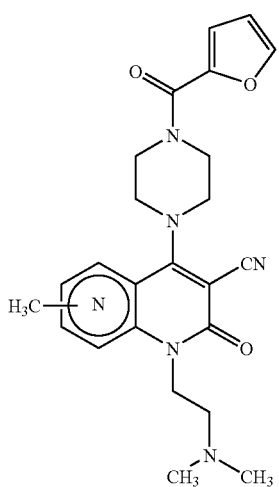
506
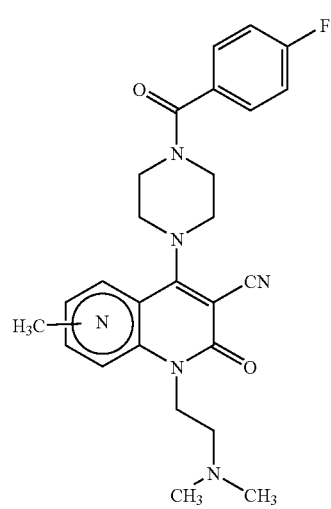
507
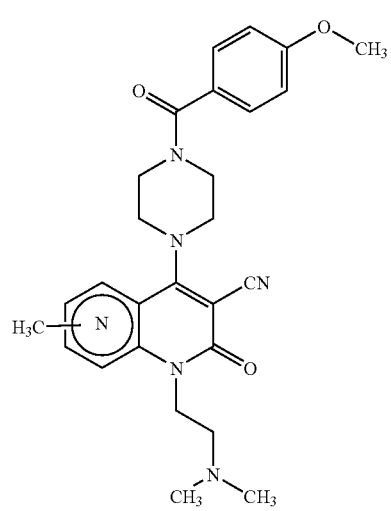
508
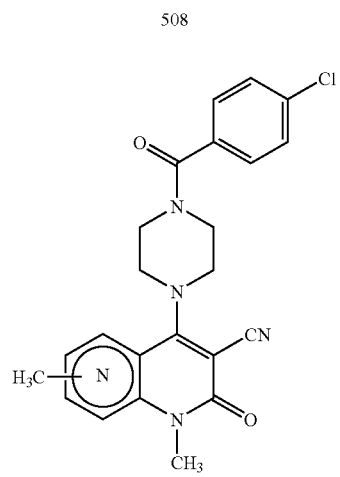
509

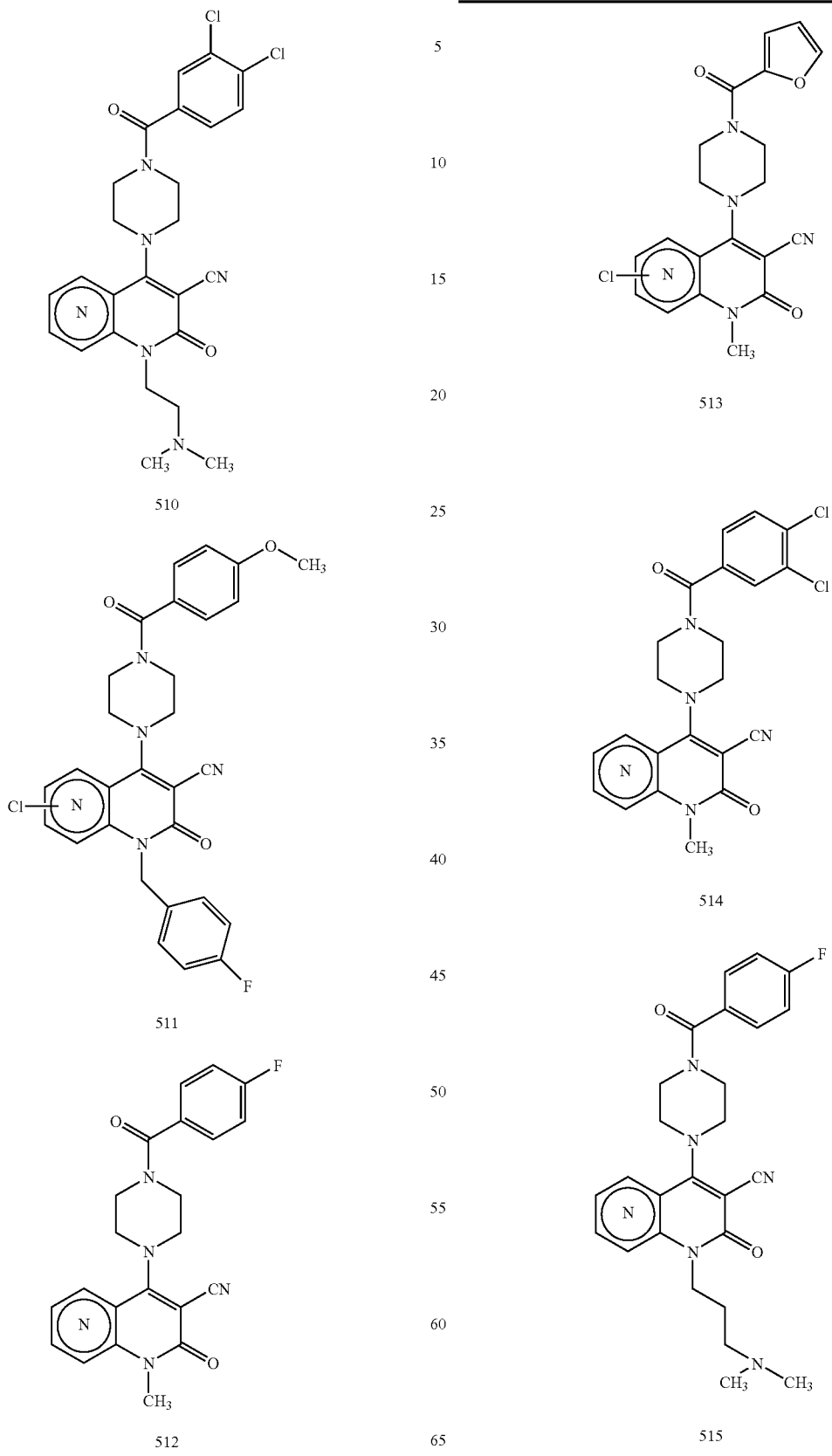

-continued
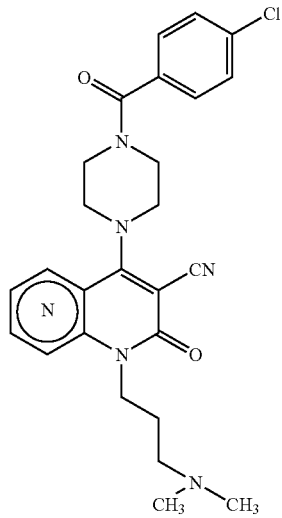
516
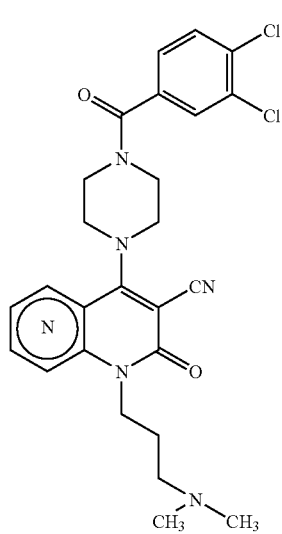
517
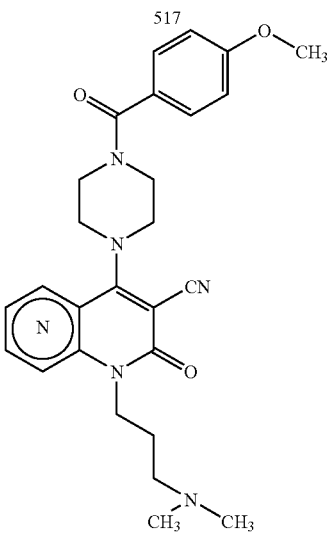
518
-continued
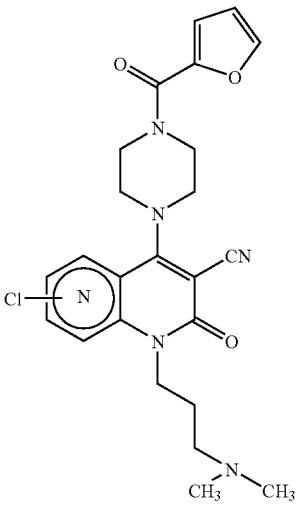
519
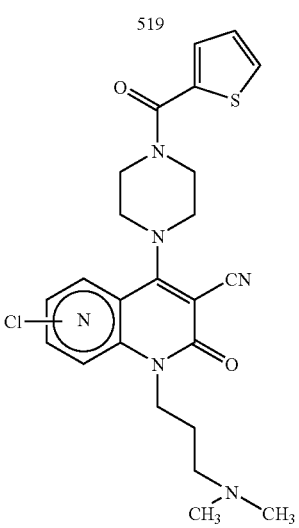
520
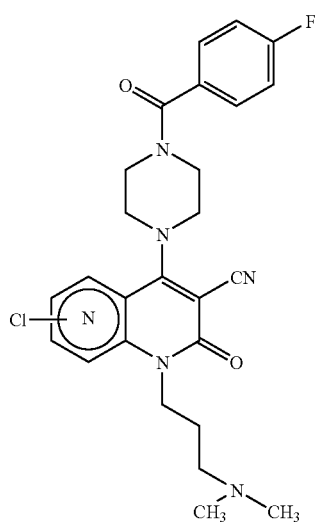
521

-continued
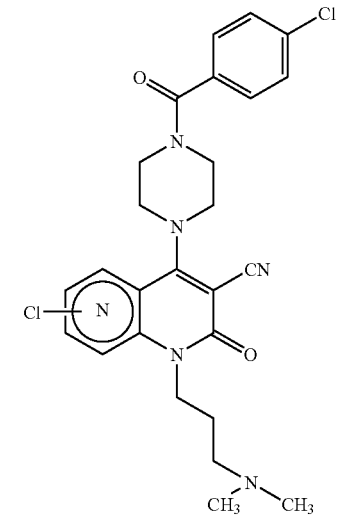
522
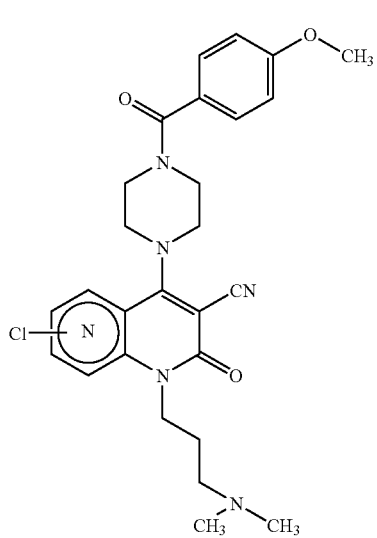
523
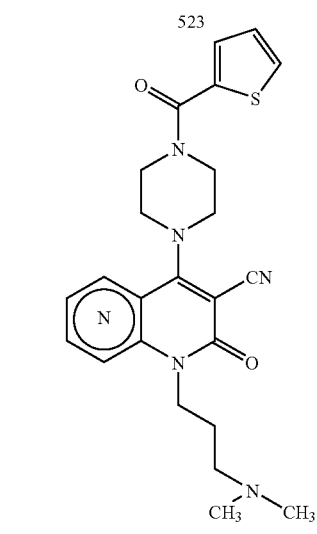
524
-continued
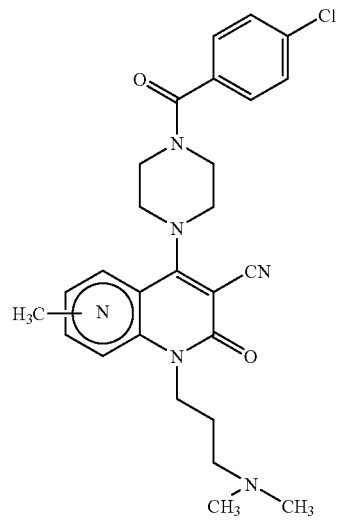
525
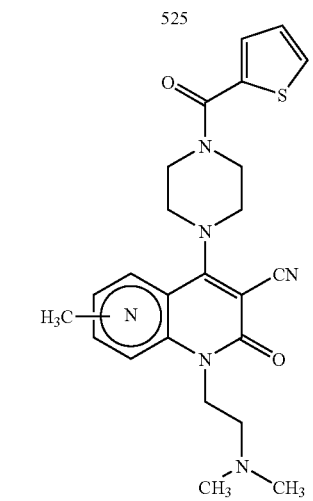
526
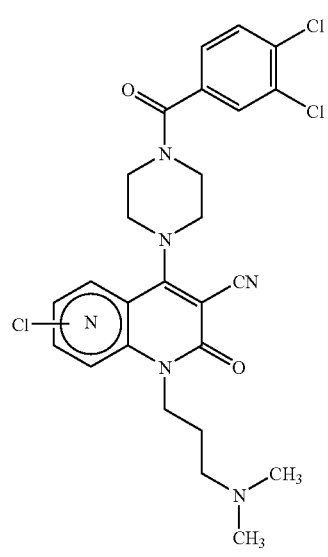
527

| 195 | 196 |
|---|---|
| -continued | -continued |
| 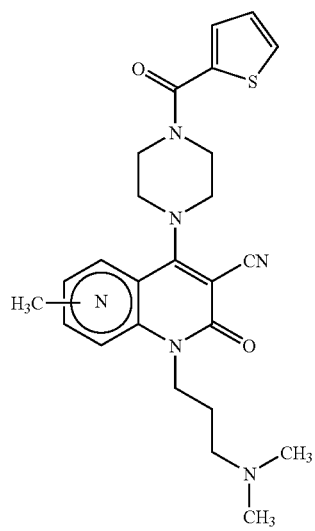 528 | 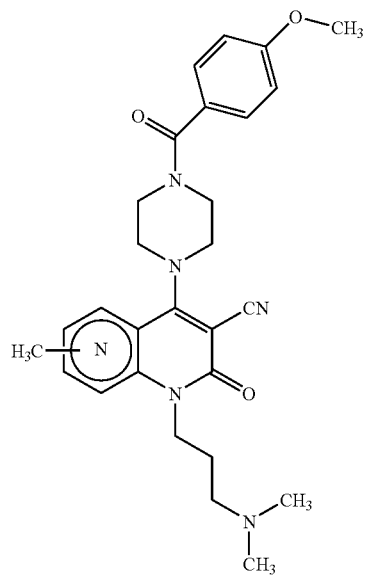 530 |
| 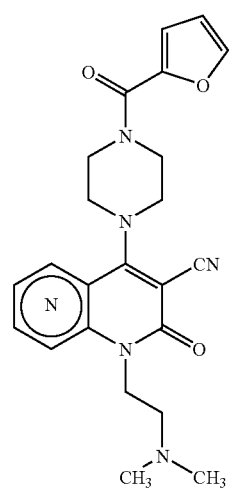 529 | 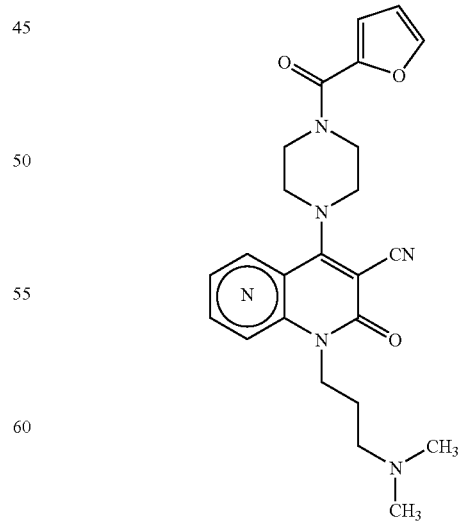 531 |

-continued
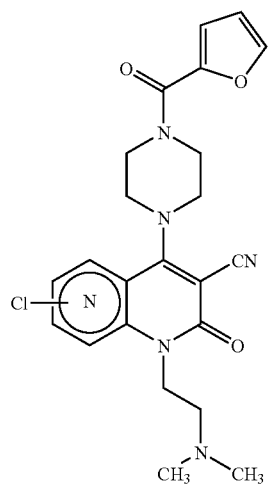
532
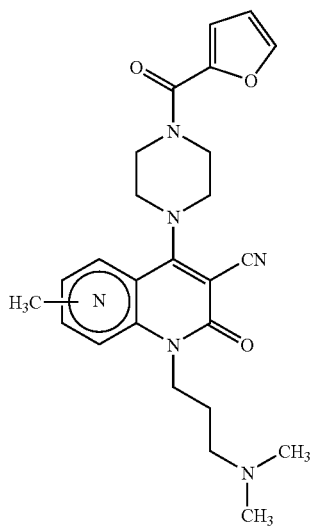
533
-continued
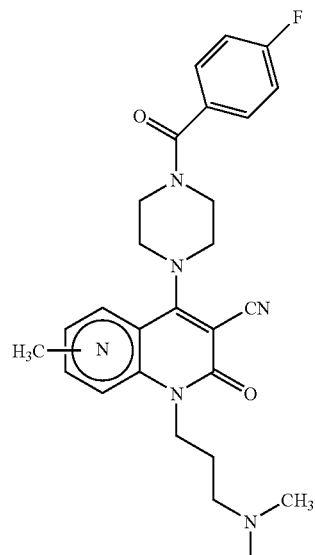
534
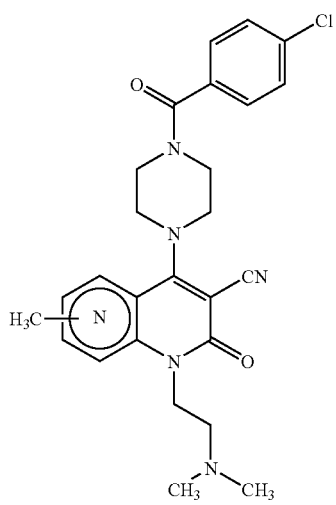
535

-continued
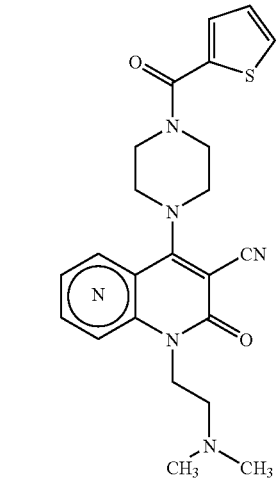
536
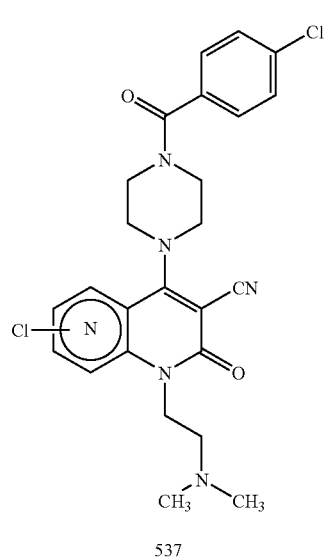
537
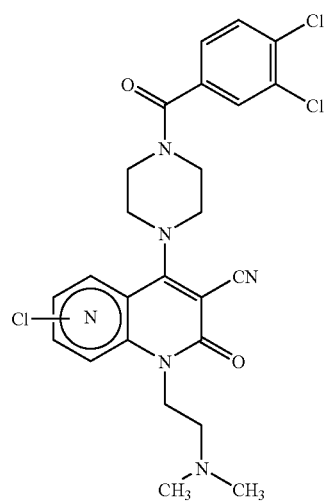
538
-continued
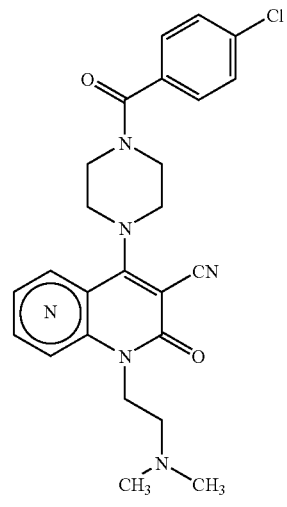
539
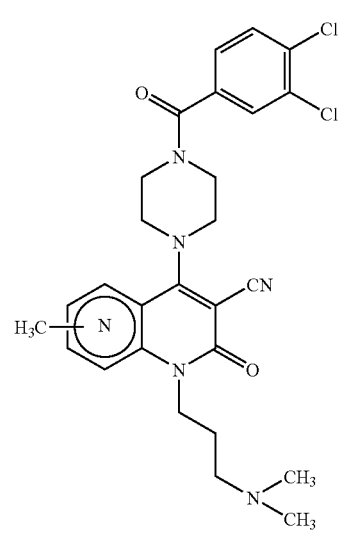
540
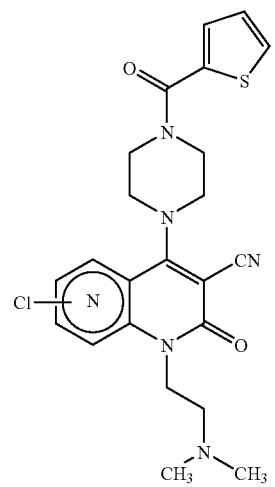
541

-continued
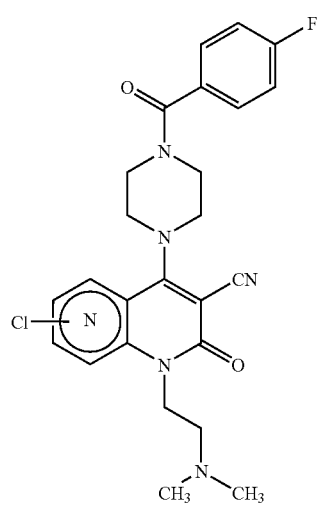
542
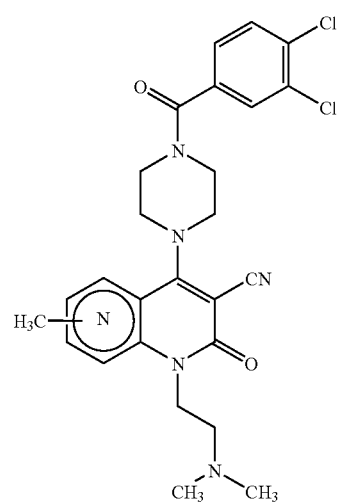
543
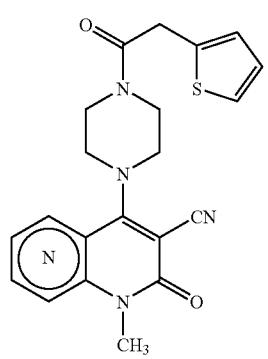
544
-continued
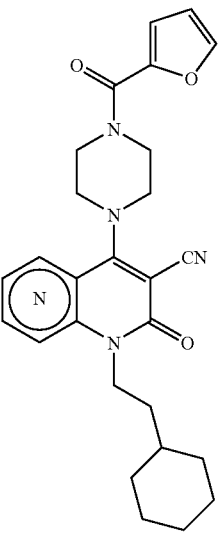
545
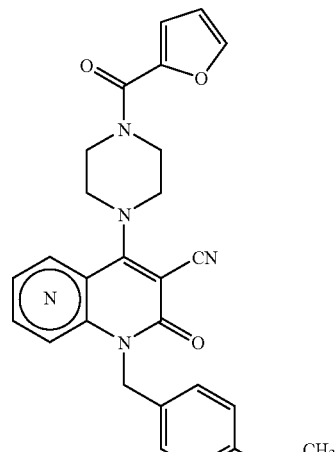
546
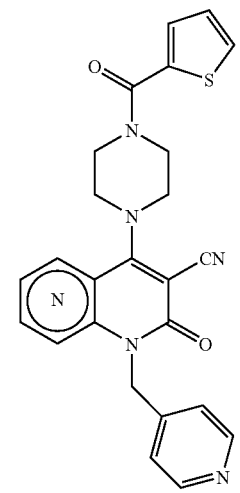
547

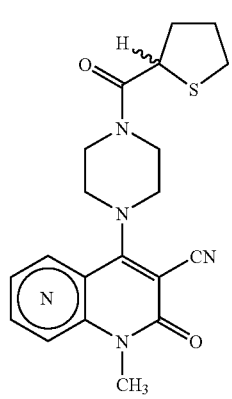
548
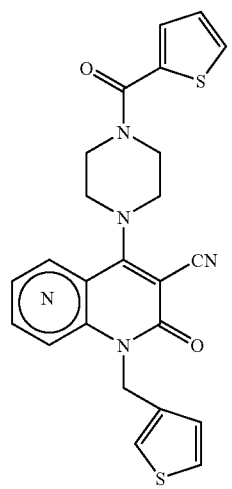
549
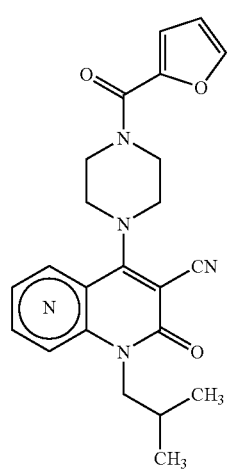
550
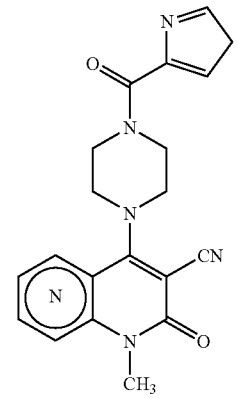
551
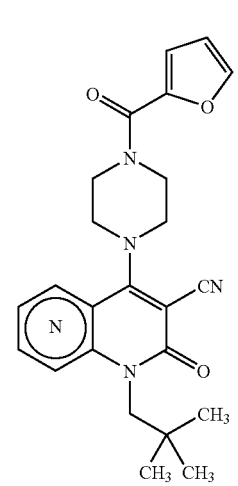
552
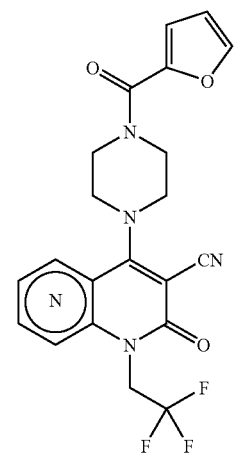
553

-continued
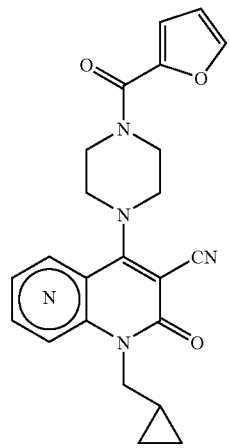
554
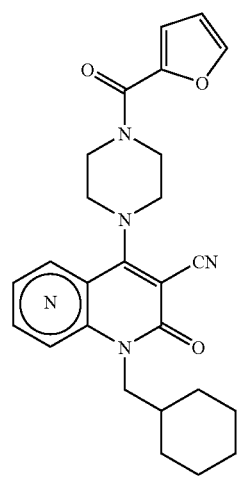
555
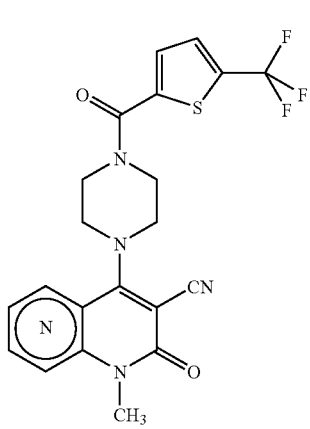
556
-continued
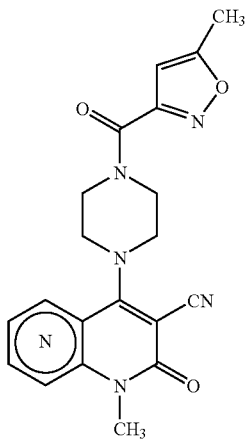
557
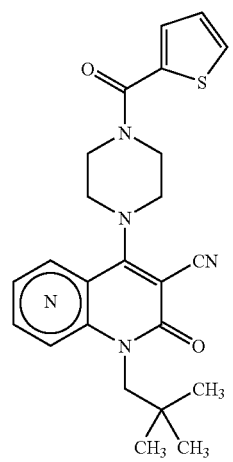
558
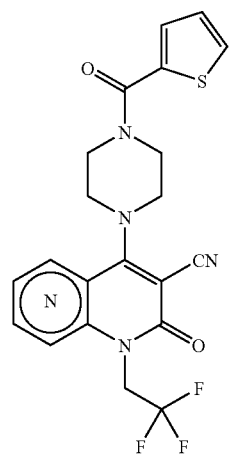
559

-continued
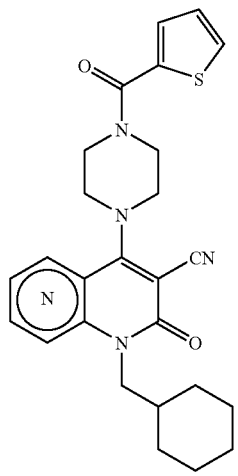
560
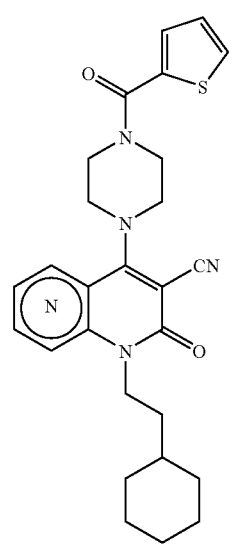
561
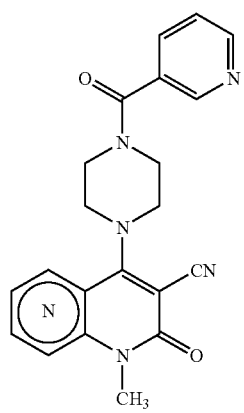
562
-continued
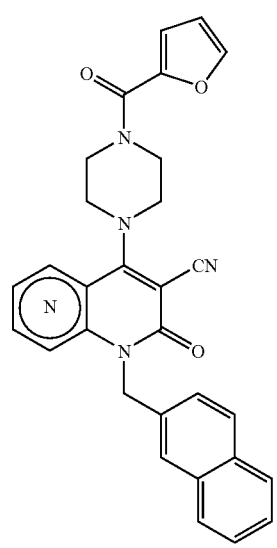
563
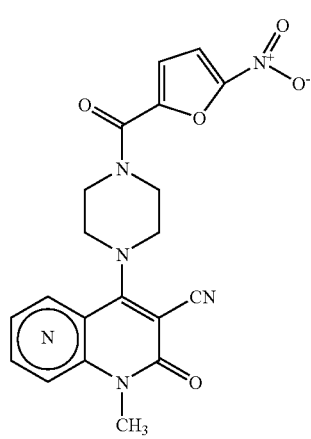
564
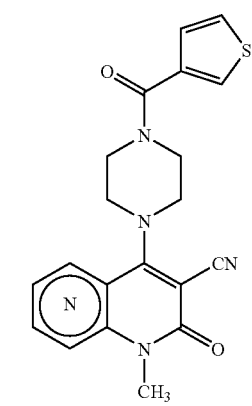
565

-continued
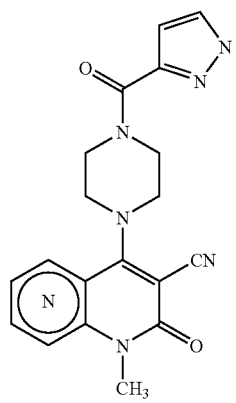
566
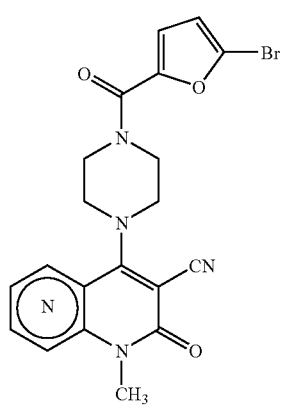
567
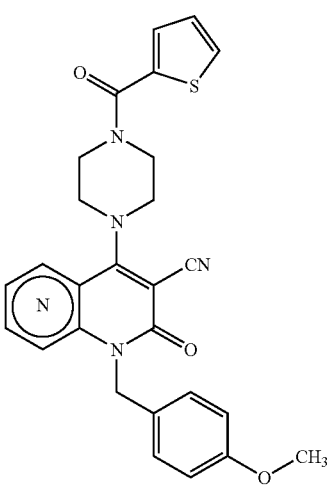
568
-continued
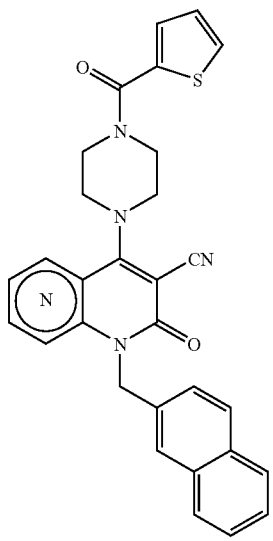
569
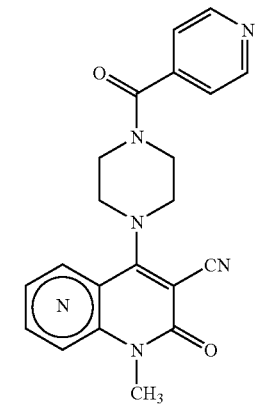
570
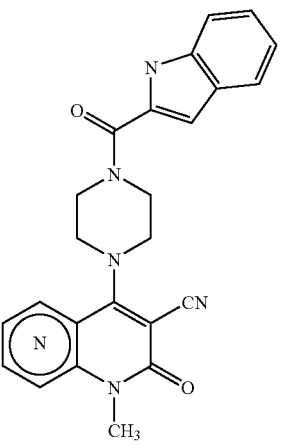
571

-continued
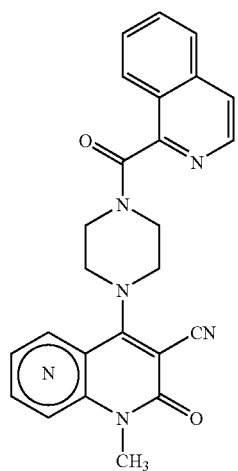
572
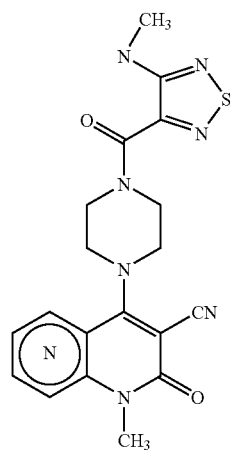
573
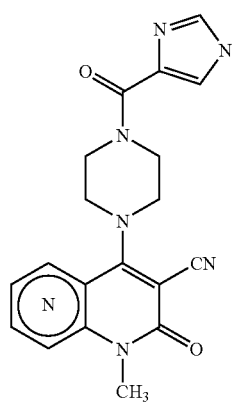
574
-continued
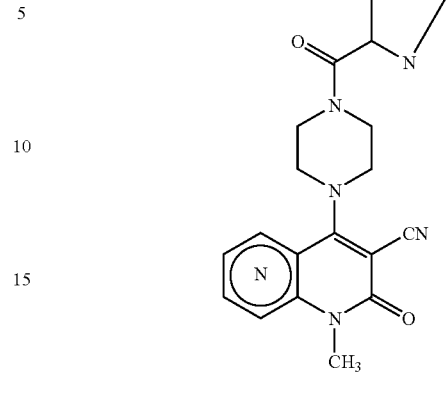
575
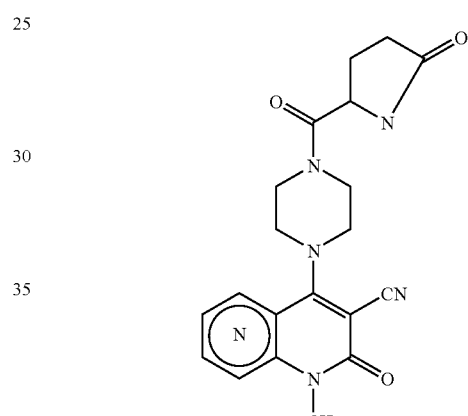
576
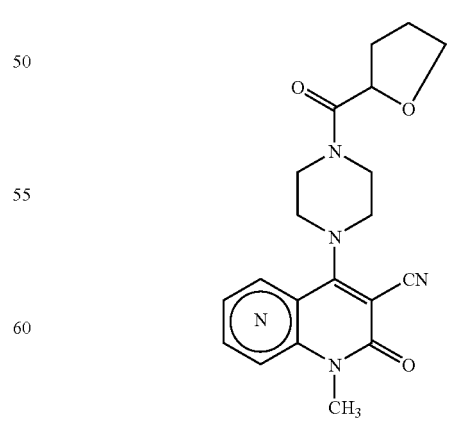
577

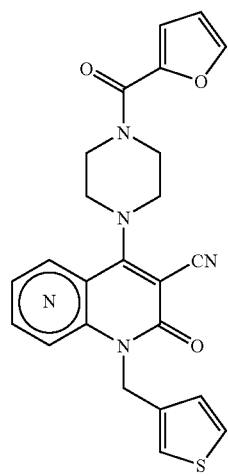
578
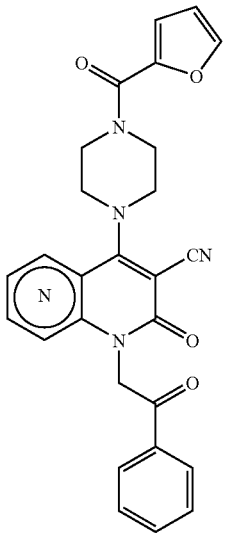
580
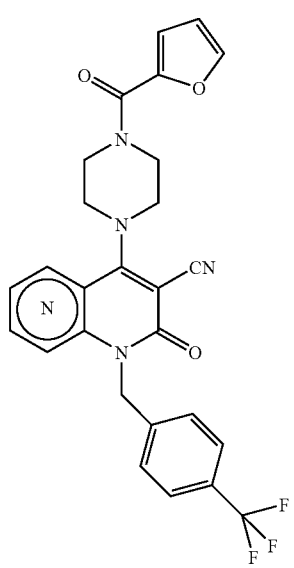
579
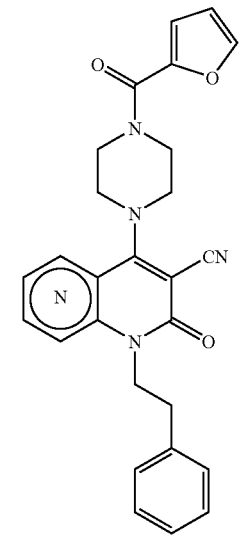
581

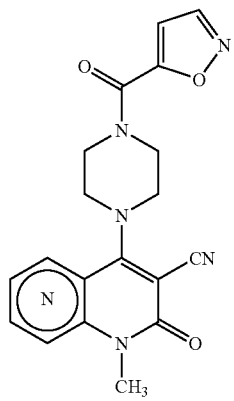
582
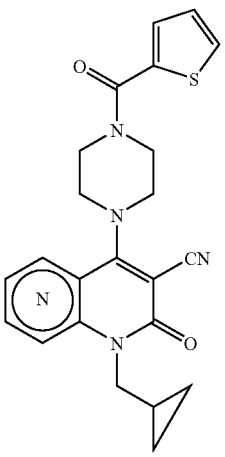
585
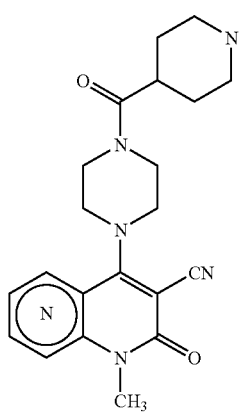
583
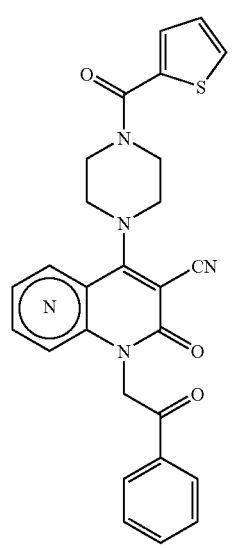
586
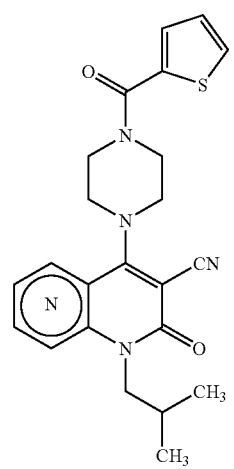
584
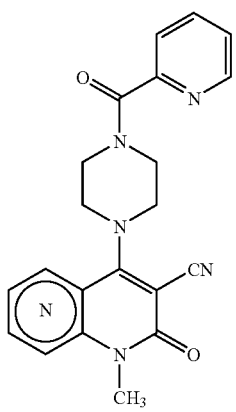
587

-continued
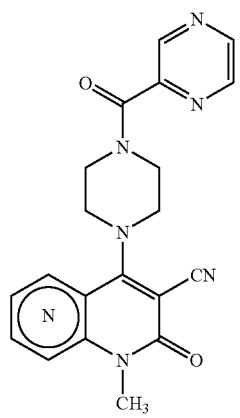
588
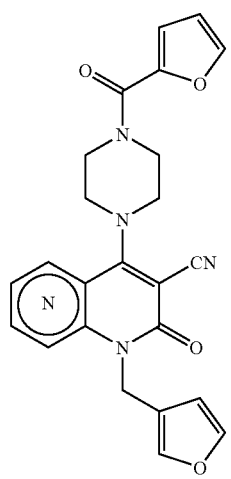
589
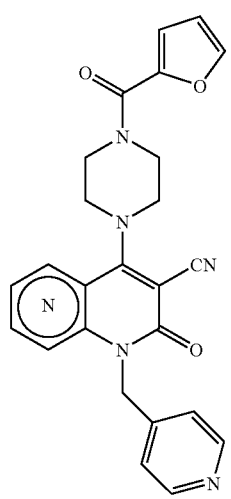
590
-continued
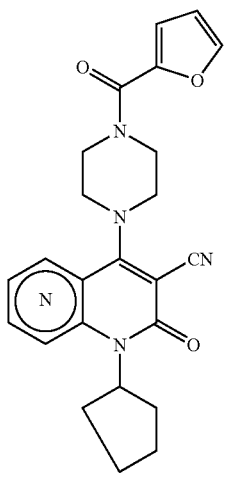
591
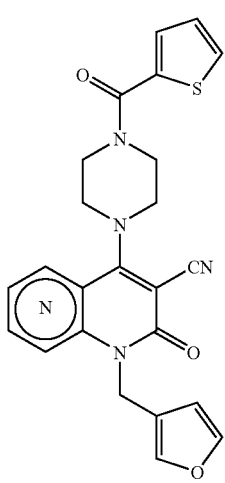
592
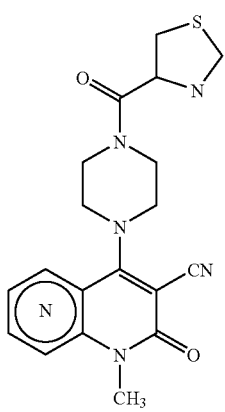
593

-continued
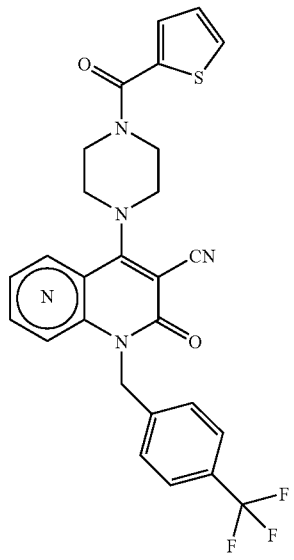
594
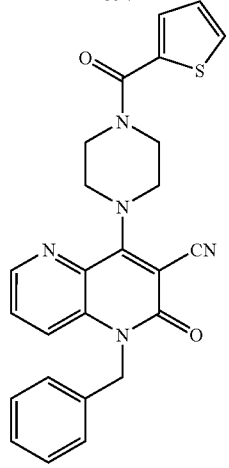
595
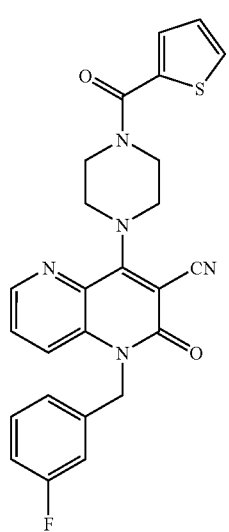
596
-continued
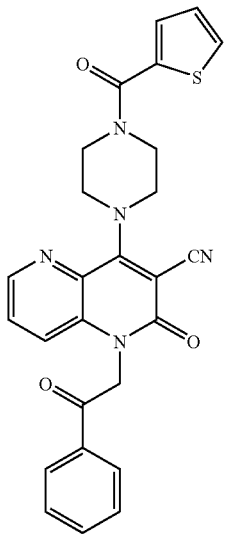
597
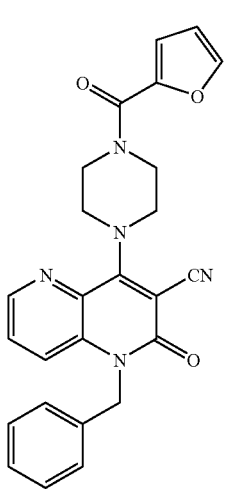
598
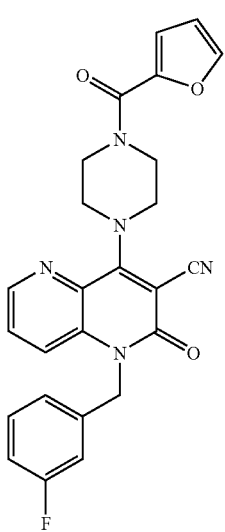
599

-continued
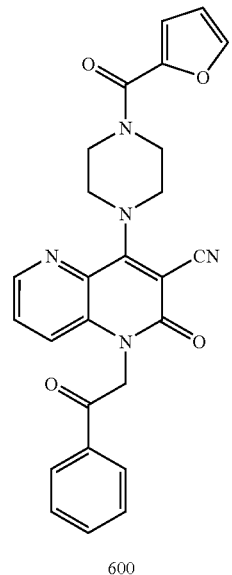
600
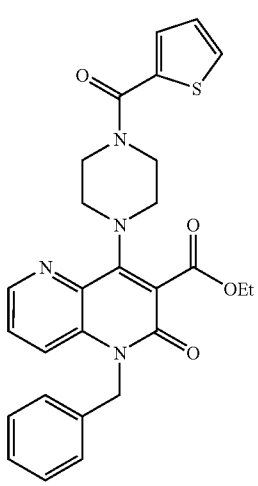
601
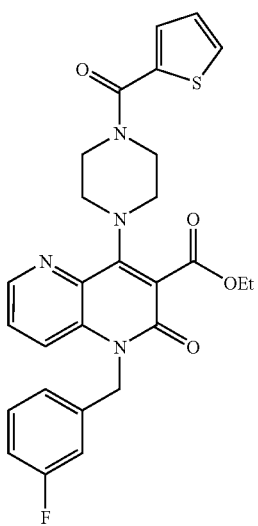
602
-continued
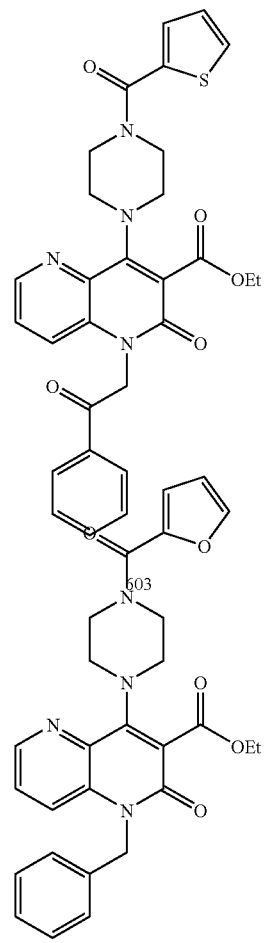
603
604
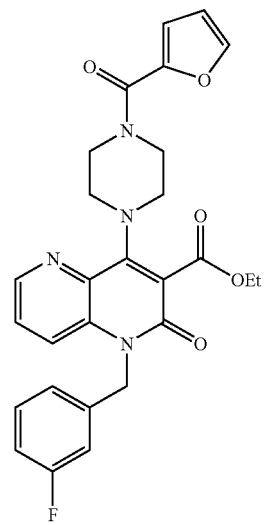
605

-continued
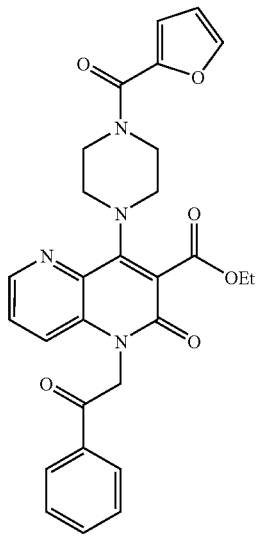
606
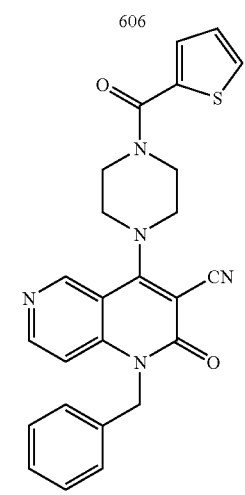
607
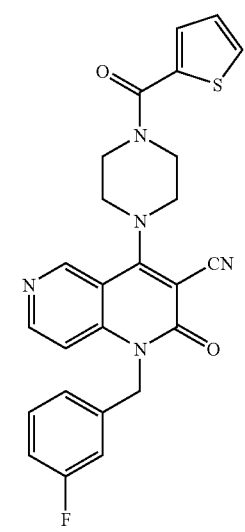
608
-continued
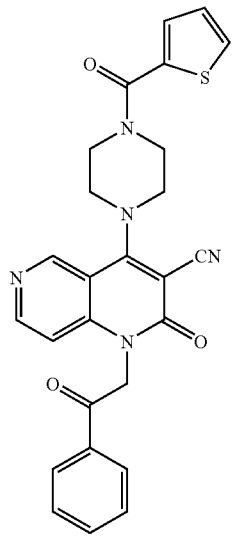
609
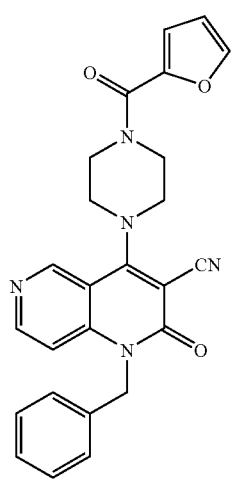
610
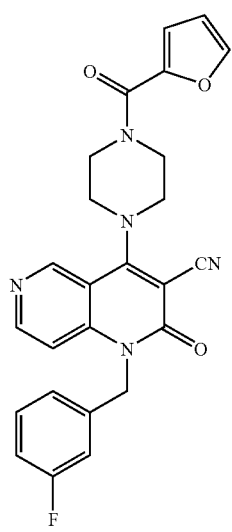
611

225 -continued
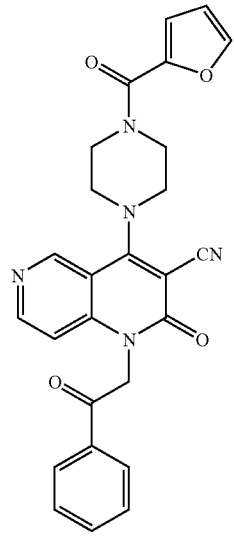
612
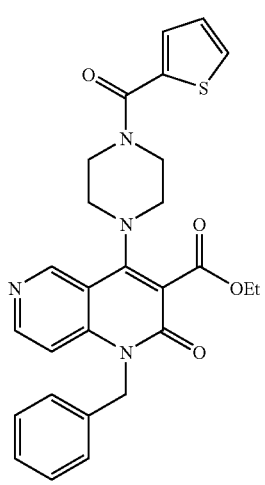
613
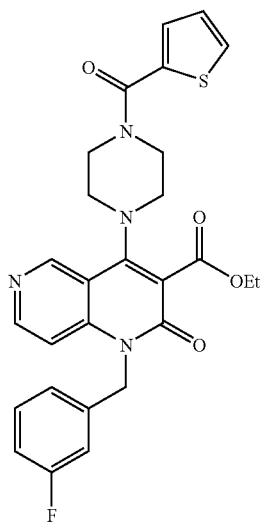
614
226 -continued
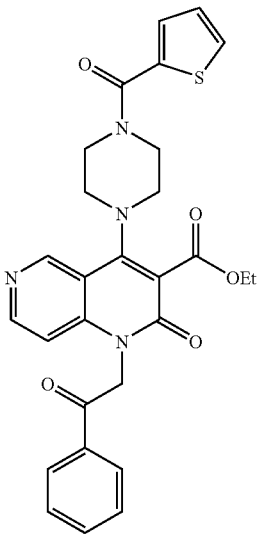
615
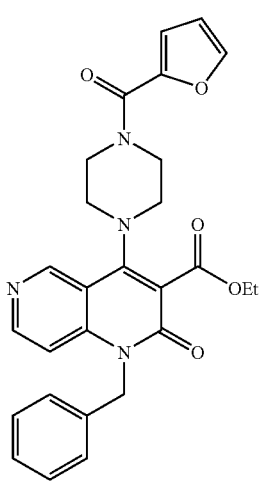
616
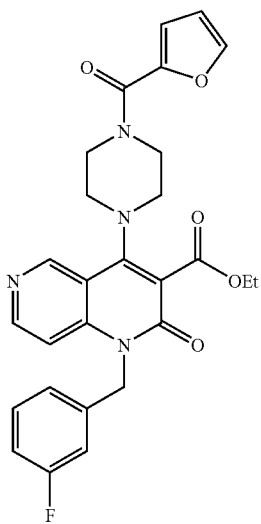
617

-continued
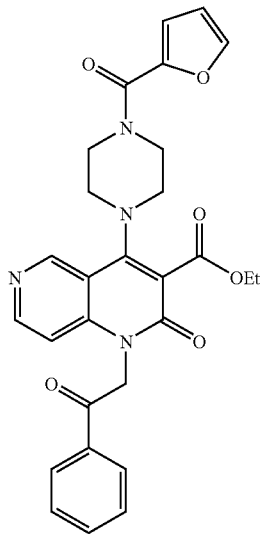
618
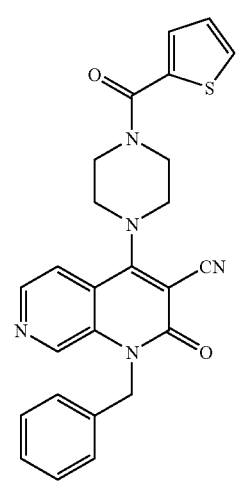
619
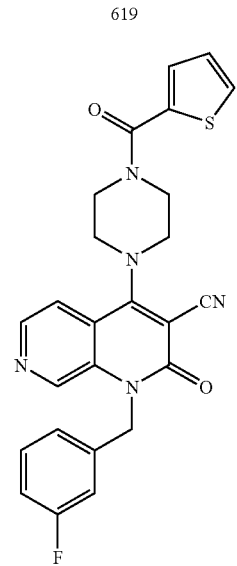
620
-continued
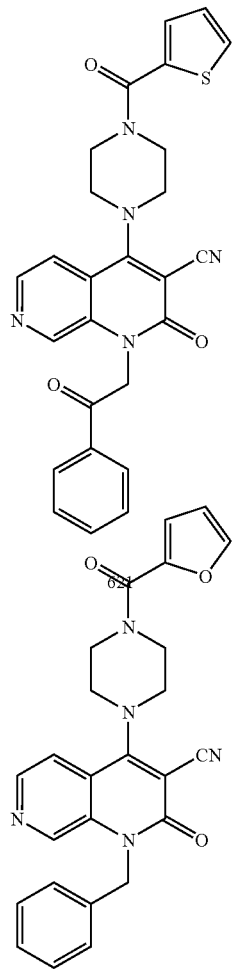
622
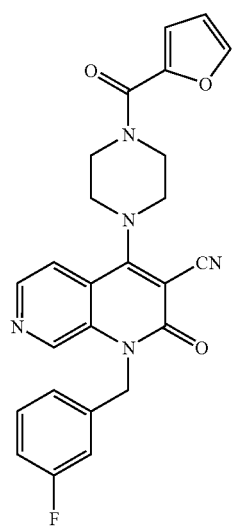
623

-continued
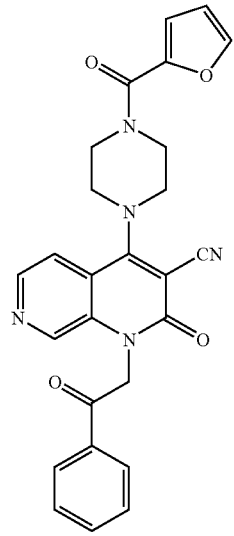
624
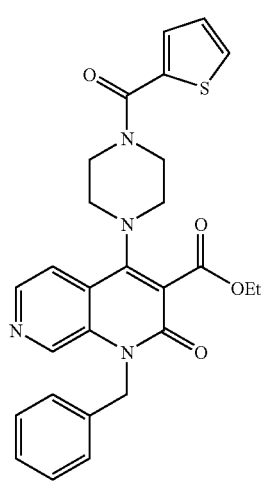
625
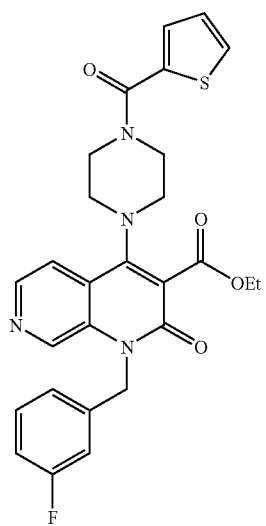
626
-continued
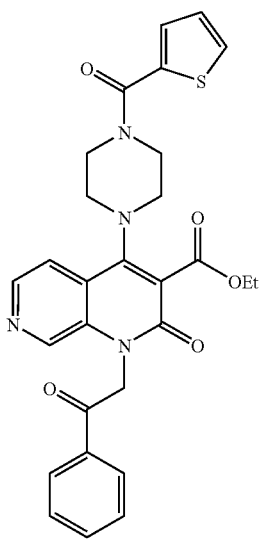
627
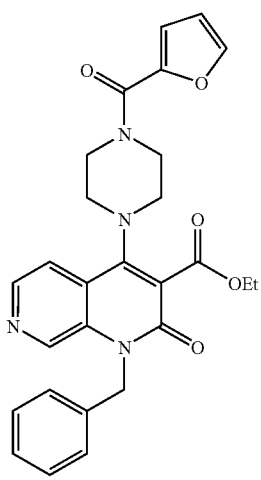
628
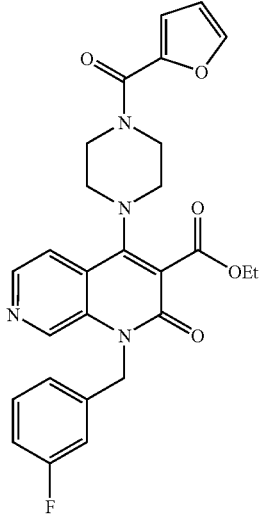
629

-continued

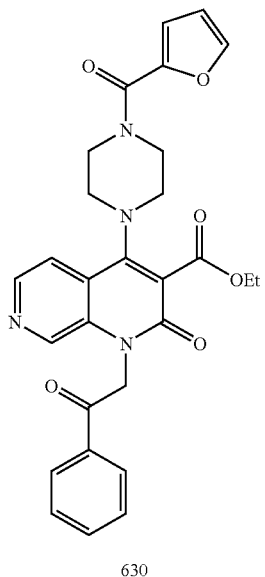

630

The compounds of preferred embodiments can generally be employed as the free acid or free base. Alternatively, the compounds of preferred embodiments can preferably be in the form of acid or base addition salts. Acid addition salts of the free base amino compounds of preferred embodiments can be prepared by methods well known in the art, and can be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts of the free acid can similarly be prepared by methods well known in the art, and can be formed from suitable bases, such as cations chosen from the alkali and alkaline earth metals (e.g. lithium, sodium, potassium, magnesium, barium or calcium) as well as the ammonium cation. The term "pharmaceutically acceptable salt" of structure (Ia), (Ib), (Ic), or (Id) is intended to encompass any and all acceptable salt forms.

The compounds of structure (Ia), (Ib), (Ic), and (Id) can be made according to the organic synthesis techniques known to those skilled in this field, as well as by the representative methods set forth in the Example. In general, compounds of structure (Ia) can be made according to the following Reaction Schemes. It is noted that in these synthetic routes the nitrogen atom of the naphthyridine ring occupies the 8 ring position. However, the synthetic routes are also effective in preparation of compounds of the preferred embodiments where in the nitrogen atom of the naphthyridine ring occupies the 5, 6, or 7 ring position, as discussed below.

Preparation of Intermediate 1-Benzyl-4-hydroxy-2-oxo-1,2-dihydro-[1,8]-naphthyridine-3-carboxylic acid ethyl ester A preferred intermediate in the preparation of compounds of formula (Ia) is 1-benzyl-4-hydroxy-2-oxo-1,2-dihydro-[1,8]-naphthyridine-3-carboxylic acid ethyl ester, depicted by formula (3) below. The starting material used for this synthesis was 2-chloro-3-pyridinecarboxylic acid. To prepare compounds of formula (Ib), The chloropyridine carboxylic acid is reacted with a secondary amino compound. For illustrative purposes in the following synthetic route, benzylamine is employed as a starting material. However, it is noted that other secondary amines can also be employed as starting materials, including substituted benzylamines such as 4-methoxybenzylamine or 4-fluorobenzylamine.

The first step in the synthesis of the intermediate 1-benzyl-4-hydroxy-2-oxo-1,2-dihydro-[1,8]-naphthyridine-3-carboxylic acid ethyl ester is the production of 2-benzylamino nicotinic acid, depicted by formula (1) as shown in Scheme 1:

Scheme 1

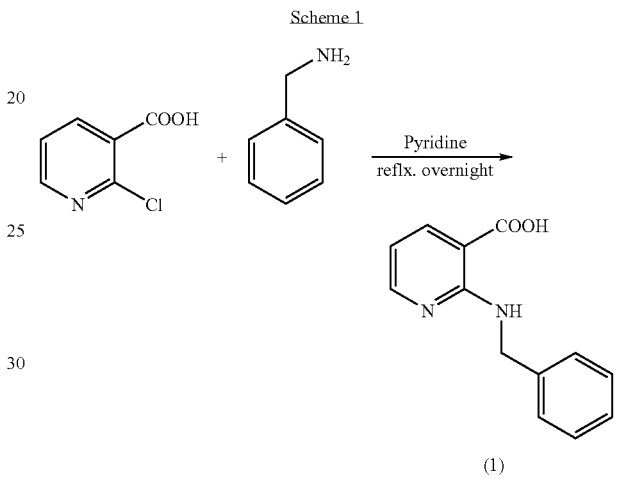

2-Benzylamino nicotinic acid (1) can then be employed to prepare 1-benzyl-1H-pyrido[2,3-d][1,3]oxazine-2,4-dione, depicted by formula (2) as shown in Scheme 2.

Scheme 2

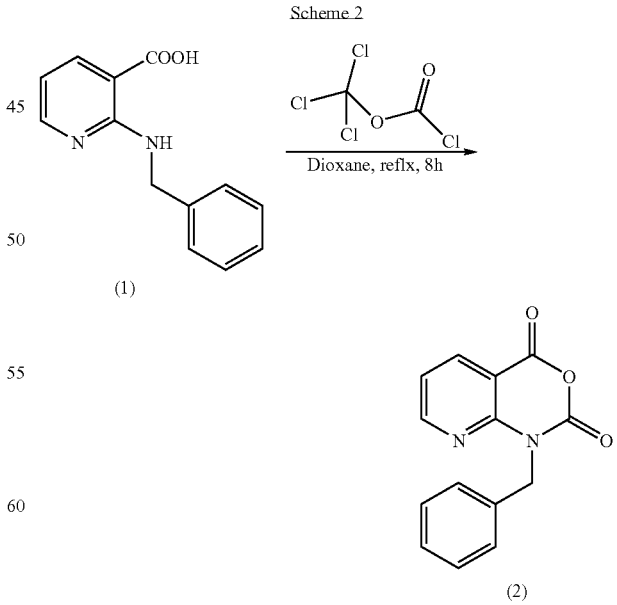

Diethyl malonate can then be reacted with the 1-benzyl-1H-pyrido[2,3-d][1,3]oxazine-2,4-dione (2) to yield the intermediate 1-benzyl-4-hydroxy-2-oxo-1,2-dihydro-[1,8]-naphthyridine-3-carboxylic acid ethyl ester (3) as shown in Scheme 3:

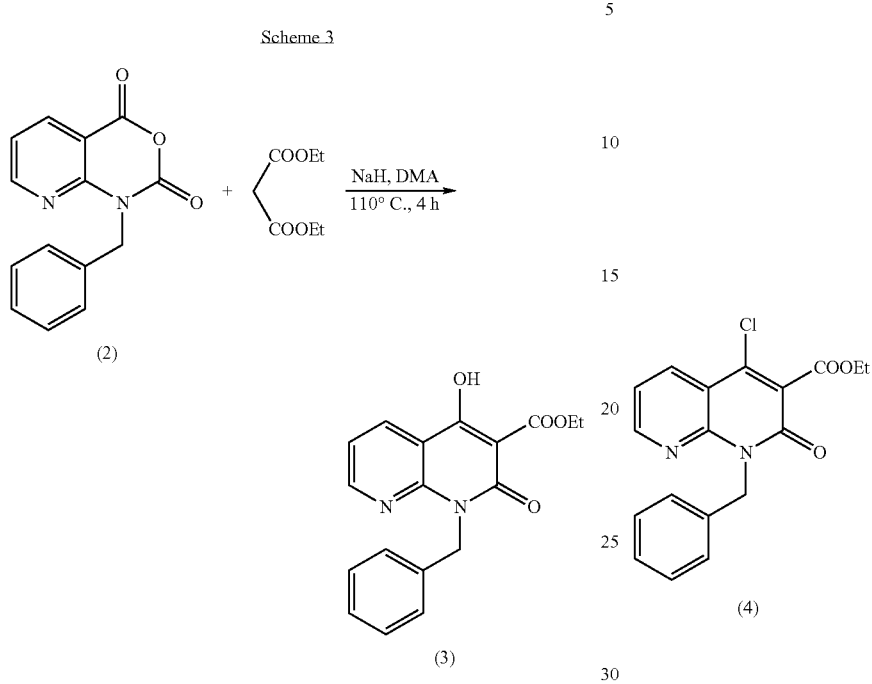

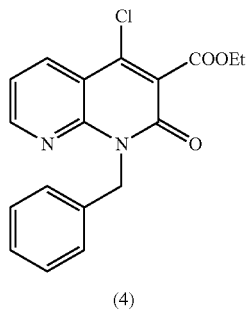

Other diesters can be employed in this reaction if a different carboxylate substitutent is preferred for the substitutent $R_1$ of the resulting compound of formula (Ia) (or formula (Ib), (Ic), or (Id)), for example, dimethyl malonate, dipropyl malonate, and the like. Otherwise, the carboxylate group can be substituted by another moiety, for example cyano, as discussed below.

Preparation of Compound of Formula (Ia)—1-Benzyl-2-oxo-4-[(4-thiophene-2-carbonyl)-piperazin-1-yl]-1,2-dihydro-[1,8]-naphthyridine-3-carboxylic acid ethyl ester One compound of a preferred embodiment can be prepared using the intermediate 1-benzyl-4-hydroxy-2-oxo-1,2-dihydro-[1,8]-naphthyridine-3-carboxylic acid ethyl ester as a starting material. This compound was prepared by applying sequence of reactions as shown in Scheme 4.

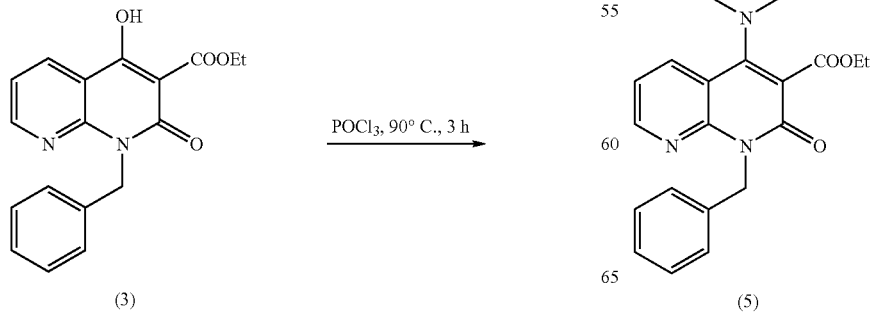

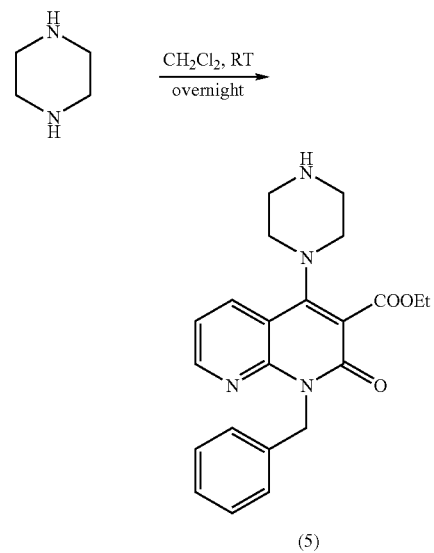

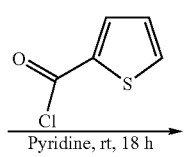

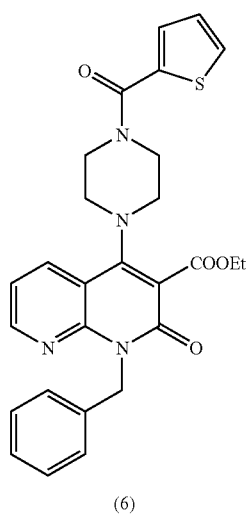

(6)

In the above-described reaction, 2-thiophene carbonyl chloride is reacted with 1-benzyl-2-oxo-4-piperazin-1-yl-1,2-dihydro-[1,8]-naphthyridine-3-carboxylic acid ethyl ester to yield the target compound, 1-benzyl-4-[4-(thiophene-2-carbonyl)-piperazin-1-yl]-2-oxo-1,2-dihydro-[1,8]-naphthyridine-3-carboxylic acid ethyl ester, depicted by formula (6) in Scheme 4. If it is preferred that the substitutent R is other than 2-thiophene, another carbonyl chloride compound can be substituted in the reaction.

Cyano Derivative of Intermediate 1-Benzyl-4-hydroxy-2-oxo-1,2-dihydro-[1,8]-naphthyridine-3-carboxylic acid ethyl ester A compound of formula (Ia) including a cyano group as the substitutent $R_1$ can be prepared starting from intermediate 1-benzyl-4-hydroxy-2-oxo-1,2-dihydro-[1,8]-naphthyridine-3-carboxylic acid ethyl ester. The intermediate is functionalized with cyano by the reactions as shown in Scheme 5:

Scheme 5

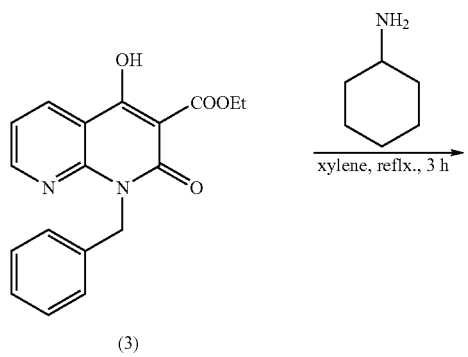

(3)

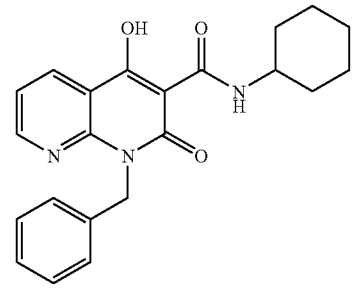

(7)

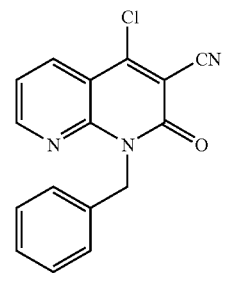

(7)

POCl$_3$, 90° C.
Overnight

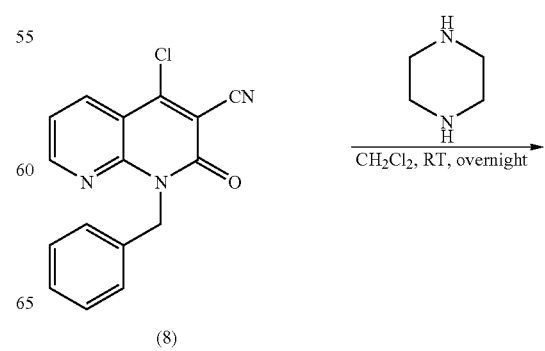

(8)

Preparation of Compound of Formula (Ia)—1-Benzyl-4-[4-(thiophene-2-carbonyl)-piperazin-1-yl]-2-oxo-1,2-dihydro-3-cyano[1,8]-naphthyridine The final product is then prepared by reaction with piperazine, followed by reaction with 2-thiophene carbonyl chloride, as discussed above in the preparation of the compounds of formulae (5) and (6) in Scheme 4. As also discussed above, if it is preferred that the substitutent R is other than 2-thiophene, another carbonyl chloride compound can be substituted in the reaction. The reaction sequences used for the preparation of 1-benzyl-4-[4-(thiophene-2-carbonyl)-piperazin-1-yl]-2-oxo-1,2-dihydro-3-cyano[1,8]-naphthyridine is shown in Scheme 6

Scheme 6

(8)

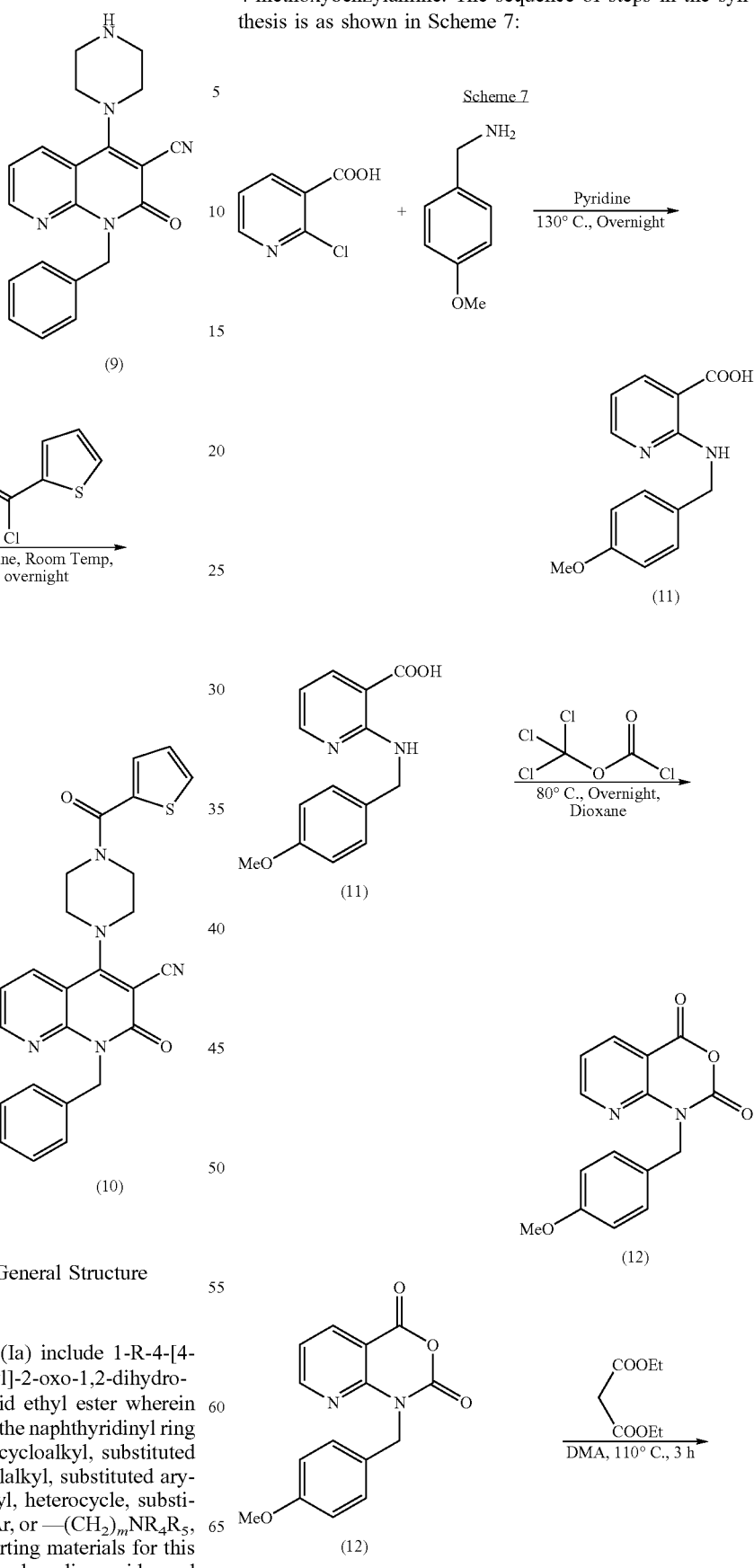

4-methoxybenzylamine. The sequence of steps in the synthesis is as shown in Scheme 7:

Preparation of Compounds of General Structure (Ia)

Preferred compounds of formula (Ia) include 1-R-4-[4-(thiophene-2-carbonyl)-piperazin-1-yl]-2-oxo-1,2-dihydro-[1,8]-naphthyridines-3-carboxylic acid ethyl ester wherein the substitutent R on the 1 position of the naphthyridinyl ring is hydrogen, alkyl substituted alkyl cycloalkyl, substituted cycloalkyl, aryl, substituted aryl, arylalkyl, substituted arylalkyl, acylalkyl, substituted acylalkyl, heterocycle, substituted heterocycle, —$(CH_2)_mC(=O)Ar$, or —$(CH_2)_mNR_4R_5$, wherein m is 0, 1, 2, 3, or 4. The starting materials for this synthesis are 2-chloro-3-pyridinecarboxylic acid and

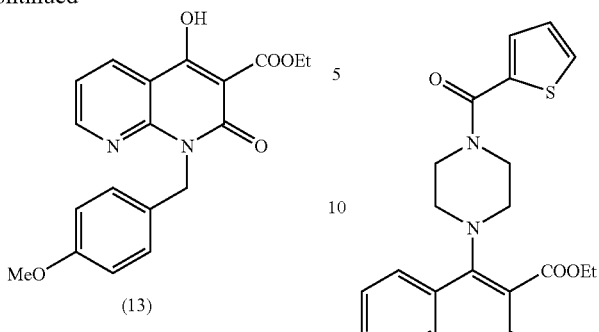
(13)
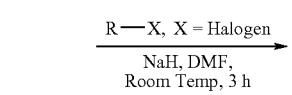
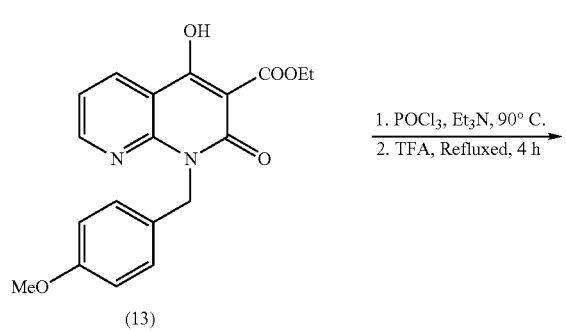
(13)
1. POCl₃, Et₃N, 90° C.
2. TFA, Refluxed, 4 h
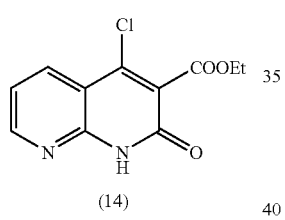
(14)
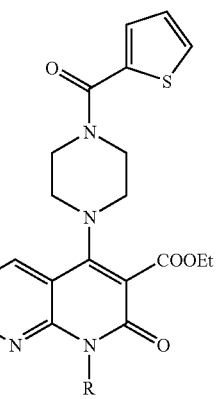
(15)
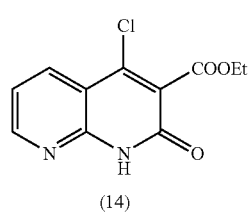
(14)
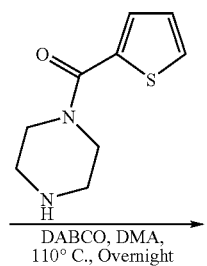
DABCO, DMA,
110° C., Overnight
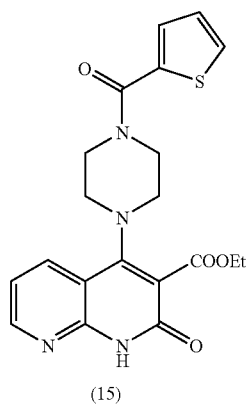
(15)
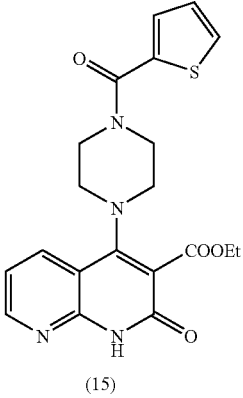
(15)
R—X, X = Halogen
DMF, K₂CO₃
90° C., 24 h
In the final step of the reaction, an appropriate halide (R—X) can be selected as a reactant so as to yield the desired substitutent (R) at the 1 position of the naphthyridinyl ring. An alternate final step in preparing the product is as shown in Scheme 8:
Scheme 8

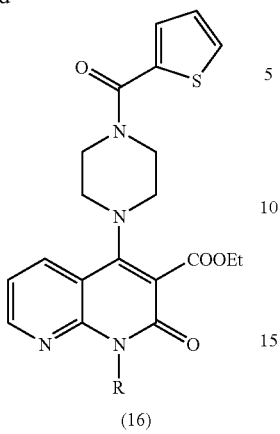

If it is preferred the substitutent in piperazine moiety is other than 2-thiophene corresponding N-acyl piperazine, prepared from acylation of t-butyl-1-piperazinecarboxylate with corresponding acid chloride followed by deprotection, can be used instead of piperazine-1-yl-thiophene-2-yl-methanone.

Preparation of Compounds of General Structure (Ia) with Carbonitrile at 3-position of Naphthyridine Moiety Preferred compounds of formula (Ia) include 1-R-2-oxo-4-[4-(thiophene-2-carbonyl)-piperazin-1-yl]-1,2-dihydro-[1,8]naphthyridine-3-carbonitriles wherein the substituent R on the 1 position of the naphthyridinyl ring is hydrogen, alkyl, substituted alkyl, cycloalkyl, substituted cycloalkyl, aryl, substituted aryl, arylalkyl, substituted arylalkyl, acylalkyl, substituted acylalkyl, heterocycle, substituted heterocycle, —(CH$_2$)$_m$C(=O)Ar, or —(CH$_2$)$_m$NR$_4$R$_5$, wherein m is 0, 1, 2, 3, or 4. 2-Oxo-4-[4-(thiophene-2-carbonyl)-piperazin-1-yl]-1,2-dihydro-[1,8]-naphthyridine-3-carbonitriles, depicted by formula 20 in Scheme 9, was prepared as a key intermediate starting from 4-hydroxy-1-(4-methoxybenzyl)-2-oxo-1,2-dihydro-[1,8]-naphthyridine-3-carboxylic acid ethyl ester, depicted by formula 13 in Scheme 7. This key intermediate was then reacted with appropriate halides (R—X) to yield target compounds. The sequence of steps used in the synthesis is as shown in Scheme 9:

Scheme 9

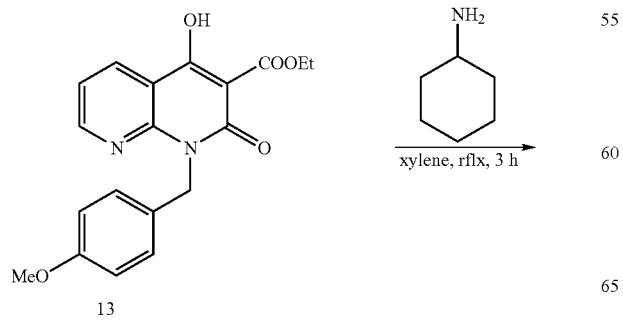

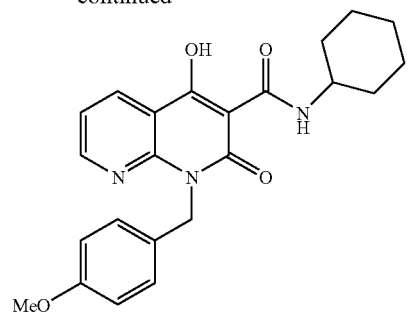

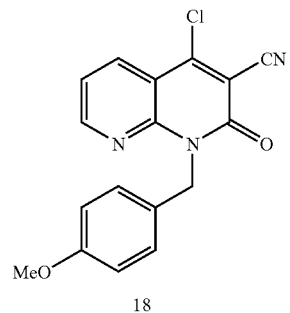

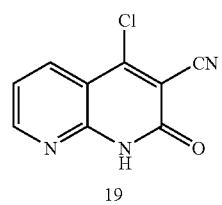

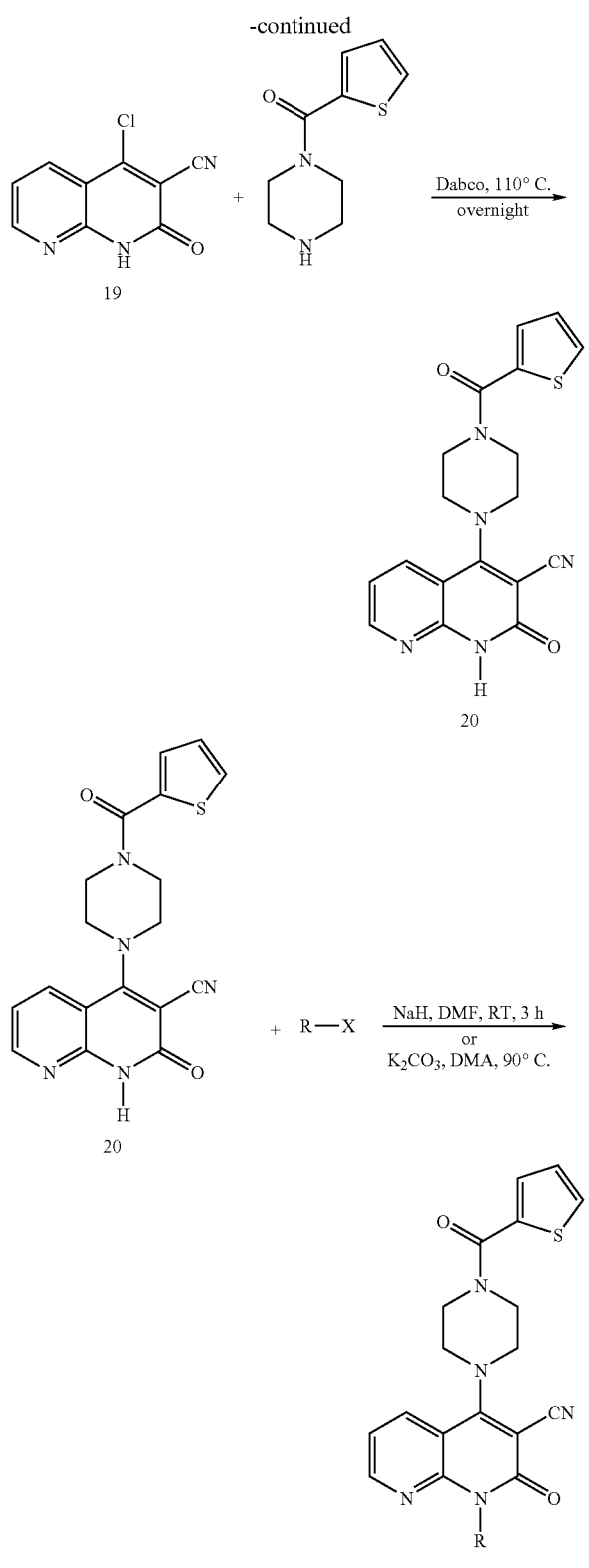

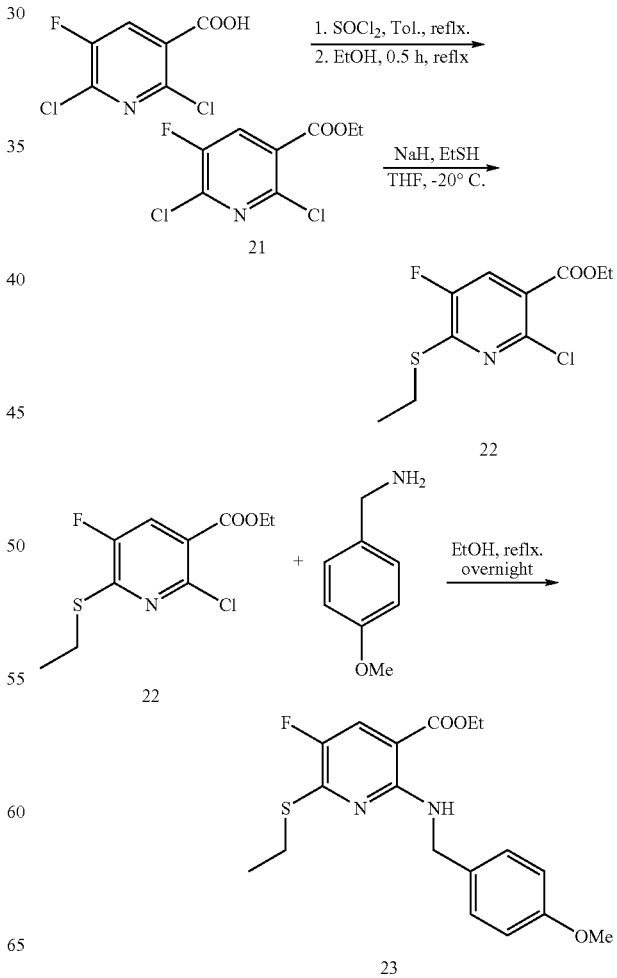

Preparation of Compounds of General Structure (Ia) with Substitution at 6-Position of Naphthyridine Moiety.

2,6 Dichloro-5-fluoro-nicotinic acid was selected as a starting material to make the compounds of structure (Ia) with fluoro substitution at 6-position of naphthyridine moiety. 2,6 Dichloro-5-fluoro-nicotinic acid was esterified by treating with thionyl chloride followed by refluxing with dry ethanol to yield 2,6-dichloro-5-fluoro-nicotinic acid ethyl ester, depicted by formula 21 in Scheme 10. This ester gave 2-chloro-6-ethylsulfanyl-5-fluoro-nicotinic acid ethyl ester, depicted by formula 22 in Scheme 10, when reacted with ethanethiol and sodium hydride. 6-Ethylsulfanyl-5-fluoro-2-(4-methoxy-benzylamino)-nicotinic acid ethyl ester, depicted by formula 23 in Scheme 10, was prepared by amination of 2-chloro-6-ethylsulfanyl-5-fluoro-nicotinic acid ethyl ester, which was converted into 5-fluoro-2-(4-methoxy-benzylamino)-nicotinic acid ethyl ester, depicted by formula 24 in Scheme 10, by refluxing with ethanol and raney nickel. 5-Fluoro-2-(4-methoxy-benzylamino)-nicotinic acid ethyl ester was then reacted with trichloromethylchloroformate to yield 6-fluoro-1-(4-methoxy-benzyl)-1H-pyrido[2,3-d][1,3]oxazine-2,4-dione, depicted by formula 25 in Scheme 10. The sequence of reactions is shown in Scheme 10.

If it is preferred the substitutent in piperazine moiety is other than 2-thiophene corresponding N-acyl piperazine, prepared from acylation of t-butyl-1-piperazinecarboxylate with corresponding acid chloride followed by deprotection, can be used instead of piperazine-1-yl-thiophene-2-yl-methanone.

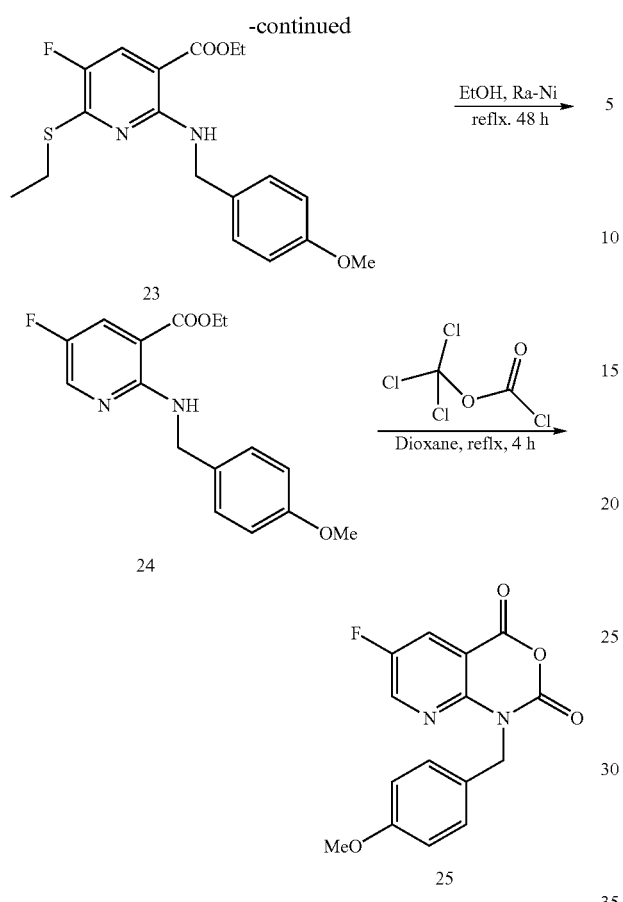

2-Hydroxy nicotinic acid was selected as a starting material for the synthesis of compounds with chloro substitution at 6-position of naphthyridine moiety. Chlorination of 2-hydroxynicotinic acid by sodium hypochlorite gave 5-chloro-2-hydroxy-nicotinic acid, depicted by formula 26 in Scheme 11. This intermediate was treated with thionyl chloride followed by refluxing with methanol to yield 2,5-dichloro-nicotinic acid methyl ester, depicted by formula 27 in Scheme 11. Amination of 2,5-dichloro-nicotinic acid methyl ester by p-methoxy benzyl amine gave 5-chloro-2-(4-methoxy-benzylamino)-nicotinic acid methyl ester, depicted by formula 28 in Scheme 11, which was converted into 6-chloro-1-(4-methoxy-benzyl)-1H-pyrido[2,3-d][1,3]oxazine-2,4-dione, depicted by formula 29 in Scheme 11, by reacting with trichloromethyl chloroformate as shown in Scheme 11.

Scheme 11

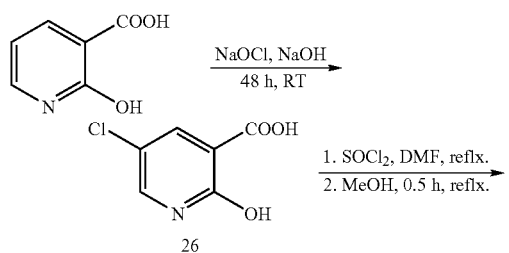

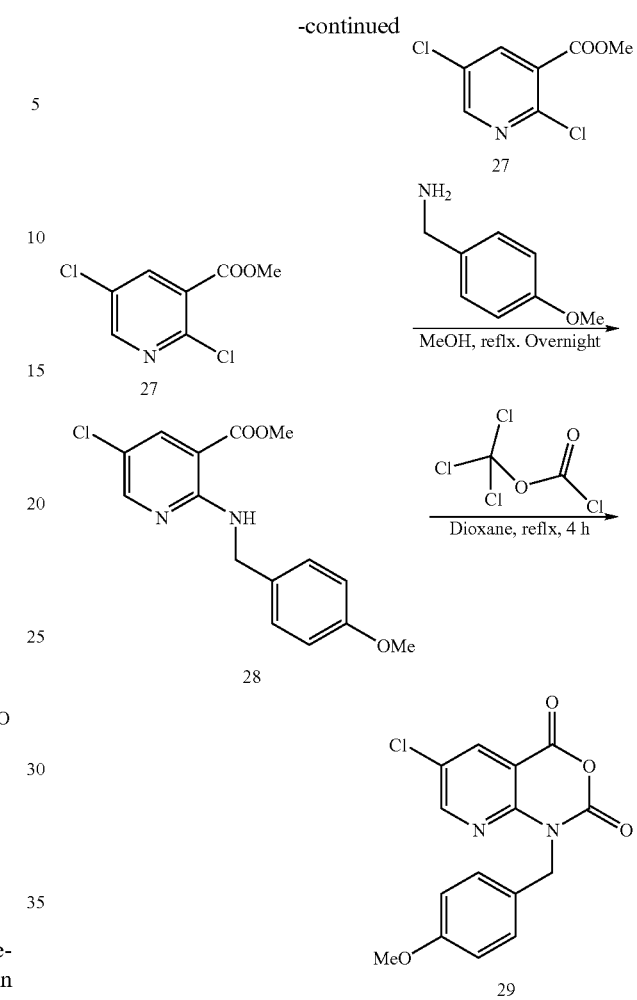

2-Bromo-5-methyl nicotinic acid ethyl ester, depicted by formula 31 in Scheme 12, was used as a starting material to prepare compounds with methyl substitution at 6-position of naphthyridine moiety. This starting material was prepared by condensation of propionaldehyde with ethyl cyanoacetate followed by cyclisation of resulted intermediate as shown in Scheme 12. Amination of 2-bromo-5-methyl nicotinic acid ethyl ester by p-methoxy benzyl amine gave 5-methyl-2-(4-methoxy-benzylamino)-nicotinic acid ethyl ester, depicted by formula 32 in Scheme 12, which was then converted into 6-methyl-1-(4-methoxy-benzyl)-1H-pyrido[2,3-d][1,3]oxazine-2,4-dione, depicted by formula 33 in Scheme 12, by reacting with trichloromethyl chloroformate as shown in Scheme 12.

Scheme 12

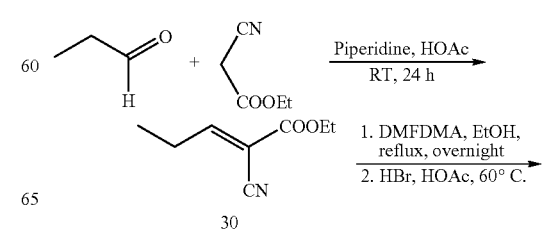

-continued

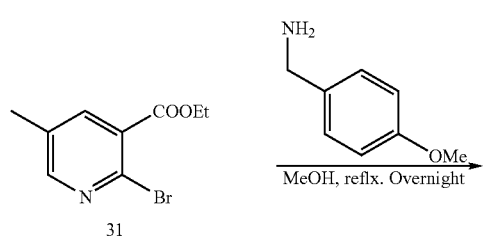

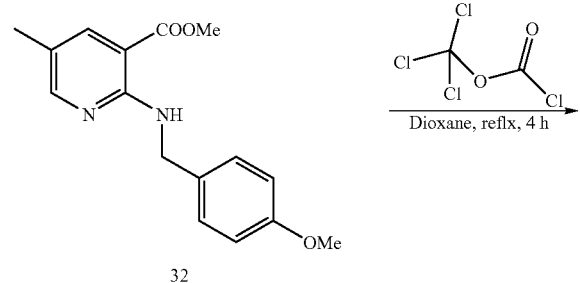

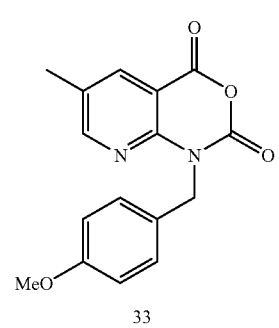

-continued

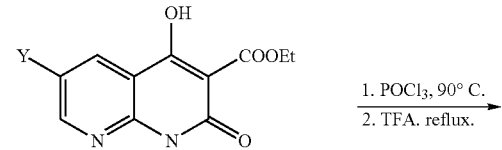

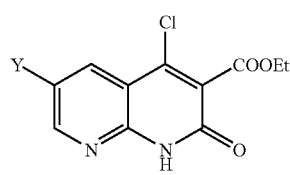

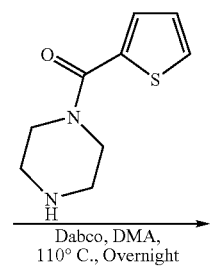

The compound with 6-substitution at naphthyridine moiety were prepared from the anhydride intermediates depicted by formula 25, 29 and 33 in Schemes 10, 11 and 12 respectively. The synthetic route applied for these compounds were similar to that of unsubstituted analogs as described above. The sequence of reactions used to prepare these compounds are shown in Scheme 13 and 14.

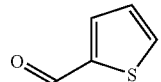

Scheme 13

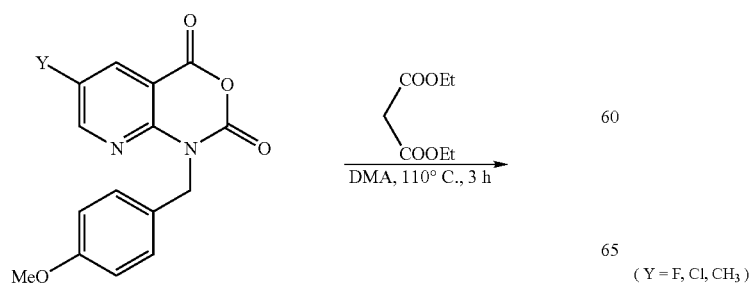

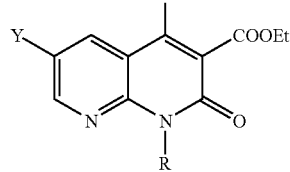

( Y = F, Cl, CH$_3$ )

Scheme 14

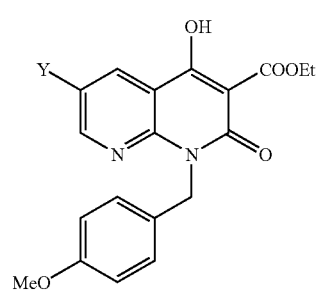
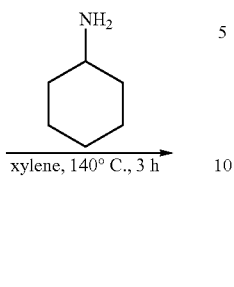

xylene, 140° C., 3 h

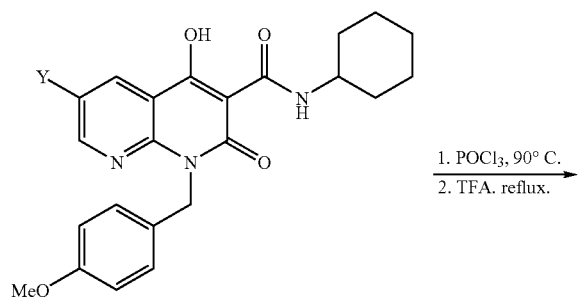

1. POCl₃, 90° C.
2. TFA. reflux.

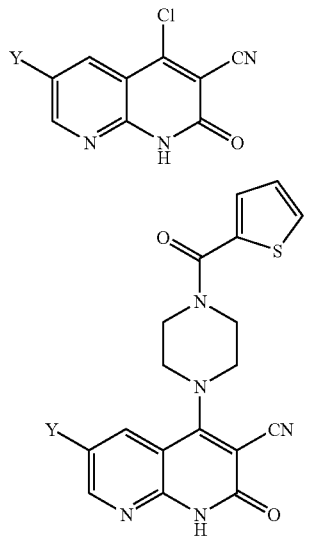

R—X
NaH, DMF, RT, 3 h
or
K₂CO₃, DMF, 90° C.

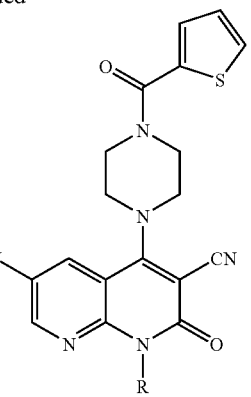

(Y = F, Cl, CH₃)

If it is preferred the substitutent in piperazine moiety is other than 2-thiophene corresponding N-acyl piperazine, prepared from acylation of t-butyl-1-piperazinecarboxylate with corresponding acid chloride followed by deprotection, can be used instead of piperazine-1-yl-thiophene-2-yl-methanone in Scheme 13 and 14.

Preparation of Compounds of General Structure
(Ic)

Preferred compounds of formula (Ic) include 1-R-4-[4-(thiophene-2-carbonyl)-piperazin-1-yl]-2-oxo-1,2-dihydro-[1,6]-naphthyridines-3-carboxylic acid ethyl ester wherein the substitutent R on the 1 position of the naphthyridinyl ring is hydrogen, alkyl, substituted alkyl, cycloalkyl, substituted cycloalkyl, aryl, substituted aryl, arylalkyl, substituted arylalkyl, acylalkyl, substituted acylalkyl, heterocycle, substituted heterocycle, —(CH₂)ₘC(=O)Ar, or —(CH₂)ₘNR₄R₅, wherein m is 0, 1, 2, 3, or 4.

The starting materials for this synthesis was 4-aminopyridine which was protected by boc group and converted to 4-tert-butoxycarbonylamino-nicotinic acid, depicted as formula 35 in Scheme 15, by ortholithiation followed by quenching with dry ice. This intermediate was reacted with trichloromethyl chloroformate to yield 1H-pyrido[4,3-d][1,3]oxazine-2,4-dione, depicted by formula 36 in Scheme 15, which was then converted to 4-chloro-2-oxo-1,2-dihydro-[1,6]-naphthyridine-3-carboxylic acid ethyl ester, depicted by formula 37 in Scheme 15. The reaction of 4-chloro-2-oxo-1,2-dihydro-[1,6]-naphthyridine-3-carboxylic acid ethyl ester with piperazine-1-yl-thiophene-2-yl-methanone gave 2-oxo-4-[4-(thiophene-2-carbonyl)-piperazin-1-yl]-1,2-dihydro-[1,6]-naphthyridin-3-carboxylic acid ethyl ester, depicted by formula 38 in Scheme 15, which was reacted with corresponding alkyl halides (R—X) to yield 1-N-substituted-2-oxo-4-[4-(thiophene-2-carbonyl)-piperazin-1-yl]-1,2-dihydro-[1,6]-naphthyridine-3-carboxylic acid ethyl esters as shown in Scheme 15.

Scheme 15

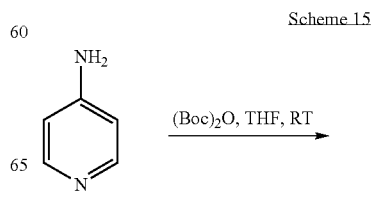

(Boc)₂O, THF, RT

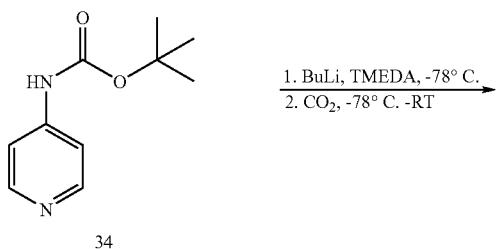

34

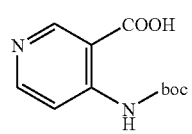

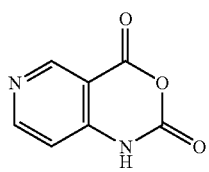

36

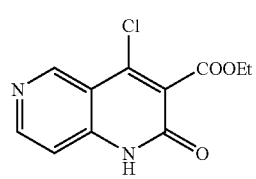

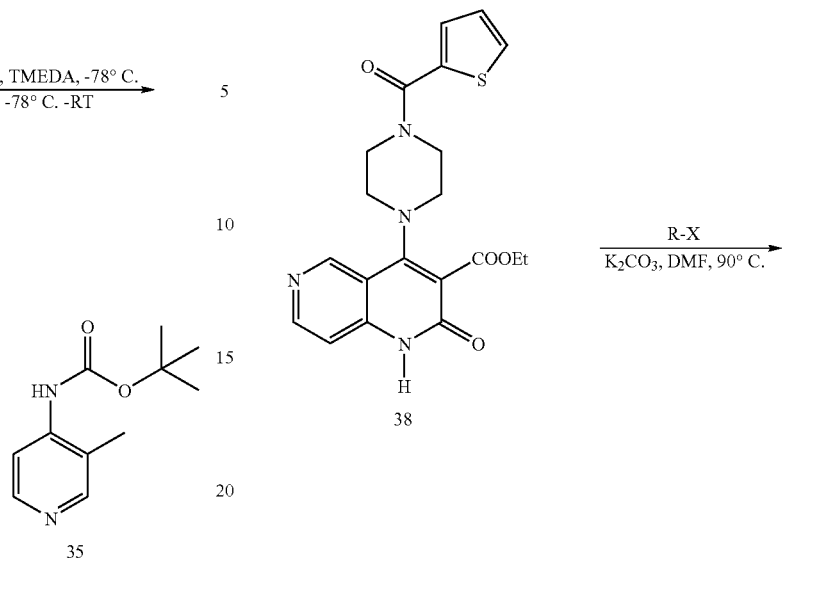

38

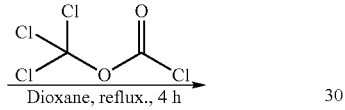

35

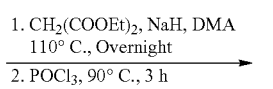

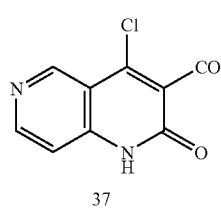

37

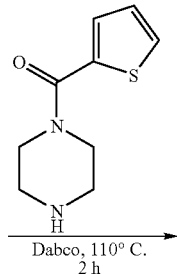

If it is preferred the substitutent in piperazine moiety is other than 2-thiophene corresponding N-acyl piperazine, prepared from acylation of t-butyl-1-piperazinecarboxylate with corresponding acid chloride followed by deprotection, can be used instead of piperazine-1-yl-thiophene-2-yl-methanone.

Alternatively, the intermediate 4-chloro-2-oxo-1,2-dihydro-[1,6]-naphthyridine-3-carboxylic acid ethyl ester, depicted by formula 37 in Scheme 15 can be prepared from 4-chloro pyridine or nicotinic acid as shown in Scheme 16. Ortholithiation of 4-chloropyridine by LDA followed by quenching with dry ice or lithiation of nicotinic acid followed by quenching with hexachloroethane can give chloronicotinic acid intermediate, depicted by formula 39 in Scheme 16. Amination of this intermediate can give 3-(4-methoxy-benzylamino)-nicotinic acid, depicted by formula 40 in Scheme 16, which was converted to 1-(4-methoxy-benzyl)-1H-pyrido[4,3-d][1,3]oxazine-2,4-dione depicted by formula 41 in Scheme 16, by treating with trichloromethyl chloroformate. This intermediate can be converted into 4-chloro-2-oxo-1,2-dihydro-[1,6]-naphthyridine-3-carboxylic acid ethyl ester, depicted by formula 37 in Scheme 15, as shown in Scheme 16.

Scheme 16

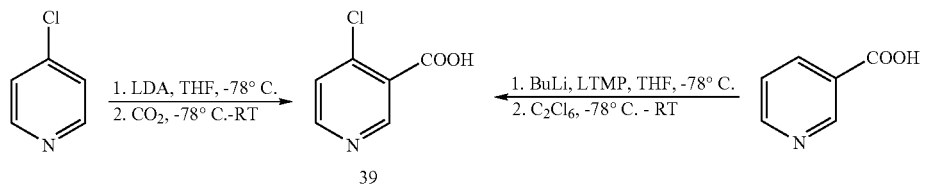

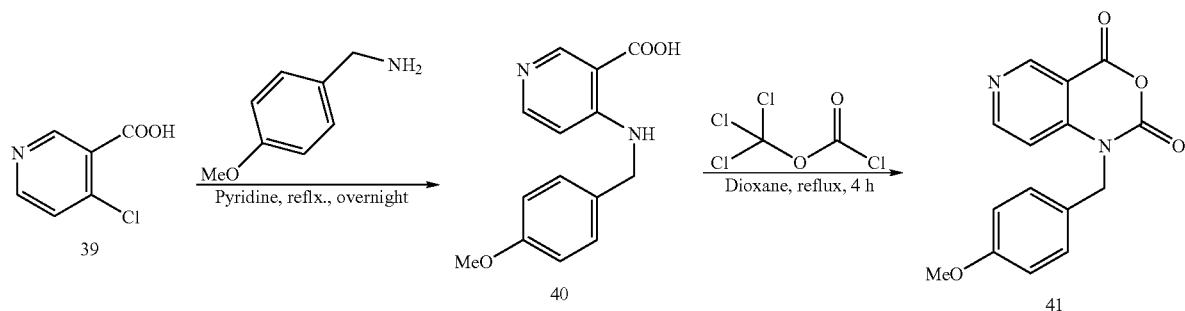

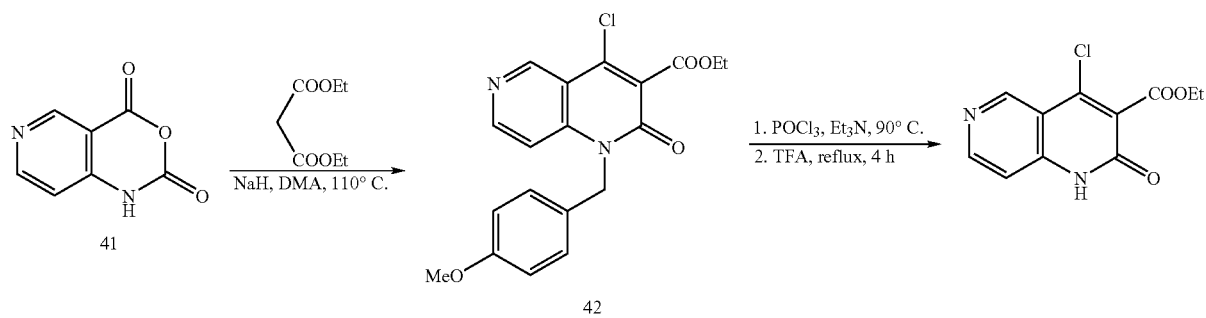

Preparation of Compounds of General Structure (Ic) with Carbonitrile Group at 3 Position of Naphthyridine Moiety Preferred compounds of formula (Ic) include 1-R-4-[4-(thiophene-2-carbonyl)-piperazin-1-yl]-2-oxo-1,2-dihydro-[1,6]-naphthyridines-3-carbonitrile wherein the substitutent R on the 1 position of the naphthyridinyl ring with nitrile group at 3-position is hydrogen, alkyl, substituted alkyl, cycloalkyl, substituted cycloalkyl, aryl, substituted aryl, arylalkyl, substituted arylalkyl, acylalkyl, substituted acylalkyl, heterocycle, substituted heterocycle, —$(CH_2)_mC(=O)$Ar, or —$(CH_2)_mNR_4R_5$, wherein m is 0, 1, 2, 3, or 4. These compounds can be prepared from intermediate 4-chloro-1-(4-methoxy-benzyl)-2-oxo-1,2-dihydro-[1,6]-naphthyridine-3-carboxylic acid ethyl ester, depicted by formula 42 in Scheme 16 by applying the reaction sequences and methods similar to that of [1,8]naphthyridine series described above. The sequence of steps in the synthesis of these compounds are shown in Scheme 17.

Scheme 17

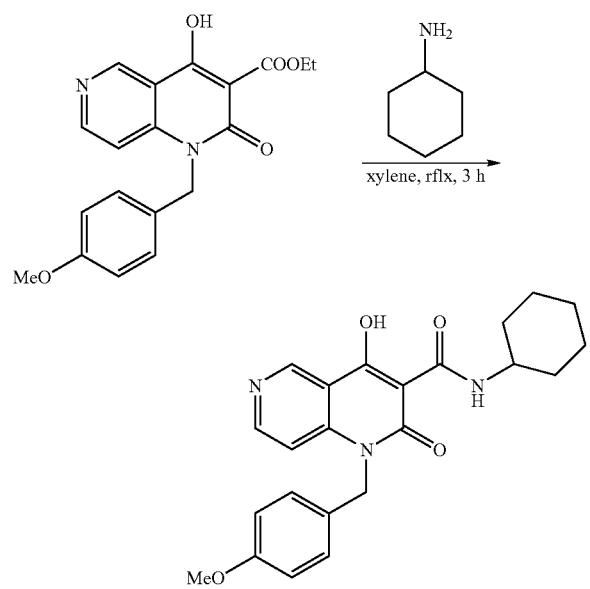

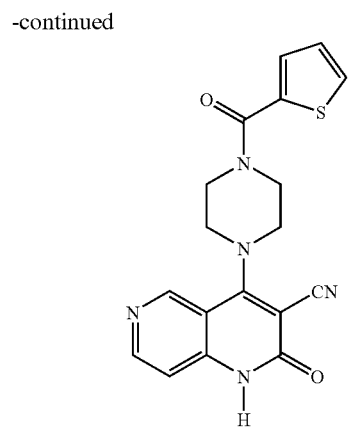
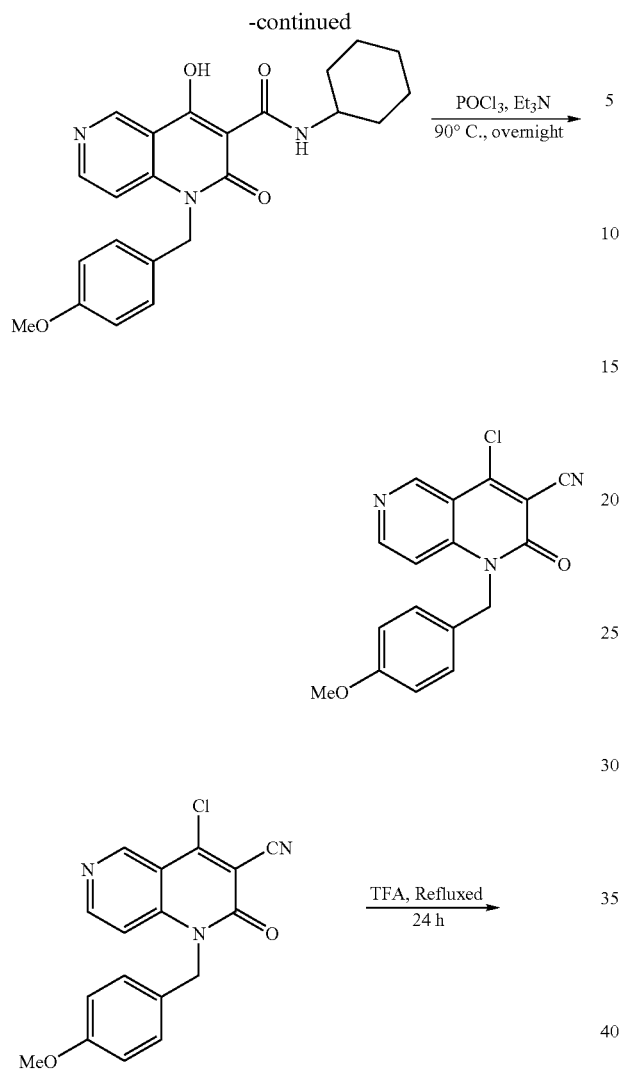
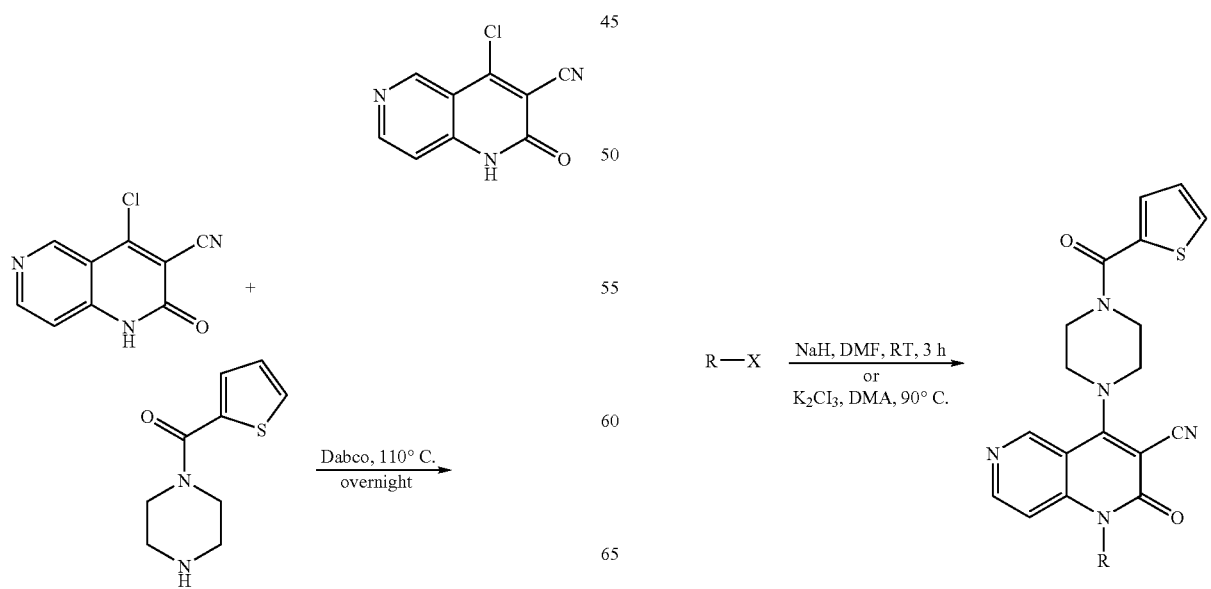

If it is preferred the substitutent in piperazine moiety is other than 2-thiophene corresponding N-acyl piperazine, prepared from acylation of t-butyl-1-piperazinecarboxylate with corresponding acid chloride followed by deprotection, can be used instead of piperazine-1-yl-thiophene-2-yl-methanone.

Preparation Compounds of General Structure (Ib)

Preferred compounds of formula (Ib) include 1-R-4-[4-(thiophene-2-carbonyl)-piperazin-1-yl]-2-oxo-1,2-dihydro-[1,7]-naphthyridines-3-carboxylic acid ethyl ester wherein the substitutent R on the 1 position of the naphthyridinyl ring is hydrogen, alkyl, substituted alkyl, cycloalkyl, substituted cycloalkyl, aryl, substituted aryl, arylalkyl, substituted arylalkyl, acylalkyl, substituted acylalkyl, heterocycle, substituted heterocycle, —$(CH_2)_m C(=O)Ar$, or —$(CH_2)_m NR_4 R_5$, wherein m is 0, 1, 2, 3, or 4. These compounds can be prepared by using pyridine 3,4-dicarboxylic acid as a starting material. Pyridine 3,4-dicarboxylic acid can react with acetic anhydride to give furo[3,4-c]pyridine-1,3-dione, depicted by formula 43 in Scheme 18, which can be converted to pyrrolo[3,4-c]pyridine-1,3-dione, depicted by formula 44 in Scheme 18, by reacting with acetamide. 3-Amino isonicotinic acid can be prepared from Hoffmann degradation of this intermediate. Reductive amination of 3-amino isonicotinic acid can give 3-(4-methoxy-benzylamino)isonicotinic acid, depicted by formula 46 in Scheme 18. This intermediate can also be prepared from alkylation of 3-amino isonicotinic acid by using lithium hexamethyl disilazide and p-methoxybenzylchloride as shown in Scheme 18.

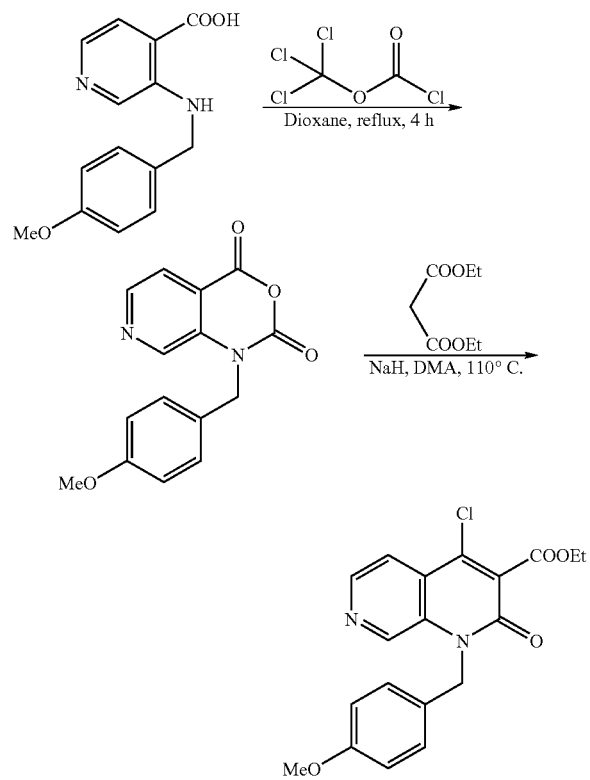

Scheme 19

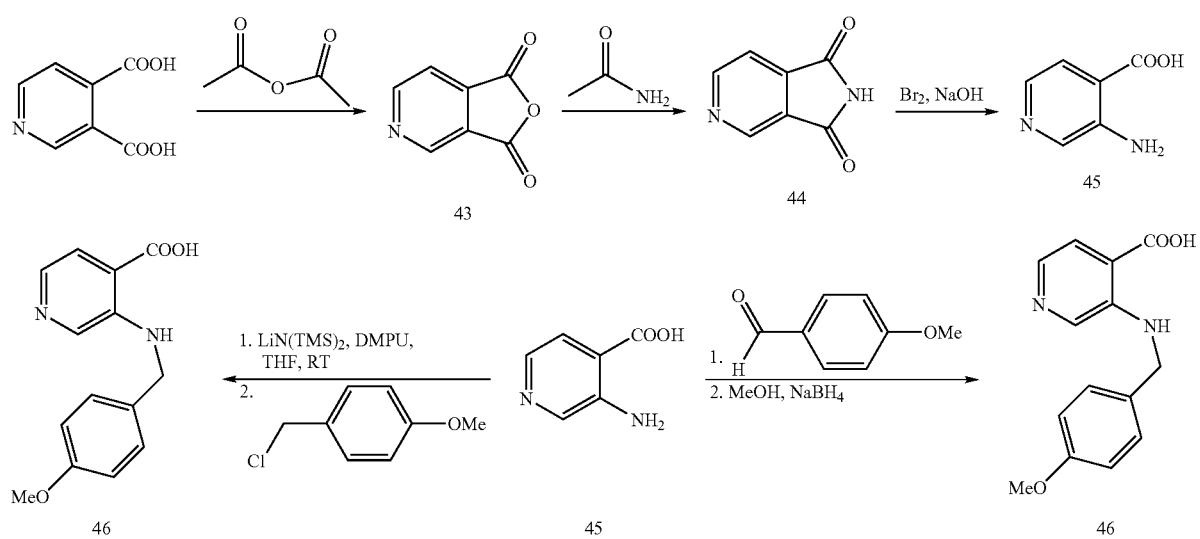

Scheme 18

The intermediate 3-(4-methoxy-benzylamino)isonicotinic acid, depicted by formula 46 in Scheme 18, can be used to synthesized compounds of the general structure (Ib) by applying similar reaction sequences and methods used for the synthesis of compounds of general structure (Ia). The sequence of the reactions that can be used to prepare these compounds are given in Scheme 19.

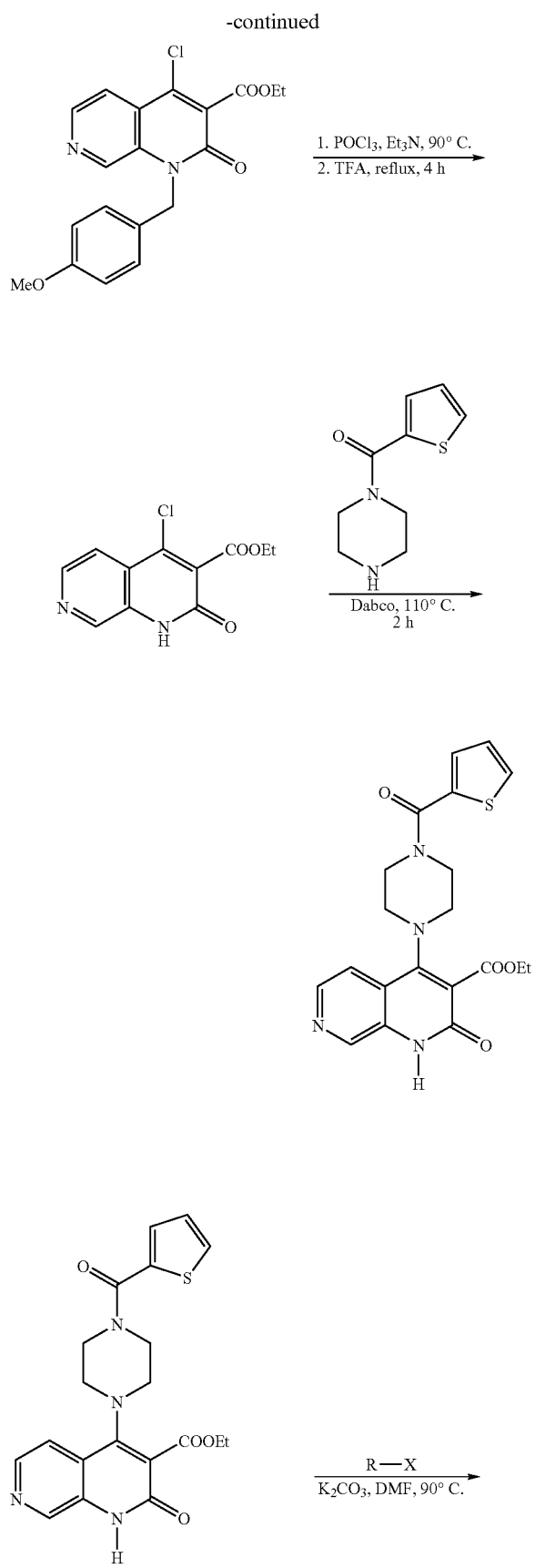

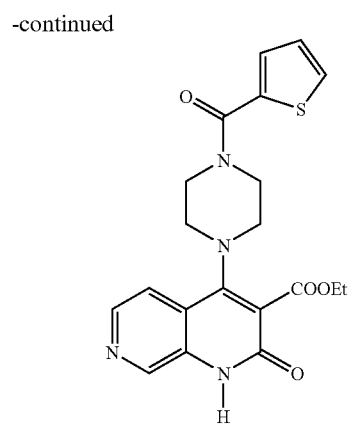

Preparation of Compounds of General Structure (Ib) with Carbonitrile Group at 3 Position of Naphthyridine Moiety Preferred compounds of formula (Ib) include 1-R-4-[4-(thiophene-2-carbonyl)-piperazin-1-yl]-2-oxo-1,2-dihydro-[1,7]-naphthyridines-3-carbonitrile wherein the substitutent R on the 1 position of the naphthyridinyl ring with nitrile group at 3-position is hydrogen, alkyl, substituted alkyl, cycloalkyl, substituted cycloalkyl, aryl, substituted aryl, arylalkyl, substituted arylalkyl, acylalkyl, substituted acylalkyl, heterocycle, substituted heterocycle, —$(CH_2)_mC(=O)$Ar, or —$(CH_2)_mNR_4R_5$, wherein m is 0, 1, 2, 3, or 4. These compounds can be prepared from intermediate 4-hydroxy-1-(4-methoxy-benzyl)-2-oxo-1,2-dihydro-[1,7]-naphthyridine-3-carboxylic acid ethyl ester, depicted by formula 47 in Scheme 20 by applying the reaction sequences and methods similar to that of [1,8]naphthyridine series described above. The sequence of steps in the synthesis of these compounds are shown in Scheme 21.

Scheme 20

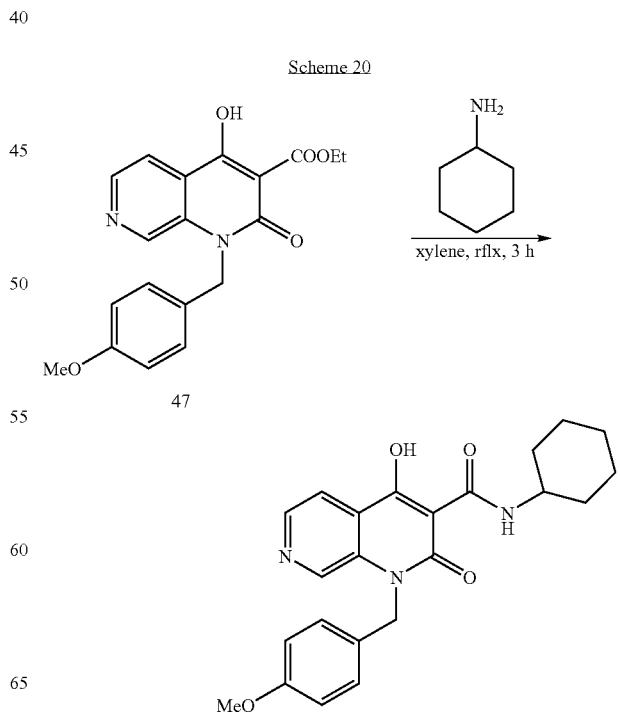

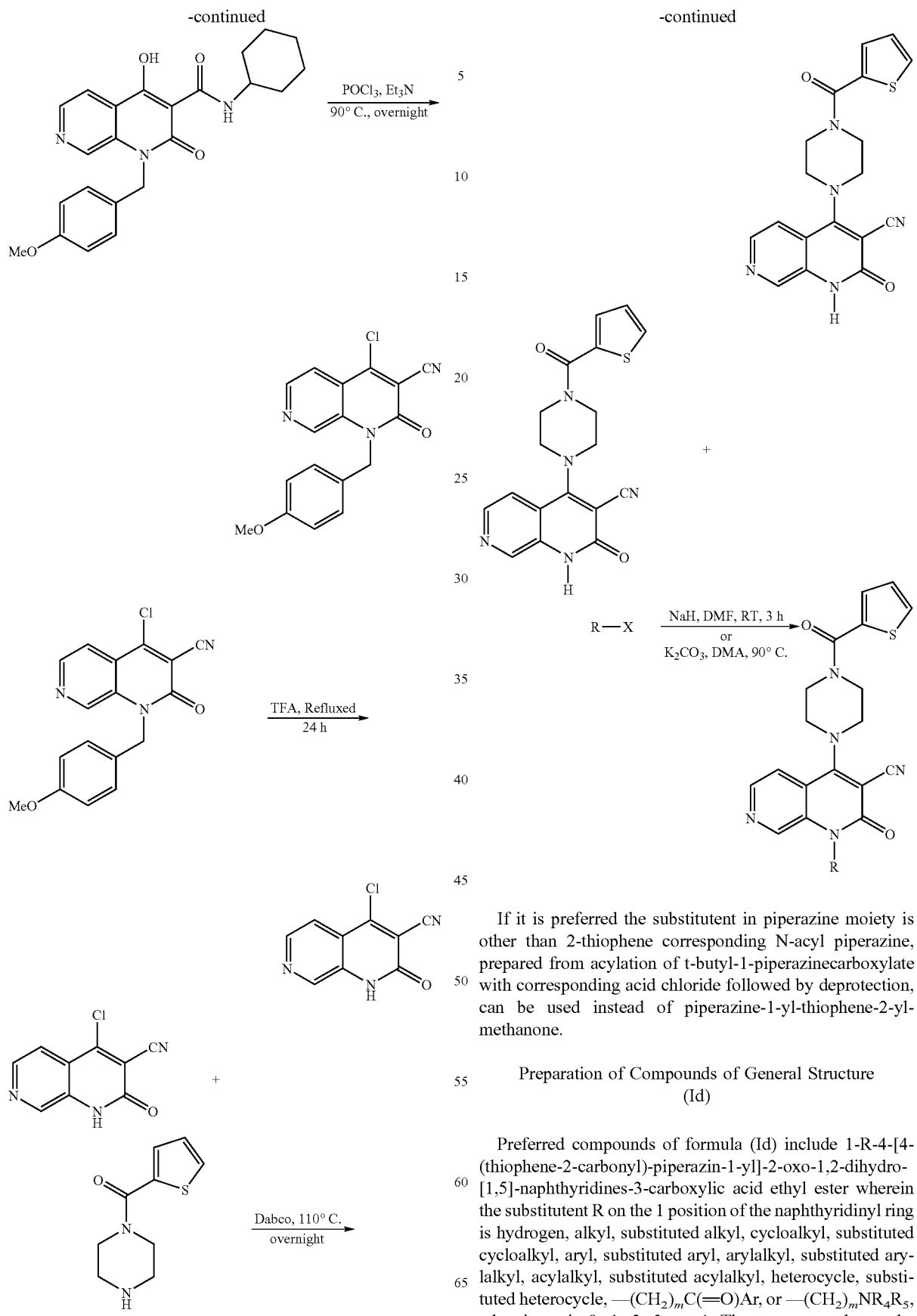

If it is preferred the substitutent in piperazine moiety is other than 2-thiophene corresponding N-acyl piperazine, prepared from acylation of t-butyl-1-piperazinecarboxylate with corresponding acid chloride followed by deprotection, can be used instead of piperazine-1-yl-thiophene-2-yl-methanone.

Preparation of Compounds of General Structure
(Id)

Preferred compounds of formula (Id) include 1-R-4-[4-(thiophene-2-carbonyl)-piperazin-1-yl]-2-oxo-1,2-dihydro-[1,5]-naphthyridines-3-carboxylic acid ethyl ester wherein the substitutent R on the 1 position of the naphthyridinyl ring is hydrogen, alkyl, substituted alkyl, cycloalkyl, substituted cycloalkyl, aryl, substituted aryl, arylalkyl, substituted arylalkyl, acylalkyl, substituted acylalkyl, heterocycle, substituted heterocycle, —(CH$_2$)$_m$C(=O)Ar, or —(CH$_2$)$_m$NR$_4$R$_5$, wherein m is 0, 1, 2, 3, or 4. These compounds can be prepared by using pyridine 2,3-dicarboxylic acid as a starting material. Pyridine 2,3-dicarboxylic acid can react with acetic anhydride to give furo[3,4-b]pyridine-5,7-dione, depicted by formula 48 in Scheme 21, which can be converted to pyrrolo[3,4-b]pyridine-5,7-dione, depicted by formula 49 in Scheme 21, by reacting with acetamide. 3-Amino pyridine-2-carboxylic acid can be prepared from Hoffmann degradation of this intermediate. Reductive amination of 3-Amino pyridine-2-carboxylic acid can give 3-(4-methoxy-benzylamino)-pyridine-2-carboxylic acid, depicted by formula 51 in Scheme 21. This intermediate can also be prepared from alkylation of 3-amino isonicotinic acid by using lithium hexamethyl disilazide and p-methoxybenzylchloride as shown in Scheme 21.

-continued

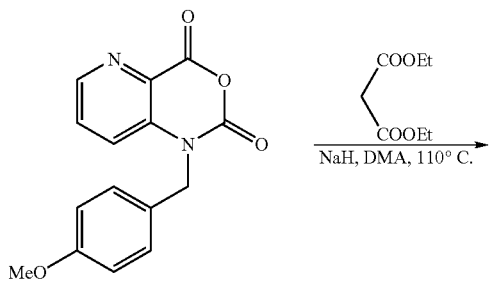

Scheme 21

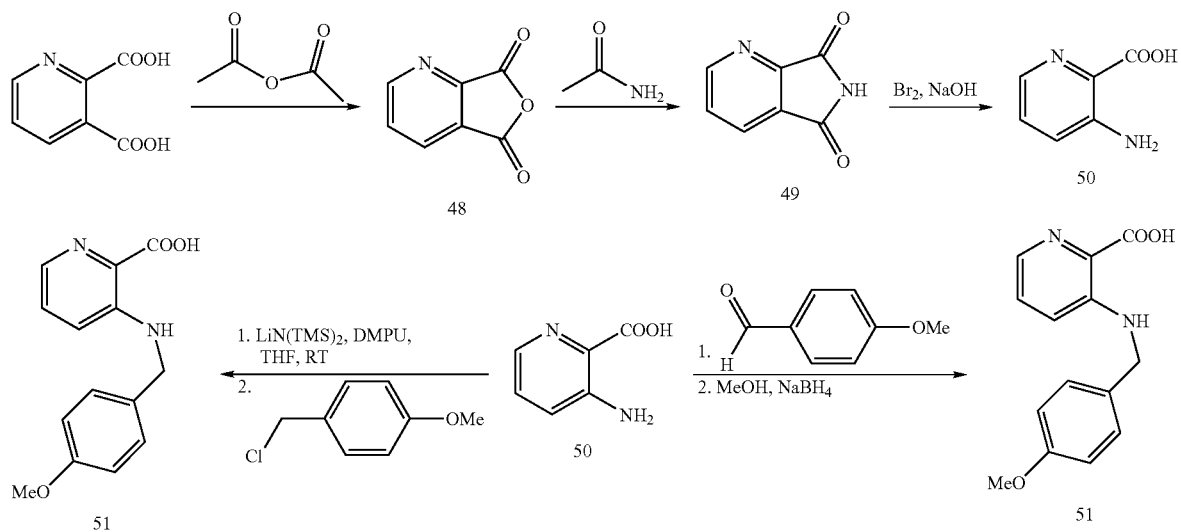

The intermediate 3-(4-methoxy-benzylamino)-pyridine-2-carboxylic acid, depicted by formula 51 in Scheme 21, can be used to synthesized compounds of the general structure (Id) by applying similar reaction sequences and methods used for the synthesis of compounds of general structure (Ia). The sequence of the reactions that can be used to prepare these compounds are given in Scheme 22.

-continued

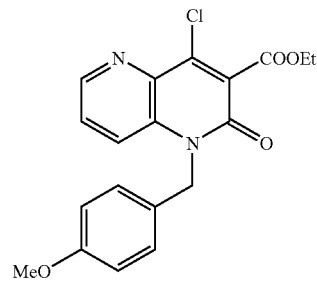

Scheme 22

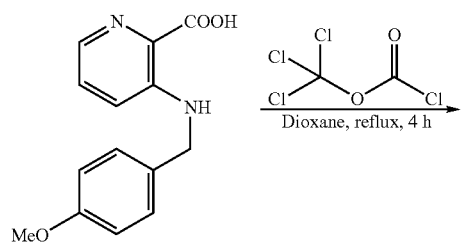

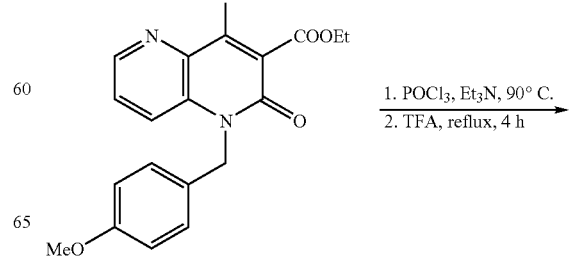

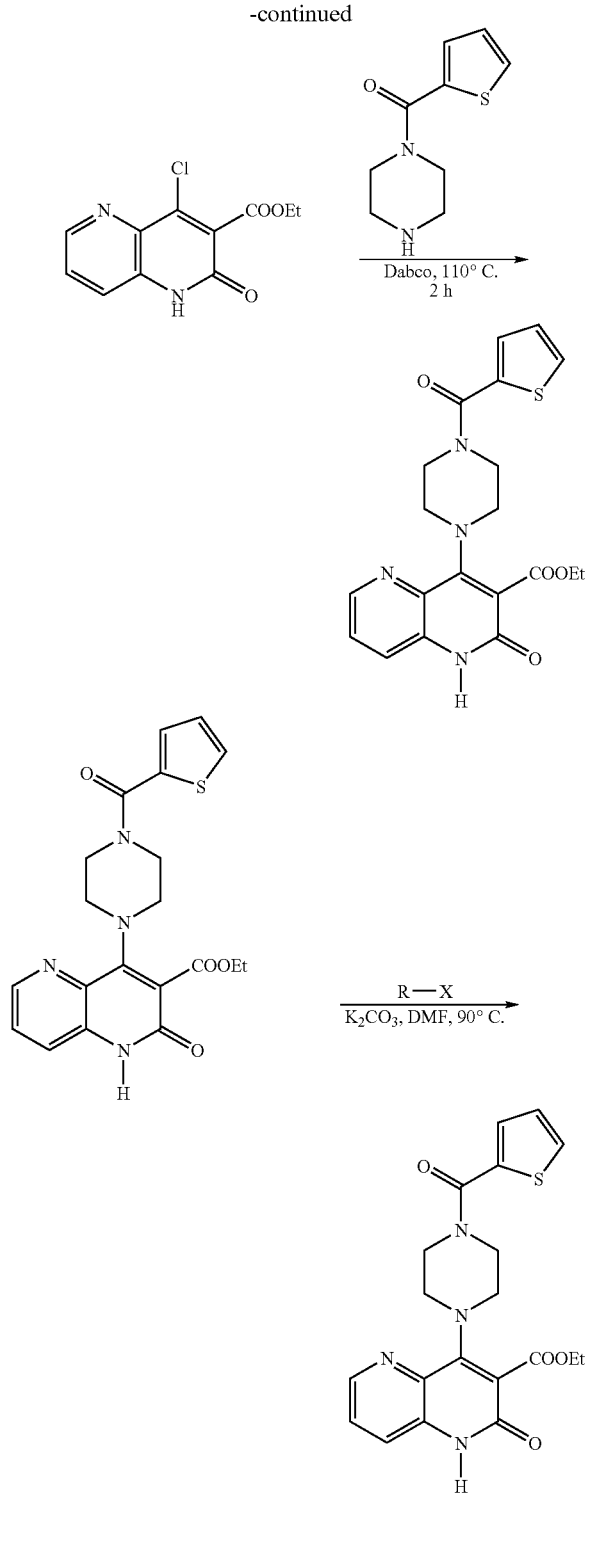

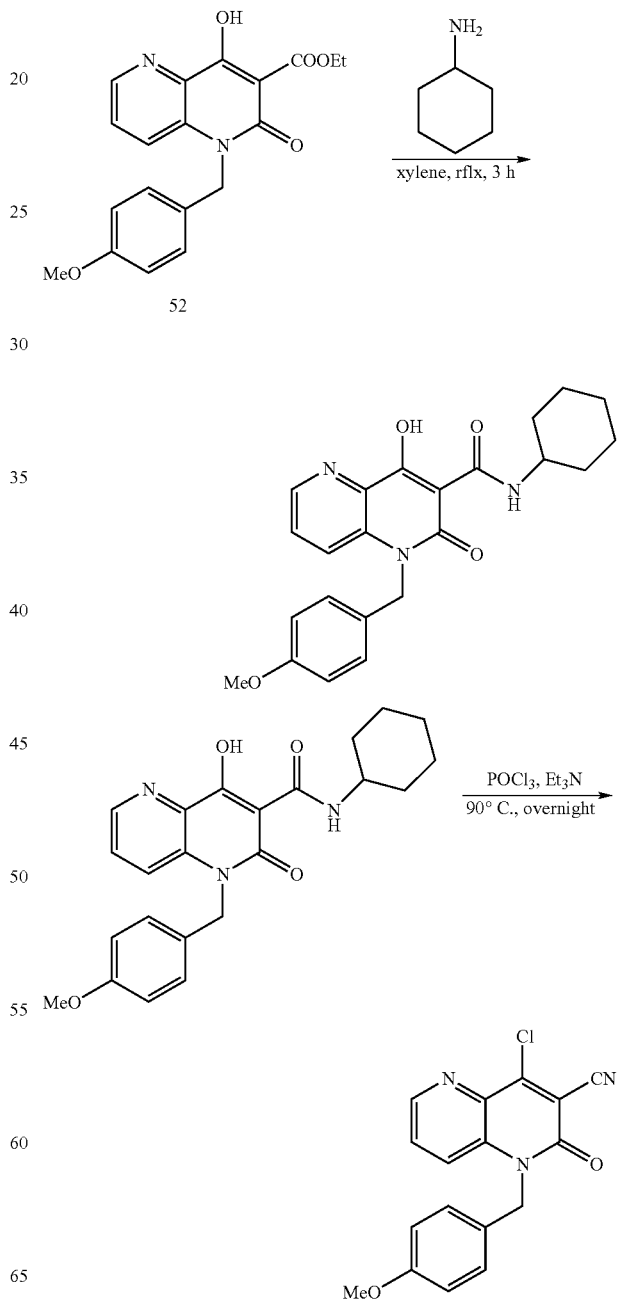

group at 3-position is hydrogen, alkyl, substituted alkyl, cycloalkyl, substituted cycloalkyl, aryl, substituted aryl, arylalkyl, substituted arylalkyl, acylalkyl, substituted acylalkyl, heterocycle, substituted heterocycle, —$(CH_2)_mC(=O)$Ar, or —$(CH_2)_mNR_4R_5$, wherein m is 0, 1, 2, 3, or 4. These compounds can be prepared from intermediate 4-hydroxy-1-(4-methoxy-benzyl)-2-oxo-1,2-dihydro-[1,5]-naphthyridine-3-carboxylic acid ethyl ester, depicted by formula 52 in Scheme 23 by applying the reaction sequences and methods similar to that of [1,8]naphthyridine series described above. The sequence of steps in the synthesis of these compounds are shown in Scheme 23.

Preparation of Compounds of General Structure (Id) with Carbonitrile Group at 3 Position of Naphthyridine Moiety Preferred compounds of formula (Id) include 1-R-4-[4-(thiophene-2-carbonyl)-piperazin-1-yl]-2-oxo-1,2-dihydro-[1,5]-naphthyridines-3-carbonitrile wherein the substitutent R on the 1 position of the naphthyridinyl ring with nitrile

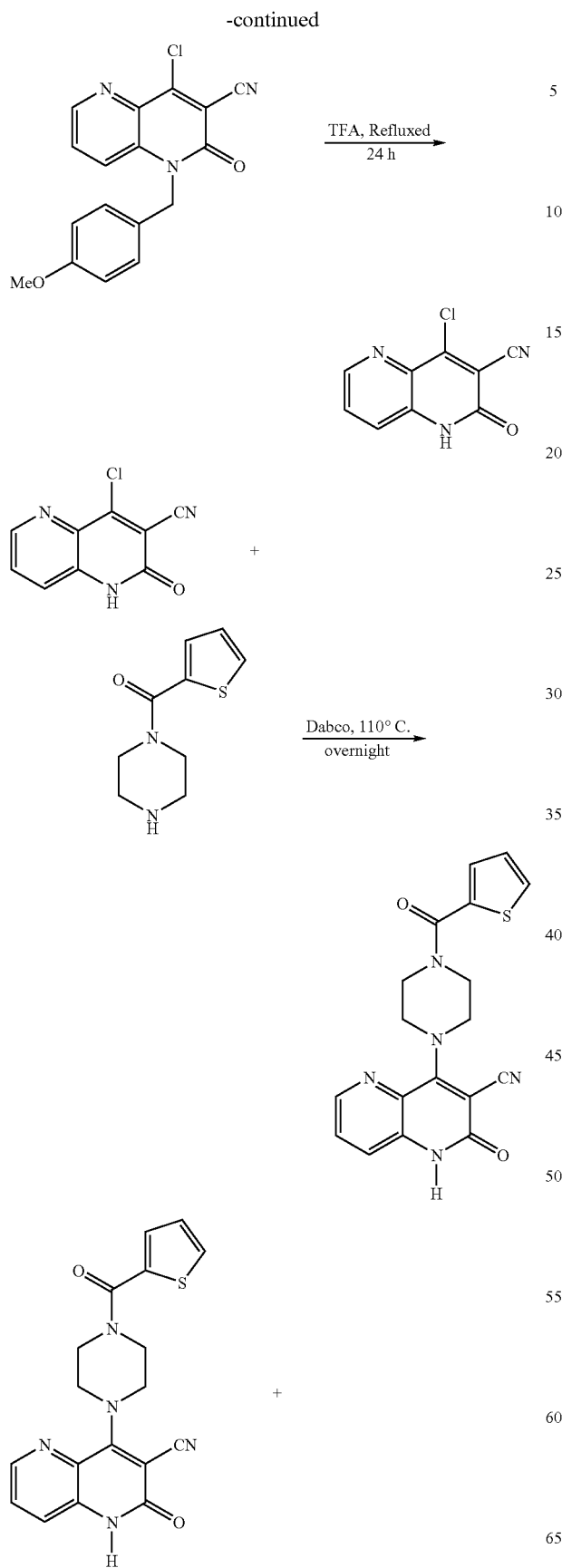

If it is preferred the substitutent in piperazine moiety is other than 2-thiophene corresponding N-acyl piperazine, prepared from acylation of t-butyl-1-piperazinecarboxylate with corresponding acid chloride followed by deprotection, can be used instead of piperazine-1-yl-thiophene-2-yl-methanone.

MIF as a Drug Target

Macrophage migration inhibitory factor (MIF) can be well suited for analysis as a drug target as its activity has been implicated in a variety of pathophysiological conditions. For instance, MIF has been shown to be a significant mediator in both inflammatory responses and cellular proliferation. In this regard, MIF has been shown to play roles as a cytokine, a pituitary hormone, as glucocorticoid-induced immunomodulator, and just recently as a neuroimmunomodulator and in neuronal function. Takahashi et al., *Mol. Med.* 4:707-714, 1998; Bucala, *Ann. N.Y. Acad. Sci.* 840:74-82, 1998; Bacher et al., *Mol. Med.* 4(4):217-230, 1998. Further, it has been recently demonstrated that anti-MIF antibodies have a variety of uses, notably decreased tumor growth, along with an observed reduction in angiogenesis. Ogawa et al., *Cytokine* 12(4):309-314, 2000; Metz and Bucala (supra). Accordingly, small molecules that can inhibit MIF have significant value in the treatment of inflammatory responses, reduction of angiogenesis, viral infection, bacterial infection, treatment of cancer (specifically tumorigenesis and apoptosis), treatment of graft versus host disease and associated tissue rejection. A MIF inhibitor can be particularly useful in a variety of immune related responses, tumor growth, glomerulonephritis, inflammation, malarial anemia, septic shock, tumor associated angiogenesis, vitreoretinopathy, psoriasis, graft versus host disease (tissue rejection), atopic dermatitis, rheumatoid arthritis, inflammatory bowel disease, inflammatory lung disorders, otitis media, Crohn's disease, acute respiratory distress syndrome, delayed-type hypersensitivity. A MIF inhibitor can also be useful in the treatment of stress and glucocorticoid function disorders, e.g. counter regulation of glucocorticoid action; or overriding of glucocorticoid mediated suppression of arachidonate release (Cys-60 based catalytic MIF oxidoreductase activity or JAB1/CSN5-MIF-interaction based mechanism).

One example of the utility of a MIF inhibitor can be evidenced by the fact that following endotoxin exposure detectable serum concentrations of MIF gradually increase during the acute phase (1-8 hours), peak at 8 hours and persist during the post-acute phase (>8 hours) for up to 20 hours. While not limited to any theory of operation, MIF may likely be produced by activated T-cells and macrophages during the proinflammatory stage of endotoxin-induced shock, e.g. as part of the localized response to infection. Once released by a pro-inflammatory stimulus, e.g. low concentrations of LPS, or by TNF-α and IFN-γ, macrophage-derived MIF may be the probable source of MIF produced during the acute phase of endotoxic shock. Both the pituitary, which releases MIF in response to LPS, and macrophages are the probable source of MIF in the post-acute phase of endotoxic shock, when the infection is no longer confined to a localized site. See, e.g. U.S. Pat. No. 6,080,407, incorporated herein by reference in its entirety and describing these results with anti-MIF antibodies.

Inhibitors of preferred embodiments inhibit lethality in mice following LPS challenge and likely attenuate IL-1β and TNF-α levels. Accordingly, a variety of inflammatory conditions can be amenable to treatment with a MIF inhibitor. In this regard, among other advantages, the inhibition of MIF activity and/or release can be employed to treat inflammatory response and shock. Beneficial effects can be achieved by intervention at both early and late stages of the shock response. In this respect, while not limited to any theory or mechanism responsible for the protective effect of MIF inhibition, anti-MIF studies have demonstrated that introduction of anti-MIF antibodies is associated with an appreciable (up to 35-40%) reduction in circulating serum TNF-α levels. This reduction is consistent with the TNF-α-inducing activity of MIF on macrophages in vitro, and suggests that MIF may be responsible, in part, for the extremely high peak in serum TNF-α level that occurs 1-2 hours after endotoxin administration despite the fact that MIF cannot be detected in the circulation at this time. Thus, MIF inhibition therapy can be beneficial at the early stages of the inflammatory response.

MIF also plays a role during the post-acute stage of the shock response, and therefore, offers an opportunity to intervene at late stages where other treatments, such as anti-TNF-α therapy, are ineffective. Inhibition of MIF can protect against lethal shock in animals challenged with high concentrations of endotoxin (i.e., concentrations that induce release of pituitary MIF into the circulation), and in animals challenged with TNF-α. Accordingly, the ability to inhibit MIF and protect animals challenged with TNF indicates that neutralization of MIF during the later, post-acute phase of septic shock can be efficacious.

TNF-α and IL-1β levels are correlated at least in some instances to MIF levels. Accordingly, an anti-MIF small molecule can be useful in a variety of TNF-α and/or IL-1β associated disease states including transplant rejection, immune-mediated and inflammatory elements of CNS disease (e.g., Alzheimer's, Parkinson's, multiple sclerosis, etc.), muscular dystrophy, diseases of hemostasis (e.g., coagulopathy, veno occlusive diseases, etc.), allergic neuritis, granuloma, diabetes, graft versus host disease, chronic renal damage, alopecia (hair loss), acute pancreatitis, joint disease, congestive heart failure, cardiovascular disease (restenosis, atherosclerosis), joint disease, and osteoarthritis.

Further, additional evidence in the art has indicated that steroids while potent inhibitors of cytokine production actually increase MIF expression. Yang et al., *Mol. Med.* 4(6): 413-424, 1998; Mitchell et al., *J. Biol. Chem.* 274(25): 18100-18106, 1999; Calandra and Bucala, *Crit. Rev. Immunol.* 17(1):77-88, 1997; Bucala, *FASEB J.* 10(14): 1607-1613, 1996. Accordingly, it can be of particular utility to utilize MIF inhibitors in combination with steroidal therapy for the treatment of cytokine mediated pathophysiological conditions, such as inflammation, shock, and other cytokine-mediated pathological states, particularly in chronic inflammatory states such as rheumatoid arthritis. Such combination therapy can be beneficial even subsequent to the onset of pathogenic or other inflammatory responses. For example, in the clinical setting, the administration of steroids subsequent to the onset of septic shock symptoms has proven of little benefit. See Bone et al., *N. Engl. J. Med.* 317: 653-658, 1987; Spring et al., *N. Engl. J. Med.* 311: 1137-1141, 1984. Combination steroids/MIF inhibition therapy can be employed to overcome this obstacle. Further, one of skill in the art understands that such therapies can be tailored to inhibit MIF release and/or activity locally and/or systemically.

Assays

The effectiveness of a compound as an inhibitor of MIF can be determined by various assay methods. Suitable inhibitors of preferred embodiments are capable of decreasing one or more activities associated with MIF and/or MIF export. A compound of structure (Ia), (Ib), (Ic), (Id) or any other structure can be assessed for activity as an inhibitor of MIF by one or more generally accepted assays for this purpose, including (but not limited to) the assays described below.

The assays can generally be divided into three categories, including assays which monitor export, those that monitor effector or small molecule binding, and those that monitor MIF activity. However, combinations of these assays are within the scope of the preferred embodiments. Surprisingly, it appears that epitope mapping of MIF acts as surrogate for biological activity. For example, in one assay, the presence of a candidate inhibitor blocks the detection of export of MIF from cells (e.g. THP-1 cells) measured using a monoclonal antibody such as that commercially available from R&D systems (Minneapolis, Minn.) whereas a polyclonal antibody demonstrates that MIF is present. Further, cellular based or in vitro assays can be employed to demonstrate that these potential inhibitors inhibit MIF activity. In an alternative, these two assays (i.e., binding and activity assays) can be combined into a singular assay which detects binding of a test compound (e.g. the ability to displace monoclonal antibodies or inhibit their binding) while also affecting MIF activity. Such assays include combining an ELISA type assay (or similar binding assay) with a MIF tautomerism assay or similar functional assay. As one of ordinary skill in the art readily recognizes, the exact assay employed is irrelevant, provided it is able to detect the ability of the compound of interest to bind MIF. In addition, the assay preferably detects the ability of the compound to inhibit a MIF activity because it selects for compounds that interact with biologically active MIF and not inactive MIF.

Compounds demonstrating the ability to inhibit monoclonal antibody binding to biologically active and not inactive MIF (e.g. small molecule inhibited), necessarily indicate the presence of a compound (e.g. a small molecule) that is interacting with MIF either in a fashion which changes the conformation of MIF or blocks an epitope necessary for antibody binding. In other embodiments, MIF inhibitory activity can also be recognized as a consequence of interfering with the formation of a polypeptide complex that includes MIF; disturbing such a complex can result in a conformational change inhibiting detection. Accordingly, the use of assays that monitor conformational changes in MIF are advantageous when employed either in addition to assays measuring competition between compounds, such as small molecules with mAb, or as a replacement of such an assay. A variety of such assays are known in the art and include, calorimetry, circular-dichroism, fluorescence energy transfer, light-scattering, nuclear magnetic resonance (NMR), surface plasmon resonance, scintillation proximity assays (see U.S. Pat. No. 5,246,869), and the like. See also WO02/07720-A1 and WO97/29635-A1. Accordingly, one of skill in the art recognizes that any assay that indicates binding and preferably conformational change or placement near the active site of MIF can be utilized. Descriptions of several of the more complicated proximity assays and conformational assays are set forth below, this discussion is merely exemplary and in no way should be construed as limiting to the type of techniques that can be utilized in preferred embodiments.

In one example, circular dichroism can be utilized to determine candidate inhibitor binding. Circular dichroism (CD) is based in part on the fact that most biological protein macromolecules are made up of asymmetric monomer units, L-amino acids, so that they all possess the attribute of optical activity. Additionally, rigid structures like DNA or an alpha helical polypeptide have optical properties that can be measured using the appropriate spectroscopic system. In fact, large changes in an easily measured spectroscopic parameter can provide selective means to identify conformational states and changes in conformational states under various circumstances, and sometimes to observe the perturbation of single groups in or attached to the macromolecule. Further, CD analysis has been frequently employed to probe the interactions of various macromolecules with small molecules and ligands. See Durand et al., *Eur. Biophys. J.* 27(2):147-151, 1998; Kleifeld et al., *Biochem.* 39(26):7702-7711, 2000; Bianchi et al., *Biochem.* 38(42):13844-13852, 1999; Sarver et al., *Biochim. Biophys. Acta* 1434(2):304-316, 1999.

The Pasteur principle states that an optically active molecule must be asymmetric; that is, the molecule and its mirror image cannot be superimposed. Plane polarized light is a combination of left circularly polarized light and right circularly polarized light traveling in phase. The interaction of this light with an asymmetric molecule results in a preferential interaction of one circularly polarized component which, in an absorption region, is seen as a differential absorption (i.e., a dichroism). See Urry, D. W., Spectroscopic Approaches to Biomolecular Conformation, American Medical Association Press, Chicago, Ill., pp. 33-120 (1969); Berova and Woody, Circular Dichroism: Principles and Applications, John Wiley & Sons, N.Y., (2000).

Circular dichroism, then, is an absorptive phenomenon that results when a chromophore interacts with plane polarized light at a specific wavelength. The absorption band can be either negative or positive depending on the differential absorption of the right and left circularly polarized components for that chromophore. Unlike optical rotatory dispersion (ORD) that measures the contributions of background and the chromophore of interest many millimicrons from the region of actual light interaction, CD offers the advantage of measuring optical events at the wavelength at which the event takes place. Circular dichroism, then, is specific to the electronic transition of the chromophore. See Berova and Woody, Circular Dichroism: Principles and Applications, John Wiley & Sons, N.Y., (2000).

Application of circular dichroism to solutions of macromolecules has resulted in the ability to identify conformation states (Berova and Woody, Circular Dichroism: Principles and Applications, John Wiley & Sons, N.Y., (2000)). The technique can distinguish random coil, alpha helix, and beta chain conformation states of macromolecules. In proteins, alpha helical fibrous proteins show absorption curves closely resembling those of alpha helical polypeptides, but in globular proteins of known structure, like lysozyme and ribonuclease, the helical structures are in rather poor agreement with X-ray crystallography work. A further source of difficulty in globular proteins is the prevalence of aromatic chromophores on the molecules around 280 nm. An interesting example of helical changes has been demonstrated using myoglobin and apomyoglobin. After removing the prosthetic group heme, the apoprotein remaining has a residual circular dichroic ellipticity reduced by 25%. This loss of helix is attributable to an uncoiling of 10-15 residues in the molecule. Other non-peptide, optically active chromophores include tyrosine, tryptophan, phenylalanine, and cysteine when located in the primary amino acid sequence of a macromolecule. Examples of non-peptide ellipticities include the disulfide transition in ribonuclease and the cysteine transitions of insulin.

Accordingly, circular dichroism can be employed to screen candidate inhibitors for the ability to affect the conformation of MIF.

In certain embodiments, MIF-binding agent or inhibitor complex formation can be determined by detecting the presence of a complex including MIF and a detectably labeled binding agent. As described in greater detail below, fluorescence energy signal detection, for example by fluorescence polarization, provides determination of signal levels that represent formation of a MIF-binding agent molecular complex. Accordingly, and as provided herein, fluorescence energy signal-based comparison of MIF-binding agent complex formation in the absence and in the presence of a candidate inhibitor provides a method for identifying whether the agent alters the interaction between MIF and the binding agent. For example, the binding agent can be a MIF substrate, an anti-MIF antibody, or a known inhibitor, while the candidate inhibitor can be the compound to be tested or vice versa.

As noted above, fluorescence energy signal-based determination of MIF-binding agent complex formation can be employed. Fluorescence energy signal detection can be, for example, by fluorescence polarization or by fluorescence resonance energy transfer, or by other fluorescence methods known in the art. As an example, the MIF polypeptide can be labeled as well as the candidate inhibitor and can comprise an energy transfer molecule donor-acceptor pair, and the level of fluorescence resonance energy transfer from energy donor to energy acceptor is determined.

The candidate inhibitor and/or binding agent can be detectably labeled, and in particularly preferred embodiments the candidate inhibitor and/or binding agent is capable of generating a fluorescence energy signal. The candidate inhibitor and/or binding agent can be detectably labeled by covalently or non-covalently attaching a suitable reporter molecule or moiety, for example any of various fluorescent materials (e.g. a fluorophore) selected according to the particular fluorescence energy technique to be employed, as known in the art and based upon the methods described herein. Fluorescent reporter moieties and methods for as provided herein can be found, for example in Haugland (1996 *Handbook of Fluorescent Probes and Research Chemicals—Sixth Ed.*, Molecular Probes, Eugene, Oreg.; 1999 *Handbook of Fluorescent Probes and Research Chemicals—Seventh Ed.*, Molecular Probes, Eugene, Oreg., http://www.probes.com/lit/) and in references cited therein.

Particularly preferred for use as such a fluorophore in preferred embodiments are fluorescein, rhodamine, Texas Red, AlexaFluor-594, AlexaFluor-488, Oregon Green, BODIPY-FL, and Cy-5. However, any suitable fluorophore can be employed, and in certain embodiments fluorophores other than those listed can be preferred.

As provided herein, a fluorescence energy signal includes any fluorescence emission, excitation, energy transfer, quenching, dequenching event, or the like. Typically a fluorescence energy signal can be mediated by a fluorescent detectably labeled candidate inhibitor and/or binding agent in response to light of an appropriate wavelength. Briefly, and without wishing to be bound by theory, generation of a fluorescence energy signal generally involves excitation of a fluorophore by an appropriate energy source (e.g., light of a suitable wavelength for the selected fluorescent reporter moiety, or fluorophore) that transiently raises the energy state of the fluorophore from a ground state to an excited state. The excited fluorophore in turn emits energy in the form of detectable light typically having a different (e.g., usually longer) wavelength from that preferred for excitation, and in so doing returns to its energetic ground state. The methods of preferred embodiments contemplate the use of any fluorescence energy signal, depending on the particular fluorophore, substrate labeling method and detection instrumentation, which can be selected readily and without undue experimentation according to criteria with which those having ordinary skill in the art are familiar.

In certain embodiments, the fluorescence energy signal is a fluorescence polarization (FP) signal. In certain other embodiments, the fluorescence energy signal can be a fluorescence resonance energy transfer (FRET) signal. In certain other preferred embodiments the fluorescence energy signal can be a fluorescence quenching (FQ) signal or a fluorescence resonance spectroscopy (FRS) signal. (For details regarding FP, FRET, FQ and FRS, see, for example, WO97/39326; WO99/29894; Haugland, *Handbook of Fluorescent Probes and Research Chemicals—6th Ed.,* 1996, Molecular Probes, Inc., Eugene, Oreg., p. 456; and references cited therein.)

FP, a measurement of the average angular displacement (due to molecular rotational diffusion) of a fluorophore that occurs between its absorption of a photon from an energy source and its subsequent emission of a photon, depends on the extent and rate of rotational diffusion during the excited state of the fluorophore, on molecular size and shape, on solution viscosity and on solution temperature (Perrin, 1926 *J. Phys. Rad.* 1:390). When viscosity and temperature are held constant, FP is directly related to the apparent molecular volume or size of the fluorophore. The polarization value is a ratio of fluorescence intensities measured in distinct planes (e.g., vertical and horizontal) and is therefore a dimensionless quantity that is unaffected by the intensity of the fluorophore. Low molecular weight fluorophores, such as the detectably labeled candidate inhibitor and/or binding agent provided herein, are capable of rapid molecular rotation in solution (i.e., low anisotropy) and thus give rise to low fluorescence polarization readings. When complexed to a higher molecular weight molecule such as MIF as provided herein, however, the fluorophore moiety of the substrate associates with a complex that exhibits relatively slow molecular rotation in solution (i.e., high anisotropy), resulting in higher fluorescence polarization readings.

This difference in the polarization value of free detectably labeled candidate inhibitor and/or binding agent compared to the polarization value of MIF:candidate inhibitor and/or binding agent complex can be employed to determine the ratio of complexed (e.g., bound) to free. This difference can also be employed to detect the influence of a candidate agent (i.e., candidate inhibitor) on the formation of such complexes and/or on the stability of a pre-formed complex, for example by comparing FP detected in the absence of an agent to FP detected in the presence of the agent. FP measurements can be performed without separation of reaction components.

As noted above, one aspect of a preferred embodiment utilizes the binding or displacement of a monoclonal antibody, known inhibitor, or other binding agent and/or complex formation of the candidate inhibitor with MIF to provide a method of identifying an inhibitor that alters the activity of MIF. In this regard, a class of compounds demonstrated the ability to inhibit/decrease monoclonal antibody binding to a biologically active MIF that is naturally produced from cells while not affecting the antibody's ability to recognize inactive (recombinant) MIF (as is available from commercial sources) and also demonstrated pronounced modulation of MIF activity in vivo. Accordingly, antibody binding can be preferred as a surrogate for enzyme activity, thus eliminating the need to run expensive and complex enzymatic assays on each candidate compound. As those of ordinary skill in the art readily appreciate, the ability to avoid enzymatic assays leads to an assay that can be extremely well suited for high throughput use.

Further, as those of ordinary skill in the art can readily appreciate, such an assay can be employed outside of the MIF context and wherever enzyme or biological activity can be replaced by a binding assay. For example, any enzyme or other polypeptide whose biologically active form is recognized by a monoclonal antibody that does not recognize the inactive form (e.g. small molecule inhibited form) can be preferred. Within the context of an enzyme, the monoclonal antibody can bind the active site, but be displaced by a small molecule. Thus, any small molecule that displaces the antibody can be a strong lead as a potential enzyme inhibitor. As those of skill in the art appreciate, the antibody can recognize an epitope that changes conformation depending on the active state of the enzyme, and that binding of a small molecule such that it precludes antibody binding to this epitope can also act as a surrogate for enzymatic activity even though the epitope may not be at the active site. Accordingly, the type of assay utilized herein can be expanded to be employed with essentially any polypeptide wherein antibody displacement is predictive of activity loss. Thus, in its simplest form any polypeptide, e.g. enzyme and its associated neutralizing antibody can be employed to screen for small molecules that displace this antibody, thereby identifying likely inhibitors.

A MIF-binding agent/candidate inhibitor complex can be identified by any of a variety of techniques known in the art for demonstrating an intermolecular interaction between MIF and another molecule as described above, for example, co-purification, co-precipitation, co-immunoprecipitation, radiometric or fluorimetric assays, western immunoblot analyses, affinity capture including affinity techniques such as solid-phase ligand-counterligand sorbent techniques, affinity chromatography and surface affinity plasmon resonance, NMR, and the like (see, e.g. U.S. Pat. No. 5,352,660). Determination of the presence of such a complex can employ antibodies, including monoclonal, polyclonal, chimeric and single-chain antibodies, and the like, that specifically bind to MIF or the binding agent.

Labeled MIF and/or labeled binding agents/candidate inhibitors can also be employed to detect the presence of a complex. The molecule of interest can be labeled by covalently or non-covalently attaching a suitable reporter molecule or moiety, for example any of various enzymes, fluorescent materials, luminescent materials, and radioactive materials. Examples of suitable enzymes include, but are not limited to, horseradish peroxidase, alkaline phosphatase, β-galactosidase, and acetylcholinesterase. Examples of suitable fluorescent materials include, but are not limited to, umbelliferone, fluorescein, fluorescein isothiocyanate, rhodamine, dichlorotriazinylamine fluorescein, dansyl chloride, phycoerythrin, Texas Red, AlexaFluor-594, AlexaFluor-488, Oregon Green, BODIPY-FL and Cy-5. Appropriate luminescent materials include, but are not limited to, luminol and suitable radioactive materials include radioactive phosphorus [$^{32}$P], iodine [$^{125}$I or $^{131}$I] or tritium [$^{3}$H].

MIF and the binding agent and/or the candidate inhibitor are combined under conditions and for a time sufficient to permit formation of an intermolecular complex between the components. Suitable conditions for formation of such complexes are known in the art and can be readily determined based on teachings provided herein, including solution conditions and methods for detecting the presence of a complex and/or for detecting free substrate in solution.

Association of a detectably labeled binding agent(s) and/or candidate inhibitor(s) in a complex with MIF, and/or binding agent or candidate inhibitor that is not part of such a complex, can be identified according to a preferred embodiment by detection of a fluorescence energy signal generated by the substrate. Typically, an energy source for detecting a fluorescence energy signal is selected according to criteria with which those having ordinary skill in the art are familiar, depending on the fluorescent reporter moiety with which the substrate is labeled. The test solution, containing (a) MIF and (b) the detectably labeled binding agent and/or candidate inhibitor, is exposed to the energy source to generate a fluorescence energy signal, which is detected by any of a variety of well known instruments and identified according to the particular fluorescence energy signal. In preferred embodiments, the fluorescence energy signal is a fluorescence polarization signal that can be detected using a spectrofluorimeter equipped with polarizing filters. In particularly preferred embodiments the fluorescence polarization assay is performed simultaneously in each of a plurality of reaction chambers that can be read using an LJL CRITERION™ Analyst (LJL Biosystems, Sunnyvale, Calif.) plate reader, for example, to provide a high throughput screen (HTS) having varied reaction components or conditions among the various reaction chambers. Examples of other suitable instruments for obtaining fluorescence polarization readings include the POLARSTAR™ (BMG Lab Technologies, Offenburg, Germany), BEACON™ (Panvera, Inc., Madison, Wis.) and the POLARION™ (Tecan, Inc., Research Triangle Park, N.C.) devices.

Determination of the presence of a complex that has formed between MIF and a binding agent and/or a candidate inhibitor can be performed by a variety of methods, as noted above, including fluorescence energy signal methodology as provided herein and as known in the art. Such methodologies can include, by way of illustration and not limitation FP, FRET, FQ, other fluorimetric assays, co-purification, co-precipitation, co-immunoprecipitation, radiometric, western immunoblot analyses, affinity capture including affinity techniques such as solid-phase ligand-counterligand sorbent techniques, affinity chromatography and surface affinity plasmon resonance, circular dichroism, and the like. For these and other useful affinity techniques, see, for example, Scopes, R. K., *Protein Purification: Principles and Practice*, 1987, Springer-Verlag, NY; Weir, D. M., *Handbook of Experimental Immunology*, 1986, Blackwell Scientific, Boston; and Hermanson, G. T. et al., *Immobilized Affinity Ligand Techniques*, 1992, Academic Press, Inc., California; which are hereby incorporated by reference in their entireties, for details regarding techniques for isolating and characterizing complexes, including affinity techniques. In various embodiments, MIF can interact with a binding agent and/or candidate inhibitor via specific binding if MIF binds the binding agent and/or candidate inhibitor with a $K_a$ of greater than or equal to about $10^4$ M$^{-1}$, preferably of greater than or equal to about $10^5$ M$^{-1}$, more preferably of greater than or equal to about $10^6$ M$^{-1}$ and still more preferably of greater than or equal to about $10^7$ M$^{-1}$ to $10^{11}$ M$^{-1}$. Affinities of binding partners can be readily calculated from data generated according to the fluorescence energy signal methodologies described above and using conventional data handling techniques, for example, those described by Scatchard et al., *Ann. N.Y. Acad. Sci.* 51:660 (1949).

For example, in various embodiments where the fluorescence energy signal is a fluorescence polarization signal, fluorescence anisotropy (in polarized light) of the free detectably labeled candidate inhibitor and/or binding agent can be determined in the absence of MIF, and fluorescence anisotropy (in polarized light) of the fully bound substrate can be determined in the presence of a titrated amount of MIF. Fluorescence anisotropy in polarized light varies as a function of the amount of rotational motion that the labeled candidate inhibitor and/or binding agent undergoes during the lifetime of the excited state of the fluorophore, such that the anisotropies of free and fully bound candidate inhibitor and/or binding agent can be usefully employed to determine the fraction of candidate inhibitor and/or binding agent bound to MIF in a given set of experimental conditions, for instance, those wherein a candidate agent is present (see, e.g. Lundblad et al., 1996 *Molec. Endocrinol.* 10:607; Dandliker et al., 1971 *Immunochem.* 7:799; Collett, E., *Polarized Light: Fundamentals and Applications*, 1993 Marcel Dekker, New York).

Certain of the preferred embodiments pertain in part to the use of intermolecular energy transfer to monitor MIF-binding agent complex formation and stability and/or MIF-candidate inhibitor complex formation.

Energy transfer (ET) is generated from a resonance interaction between two molecules: an energy-contributing "donor" molecule and an energy-receiving "acceptor" molecule. Energy transfer can occur when (1) the emission spectrum of the donor overlaps the absorption spectrum of the acceptor and (2) the donor and the acceptor are within a certain distance (for example, less than about 10 nm) of one another. The efficiency of energy transfer is dictated largely by the proximity of the donor and acceptor, and decreases as a power of 6 with distance. Measurements of ET thus strongly reflect the proximity of the acceptor and donor compounds, and changes in ET sensitively reflect changes in the proximity of the compounds such as, for example, association or dissociation of the donor and acceptor.

It is therefore an aspect of a preferred embodiment to provide a method for assaying a candidate MIF inhibitor, in pertinent part, by contacting MIF or an MIF-binding agent complex including one or more ET donor and an ET acceptor molecules, exciting the ET donor to produce an excited ET donor molecule and detecting a signal generated by energy transfer from the ET donor to the ET acceptor. As also provided herein, the method can employ any suitable ET donor molecule and ET acceptor molecule that can function as a donor-acceptor pair.

In certain preferred embodiments, a detectable signal that is generated by energy transfer between ET donor and acceptor molecules results from fluorescence resonance energy transfer (FRET), as discussed above. FRET occurs within a molecule, or between two different types of molecules, when energy from an excited donor fluorophore is transferred directly to an acceptor fluorophore (for a review, see Wu et al., *Analytical Biochem.* 218:1-13, 1994).

In other aspects of preferred embodiments, the ability of a candidate inhibitor to effect MIF export is tested.

The first step of such an assay is performed to detect MIF extracellularly. For this assay, test cells expressing MIF are employed (e.g. THP-1 cells). Either the test cells can naturally produce the protein or produce it from a transfected expression vector. Test cells preferably normally express the protein, such that transfection merely increases expressed levels. Thus, for expression of MIF and IL-1, THP1 cells are preferred. When one is assaying virally-derived proteins, such as HIV tat, if the test cells do not "naturally" produce the protein, they can readily be transfected using an appropriate vector, so that the test cells express the desired protein, as those of skill in the art readily appreciate.

Following expression, MIF is detected by any one of a variety of well-known methods and procedures. Such methods include staining with antibodies in conjunction with flow cytometry, confocal microscopy, image analysis, immunoprecipitation of cell cytosol or medium, Western blot of cell medium, ELISA, 1- or 2-D gel analysis, HPLC, bioassay, or the like. A convenient assay for initial screening is ELISA. MIF export can be confirmed by one of the other assays, preferably by immunoprecipitation of cell medium following metabolic labeling. Briefly, cells expressing MIF protein are pulse labeled for 15 minutes with $^{35}$S-methionine and/or $^{35}$S-cysteine in methionine and/or cysteine free medium and chased in medium supplemented with excess methionine and/or cysteine. Media fractions are collected and clarified by centrifugation, such as in a microfuge. Lysis buffer containing 1% NP-40, 0.5% deoxycholate (DOC), 20 mM Tris, pH 7.5, 5 mM EDTA, 2 mM EGTA, 10 nM PMSF, 10 ng/ml aprotinin, 10 ng/ml leupeptin, and 10 ng/ml pepstatin is added to the clarified medium. An antibody to MIF is added and following incubation in the cold, a precipitating second antibody or immunoglobulin binding protein, such as protein A-Sepharose® or GammaBind™-Sepharose®, is added for further incubation. In parallel, as a control, a cytosolic protein is monitored and an antibody to the cytosolic protein is preferred in immunoprecipitations. Immune complexes are pelleted and washed with ice-cold lysis buffer. Complexes are further washed with ice-cold IP buffer (0.15 M NaCl, 10 mM Na-phosphate, pH 7.2, 1% DOC, 1% NP-40, 0.1% SDS). Immune complexes are eluted directly into SDS-gel sample buffer and electrophoresed in SDS-PAGE. The gel is processed for fluorography, dried and exposed to X-ray film. Alternatively cells can be engineered to produce a MIF that is tagged with a reporter so that the presence of an active MIF can be through the surrogate activity of the reporter.

While not wishing to be bound to theory, it is believed that the present inhibitors function by interacting directly with the naturally produced MIF complex in such a fashion as to alter the protein's conformation enough to block its biological activity. This interaction can be mapped by X-ray crystallography of MIF-compound co-crystals to determine the exact site of interaction. One site localizes to the pocket that is responsible for the tautomerase activity of MIF.

Screening assays for inhibitors of MIF export vary according to the type of inhibitor and the nature of the activity that is being affected. Assays can be performed in vitro or in vivo. In general, in vitro assays are designed to evaluate MIF activity, or multimerization, and in vivo assays are designed to evaluate MIF activity, extracellular localization, and intracellular localization in a model cell or animal system. In any of the assays, a statistically significant increase or decrease compared to a proper control is indicative of enhancement or inhibition.

One in vitro assay can be performed by examining the effect of a candidate compound on the ability of MIF to inhibit macrophage migration. Briefly, human peripheral blood monocytes are preferred as indicator cells in an agarose-droplet assay system essentially as described by Weiser et al., *Cell. Immunol.* 90:167-178, 1985 and Harrington et al., *J. Immunol.* 110:752-759, 1973. Other assay systems of analyzing macrophage migration can also be employed. Such an assay is described by Hermanowski-Vosatka et al., Biochem. 38:12841-12849, 1999.

An alternative in vitro assay is designed to measure the ability of MIF to catalyze tautomerization of the D-isomer of dopachrome (see Rosengren et al., *Mol. Med.* 2:143-149, 1996; Winder et al., *J. Cell Sci.* 106:153-166, 1993; Aroca et al., *Biochem. J.* 277:393-397). Briefly, in this method, D-dopachrome is provided to MIF in the presence and absence of a candidate inhibitor and the ability to catalyze the tautomerization to 5,6-dihydroxyindole-2-carboxylic acid (DHICA) is monitored. However, use of methyl esters of D-dopachrome can be preferred in that a faster reaction rate is observed. Detection of the tautomerization can be performed by any one of a variety of standard methods.

In a similar assay, the ability of MIF to catalyze the tautomerization of phenylpyruvate can be tested (see Johnson et al., *Biochem.* 38(48):16024-16033, 1999). Briefly, in this method, typically ketonization of phenylpyruvate or (p-hydroxyphenyl)pyruvate is followed by spectroscopy. Further, product formation can be verified by treatment of these compounds with MIF and subsequent conversion to malate for $^1$H NMR analysis.

In vivo assays can be performed in cells transfected either transiently or stably with an expression vector containing a MIF nucleic acid molecule, such as those described herein. These cells are preferred to measure MIF activity (e.g. modulation of apoptosis, proliferation, etc.) or extracellular and intracellular localization in the presence or absence of a candidate compound. When assaying for apoptosis, a variety of cell analyses can be employed, including, for example, dye staining and microscopy to examine nucleic acid fragmentation and porosity of the cells.

Other assays can be performed in model cell or animal systems by providing to the system a recombinant or naturally occurring form of MIF or inducing endogenous MIF expression in the presence or absence of test compound, thereby determining a statistically significant increase or decrease in the pathology of that system. For example, LPS can be employed to induce a toxic shock response.

The assays briefly described herein can be employed to identify an inhibitor that is specific for MIF.

In any of the assays described herein, a test cell can express the MIF naturally (e.g. THP-1 cells) or following introduction of a recombinant DNA molecule encoding the protein. Transfection and transformation protocols are well known in the art and include $Ca_2PO_4$-mediated transfection, electroporation, infection with a viral vector, DEAE-dextran mediated transfection, and the like. As an alternative to the proteins described above, chimeric MIF proteins (i.e., proteins prepared by fusion of MIF protein with another protein or protein fragment), or protein sequences engineered to lack a leader sequence can be employed. In a similar fashion, a fusion can be constructed to direct secretion, export, or cytosolic retention. Any and all of these sequences can be employed in a fusion construct with MIF to assist in assaying inhibitors. The host cell can also express MIF as a result of being diseased, infected with a virus, and the like. Secreted proteins that are exported by virtue of a leader sequence are well known and include, human chorionic gonadatropin (hCGα), growth hormone, hepatocyte growth factor, transferrin, nerve growth factor, vascular endothelial growth factor, ovalbumin, and insulin-like growth factor. Similarly, cytosolic proteins are well known and include, neomycin phosphotransferase, β-galactosidase, actin and other cytoskeletal proteins, and enzymes, such as protein kinase A or C. The most useful cytosolic or secreted proteins are those that are readily measured in a convenient assay, such as ELISA. The three proteins (leaderless, secreted, and cytosolic) can be co-expressed naturally, by co-transfection in the test cells, or transfected separately into separate host cells. Furthermore, for the assays described herein, cells can be stably transformed or express the protein transiently.

Immunoprecipitation is one such assay that can be employed to determine inhibition. Briefly, cells expressing MIF naturally or from an introduced vector construct are labeled with $^{35}$S-methionine and/or $^{35}$S-cysteine for a brief period of time, typically 15 minutes or longer, in methionine- and/or cysteine-free cell culture medium. Following pulse labeling, cells are washed with medium supplemented with excess unlabeled methionine and cysteine plus heparin if the leaderless protein is heparin binding. Cells are then cultured in the same chase medium for various periods of time. Candidate inhibitors or enhancers are added to cultures at various concentrations. Culture supernatant is collected and clarified. Supernatants are incubated with anti-MIF immune serum or a monoclonal antibody, or with anti-tag antibody if a peptide tag is present, followed by a developing reagent such as *Staphylococcus aureus* Cowan strain I, protein A-Sepharose®, or Gamma-bind™ G-Sepharose®. Immune complexes are pelleted by centrifugation, washed in a buffer containing 1% NP-40 and 0.5% deoxycholate, EGTA, PMSF, aprotinin, leupeptin, and pepstatin. Precipitates are then washed in a buffer containing sodium phosphate pH 7.2, deoxycholate, NP-40, and SDS. Immune complexes are eluted into a SDS gel sample buffer and separated by SDS-PAGE. The gel is processed for fluorography, dried, and exposed to x-ray film.

Alternatively, ELISA can be preferred to detect and quantify the amount of MIF in cell supernatants. ELISA is preferred for detection in high throughput screening. Briefly, 96-well plates are coated with an anti-MIF antibody or anti-tag antibody, washed, and blocked with 2% BSA. Cell supernatant is then added to the wells. Following incubation and washing, a second antibody (e.g. an antibody to MIF) is added. The second antibody can be coupled to a label or detecting reagent, such as an enzyme, or to biotin. Following further incubation, a developing reagent is added and the amount of MIF determined using an ELISA plate reader. The developing reagent is a substrate for the enzyme coupled to the second antibody (typically an anti-isotype antibody) or for the enzyme coupled to streptavidin. Suitable enzymes are well known in the art and include horseradish peroxidase, which acts upon a substrate (e.g. ABTS) resulting in a calorimetric reaction. It is recognized that rather than using a second antibody coupled to an enzyme, the anti-MIF antibody can be directly coupled to the horseradish peroxidase, or other equivalent detection reagent. If desired, cell supernatants can be concentrated to raise the detection level. Further, detection methods, such as ELISA and the like can be employed to monitor intracellular as well as extracellular levels of MIF. When intracellular levels are desired, a cell lysate is preferred. When extracellular levels are desired, media can be screened.

ELISA can also be readily adapted for screening multiple candidate inhibitors or enhancers with high throughput. Briefly, such an assay is conveniently cell-based and performed in 96-well plates. Test cells that naturally or stably express MIF are plated at a level sufficient for expressed product detection, such as, about 20,000 cells/well. However, if the cells do not naturally express the protein, transient expression is achieved, such as by electroporation or $Ca_2PO_4$-mediated transfection. For electroporation, 100 μl of a mixture of cells (e.g., 150,000 cells/ml) and vector DNA (5 μg/ml) is dispensed into individual wells of a 96-well plate. The cells are electroporated using an apparatus with a 96-well electrode (e.g. ECM 600 Electroporation System, BTX, Genetronics, Inc.). Optimal conditions for electroporation are experimentally determined for the particular host cell type. Voltage, resistance, and pulse length are the typical parameters varied. Guidelines for optimizing electroporation can be obtained from manufacturers or found in protocol manuals, such as *Current Protocols in Molecular Biology* (Ausubel et al. (ed.), Wiley Interscience, 1987). Cells are diluted with an equal volume of medium and incubated for 48 hours. Electroporation can be performed on various cell types, including mammalian cells, yeast cells, bacteria, and the like. Following incubation, medium with or without inhibitor is added and cells are further incubated for 1-2 days. At this time, culture medium is harvested and the protein is assayed by any of the assays herein. Preferably, ELISA is employed to detect the protein. An initial concentration of 50 μM is tested. If this amount gives a statistically significant reduction of export or reduction of monoclonal Ab detection, the candidate inhibitor is further tested in a dose response.

Alternatively, concentrated supernatant can be electrophoresed on a SDS-PAGE gel and transferred to a solid support, such as nylon or nitrocellulose. MIF is then detected by an immunoblot (see Harlow, *Antibodies: A Laboratory Manual*, Cold Spring Harbor Laboratory, 1988), using an antibody to MIF containing an isotopic or non-isotopic reporter group. These reporter groups include, but are not limited to enzymes, cofactors, dyes, radioisotopes, luminescent molecules, fluorescent molecules, and biotin. Preferably, the reporter group is $^{125}$I or horseradish peroxidase, which can be detected by incubation with 2,2'-azino-di-3-ethylbenzthiazoline sulfonic acid. These detection assays described above are readily adapted for use if MIF contains a peptide tag. In such case, the antibody binds to the peptide tag. Other assays include size or charge-based chromatography, including HPLC and affinity chromatography.

Alternatively, a bioassay can be employed to quantify the amount of active MIF present in the cell medium. For example, the bioactivity of the MIF can be measured by a macrophage migration assay. Briefly, cells transfected with an expression vector containing MIF are cultured for approximately 30 hours, during which time a candidate inhibitor or enhancer is added. Following incubation, cells are transferred to a low serum medium for a further 16 hours of incubation. The medium is removed and clarified by centrifugation. A lysis buffer containing protease inhibitors is added to the medium or, in the alternative, cells are lysed and internal levels are determined as follows. Bioactivity of MIF is then measured by macrophage migration assay, isomerase activity, or a proliferation assay. A proliferation assay is performed by adding various amounts of the eluate to cultured quiescent 3T3 cells. Tritiated thymidine is added to the medium and TCA precipitable counts are measured approximately 24 hours later. Reduction of the vital dye MTT is an alternative way to measure proliferation. For a standard, purified recombinant human FGF-2 can be employed. Other functions can be assayed in other appropriate bioassays available in the art, such as CPS induced toxic shock, TSST-1 induced toxic shock, collagen induced arthritis, etc.

Other in vitro angiogenic assays include bioassays that measure proliferation of endothelial cells within collagen gel (Goto et al., *Lab Invest.* 69:508, 1993), co-culture of brain capillary endothelial cells on collagen gels separated by a chamber from cells exporting the MIF protein (Okamure et al., *B. B. R. C.* 186:1471, 1992; Abe et al., *J. Clin. Invest.* 92:54, 1993), or a cell migration assay (see Warren et al., *J. Clin. Invest.* 95:1789, 1995).

Production of Antibodies

The term "antibody," as used herein is a broad term and is used in its ordinary sense, including, without limitation, to refer to polyclonal, monospecific, and monoclonal antibodies, as well as antigen binding fragments of such antibodies. With regard to an anti-MIF/target antibody of preferred embodiments, the term "antigen" as used herein is a broad term and is used in its ordinary sense, including, without limitation, to refer to a macrophage migration inhibitory factor polypeptide or a target polypeptide, variant, or functional fragment thereof. An anti-MIF/target antibody, or antigen binding fragment of such an antibody, can be characterized as having specific binding activity for the target polypeptide or epitope thereof of at least about $1\times10^5$ $M^{-1}$, generally at least about $1\times10^6$ $M^{-1}$, and preferably at least about $1\times10^8$ $M^{-1}$. Fab, F(ab')$_2$, Fd and Fv fragments of an anti-MIF/target antibody, which retain specific binding activity for a MIF/target polypeptide-specific epitope, are encompassed within preferred embodiments. Of particular interest are those antibodies that bind active polypeptides and are displaced upon binding of an inhibitory small molecule. Those of skill in the art readily appreciate that such displacement can be the result of a conformational change, thus changing the nature of the epitope, competitive binding with the epitope, or steric exclusion of the antibody from its epitope. In one example, the active site of an enzyme can be the epitope for a particular antibody and upon binding of a small molecule at or near the active site, immunoreactivity of the antibody is lost, thereby allowing the use of loss of immunoreactivity with an antibody as a surrogate marker for enzyme activity.

In addition, the term "antibody" as used herein is a broad term and is used in its ordinary sense, including, without limitation, to refer to naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly, or can be obtained, for example, by screening combinatorial libraries including variable heavy chains and variable light chains (Huse et al., *Science* 246: 1275-1281 (1989)). These and other methods of making, for example, chimeric, humanized, CDR-grafted, single chain, and bifunctional antibodies are well known in the art (Winter and Harris, *Immunol. Today* 14:243-246 (1993); Ward et al., *Nature* 341:544-546 (1989); Harlow and Lane, *Antibodies: A Laboratory Manual*, Cold Spring Harbor Laboratory, New York (1992); Borrabeck, *Antibody Engineering*, 2d ed., Oxford Univ. Press (1995); Hilyard et al., *Protein Engineering: A practical approach*, IRL Press (1992)).

In certain preferred embodiments, an anti-MIF/target antibody can be raised using as an immunogen, for example, an isolated peptide including the active site region of MIF or the target polypeptide, which can be prepared from natural sources or produced recombinantly, as described above, or an immunogenic fragment of a MIF/target polypeptide (e.g. immunogenic sequences including 8-30 or more contiguous amino acid sequences), including synthetic peptides, as described above. A non-immunogenic peptide portion of a MIF/target polypeptide can be made immunogenic by coupling the hapten to a carrier molecule such as bovine serum albumin (BSA) or keyhole limpet hemocyanin (KLH), or by expressing the peptide portion as a fusion protein. Various other carrier molecules and methods for coupling a hapten to a carrier molecule are well known in the art (Harlow and Lane, supra, 1992).

Methods for raising polyclonal antibodies, for example, in a rabbit, goat, mouse, or other mammal, are well known in the art. In addition, monoclonal antibodies can be obtained using methods that are well known and routine in the art (Harlow and Lane, supra, 1992). For example, spleen cells from a target polypeptide-immunized mammal can be fused to an appropriate myeloma cell line such as SP/02 myeloma cells to produce hybridoma cells. Cloned hybridoma cell lines can be screened using a labeled target polypeptide or functional fragment thereof to identify clones that secrete target polypeptide monoclonal antibodies having the desired specificity. Hybridomas expressing target polypeptide monoclonal antibodies having a desirable specificity and affinity can be isolated and utilized as a continuous source of the antibodies, which are useful, for example, for preparing standardized kits. Similarly, a recombinant phage that expresses, for example, a single chain anti-target polypeptide also provides a monoclonal antibody that can be employed for preparing standardized kits.

Applications and Methods Utilizing Inhibitors of MIF

Inhibitors of MIF have a variety of applicable uses, as noted above. Candidate inhibitors of MIF can be isolated or procured from a variety of sources, such as bacteria, fungi, plants, parasites, libraries of chemicals (small molecules), peptides or peptide derivatives, and the like. Further, one of skill in the art recognizes that inhibition has occurred when a statistically significant variation from control levels is observed.

Given the various roles of MIF in pathology and homeostasis, inhibition of MIF activity or MIF extracellular localization can have a therapeutic effect. For example, recent studies have demonstrated that MIF is a mediator of endotoxemia, where anti-MIF antibodies fully protected mice from LPS-induced lethality. See Bernhagen et al., *Nature* 365:756-759, 1993; Calandra et al., *J. Exp. Med.* 179:1895-1902, 1994; Bernhagen et al. *Trends Microbiol.* 2:198-201, 1994. Further, anti-MIF antibodies have markedly increased survival in mice challenged with gram-positive bacteria that induces septic shock. Bernhagen et al., *J. Mol. Med.* 76:151-161, 1998. Other studies have demonstrated the role of MIF in tumor cell growth and that anti-sense inhibition of MIF leads to resistance to apoptotic stimuli. Takahashi et al., *Mol. Med.* 4:707-714, 1998; Takahashi et al., *Microbiol. Immunol.* 43(1):61-67, 1999. In addition, the finding that MIF is a counterregulator of glucocorticoid action indicates that methods of inhibiting MIF extracellular localization can allow for treatment of a variety of pathological conditions, including autoimmunity, inflammation, endotoxemia, and adult respiratory distress syndrome, inflammatory bowel disease, otitis media, inflammatory joint disease, and Crohn's disease. See Bernhagen et al., *J. Mol. Med.* 76:151-161, 1998; Calandra et al., *Nature* 377:68-71, 1995; Donnelly et al., *Nat. Med.* 3:320-323, 1997. Because MIF is also recognized to be angiogenic, the inhibition of this cytokine can have anti-angiogenic activity and particular utility in angiogenic diseases that include, but are not limited to, cancer, diabetic retinopathy, psoriasis, angiopathies, fertility, obesity, and genetic diseases of glucocorticoid dysfunction like Cushing's and Addison's disease.

The inhibitors of MIF activity or export can be employed therapeutically and also utilized in conjunction with a targeting moiety that binds a cell surface receptor specific to particular cells. Administration of inhibitors or enhancers generally follows established protocols. Compositions of preferred embodiments can be formulated for the manner of administration indicated, including for example, for oral, nasal, transmucosal, transcutaneous, venous, intracranial, intraperitoneal, subcutaneous, or intramuscular administration. Within other embodiments, the compositions described herein can be administered as part of a sustained release implant. Within yet other embodiments, compositions of preferred embodiments can be formulized as a lyophilizate, utilizing appropriate excipients that provide stability as a lyophilizate, and subsequent to rehydration.

In another embodiment, pharmaceutical compositions containing one or more inhibitors of MIF are provided. For the purposes of administration, the compounds of preferred embodiments can be formulated as pharmaceutical compositions. Pharmaceutical compositions of preferred embodiments comprise one or more MIF inhibitors of preferred embodiments (i.e., a compound of structure (Ia) or (Ib)) and a pharmaceutically acceptable carrier and/or diluent. The inhibitor of MIF is present in the composition in an amount which is effective to treat a particular disorder, that is, in an amount sufficient to achieve decreased MIF levels or activity, symptoms, and/or preferably with acceptable toxicity to the patient. Preferably, the pharmaceutical compositions of preferred embodiments can include an inhibitor of MIF in an amount from less than about 0.01 mg to more than about 1000 mg per dosage depending upon the route of administration, preferably about 0.025, 0.05, 0.075, 0.1, 0.2, 0.3, 0.4, 0.5, 0.6, 0.7, 0.8, or 0.9 mg to about 65, 70, 75, 80, 85, 90, 95, 100, 125, 150, 175, 200, 225, 250, 300, 350, 375, 400, 425, 450, 500, 600, 700, 800, or 900 mg, and more preferably from about 1, 2, 3, 4, 5, 6, 7, 8, 9, 10, 15, 20, or 25 mg to about 30, 35, 40, 45, 50, 55, or 60 mg. In certain embodiments, however, lower or higher dosages than those mentioned above can be preferred. Appropriate concentrations and dosages can be readily determined by one skilled in the art.

Pharmaceutically acceptable carriers and diluents are familiar to those skilled in the art. For compositions formulated as liquid solutions, acceptable carriers and/or diluents include saline and sterile water, and can optionally include antioxidants, buffers, bacteriostats, and other common additives. The compositions can also be formulated as pills, capsules, granules, or tablets that contain, in addition to an inhibitor or inhibitors of MIF, diluents, dispersing and surface-active agents, binders, and lubricants. One skilled in this art can further formulate the inhibitor of MIF in an appropriate manner, and in accordance with accepted practices, such as those described in *Remington's Pharmaceutical Sciences*, Gennaro, Ed., Mack Publishing Co., Easton, Pa. 1990.

In addition, prodrugs are also included within the context of preferred embodiments. Prodrugs are any covalently bonded carriers that release a compound of structure (Ia) or (Ib) in vivo when such prodrug is administered to a patient. Prodrugs are generally prepared by modifying functional groups in a way such that the modification is cleaved, either by routine manipulation or in vivo, yielding the parent compound.

With regard to stereoisomers, the compounds of structures (Ia), (Ib), (Ic), and (Id) can have chiral centers and can occur as racemates, racemic mixtures and as individual enantiomers or diastereomers. All such isomeric forms are included within preferred embodiments, including mixtures thereof. Furthermore, some of the crystalline forms of the compounds of structures (Ia), (Ib), (Ic), and (Id) can exist as polymorphs, which are included in preferred embodiments. In addition, some of the compounds of structures (Ia), (Ib), (Ic), and (Id) can also form solvates with water or other organic solvents. Such solvates are similarly included within the scope of the preferred embodiments.

In another embodiment, a method is provided for treating a variety of disorders or illnesses, including inflammatory diseases, arthritis, immune-related disorders, and the like. Such methods include administering of a compound of preferred embodiments to a warm-blooded animal in an amount sufficient to treat the disorder or illness. Such methods include systemic administration of an inhibitor of MIF of preferred embodiments, preferably in the form of a pharmaceutical composition. As used herein, systemic administration includes oral and parenteral methods of administration. For oral administration, suitable pharmaceutical compositions of an inhibitor of MIF include powders, granules, pills, tablets, and capsules as well as liquids, syrups, suspensions, and emulsions. These compositions can also include flavorants, preservatives, suspending, thickening and emulsifying agents, and other pharmaceutically acceptable additives. For parenteral administration, the compounds of preferred embodiments can be prepared in aqueous injection solutions that can contain, in addition to the inhibitor of MIF activity and/or export, buffers, antioxidants, bacteriostats, and other additives commonly employed in such solutions.

As mentioned above, administration of a compound of preferred embodiments can be employed to treat a wide variety of disorders or illnesses. In particular, the compounds of preferred embodiments can be administered to a warm-blooded animal for the treatment of inflammation, cancer, immune disorders, and the like.

MIF inhibiting compounds can be used in combination therapies with other pharmaceutical compounds. In preferred embodiments, the MIF inhibiting compound is present in combination with conventional drugs used to treat diseases or conditions wherein MIF is pathogenic or wherein MIF plays a pivotal or other role in the disease process. In particularly preferred embodiments, pharmaceutical compositions are provided comprising one or more MIF inhibiting compounds, including, but not limited to compounds of structures (Ia), (Ib), (Ic), and (Id), in combination with one or more additional pharmaceutical compounds, including, but not limited to drugs for the treatment of various cancers, asthma or other respiratory diseases, sepsis, arthritis, inflammatory bowel disease (IBD), or other inflammatory diseases, immune disorders, or other diseases or disorders wherein MIF is pathogenic.

In particularly preferred embodiments, one or more MIF inhibiting compounds are present in combination with one or more nonsteroidal anti-inflammatory drugs (NSAIDs) or other pharmaceutical compounds for treating arthritis or other inflammatory diseases. Preferred compounds include, but are not limited to, celecoxib; rofecoxib; NSAIDS, for example, aspirin, celecoxib, choline magnesium trisalicylate, diclofenac potassium, diclofenac sodium, diflunisal, etodolac, fenoprofen, flurbiprofen, ibuprofen, indomethacin, ketoprofen, ketorolac, melenamic acid, nabumetone, naproxen, naproxen sodium, oxaprozin, piroxicam, rofecoxib, salsalate, sulindac, and tolmetin; and corticosteroids, for example, cortisone, hydrocortisone, methylprednisolone, prednisone, prednisolone, betamethesone, beclomethasone dipropionate, budesonide, dexamethasone sodium phosphate, flunisolide, fluticasone propionate, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, and dexamethasone.

In particularly preferred embodiments, one or more MIF inhibiting compounds are present in combination with one or more beta stimulants, inhalation corticosteroids, antihistamines, hormones, or other pharmaceutical compounds for treating asthma, acute respiratory distress, or other respiratory diseases. Preferred compounds include, but are not limited to, beta stimulants, for example, commonly prescribed bronchodilators; inhalation corticosteroids, for example, beclomethasone, fluticasone, triamcinolone, mometasone, and forms of prednisone such as prednisone, prednisolone, and methylprednisolone; antihistamines, for example, azatadine, carbinoxamine/pseudoephedrine, cetirizine, cyproheptadine, dexchlorpheniramine, fexofenadine, loratadine, promethazine, tripelennamine, brompheniramine, cholopheniramine, clemastine, diphenhydramine; and hormones, for example, epinephrine.

In particularly preferred embodiments, one or more MIF inhibiting compounds are present in combination with pharmaceutical compounds for treating IBD, such as azathioprine or corticosteroids, in a pharmaceutical composition.

In particularly preferred embodiments, one or more MIF inhibiting compounds are present in combination with pharmaceutical compounds for treating cancer, such as paclitaxel, in a pharmaceutical composition.

In particularly preferred embodiments, one or more MIF inhibiting compounds are present in combination with immunosuppressive compounds in a pharmaceutical composition. In particularly preferred embodiments, one or more MIF inhibiting compounds are present in combination with one or more drugs for treating an autoimmune disorder, for example, Lyme disease, Lupus (e.g., Systemic Lupus Erythematosus (SLE)), or Acquired Immune Deficiency Syndrome (AIDS). Such drugs can include protease inhibitors, for example, indinavir, amprenavir, saquinavir, lopinavir, ritonavir, and nelfinavir; nucleoside reverse transcriptase inhibitors, for example, zidovudine, abacavir, lamivudine, idanosine, zalcitabine, and stavudine; nucleotide reverse transcriptase inhibitors, for example, tenofovir disoproxil fumarate; non nucleoside reverse transcriptase inhibitors, for example, delavirdine, efavirenz, and nevirapine; biological response modifiers, for example, etanercept, infliximab, and other compounds that inhibit or interfere with tumor necrosing factor; antivirals, for example, amivudine and zidovudine.

In particularly preferred embodiments, one or more MIF inhibiting compounds are present in combination with pharmaceutical compounds for treating sepsis, such as steroids or anti-infective agents. Examples of steroids include corticosteroids, for example, cortisone, hydrocortisone, methylprednisolone, prednisone, prednisolone, betamethesone, beclomethasone dipropionate, budesonide, dexamethasone sodium phosphate, flunisolide, fluticasone propionate, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, and dexamethasone. Examples of anti-infective agents include anthelmintics (mebendazole), antibiotics including aminoclycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin; clindamycin; colistimethate sodium; polymyxin b sulfate; vancomycin; antivirals including acyclovir, amantadine, didanosine, efavirenz, foscarnet, ganciclovir, indinavir, lamivudine, nelfinavir, ritonavir, saquinavir, stavudine, valacyclovir, valganciclovir, zidovudine; quinolones (ciprofloxacin, levofloxacin); sulfonamides (sulfadiazine, sulfisoxazole); sulfones (dapsone); furazolidone; metronidazole; pentamidine; sulfanilamidum crystallinum; gatifloxacin; and sulfamethoxazole/trimethoprim.

In the treatment of certain diseases, it can be beneficial to treat the patient with a MIF inhibitor in combination with an anesthetic, for example, ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocalne, and phenazopyridine.

EXAMPLES

The inhibitors of MIF of preferred embodiments were prepared by the methods described in Example 1.

Example 1

Synthesis of 2-Benzylamino nicotinic acid (1)

Benzylamine (14 mL, 126.8 mmol) was added to a solution of chloronicotinic acid (10 g, 63.4 mmol) in pyridine and refluxed overnight. The pyridine was distilled and the residue was dissolved in 1N NaOH. The solution was diluted with water to adjust the pH to 10 to 11 and washed by dichloromethane. The aqueous phase was neutralized with cold aqueous 10% HCl solution to adjust the pH to 6 to 7. The solids formed were filtered, washed with cold water, and dried in a vacuum oven to yield 12.2 g (84%) of 2-benzylamino nicotinic acid (1) as white solids. MP: 148° C.; $^1$H-NMR (DMSO-$d_6$): δ 4.69 (d, J=3.6 Hz, 2H), 6.61 (dd, J=4.9, 7.7 Hz, 1H), 7.23 (m, 1H), 7.29 (m, 4H), 8.08 (dd, J=1.8, 7.0 Hz, 1H), 8.28 (dd, J=1.8, 7.0 Hz, 1H), 8.47 (br. s, 1H), 13.10 (s, 1H); EIMS: 229 (M+1), 251 (M+23).

Synthesis of 1-Benzyl-1H-pyrido[2,3-d][1,3]oxazine-2,4-dione (2)

Trichloromethyl chloroformate (2.5 mL, 21 mmol) was added slowly to a suspension of (1) (4 g, 17.5 mmol) in dioxane and refluxed for 8 h under nitrogen atmosphere. The solution was cooled and the solvent was removed under vacuum. The residue was dissolved in dichloromethane and washed by saturated $NaHCO_3$ solution. The organic phase was dried over $Na_2SO_4$ and evaporated to yield a residue. The residue was recrystallized by ether to yields 3.02 g (68%) of 1-benzyl-1H-pyrido[2,3-d][1,3]oxazine-2,4-dione (2) as white solids. MP: 168° C.; $^1$H-NMR (DMSO-$d_6$): δ 5.35 (s, 2H), 7.26 (m, 1H), 7.30 (m, 2H), 7.39 (m, 3H), 8.41 (dd, J=1.5, 7.5 Hz, 1H), 8.72 (dd, J=1.5, 7.5 Hz, 1H); EIMS: 277 (M+23).

The sequence of reactions in the preparation of 2-benzylamino nicotinic acid (1) and 1-benzyl-1H-pyrido[2,3-d][1,3]oxazine-2,4-dione (2) as described above was as follows:

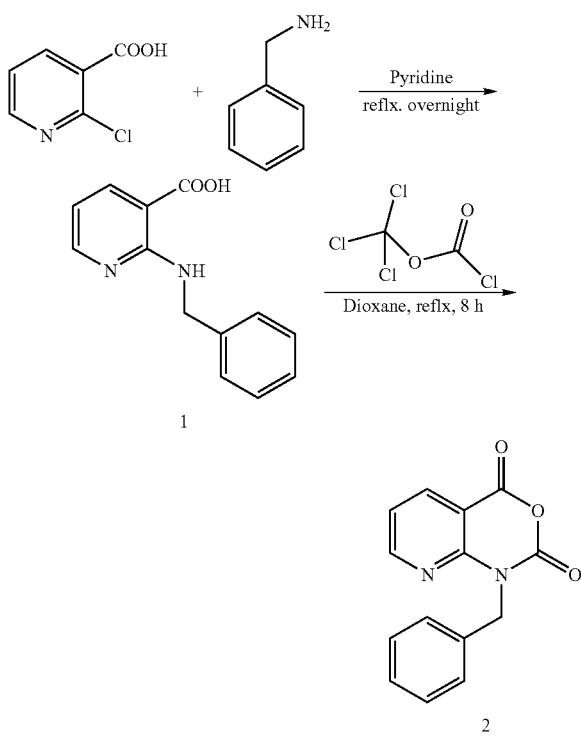

Synthesis of 1-Benzyl-4-hydroxy-2-oxo-1,2-dihydro-[1,8]-naphthyridine-3-carboxylic acid ethyl ester (3)

Diethyl malonate (0.6 mL, 4 mmol) was added slowly to a suspension of NaH (60% in mineral oil, 164 mg, 4.1 mmol) in dimethylacetamide (20 mL) and stirred at room temperature for 0.5 h under inert atmosphere. 1-Benzyl-1H-pyrido[2,3-d][1,3]oxazine-2,4-dione (2) (1 g, 4 mmol) was added to the solution and heated at 110° C. for 4 h (TLC control). The solution was cooled and poured into ice water. The pH of the solution was adjusted to 3 by cold 10% HCl. The solids formed were filtered, washed by excess water, and dried in a vacuum oven to yield 940 mg (72%) of 1-benzyl-4-hydroxy-2-oxo-1,2-dihydro-[1,8]-naphthyridine-3-carboxylic acid ethyl ester (3) as white solids. MP: 143° C.; $^1$H-NMR (DMSO-$d_6$): δ 1.29 (t, J=6.9 Hz, 3H), 4.31 (q, J=6.9 Hz, 2H), 5.55 (s, 2H), 7.23 (m, 5H), 7.36 (m, 1H), 8.45 (dd, J=1.5, 7.5 Hz, 1H), 8.70 (dd, J=1.5, 7.5 Hz, 1H); EIMS: 325 (M+1), 347 (M+23).

Synthesis of 1-Benzyl-4-chloro-2-oxo-1,2-dihydro-[1,8]-naphthyridine-3-carboxylic acid ethyl ester (4)

A solution of 1-benzyl-4-hydroxy-2-oxo-1,2-dihydro-[1,8]-naphthyridine-3-carboxylic acid ethyl ester (3) (0.94 g, 2.9 mmol) was heated in neat $POCl_3$ at 90° C. for 3 h. The solution was cooled and the excess $POCl_3$ was distilled under vacuum. The residue was suspended in water, neutralized by solid $NaHCO_3$, and extracted by dichloromethane. The organic layer was subsequently washed by saturated $NaHCO_3$ solution, water and brine, dried over $Na_2SO_4$, and evaporated to yield 0.9 g (98%) of 1-benzyl-4-chloro-2-oxo-1,2-dihydro-[1,8]-naphthyridine-3-carboxylic acid ethyl ester (4) as white solids. MP: 109° C.; $^1$H-NMR (DMSO-$d_6$): δ 1.31 (t, J=6.9 Hz, 3H), 4.37 (q, J=6.9 Hz, 2H), 5.62 (s, 2H), 7.27 (m, 5H), 7.51 (dd, J=4.7, 8.0 Hz, 1H), 8.46 (dd, J=1.5, 7.5 Hz, 1H), 8.80 (dd, J=1.5, 7.5 Hz, 1H); EIMS: 343 (M+1), 365 (M+23).

The sequence of reactions in the preparation of 1-benzyl-4-hydroxy-2-oxo-1,2-dihydro-[1,8]-naphthyridine-3-carboxylic acid ethyl ester (3) and 1-benzyl-4-chloro-2-oxo-1,2-dihydro-[1,8]-naphthyridine-3-carboxylic acid ethyl ester (4) as described above was as follows:

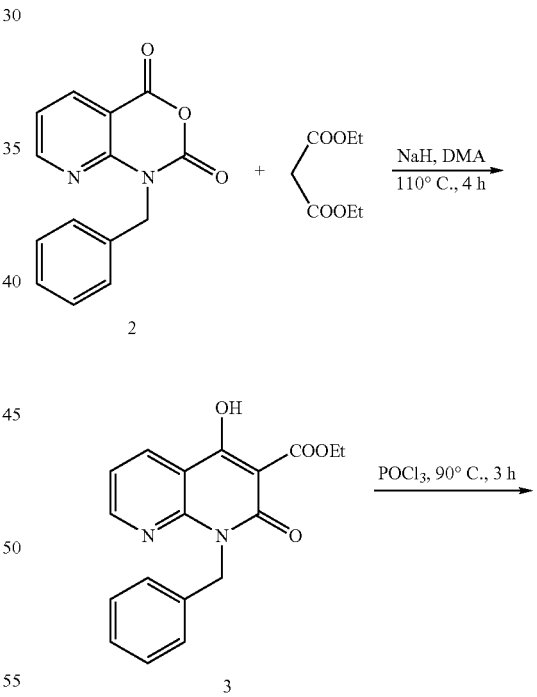

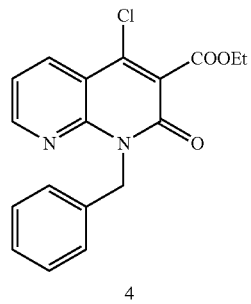

Synthesis of 1-Benzyl-2-oxo-4-piperazin-1-yl-1,2-dihydro-[1,8]-naphthyridine-3-carboxylic acid ethyl ester (5)

A solution of 1-benzyl-4-chloro-2-oxo-1,2-dihydro-[1,8]-naphthyridine-3-carboxylic acid ethyl ester (4) (1.2 g, 3.5 mmol) in dichloromethane was added slowly to a stirred solution of piperazine (0.9 g, 10.5 mmol) in dichloromethane at room temperature. The solution was stirred overnight at room temperature. The solvent was evaporated and the residue was suspended in water, sonicated briefly, and extracted with dichloromethane. The combined organic phase was subsequently washed by water and brine, dried over $Na_2SO_4$, and evaporated to yield 1.12 g (82%) of 1-benzyl-2-oxo-4-piperazin-1-yl-1,2-dihydro-[1,8]-naphthyridine-3-carboxylic acid ethyl ester (5) as yellow solids. MP: 120° C.; $^1$H-NMR (DMSO-$d_6$): δ 1.30 (t, J=6.9 Hz, 3H), 2.28 (m, 4H), 3.03 (m, 4H), 4.28 (q, J=6.9 Hz, 2H), 5.55 (s, 2H), 7.16-7.28 (m, 5H), 7.36 (m, 1H), 8.25 (dd, J=1.5, 7.5 Hz, 1H), 8.63 (dd, J=1.5, 7.5 Hz, 1H); EIMS: 393 (M+1), 415 (M+23).

Synthesis of 1-Benzyl-4-[4-(thiophene-2-carbonyl)-piperazin-1-yl]-2-oxo-1,2-dihydro-[1,8]-naphthyridine-3-carboxylic acid ethyl ester (6)

2-Thiophene carbonyl chloride (0.16 mL, 1.5 mmol) was added to a stirred solution of 1-benzyl-2-oxo-4-piperazin-1-yl-1,2-dihydro-[1,8]-naphthyridine-3-carboxylic acid ethyl ester (5) (392 mg, 1 mmol) in pyridine (5 mL) at 0° C. under inert atmosphere. The solution was allowed to come at room temperature and further stirred for 18 h. The solution was poured into ice water, the solids formed were filtered, washed by water, dried, and recrystallized by ether and ethyl acetate to yield 256 mg (51%) of 1-benzyl-4-[4-(thiophene-2-carbonyl)-piperazin-1-yl]-2-oxo-1,2-dihydro-[1,8]-naphthyridine-3-carboxylic acid ethyl ester (6) as white solids. MP: 168° C.; $^1$H-NMR (DMSO-$d_6$): δ 1.29 (t, J=6.9 Hz, 3H), 3.16 (m, 4H), 3.88 (m, 4H), 4.31 (q, J=6.9 Hz, 2H), 5.56 (s, 2H), 7.15 (dd, J=3.5, 4.9 Hz, 1H), 7.20-7.29 (m, 5H), 7.38 (dd, J=4.6, 8.2 Hz, 1H), 7.97 (d, J=4.9 Hz, 1H), 8.35 (dd, J=1.5, 7.5 Hz, 1H), 8.66 (dd, J=1.5, 7.5 Hz, 1H); EIMS: 503 (M+1), 525 (M+23). Anal. $C_{27}H_{26}N_4O_4S$ (C,H,N).

The sequence of reactions in the preparation of 1-benzyl-2-oxo-4-piperazin-1-yl-1,2-dihydro-[1,8]-naphthyridine-3-carboxylic acid ethyl ester (5) and 1-benzyl-4-[4-(thiophene-2-carbonyl)-piperazin-1-yl]-2-oxo-1,2-dihydro-[1,8]-naphthyridine-3-carboxylic acid ethyl ester (6) as described above was as follows:

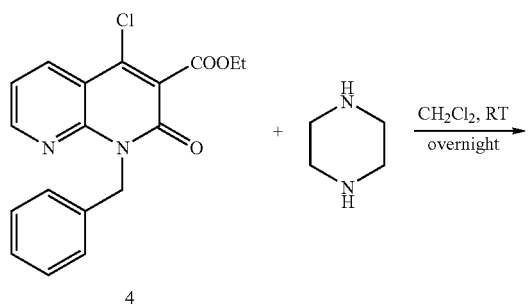

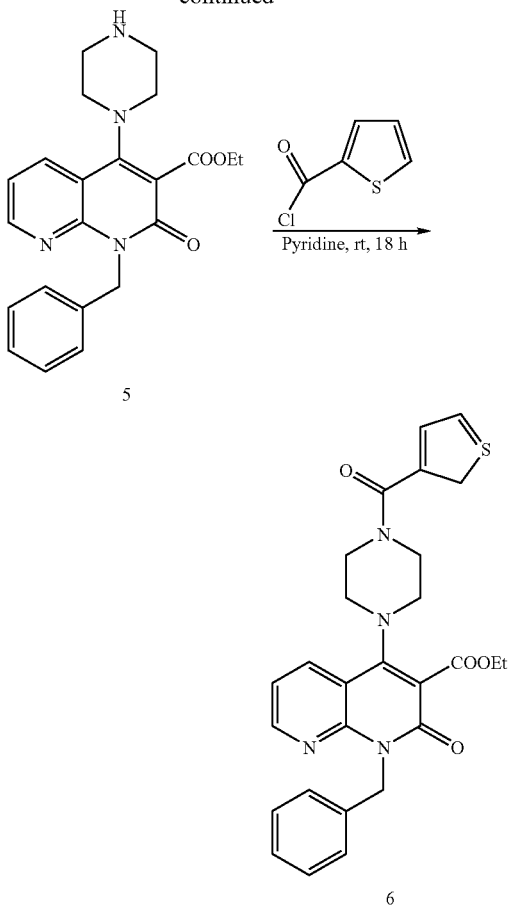

Synthesis of 1-Benzyl-4-hydroxy-2-oxo-1,2-dihydro-[1,8]-naphthyridine-3-carboxylic acid cyclohexylamide (7)

Cyclohexylamine (1.18 mL, 10.35 mmol) was added to a stirred solution of 1-benzyl-4-hydroxy-2-oxo-1,2-dihydro-[1,8]-naphthyridine-3-carboxylic acid ethyl ester (3) (1.68 g, 5.17 mmol) in xylene and heated at 140° C. for 3 h. The solution was cooled and the solvent was evaporated under vacuum. The residue was suspended in water and extracted by dichloromethane. The combined organic phase washed by water and brine, then dried over $Na_2SO_4$ and evaporated to yield 1.6 g (82%) of 1-benzyl-4-hydroxy-2-oxo-1,2-dihydro-[1,8]-naphthyridine-3-carboxylic acid cyclohexylamide (7) as white solids. MP: 143° C.; $^1$H-NMR (DMSO-$d_6$): δ 1.22-1.87 (m, 10H), 3.87 (m, 1H), 5.62 (s, 2H), 7.20-7.32 (m, 5H), 7.43 (dd, J=4.6, 8.0 Hz, 1H), 8.48 (dd, J=1.5, 7.5 Hz, 1H), 8.77 (dd, J=1.5, 7.5 Hz, 1H), 10.20 (s, 1H); EIMS: 378 (M+1).

Synthesis of 1-Benzyl-4-chloro-2-oxo-1,2-dihydro-[1,8]-naphthyridine-3-carbonitrile (8)

A solution of 1-benzyl-4-hydroxy-2-oxo-1,2-dihydro-[1,8]-naphthyridine-3-carboxylic acid cyclohexylamide (7) (1.3 g, 3.44 mmol) in neat $POCl_3$ was heated overnight at 90° C. The solution was cooled and the excess $POCl_3$ was distilled under vacuum. The residue was suspended in water, basified by saturated NaHCO$_3$ solution and extracted by dichloromethane. The combined organic phase washed subsequently by a saturated NaHCO$_3$ solution, water and brine, dried over Na$_2$SO$_4$, and evaporated. The residue was crystallized by acetone to yield 530 mg (52%) of 1-benzyl-4-chloro-2-oxo-1,2-dihydro-[1,8]-naphthyridine-3-carbonitrile (8) as white solids. MP: 188° C.; $^1$H-NMR (DMSO-d$_6$): δ 5.61 (s, 2H), 7.21-7.31 (m, 5H), 7.56 (dd, J=4.8, 8.0 Hz, 1H), 8.53 (dd, J=1.6, 8.0 Hz, 1H), 8.86 (dd, J=1.6, 8.0 Hz, 1H); EIMS: 296 (M+1).

The sequence of reactions in the preparation of 1-benzyl-4-hydroxy-2-oxo-1,2-dihydro-[1,8]-naphthyridine-3-carboxylic acid cyclohexylamide (7) and 1-benzyl-4-chloro-2-oxo-1,2-dihydro-[1,8]-naphthyridine-3-carbonitrile (8) as described above was as follows:

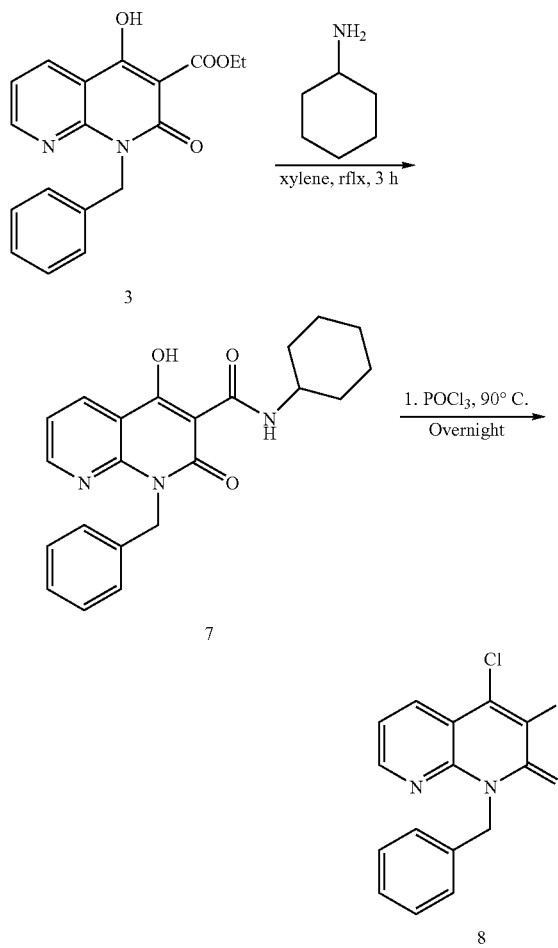

Synthesis of 1-Benzyl-2-oxo-4-piperazin-1-yl-1,2-dihydro-[1,8]-naphthyridine-3-carbonitrile (9)

A solution of 1-benzyl-4-chloro-2-oxo-1,2-dihydro-[1,8]-naphthyridine-3-carbonitrile (8) (530 mg, 1.79 mmol) in dichloromethane was added slowly to a stirred solution of piperazine (463 mg, 5.37 mmol) in dichloromethane at room temperature. The solution was further stirred overnight at room temperature and diluted by dichloromethane. The solution was subsequently washed with saturated NaHCO$_3$ solution, water and brine, then dried over Na$_2$SO$_4$ and evaporated to yield 610 mg (98%) of 1-benzyl-2-oxo-4-piperazin-1-yl-1,2-dihydro-[1,8]-naphthyridine-3-carbonitrile (9) as white solids. MP: 211° C.; $^1$H-NMR (DMSO-d$_6$): δ 2.93 (m, 4H), 3.57 (m, 4H), 5.53 (s, 2H), 7.20-7.27 (m, 5H), 7.34 (dd, J=4.8, 8.0 Hz, 1H), 8.26 (dd, J=1.6, 8.0 Hz, 1H), 8.65 (dd, J=1.6, 8.0 Hz, 1H); EIMS: 296 (M+1). EIMS: 346 (M+1).

Synthesis of 1-Benzyl-2-oxo-4-[4-(thiophene-2-carbonyl)-piperazin-1-yl]-1,2-dihydro-[1,8]-naphthyridine-3-carbonitrile (10)

2-Thiophene carbonyl chloride (0.16 mL, 1.5 mmol) was added to a stirred solution of 1-benzyl-2-oxo-4-piperazin-1-yl-1,2-dihydro-[1,8]-naphthyridine-3-carbonitrile (9) (345 mg, 1 mmol) in pyridine at 0° C. The solution was allowed to come at room temperature and further stirred overnight at room temperature. The solution was poured into ice water and the solids formed were filtered, washed by water, and dried. The crude product was purified by flash chromatography eluting with linear gradients of 0-3% MeOH in CH$_2$Cl$_2$ to yield 273 mg (45%) of 1-benzyl-2-oxo-4-[4-(thiophene-2-carbonyl)-piperazin-1-yl]-1,2-dihydro-[1,8]-naphthyridine-3-carbonitrile (10) as white solids. MP: 263° C.; $^1$H-NMR (DMSO-d$_6$): δ 3.75 (m, 4H), 3.94 (m, 4H), 5.58 (s, 2H), 7.15 (dd, J=3.5, 4.8 Hz, 1H), 7.19-7.29 (m, 5H), 7.40 (dd, J=4.8, 8.0 Hz, 1H), 7.52 (dd, J=4.0, 5.2 Hz, 1H), 8.35 (dd, J=1.6, 8.0 Hz, 1H), 8.72 (dd, J=1.6, 8.0 Hz, 1H); EIMS: 456 (M+1). Anal. C$_{25}$H$_{21}$N$_5$O$_2$S (C,H,N).

The sequence of reactions in the preparation of 1-benzyl-2-oxo-4-piperazin-1-yl-1,2-dihydro-[1,8]-naphthyridine-3-carbonitrile (9) and 1-benzyl-2-oxo-4-[4-(thiophene-2-carbonyl)-piperazin-1-yl]-1,2-dihydro-[1,8]-naphthyridine-3-carbonitrile (10) as described above was as follows:

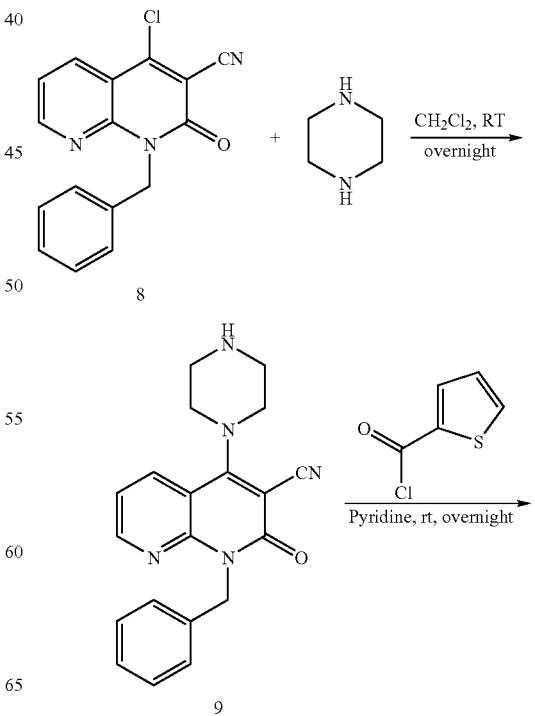

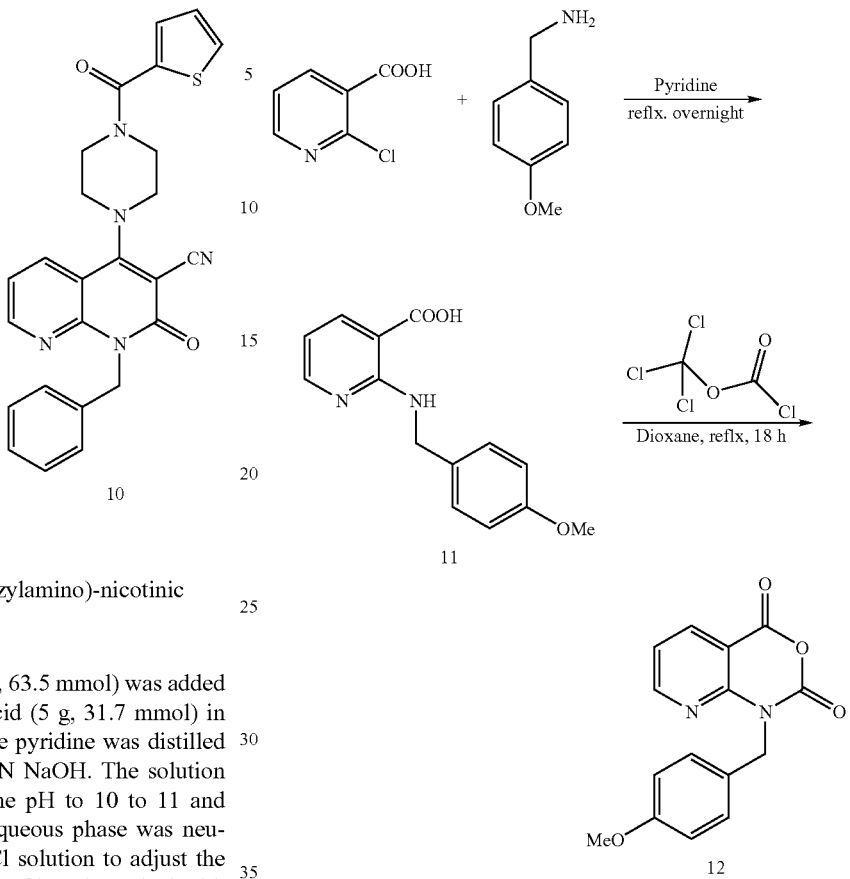

Synthesis of 2-(4-Methoxy-benzylamino)-nicotinic acid (11)

p-Methoxybenzylamine (8.24 mL, 63.5 mmol) was added to a solution of 2-chloronicotinic acid (5 g, 31.7 mmol) in pyridine and refluxed overnight. The pyridine was distilled and the residue was dissolved in 1N NaOH. The solution was diluted with water to adjust the pH to 10 to 11 and washed by dichloromethane. The aqueous phase was neutralized with cold aqueous 10% HCl solution to adjust the pH to 4 to 5. The solids formed were filtered, washed with cold water, and dried in a vacuum oven to yield 6.32 g (77%) of 2-(4-methoxy-benzylamino)-nicotinic acid (11) as white solids. MP: 229° C.; $^1$H-NMR (DMSO-$d_6$): δ 3.72 (s, 3H), 4.60 (d, J=3.6 Hz, 2H), 6.40 (dd, J=4.9, 7.7 Hz, 1H), 6.62 (d, J=7.6 Hz, 2H), 7.25 (d, J=7.6 Hz, 2H), 8.09 (dd, J=1.8, 7.0 Hz, 1H), 8.26 (dd, J=1.8, 7.0 Hz, 1H), 8.48 (br. s, 1H), 13.11 (s, 1H); EIMS: 259 (M+1), 281 (M+23).

Synthesis of 1-(4-Methoxy-benzyl)-1H-pyrido[2,3-d][1,3]oxazine-2,4-dione (12)

Trichloromethyl chloroformate (3.36 mL, 27.8 mmol) was added slowly to a suspension of 2-(4-methoxy-benzylamino)-nicotinic acid (11) (6 g, 23.23 mmol) in dioxane and refluxed for 18 h under nitrogen atmosphere. The solution was cooled and the solvent was removed under vacuum. The residue was dissolved in dichloromethane and washed by saturated NaHCO$_3$ solution. The organic phase was dried over Na$_2$SO$_4$ and evaporated to yield a residue. The residue was recrystallized by ether to yield 4.47 g (67%) of 1-(4-methoxy-benzyl)-1H-pyrido[2,3-d][1,3]oxazine-2,4-dione (12) as white solids. MP: 160° C.; $^1$H-NMR (DMSO-$d_6$): δ 3.71 (s, 1H), 5.27 (s, 2H), 6.85 (d, J=7.0 Hz, 2H), 7.33 (m, 3H), 8.40 (dd, J=1.5, 7.5 Hz, 1H), 8.75 (dd, J=1.5, 7.5 Hz, 1H); EIMS: 286 (M+23).

The sequence of reactions in the preparation of 2-(4-methoxy-benzylamino)-nicotinic acid (11) and 1-(4-methoxy-benzyl)-1H-pyrido[2,3-d][1,3]oxazine-2,4-dione (12) as described above was as follows:

Synthesis of 4-Hydroxy-1-(4-methoxy-benzyl)-2-oxo-1,2-dihydro-[1,8]-naphthyridine-3-carboxylic acid ethyl ester (13)

Diethyl malonate (2.37 mL, 15.61 mmol) was added slowly to a suspension of NaH (60% in mineral oil, 0.62 g, 15.61 mmol) in dimethylacetamide (40 mL) and stirred at room temperature for 0.5 h under inert atmosphere. 1-(4-Methoxy-benzyl)-1H-pyrido[2,3-d][1,3]oxazine-2,4-dione (12) (4.47 g, 15.61 mmol) was added to the solution and heated at 110° C. for 3 h (TLC control). The solution was cooled and poured into ice water. The pH of the solution was adjusted to 3 by cold 10% HCl. The solids formed were filtered, washed by excess water, and dried in a vacuum oven. The crude product was recrystallized by ethylacetate to yield 1.2 g (21%) of 4-hydroxy-1-(4-methoxy-benzyl)-2-oxo-1,2-dihydro-[1,8]-naphthyridine-3-carboxylic acid ethyl ester (13) as white solids. MP: 153° C.; $^1$H-NMR (DMSO-$d_6$): δ 1.31 (t, J=7.0 Hz, 3H), 3.68 (s, 3H), 4.32 (q, J=7.0 Hz, 2H), 5.47 (s, 2H), 6.81 (d, J=7.7 Hz, 2H), 7.21 (d, J=7.6 Hz, 2H), 7.36 (d, J=7.6 Hz, 1H), 8.42 (dd, J=1.5, 7.5 Hz, 1H), 8.73 (dd, J=1.5, 7.5 Hz, 1H), 13.00 (S, 1H); EIMS: 355 (M+1).

The sequence of reaction in the preparation of 4-hydroxy-1-(4-methoxy-benzyl)-2-oxo-1,2-dihydro-[1,8]-naphthyridine-3-carboxylic acid ethyl ester (13) as described above was as follows:

dine-3-carboxylic acid ethyl ester (14) and 4-chloro-2-oxo-1,2-dihydro-[1,8]-naphthyridine-3-carboxylic acid ethyl ester (15) as described above was as follows:

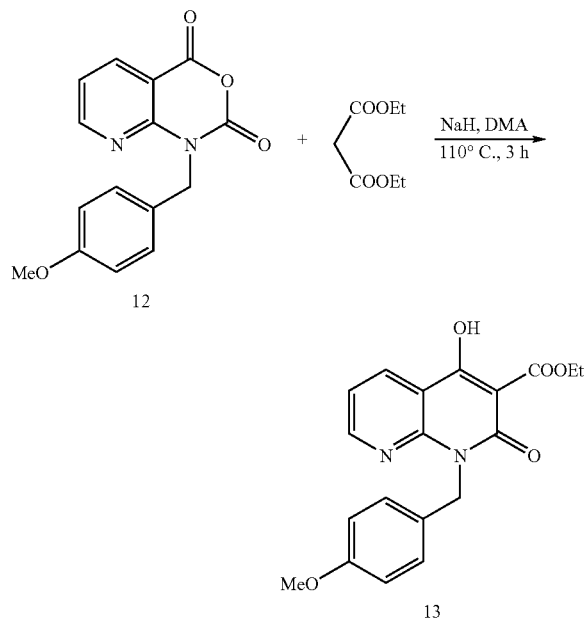

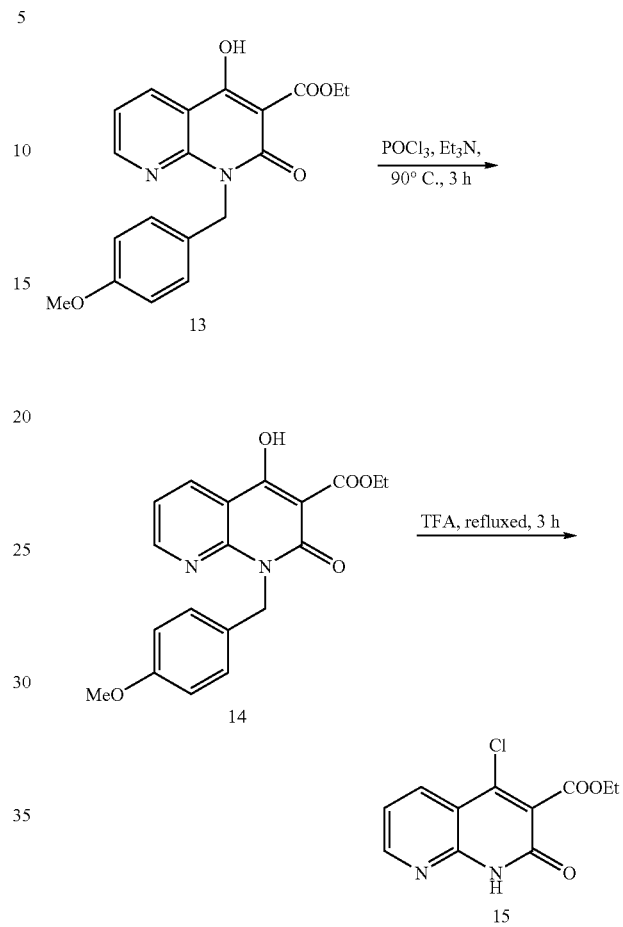

Synthesis of 4-Chloro-1-(4-methoxy-benzyl)-2-oxo-1,2-dihydro-[1,8]-naphthyridine-3-carboxylic acid ethyl ester (14)

A solution of 4-hydroxy-1-(4-methoxy-benzyl)-2-oxo-1,2-dihydro-[1,8]-naphthyridine-3-carboxylic acid ethyl ester (13) (0.40 g, 1.13 mmol) and triethylamine (393 µL, 2.82 mmol) was heated in neat $POCl_3$ at 90° C. for 3 h. The solution was cooled and the excess $POCl_3$ was distilled under vacuum. The residue was suspended in saturated $NaHCO_3$ solution, sonicated briefly and filtered. The solids were dissolved in dichloromethane, washed subsequently by saturated $NaHCO_3$ solution, water and brine. The organic phase was dried over $MgSO_4$ and evaporated to yield 400 mg (95%) of 4-chloro-1-(4-methoxy-benzyl)-2-oxo-1,2-dihydro-[1,8]-naphthyridine-3-carboxylic acid ethyl ester (14) as white solids. $^1$H-NMR (DMSO-$d_6$): δ 1.30 (t, J=7.0 Hz, 3H), 3.62 (s, 3H), 4.30 (q, J=7.0 Hz, 2H), 5.47 (s, 2H), 6.81 (d, J=7.7 Hz, 2H), 7.21 (d, J=7.6 Hz, 2H), 7.31 (d, J=7.6 Hz, 1H), 8.40 (dd, J=1.5, 7.5 Hz, 1H), 8.71 (dd, J=1.5, 7.5 Hz, 1H); EIMS: 373 (M+1).

Synthesis of 4-Chloro-2-oxo-1,2-dihydro-[1,8]-naphthyridine-3-carboxylic acid ethyl ester (15)

A solution of 4-chloro-1-(4-methoxy-benzyl)-2-oxo-1,2-dihydro-[1,8]-naphthyridine-3-carboxylic acid ethyl ester (13) (0.40 g, 1.07 mmol) in neat trifluoroacetic acid (TFA) was refluxed for 3 h. The solution was cooled and the excess TFA was distilled under vacuum. The residue was suspended in saturated NaHCO3 solution, sonicated briefly and filtered. The solids were washed by water, and dried at room temperature to yield 252 mg (93%) of 4-chloro-2-oxo-1,2-dihydro-[1,8]-naphthyridine-3-carboxylic acid ethyl ester (15) as white solids. MP: 172° C.; 1H-NMR (DMSO-d6): δ 1.31 (t, J=7.0 Hz, 3H), 4.35 (q, J=6.9 Hz, 2H), 7.41 (dd, J=4.7, 8.0 Hz, 1H), 8.34 (dd, J=1.5, 7.5 Hz, 1H), 8.69 (dd, J=1.5, 7.5 Hz, 1H), 12.90 (s, 1H); EIMS: 253 (M+1).

The sequence of reactions in the preparation of 4-chloro-1-(4-methoxy-benzyl)-2-oxo-1,2-dihydro-[1,8]-naphthyri-

Synthesis of 2-Oxo-4-[4-(thiophene-2-carbonyl)-piperazin-1-yl]-1,2-dihydro-[1,8]-naphthyridine-3-carboxylic acid ethyl ester (16)

DABCO (0.57 g, 5.14 mmol) was added to a solution of 4-chloro-2-oxo-1,2-dihydro-[1,8]-naphthyridine-3-carboxylic acid ethyl ester (15) (0.65 g, 2.57 mmol) and piperazine-1-yl-thiophene-2-yl-methanone (0.60 g, 3.08 mmol) in dimethylacetamide at room temperature. The solution was heated overnight at 110° C. The solution was cooled and poured into ice water. The solids formed were filtered, washed by water, and dried to yield 420 mg (39%) of 2-oxo-4-[4-(thiophene-2-carbonyl)-piperazin-1-yl]-1,2-dihydro-[1,8]-naphthyridine-3-carboxylic acid ethyl ester (16) as white solids. MP: 239° C.; $^1$H-NMR (DMSO-$d_6$): δ 1.30 (t, J=7.0 Hz, 3H), 3.13 (m, 4H), 3.87 (m, 4H), 4.30 (q, J=7.0 Hz, 2H), 7.15 (dd, J=3.5, 4.8 Hz, 1H), 7.40 (dd, J=4.8, 8.0 Hz, 1H), 7.45 (d, J=3.6 Hz, 1H), 7.80 (d, J=4.8 Hz, 1H), 8.24 (dd, J=1.5, 7.5 Hz, 1H), 8.56 (dd, J=1.5, 7.5 Hz, 1H) 12.25 (s, 1H); EIMS: 413 (M+1).

The sequence of reactions in the preparation of 2-oxo-4-[4-(thiophene-2-carbonyl)-piperazin-1-yl]-1,2-dihydro-[1,8]-naphthyridine-3-carboxylic acid ethyl ester (16)) as described above was as follows:

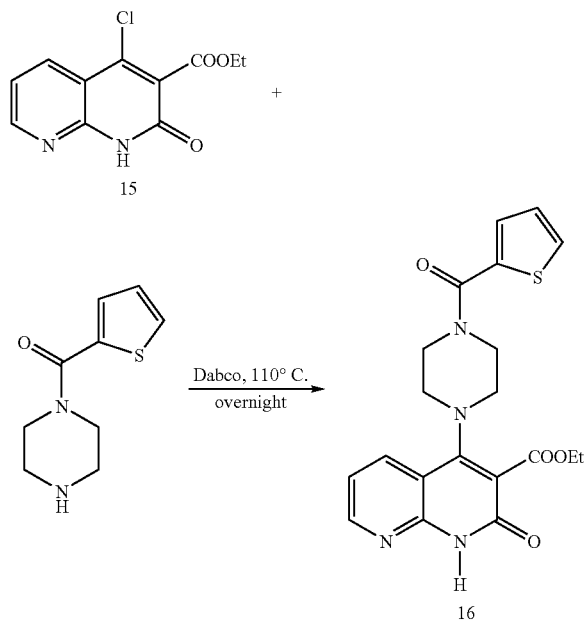

Preparation of Compounds by Alkylation at N–1 Position of Naphthyridine Moiety

The compounds referred to as compound 17 through 28 were prepared by applying either General Procedure A or General Procedure B.

General procedure A

Solid 2-oxo-4-[4-(thiophene-2-carbonyl)-piperazin-1-yl]-1,2-dihydro-[1,8]-naphthyridine-3-carboxylic acid ethyl ester (16) (455 mg, 1.1 mmol) was added in portion to a stirred suspension of NaH (60% in mineral oil, 53 mg, 1.32 mmol) in DMF at room temperature. The solution was further stirred at room temperature for 1 h to yield a yellow clear solution. Corresponding alkyl halides (1.32 mmol) were added to this solution and further stirred for 3 h. The solution was poured into ice water and the solids formed were filtered, washed by cold water, and dried. The crude product was purified by flash chromatography eluting with 0-2% methanol in dichloromethane gradient to yield title compound.

General procedure B

A solution of 2-oxo-4-[4-(thiophene-2-carbonyl)-piperazin-1-yl]-1,2-dihydro-[1,8]-naphthyridine-3-carboxylic acid ethyl ester (16) (455 mg, 1.1 mmol), corresponding alkyl halide (1.65 mmol) and anhydrous potassium carbonate (5.5 mmol) in DMF was heated overnight at 90° C. The solution was cooled and DMF was removed under vacuum. The residue was suspended in water, sonicated briefly, filtered, and dried at room temperature. The crude product was purified by flash chromatography eluting with 0-2% methanol in dichloromethane gradient to yield title compound.

Synthesis of 1-(4-Acetoxy-benzyl)-2-oxo-4-[4-(thiophene-2-carbonyl)-piperazin-1-yl]-1,2-dihydro-[1,8]-naphthyridine-3-carboxylic acid ethyl ester (17)

The compound was prepared by using 4-acetoxy benzyl bromide (305 mg, 1.32 mmol) according to General Procedure A to yield 275 mg (45% of white solids. MP: 123° C.; $^1$H-NMR (DMSO-$d_6$): δ 1.37 (t, J=6.9 Hz, 3H), 2.19 (s, 3H), 3.22 (m, 4H), 3.95 (m, 4H), 4.40 (q, J=6.9 Hz, 2H), 5.81 (s, 2H), 7.10 (d, J=8.0 Hz, 2H), 7.16 (m, 1H), 7.22 (d, J=8.0 Hz, 2H), 7.45 (m, 1H), 7.47 (d, J=3.2 Hz, 1H), 7.84 (d, J=4.8 Hz, 1H), 8.41 (dd, J=1.5, 7.5 Hz, 1H), 8.70 (dd, J=1.5, 7.5 Hz, 1H); EIMS: 561 (M+1). Anal. ($C_{29}H_{28}N_4O_6S$) C, H, N.

Synthesis of 1-(2-Dimethylaminoethyl)-2-oxo-4-[4-(thiophene-2-carbonyl)-piperazin-1-yl]-1,2-dihydro-[1,8]-naphthyridine-3-carboxylic acid ethyl ester (18)

The compound was prepared by using 2-dimethylaminoethyl chloride hydrochloride (188 mg, 1.32 mmol) according to General Procedure B to yield 223 mg (35%) of white solids. MP: 134° C.; $^1$H-NMR (DMSO-$d_6$): δ 1.35 (t, J=7.0 Hz, 3H), 2.20 (S, 6H), 3.02 (m, 4H), 3.90 (m, 4H), 4.30 (q, J=7.0 Hz, 2H), 4.50 (m, 2H), 7.15 (dd, J=3.5, 4.8 Hz, 1H), 7.41 (dd, J=4.8, 8.0 Hz, 1H), 7.45 (d, J=3.6 Hz, 1H), 7.81 (d, J=4.8 Hz, 1H), 8.38 (dd, J=1.5, 7.5 Hz, 1H), 8.76 (dd, J=1.5, 7.5 Hz, 1H); EIMS: 484 (M+1). Anal. ($C_{24}H_{29}N_5O_4S$) C, H, N.

Synthesis of 1-Methyl-2-oxo-4-[4-(thiophene-2-carbonyl)-piperazine-1-yl]-1,2-dihydro-[1,8]-naphthyridine-3-carboxylic acid ethyl ester (19)

The compound was prepared by using methyl iodide (82 μL, 1.32 mmol) according to General Procedure A to yield 102 mg (22%) of white solids. MP 164° C.; $^1$H-NMR (DMSO-$d_6$): δ 1.31 (t, J=6.8 Hz, 3H), 3.13 (m, 4H), 3.64 (s, 3H), 3.88 (m, 4H), 4.31 (q, J=6.8 Hz, 2H), 7.15 (dd, J=3.6, 4.8 Hz, 1H), 7.38 (dd, J=4.8, 8.0 Hz, 1H), 7.45 (d, J=3.6 Hz, 1H), 7.79 (d, J=4.8 Hz, 1H), 8.34 (dd, J=1.6, 8.0 Hz, 1H), 8.70 (dd, J=1.6, 4.8 Hz, 1H); EIMS: 427 (M+1). Anal. ($C_{21}H_{22}N_4O_4S$) C, H, N.

Synthesis of 1-(4-Fluoro-benzyl)-2-oxo-4-[4-(thiophene-2-carbonyl)-piperazine-1-yl]-1,2-dihydro-[1,8]-naphthyridine-3-carboxylic acid ethyl ester (20)

The compound was prepared by using 4-fluorobenzylbromide (162 μL, 1.32 mmol) according to General Procedure A to yield 355 mg (62%) of white solids. MP 196° C.; $^1$H-NMR (DMSO-$d_6$): δ 1.24 (t, J=6.8 Hz, 3H), 3.20 (m, 4H), 3.90 (m, 4H), 4.31 (q, J=6.8 Hz, 2H), 5.57 (s, 2H), 7.10-7.20 (m, 3H), 7.30-7.40 (m, 3H), 7.56 (d, J=3.6 Hz, 1H), 7.81 (d, J=4.8 Hz, 1H), 8.30 (dd, J=1.6, 8.0 Hz, 1H), 8.70 (dd, J=1.6, 4.4 Hz, 1H); EIMS: 521 (M+1). Anal. ($C_{27}H_{25}FN_4O_4S$) C, H, N.

Synthesis of 2-Oxo-1-propyl-4-[4-(thiophene-2-carbonyl)-piperazin-1-yl]-1,2-dihydro-[1,8]-naphthyridine-3-carboxylic acid ethyl ester (21)

The compound was prepared by using 1-iodopropane (129 μL, 1.32 mmol) according to General Procedure B to yield 140 mg (28%) of yellow solids. MP 92-96° C.; $^1$H-NMR (DMSO-$d_6$): δ 0.91 (t, J=7.2 Hz, 3H), 1.30 (t, J=7.2 Hz, 3H), 1.6 (m, 2H), 3.13 (s, 4H), 3.88 (s, 4H), 4.3 (m, 4H), 7.1 (m, 1H), 7.4 (dd, J=1.2, 3.6 Hz, 1H), 7.79 (d, J=0.8, 4.8 Hz, 1H), 8.34 (dd, J=1.6, 8.0 Hz, 1H), 8.70 (dd, J=1.6, 4.4 Hz, 1H); EIMS m/z 455 (M+H).

Synthesis of 1-Butyl-2-oxo-4-[4-(thiophene-2-carbonyl)-piperazin-1-yl]-1,2-dihydro-[1,8]-naphthyridine-3-carboxylic acid ethyl ester (22)

The compound was prepared by using iodobutane (151 µL, 1.32 mmol) according to General Procedure B to yield 200 mg (39%) of yellow solids. MP 90-96° C.; $^1$H-NMR (DMSO-d$_6$): 0.92 (t, J=7.2 Hz, 3H), 1.3 (m, 5H), 1.6 (m, 2H), 3.13 (s, 4H), 3.88 (s, 4H), 4.32 (m, 4H), 7.15 (m, 1H), 7.38 (m, 1H), 7.45 (dd, J=1.2, 3.6, 1H), 7.79 (dd, J=1.2, 5.2 Hz, 1H), 8.34 (dd, J=1.6, 8.0 Hz, 1H), 8.70 (dd, J=1.6, 4.4 Hz, 1H); EIMS m/z 469 (M+H).

Synthesis of 1-Allyl-2-oxo-4-[4-(thiophene-2-carbonyl)-piperazin-1-yl]-1,2-dihydro-[1,8]-naphthyridine-3-carboxylic acid ethyl ester (23)

The compound was prepared by using allyliodide (134 µL, 1.32 mmol) according to General Procedure B to yield 170 mg (34%) of yellow solids. MP 89-96° C.; $^1$H-NMR (DMSO-d$_6$): δ 1.30 (t, J=7.2 Hz, 3H), 3.15 (s, 4H), 3.89 (s, 4H), 4.31 (q, J=7.2 Hz, 2H), 5.0 (m, 4H), 5.9 (m, 1H), 7.15 (m, 1H), 7.39 (dd, J=4.8, 8.0 Hz, 1H), 7.46 (dd, J=0.8, 3.6 Hz), 7.79 (dd, J=0.8, 4.8 Hz, 1H), 8.34 (dd, J=1.6, 8.0 Hz, 1H), 8.68 (dd, J=1.6, 4.8 Hz, 1H); EIMS m/z 453 (M+H).

Synthesis of 1-(2-Fluoro-benzyl)-2-oxo-4-[4-(thiophene-2-carbonyl)-piperazin-1-yl]-1,2-dihydro-[1,8]-naphthyridine-3-carboxylic acid ethyl ester (24)

The compound was prepared by using 2-fluorobenzylbromide (162 µL, 1.32 mmol) according to General Procedure B to yield 170 mg (30%) of yellow solids. MP 105-110° C.; $^1$H-NMR (DMSO-d$_6$): δ 1.29 (t, J=7.2 Hz, 3H), 3.19 (s, 4H), 3.91 (s, 4H), 4.30 (q, J=7.2 Hz, 2H), 5.60 (s, 2H), 6.81 (m, 1H), 7.04 (m, 1H), 7.2 (m, 3H), 7.39 (m, 1H), 7.46 (dd, J=0.8, 3.6 Hz, 1H), 7.80 (dd, J=0.8, 4.8 Hz, 1H), 8.38 (dd, J=1.6, 8.0 Hz, 1H), 8.63 (dd, J=1.6, 4.4 Hz, 1H); EIMS m/z 521 (M+H).

Synthesis of 1-(3-Fluoro-benzyl)-2-oxo-4-[4-(thiophene-2-carbonyl)-piperazin-1-yl]-1,2-dihydro-[1,8]-naphthyridine-3-carboxylic acid ethyl ester (25)

The compound was prepared by using 3-fluorobenzylbromide (162 µL, 1.32 mmol) according to General Procedure B to yield 190 mg (33%) of yellow solids. MP 105-110° C.; $^1$H-NMR (DMSO-d$_6$): δ 1.29 (t, J=6.8 Hz, 3H), 3.18 (s, 4H), 3.89 (s, 4H), 4.31 (q, J=6.8 Hz, 2H), 5.56 (s, 2H), 7.1 (m, 4H), 7.4 (m, 3H), 7.79 (d, J=4.4 Hz, 1H), 8.36 (d, J=7.6 Hz, 1H), 8.67 (d, J=3.2 Hz, 1H); EIMS m/z 521 (M+H).

Synthesis of 1-(3-Dimethylamino-propyl)-2-oxo-4-[4-(thiophene-2-carbonyl)-piperazin-1-yl]-1,2-dihydro-[1,8]-naphthyridine-3-carboxylic acid ethyl ester (26)

The compound was prepared by using β-dimethylaminopropyl hydrochloride (209 mg, 1.32 mmol) according to General Procedure B to yield 110 mg (20%) of yellow solids. MP 84-94° C.; $^1$H-NMR (DMSO-d$_6$): δ 1.30 (t, J=7.2 Hz, 3H), 1.7 m, 2H), 2.14 (s, 6H), 2.30 (t, J=6.8 Hz, 2H), 3.13 (b, 4H), 3.88 (b, 4H), 4.3 (m, 4H), 7.2 (m, 1H), 7.3 (m, 1H), 7.45 (dd, J=1.2, 3.6 Hz, 1H), 7.79 (dd, J=0.8, 4.8 Hz, 1H), 8.34 (dd, J=2.0, 8.0 Hz, 1H), 8.70 (dd, J=2.0, 4.8 Hz, 1H); EIMS m/z 498 (M+H).

Synthesis of 2-Oxo-1-(2-oxo-2-phenyl-ethyl)-4-[4-(thiophene-2-carbonyl)-piperazin-1-yl]-1,2-dihydro-[1,8]-naphthyridine-3-carboxylic acid ethyl ester (27)

The compound was prepared by using 2-bromoacetophenone (262 µL, 1.32 mmol) according to General Procedure B to yield 58 mg (10%) red solid. MP 115° C.; $^1$H-NMR (DMSO-d$_6$): δ 1.29 (t, J=7.2 Hz, 3H), 3.21 (s, 4H), 3.92 (s, 4H), 4.31 (q, J=7.2 Hz, 2H), 5.89 (s, 2H), 7.16 (t, J=4.4 Hz, 1H), 7.4 (m, 1H), 7.47 (d, J=3.2 Hz, 1H), 7.61 (t, J=7.6 Hz, 2H), 7.74 (t, J=7.2 Hz, 1H), 7.80 (d, J=5.2 Hz, 1H), 8.12 (d, J=7.6 Hz, 2H), 8.38 (d, J=8.0 Hz, 1H), 8.56 (d, J=4.8 Hz, 1H); EIMS m/z 531 (M+1).

Synthesis of 4-Hydroxy-1-(4-methoxybenzyl)-2-oxo-1,2-dihydro-[1,8]-naphthyridine-3-carboxylic acid cyclohexylamide (29)

Cyclohexylamine (1.18 mL, 10.35 mmol) was added to a stirred solution of 4-hydroxy-1-(4-methoxy-benzyl)-2-oxo-1,2-dihydro-[1,8]-naphthyridine-3-carboxylic acid ethyl ester (13) (1.80 g, 5.17 mmol) in xylene and heated at 140° C. for 3 h. The solution was cooled and the solvent was evaporated under vacuum. The residue was suspended in water and extracted by dichloromethane. The combined organic phase washed by water and brine, then dried over Na2SO4 and evaporated to yield 1.68 g (82%) of 4-hydroxy-1-(4-methoxy-benzyl)-2-oxo-1,2-dihydro-[1,8]-naphthyridine-3-carboxylic acid cyclohexylamide (29) as white solids. MP: 149° C.; 1H-NMR (DMSO-d6): δ 1.2-1.4 (m, 5H), 1.55 (m, 1H), 1.70 (m, 2H), 1.90 (m, 2H), 3.69 (s, 3H), 3.86 (m, 1H), 5.54 (s, 2H), 6.81 (d, J=8.8 Hz, 2H), 7.20 (d, J=8.8 Hz, 2H), 7.43 (m, 1H), 8.47 (dd, J=2.0, 8.0 Hz, 1H), 8.79 (dd, J=1.6, 4.8 Hz, 1H), 10.22 (d, J=7.2 Hz, 1H); EIMS m/z 408 (M+1).

Synthesis of 2,4-Dichloro-[1,8]-naphthyridine-3-carbonitrile (30)

A solution of 4-hydroxy-1-(4-methoxy-benzyl)-2-oxo-1,2-dihydro-[1,8]-naphthyridine-3-carboxylic acid cyclohexylamide (29) (1.4 g, 3.44 mmol) in neat POCl$_3$ was heated overnight at 90° C. The solution was cooled and the excess POCl$_3$ was distilled under vacuum. The residue was suspended in water, basified by saturated NaHCO$_3$ solution and extracted by dichloromethane. The combined organic phase washed subsequently by a saturated NaHCO$_3$ solution, water and brine, dried over Na$_2$SO$_4$, and evaporated. The residue was crystallized by acetone to yield 624 mg (81%) of 2,4-dichloro-[1,8]-naphthyridine-3-carbonitrile (30) as brown solids. MP: 231; $^1$H-NMR (DMSO-d$_6$): δ 7.95 (m, 1H), 8.78 (dd, J=2.0, 8.4 Hz, 1H), 9.33 (dd, J=2.0, 4.4 Hz, 1H); EIMS m/z 224 (M+1).

The sequence of reactions in the preparation of 4-hydroxy-1-(4-methoxy-benzyl)-2-oxo-1,2-dihydro-[1,8]-naphthyridine-3-carboxylic acid cyclohexylamide (29) and 2,4-dichloro-[1,8]-naphthyridine-3-carbonitrile (30) as described above was as follows:

301

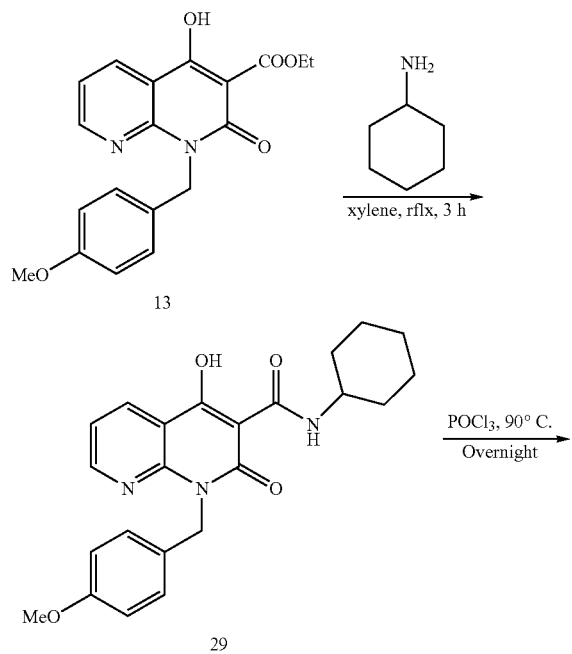

Synthesis of 4-Chloro-2-oxo-1,2-dihydro-[1,8]-naphthyridine-3-carbonitrile (31)

Ammonium acetate (6.81 g, 88.37 mmol) was added to a suspension of 2,4-Dichloro-[1,8]-naphthyridine-3-carbonitrile (30) in acetic acid at room temperature and heated at 140° C. for 45 min. The solution was cooled and poured into ice water. The solids formed were filtered, washed with cold water and suspended in saturated sodium bicarbonate solution. After stirring overnight at room temperature, the solids were filtered, washed by cold water, and dried at room temperature under vacuum to yield 8.0 g (48%) of 4-chloro-2-oxo-1,2-dihydro-[1,8]-naphthyridine-3-carbonitrile (31) as white solids. MP: 310° C.; $^1$H-NMR (DMSO-d$_6$): δ 7.58 (dd, J=4.4, 8.0 Hz, 1H), 8.50 (d, J=2.0, 8.0 Hz, 1H), 8.83 (dd, J=4.4, 1.6 Hz, 1H), 13.03 (S, 1H); EIMS: 206 (M+1).

Alternative Method

A solution of 1-(4-methoxybenzyl)-4-chloro-1,2-dihydro-2-oxo-1,8-naphthyridine-3-carbonitrile (32) (326 mg, 1 mmol) in TFA was refluxed for 24 h. The solution was cooled and excess TFA was distilled off under reduced pressure. The residue was taken in water, basified by solid NaHCO$_3$ and filtered. The solids were washed with excess water and dried to yield 197 mg (95%) of 4-chloro-2-oxo-1,2-dihydro-[1,8]-naphthyridine-3-carbonitrile (31) as white solids. MP: 310° C.; $^1$H-NMR (DMSO-d$_6$): δ 7.58 (dd, J=4.4, 8.0 Hz, 1H), 8.50 (d, J=2.0, 8.0 Hz, 1H), 8.83 (dd, J=4.4, 1.6 Hz, 1H), 13.03 (s, 1H); EIMS: 206 (M+1).

302

Synthesis of 1-(4-methoxybenzyl)-4-chloro-1,2-dihydro-2-oxo-1,8-naphthyridine-3-carbonitrile (32)

A solution of 4-hydroxy-1-(4-methoxy-benzyl)-2-oxo-1,2-dihydro-[1,8]-naphthyridine-3-carboxylic acid cyclohexylamide (29) (1.22 g, 3 mmol) and triethylamine (1.04 mL, 7.5 mmol) was heated in neat POCl$_3$ overnight at 90° C. The solution was cooled and the excess POCl$_3$ was distilled under vacuum. The residue was suspended in saturated NaHCO$_3$ solution, sonicated briefly and filtered. The solids were dissolved in dichloromethane, washed subsequently by saturated NaHCO$_3$ solution, water and brine. The organic phase was dried over MgSO$_4$ and evaporated to yield 0.83 g (85%), of 1-(4-methoxybenzyl)-4-chloro-1,2-dihydro-2-oxo-1,8-naphthyridine-3-carbonitrile (32) as brown solids. MP 195° C. $^1$H-NMR (DMSO-d$_6$): δ 3.69 (s, 3H), 5.42 (s, 2H), 6.83 (d, J=8.8 Hz, 2H), 7.29 (d, J=8.8 Hz, 2H), 7.55 (m, 1H), 8.50 (dd, J=2.0, 8.0 Hz, 1H), 8.88 (dd, J=1.6, 4.8 Hz, 1H); EIMS m/z 326 (M+1).

The sequence of reactions in the preparation of 4-chloro-2-oxo-1,2-dihydro-[1,8]-naphthyridine-3-carbonitrile (31) and 1-(4-methoxybenzyl)-4-chloro-1,2-dihydro-2-oxo-1,8-naphthyridine-3-carbonitrile (32) as described above was as follows:

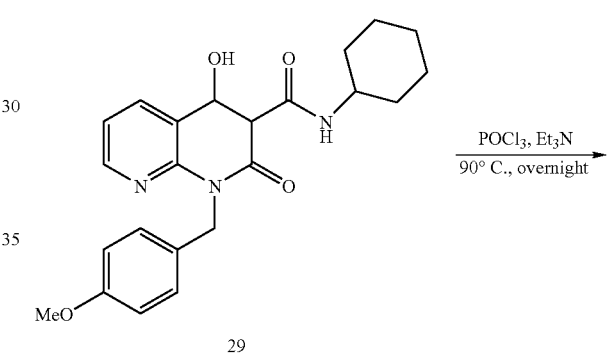

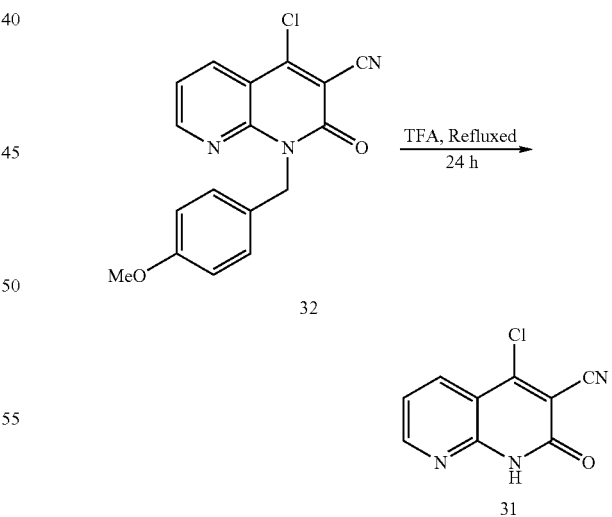

Synthesis of 2-Oxo-4-[4-(thiophene-2-carbonyl)-piperazine-1-yl]-1,2-dihydro-[1,8]-naphthyridine-3-carbonitrile (33)

1,4-Diazabicyclo[2.2.2]-octane (8.60 g, 77 mmol) was added to a solution of 4-chloro-2-oxo-1,2-dihydro-[1,8]- naphthyridine-3-carbonitrile (31) (7.9 g, 38 mmol) and piperazin-1-yl-thiophene-2-yl-methanone (11.30 g, 57 mmol) in dimethylacetamide at room temperature. The solution was heated at 110° C. overnight. The solution was cooled and poured into ice cold 10% $NH_4Cl$ solution. The solids formed were filtered, washed by cold water and dried under vacuum at room temperature to yield 7.1 g (51%) of 2-oxo-4-[4-(thiophene-2-carbonyl)-piperazine-1-yl]-1,2-dihydro-[1,8]-naphthyridine-3-carbonitrile (33) as white solids. MP 320° C.; $^1$H-NMR (DMSO-$d_6$): δ 3.69 (m, 4H), 3.90 (m, 4H), 7.16 (dd, J=3.6, 4.8 Hz, 1H), 7.30 (dd, J=4.4, 8.0 Hz, 1H), 7.49 (d, J=3.6 Hz, 1H), 7.80 (d, J=4.8 Hz, 1H), 8.20 (dd, J=2.0, 8.0 Hz, 1H), 8.60 (d, J=3.2 Hz, 1H), 12.20 (S, 1H); EIMS: 366 (M+1).

The sequence of reaction in the preparation of 2-oxo-4-[4-(thiophene-2-carbonyl)-piperazine-1-yl]-1,2-dihydro-[1,8]-naphthyridine-3-carbonitrile (33) as described above was as follows:

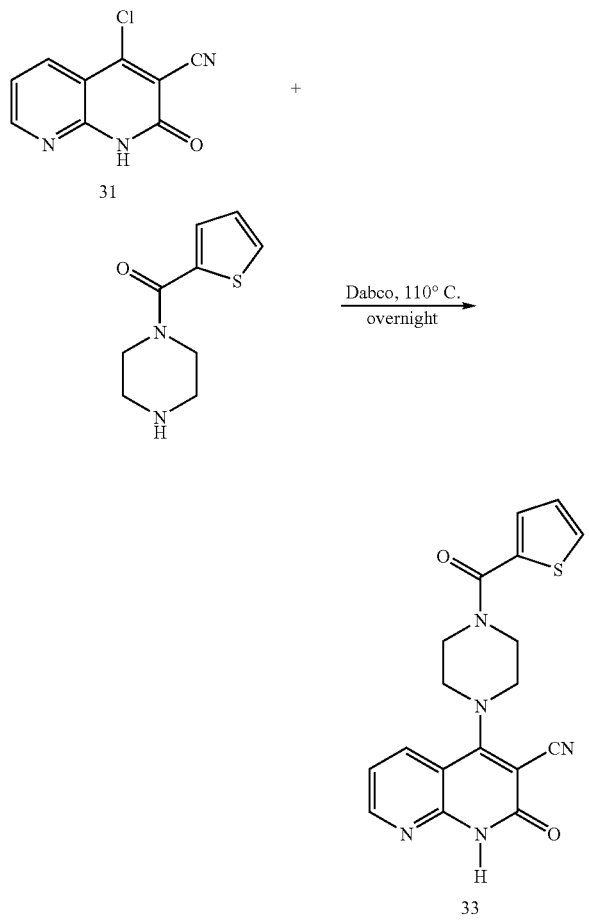

Preparation of Compounds by Alkylation at N–1 Position of Naphthyridine Moiety

The compounds referred to as compound 34 through 48 were prepared from 2-oxo-4-[4-(thiophene-2-carbonyl)-piperazine-1-yl]-1,2-dihydro-[1,8]-naphthyridine-3-carbonitrile (33) (400 mg, 1.1 mmol) and corresponding alkyl halides by applying either General Procedure A or General Procedure B as described above.

Synthesis of 1-Methyl-2-oxo-4-[4-(thiophene-2-carbonyl)-piperazine-1-yl]-1,2-dihydro-[1,8]-naphthyridine-3-carbonitrile (34)

The compound was prepared by using methyl iodide (82 μL, 1.32 mmol) according to General Procedure A to yield 221 mg (53%) of white solids. MP 266° C.; $^1$H-NMR (DMSO-$d_6$): δ 3.62 (s, 3H), 3.69 (m, 4H), 3.91 (m, 4H), 7.16 (dd, J=3.6, 4.8 Hz, 1H), 7.37 (dd, J=4.8, 8.0 Hz, 1H), 7.48 (d, J=4.4 Hz, 1H), 7.79 (d, J=4.8 Hz, 1H), 8.29 (dd, J=1.6, 8.0 Hz, 1H), 8.74 (dd, J=1.6, 4.8 Hz, 1H); EIMS: 380 (M+1). Anal. ($C_{19}H_{17}N_5O_2S$) C, H, N.

Synthesis of 2-Oxo-4-[4-(thiophene-2-carbonyl)-piperazine-1-yl]-1-vinyl-1,2-dihydro-[1,8]-naphthyridine-3-carbonitrile (35)

The compound was prepared by using allyl iodide (121 μL, 1.32 mmol) according to General Procedure A to yield 283 mg (63%) of white solids. MP 228° C.; $^1$H-NMR (DMSO-$d_6$): δ 3.71 (m, 4H), 3.92 (m, 4H), 4.94 (d, J=5.2 Hz, 2H), 5.02 (dd, J=1.2, 10.4 Hz, 1H), 5.08 (dd, J=1.2, 10.4 Hz, 1H), 5.92 (m, 1H), 7.16 (dd, J=3.6, 4.8 Hz, 1H), 7.37 (dd, J=4.8, 8.0 Hz, 1H), 7.49 (d, J=3.6 Hz, 1H), 7.81 (d, J=4.8 Hz, 1H), 8.32 (dd, J=1.6, 8.0 Hz, 1H), 8.71 (dd, J=1.6, 4.4 Hz, 1H); EIMS: 405 (M+1). Anal. ($C_{21}H_{19}N_5O_2S$) C, H, N.

Synthesis of 1-Butyl-2-oxo-4-[4-(thiophene-2-carbonyl)-piperazine-1-yl]-1,2-dihydro-[1,8]-naphthyridine-3-carbonitrile (36)

The compound was prepared by using iodobutane (151 μL, 1.32 mmol) according to General Procedure A to yield 296 mg (64%) of white solids. MP 143° C.; $^1$H-NMR (DMSO-$d_6$): δ 0.91 (t, J=7.2 Hz, 3H), 1.32 (m, 2H), 1.59 (m, 2H), 3.67 (m, 4H), 3.90 (m, 4H), 4.34 (t, J=7.6 Hz, 2H), 7.16 (dd, J=4.4, 5.2 Hz, 1H), 7.36 (dd, J=4.8, 8.2 Hz, 1H), 7.49 (dd, J=1.2, 3.6 Hz, 1H), 7.80 (dd, J=1.2, 4.2 Hz, 1H), 8.32 (dd, J=2.0, 8.2 Hz, 1H), 8.71 (dd, J=1.6, 4.8 Hz, 1H); EIMS: 422 (M+1). Anal. ($C_{22}H_{23}N_5O_2S$) C, H, N.

Synthesis of 1-(3-Fluoro-benzyl)-2-oxo-4-[4-(thiophene-2-carbonyl)-piperazine-1-yl]-1,2-dihydro-[1,8]-naphthyridine-3-carbonitrile (37)

The compound was prepared by using 3-fluorobenzylbromide (162 μL, 1.32 mmol) according to General Procedure A to yield 262 mg (50%) of white solids. MP 231° C.; $^1$H-NMR (DMSO-$d_6$): δ 3.73 (m, 4H), 3.93 (m, 4H), 5.55 (s, 2H), 7.06 (m, 3H), 7.17 (m, 1H), 7.30 (m, 2H), 7.49 (d, J=3.6 Hz, 1H), 7.80 (d, J=5.2 Hz, 1H), 8.33 (d, J=8.0 Hz, 1H), 8.68 (d, J=4.4 Hz, 1H); EIMS: 474 (M+1). Anal. ($C_{25}H_{20}FN_5O_2S$) C, H, N.

Synthesis of 2-Oxo-1-(2-oxo-2-phenyl-ethyl)-4-[4-(thiophene-2-carbonyl)-piperazine-1-yl]-1,2-dihydro-[1,8]-naphthyridine-3-carbonitrile (38)

The compound was prepared by using 2-bromoacetophenone (262 mg, 1.32 mmol) according to General Procedure A to yield 113 mg (21%) of white solids. MP 269° C.; $^1$H-NMR (DMSO-$d_6$): δ 3.78 (m, 4H), 3.94 (m, 4H), 5.88 (s, 2H), 7.17 (dd, J=3.6, 4.8 Hz, 1H), 7.37 (dd, J=4.4, 8.0 Hz, 1H), 7.50 (d, J=3.6 Hz, 1H), 7.59 (m, 2H), 7.74 (m, 1H), 7.80 (dd, J=1.2, 4.2 Hz, 1H), 8.12 (d, J=7.6 Hz, 1H), 8.39

(dd, J=1.2, 8.0 Hz, 1H), 8.59 (dd, J=1.6, 4.4 Hz, 1H); EIMS: 484 (M+1). Anal. ($C_{26}H_{21}N_5O_3S$) C, H, N.

Synthesis of 1-(4-Fluoro-benzyl)-2-oxo-4-[4-(thiophene-2-carbonyl)-piperazine-1-yl]-1,2-dihydro-[1,8]-naphthyridine-3-carbonitrile (39)

The compound was prepared by using 4-fluorobenzylbromide (162 μL, 1.32 mmol) according to General Procedure A to yield 361 mg (69%) of white solids. MP 271° C.; $^1$H-NMR (DMSO-$d_6$): δ 3.72 (m, 4H), 3.92 (m, 4H), 5.52 (s, 2H), 7.10 (m, 2H), 7.16 (dd, J=3.6, 4.8 Hz, 1H), 7.33-7.39 (m, 3H), 7.49 (dd, J=1.2, 3.6 Hz, 1H), 7.80 (dd, J=1.2, 4.8 Hz, 1H), 8.33 (dd, J=1.6, 8.0 Hz, 1H), 8.70 (dd, J=1.6, 4.4 Hz, 1H); EIMS: 474 (M+1). Anal. ($C_{25}H_{20}FN_5O_2S$) C, H, N.

Synthesis of 1-(2-Fluoro-benzyl)-2-oxo-4-[4-(thiophene-2-carbonyl)-piperazine-1-yl]-1,2-dihydro-[1,8]-naphthyridine-3-carbonitrile (40)

The compound was prepared by using 2-fluorobenzylbromide (162 μL, 1.32 mmol) according to General Procedure A to yield 370 mg (71%) of white solids. MP 286° C.; $^1$H-NMR (DMSO-$d_6$): δ 3.74 (m, 4H), 3.92 (m, 4H), 5.58 (s, 2H), 6.89 (m, 1H), 7.03 (m, 1H), 7.16-7.26 (m, 3H), 7.37 (dd, J=4.4, 8.0 Hz, 1H), 7.50 (dd, J=1.2, 4.0 Hz, 1H), 7.80 (d, J=4.8 Hz, 1H), 8.34 (dd, J=1.6, 8.4 Hz, 1H), 8.65 (dd, J=1.6, 4.8 Hz, 1H); EIMS: 474 (M+1). Anal. ($C_{25}H_{20}FN_5O_2S$) C, H, N.

Synthesis of Acetic acid-2-{3-cyano-2-oxo-4-[4-(thiophene-2-carbonyl)-piperazine-1-yl]-1,2-dihydro-[1,8]-naphthyridin-1-yl}-ethyl ester (41)

The compound was prepared by using α-bromoethylacetate (145 μL, 1.32 mmol) according to General Procedure A to yield 326 mg (65%) of white solids. MP 189° C.; $^1$H-NMR (DMSO-$d_6$): δ 1.88 (s, 3H), 3.70 (m, 4H), 3.92 (m, 4H), 4.30 (t, J=5.6 Hz, 2H), 4.60 (t, J=5.6 Hz, 2H), 7.16 (dd, J=3.6, 4.8 Hz, 1H), 7.37 (dd, J=4.4, 8.0 Hz, 1H), 7.49 (dd, J=1.2, 3.2 Hz, 1H), 7.81 (dd, J=1.2, 5.2 Hz, 1H), 8.33 (dd, J=1.6, 8.0 Hz, 1H), 8.72 (dd, J=1.6, 4.4 Hz, 1H); EIMS: 452 (M+1). Anal. ($C_{22}H_{21}N_5O_4S$) C, H, N.

Synthesis of 2-Oxo-1-propyl-4-[4-(thiophene-2-carbonyl)-piperazine-1-yl]-1,2-dihydro-[1,8]-naphthyridine-3-carbonitrile (42)

The compound was prepared by using 1-iodopropane (129 μL, 1.32 mmol) according to General Procedure A to yield 234 mg (52%) of white solids. MP 196° C.; $^1$H-NMR (DMSO-$d_6$): δ 0.90 (t, J=7.6 Hz, 3H), 1.64 (m, 2H), 3.67 (m, 4H), 3.91 (m, 4H), 4.28 (m, 2H), 7.16 (dd, J=3.6, 4.8 Hz, 1H), 7.36 (dd, J=4.4, 8.0 Hz, 1H), 7.48 (dd, J=1.2, 3.6 Hz, 1H), 7.80 (dd, J=1.2, 4.2 Hz, 1H), 8.29 (dd, J=1.6, 8.0 Hz, 1H), 8.73 (dd, J=1.6, 4.4 Hz, 1H); EIMS: 408 (M+1). Anal. ($C_{21}H_{21}N_5O_2S$) C, H, N.

Synthesis of 1-(2,2-Dimethyl-propyl)-2-oxo-4-[4-(thiophene-2-carbonyl)-piperazine-1-yl]-1,2-dihydro-[1,8]-naphthyridine-3-carbonitrile (43)

The compound was prepared by using neopentyliodide (175 μL, 1.32 mmol) according to General Procedure A to yield 223 mg (46%) of white solids. MP 232° C.; $^1$H-NMR (DMSO-$d_6$): δ 0.89 (s, 9H), 3.70 (m, 4H), 3.92 (m, 4H), 4.35 (s, 2H), 7.16 (dd, J=3.6, 4.8 Hz, 1H), 7.34 (dd, J=4.8, 8.0 Hz, 1H), 7.49 (dd, J=1.2, 4.0 Hz, 1H), 7.80 (dd, J=1.2, 4.2 Hz, 1H), 8.29 (dd, J=2.0, 8.0 Hz, 1H), 8.69 (dd, J=1.6, 4.8 Hz, 1H); EIMS: 436 (M+1). Anal. ($C_{23}H_{25}N_5O_2S$) C, H, N.

Synthesis of 1-(4-Cyano-benzyl)-2-oxo-4-[4-(thiophene-2-carbonyl)-piperazine-1-yl]-1,2-dihydro-[1,8]-naphthyridine-3-carbonitrile (44)

The compound was prepared by using α-bromo-p-tolunitrile (259 mg, 1.32 mmol) according to General Procedure B to yield 353 mg (66%) of white solids. MP 241° C.; $^1$H-NMR (DMSO-$d_6$): δ 3.73 (m, 4H), 3.91 (m, 4H), 5.61 (s, 2H), 7.10 (m, 2H), 7.16 (dd, J=3.6, 4.8 Hz, 1H), 7.37 (dd, J=4.8, 8.0 Hz, 1H), 7.44 (m, 2H), 7.50 (dd, J=1.2, 3.6 Hz, 1H), 7.74 (m, 2H), 7.80 (d, J=4.8 Hz, 1H), 8.34 (dd, J=1.6, 8.0 Hz, 1H), 8.65 (d, J=4.0 Hz, 1H); EIMS: 481 (M+1). Anal. ($C_{26}H_{20}N_6O_2S$) C, H, N.

Synthesis of 1-Cyclohexyl-2-oxo-4-[4-(thiophene-2-carbonyl)-piperazine-1-yl]-1,2-dihydro-[1,8]-naphthyridine-3-carbonitrile (45)

The compound was prepared by using bromomethylcyclohexane (183 μL, 1.32 mmol) according to General Procedure B to yield 243 mg (48%) of white solids. MP 192° C.; $^1$H-NMR (DMSO-$d_6$): δ 1.05-1.13 (m, 5H), 1.53-1.65 (m, 5H), 2.80 (m, 1H), 3.69 (m, 4H), 3.91 (m, 4H), 4.21 (d, J=7.6 Hz, 2H), 7.16 (dd, J=3.6, 5.2 Hz, 1H), 7.34 (dd, J=4.8, 8.0 Hz, 1H), 7.48 (dd, J=1.2, 3.6 Hz, 1H), 7.80 (dd, J=1.2, 4.8 Hz, 1H), 8.28 (dd, J=1.6, 8.0 Hz, 1H), 8.72 (dd, J=2.0, 4.8 Hz, 1H); EIMS: 462 (M+1). Anal. ($C_{25}H_{27}N_5O_2S$) C, H, N.

Synthesis of {3-Cyano-2-oxo-4-[4-(thiophene-2-carbonyl)-piperazine-1-yl]-1,2-dihydro-[1,8]-naphthyridin-1-yl}-acetic acid ethyl ester (46)

The compound was prepared by using ethyl bromoacetate (146 μL, 1.32 mmol) according to General Procedure B to yield 267 mg (54%) of white solids. MP 236° C.; $^1$H-NMR (DMSO-$d_6$): δ 1.19 (t, J=7.2 Hz, 3H), 3.76 (m, 4H), 3.92 (m, 4H), 4.12 (q, J=7.2 Hz, 2H), 5.07 (s, 2H), 7.16 (dd, J=4.0, 5.2 Hz, 1H), 7.40 (dd, J=4.4, 8.0 Hz, 1H), 7.49 (dd, J=1.2, 3.6 Hz, 1H), 7.80 (d, J=4.8 Hz, 1H), 8.34 (dd, J=1.6, 8.0 Hz, 1H), 8.68 (dd, J=1.6, 4.4 Hz, 1H); EIMS: 452 (M+1). Anal. ($C_{22}H_{21}N_5O_4S$) C, H, N.

Synthesis of 1-(3-Dimethylamino-propyl)-2-oxo-4-[4-(thiophene-2-carbonyl)-piperazine-1-yl]-1,2-dihydro-[1,8]-naphthyridine-3-carbonitrile (47)

The compound was prepared by using β-dimethylaminopropyl hydrochloride (209 mg, 1.32 mmol) according to General Procedure B to yield 194 mg (39%) of white solids. MP 176° C.; $^1$H-NMR (DMSO-$d_6$): δ 1.73 (m, 2H), 2.11 (s, 6H), 2.29 (m, 2H), 3.68 (m, 4H), 3.91 (m, 4H), 4.34 (t, J=7.6 Hz, 2H), 7.16 (dd, J=3.6, 4.8 Hz, 1H), 7.35 (dd, J=4.4, 8.0 Hz, 1H), 7.48 (d, J=3.6 Hz, 1H), 7.80 (dd, J=1.2, 5.2 Hz, 1H), 8.31 (dd, J=1.6, 8.0 Hz, 1H), 8.74 (dd, J=1.2, 4.4 Hz, 1H); EIMS: 451 (M+1). Anal. ($C_{23}H_{26}N_6O_2S$) C, H, N.

Synthesis of 1-Cyclopropylmethyl-2-oxo-4-[4-(thiophene-2-carbonyl)-piperazine-1-yl]-1,2-dihydro-[1,8]-naphthyridine-3-carbonitrile (48)

The compound was prepared by using bromomethyl cyclopropane (128 μL, 1.32 mmol) according to General Procedure B to yield 278 mg (60%) of white solids. MP 189° C.; $^1$H-NMR (DMSO-d$_6$): δ 0.42 (m, 4H), 1.28 (m, 1H), 3.70 (m, 4H), 3.90 (m, 4H), 4.23 (d, J=7.2 Hz, 2H), 7.16 (dd, J=3.6, 4.8 Hz, 1H), 7.37 (dd, J=4.4, 8.0 Hz, 1H), 7.49 (dd, J=1.2, 3.6 Hz, 1H), 7.80 (dd, J=1.2, 5.2 Hz, 1H), 8.32 (dd, J=1.6, 8.0 Hz, 1H), 8.73 (dd, J=1.6, 4.8 Hz, 1H); EIMS: 420 (M+1). Anal. (C$_{22}$H$_{21}$N$_5$O$_2$S) C, H, N.

Preparation of Compounds by Acylation of Piperazine Substituted at Naphthyridine Moiety The compounds referred to as 49 through 55 were prepared from 1-benzyl-2-oxo-4-piperazin-1-yl-1,2-dihydro-[1,8]-naphthyridine-3-carboxylic acid ethyl ester (5) by applying either General Procedure C or General Procedure D.

General Procedure C

The corresponding acid chloride (1.5 mmol) was added to a stirred solution of 1-benzyl-2-oxo-4-piperazin-1-yl-1,2-dihydro-[1,8]-naphthyridine-3-carboxylic acid ethyl ester (5) (392 mg, 1 mmol) in pyridine (5 mL) under argon at 0° C. The solution was allowed to come at room temperature and further stirred overnight. The solution was poured into ice water and the solids formed were filtered. The solids were washed by excess water, dried, and purified by flash chromatography eluting with 0-2% MeOH in a CH2Cl2 gradient.

General Procedure D

Oxalyl chloride (2 mmol) and DMF (2 drops) were added sequentially to a stirred solution of the corresponding acid (1.5 mmol) in CH$_2$Cl$_2$ at room temperature, then further stirred for 2 h under argon atmosphere. The solvent was removed under vacuum at room temperature to yield corresponding acid chloride. A solution of 1-benzyl-2-oxo-4-piperazin-1-yl-1,2-dihydro-[1,8]-naphthyridine-3-carboxylic acid ethyl ester (5) (392 mg, 1 mmol) in dry pyridine (5 mL) was added to the residue under argon atmosphere and briefly sonicated. The solution was stirred overnight at room temperature under argon atmosphere. The solution was poured into ice water and the solids formed were filtered. The solids were washed by excess water, dried, and purified by flash chromatography eluting with 0-2% MeOH in a CH$_2$Cl$_2$ gradient.

Synthesis of 1-Benzyl-4-(4-cyclopentanecarbonyl-piperazin-1-yl)-2-oxo-1,2-dihydro-[1,8]-naphthyridine-3-carboxylic acid ethyl ester (49)

The compound was prepared according to General Procedure C. White solid, yield 64%, mp 170° C. $^1$H-NMR (DMSO-d$_6$): δ 1.28 (t, J=6.8 Hz, 3H), 1.6 (m, 8H), 3.05 (m, 5H), 3.74 (m, 4H), 4.29 (q, J=7.2 Hz, 2H), 5.56 (s, 2H), 7.25 (m, 5H), 7.38 (m, 1H), 8.34 (dd, J=1.6, 7.6 Hz, 1H), 8.67 (dd, J=1.6, 4.4 Hz, 1H); EIMS m/z 489 (M+1).

Synthesis of 4-(4-Benzoyl-piperazin-1-yl)-1-benzyl-2-oxo-1,2-dihydro-[1,8]-naphthyridine-3-carboxylic acid ethyl ester (50)

The compound was prepared according to General Procedure C. White solid, yield 90%, mp 220° C. $^1$H-NMR (DMSO-d$_6$): δ 1.29 (t, J=6.8 Hz, 3H), 3.1 (m, 4H), 3.5-4.0 (m, 4H), 4.30 (q, J=6.8 Hz, 2H), 5.56 (s, 2H), 7.23 (m, 5H), 7.40 (m, 6H), 8.33 (dd, J=2.0, 8.4 Hz, 1H), 8.66 (dd, J=2.0, 4.8 Hz, 1H); EIMS m/z 497 (M+1).

Synthesis of 1-Benzyl-4-[4-(4-chloro-benzoyl)-piperazin-1-yl]-2-oxo-1,2-dihydro-[1,8]-naphthyridine-3-carboxylic acid ethyl ester (51)

The compound was prepared according to General Procedure C. White solid, yield, 86%, mp 110-115° C. $^1$H-NMR (DMSO-d$_6$): δ 1.29 (t, J=7.2 Hz, 3H), 3.1 (m, 4H), 3.5-4.0 (m, 4H), 4.31 (q, J=7.2 Hz, 2H), 5.56 (s, 2H), 7.25 (m, 5H), 7.38 (m, 1H), 7.46 (d, J=6.4 Hz, 2H), 7.54 (d, J=6.4 Hz, 2H), 8.33 (dd, J=1.6, 8.0 Hz, 1H), 8.66 (J=1.6, 4.8 Hz, 1H); EIMS m/z 531 (M+1).

Synthesis of 1-Benzyl-4-[4-(6-chloro-pyridine-3-carbonyl)-piperazin-1-yl]-2-oxo-1,2-dihydro-[1,8]-naphthyridine-3-carboxylic acid ethyl ester (52)

The compound was prepared according to General Procedure C. Yellow solid, yield 89%, mp 125-130° C. $^1$H-NMR (DMSO-d$_6$): δ 1.29 (t, J=6.8 Hz, 3H), 3.15 (m, 4H), 3.5-4.0 (m, 4H), 4.31 (q, J=6.8 Hz, 2H), 5.56 (s, 2H), 7.27 (m, 5H), 7.38 (m, 1H), 7.65 (d, J=6.8 Hz, 1H), 7.96 (dd, J=2.4, 8.0 Hz, 1H), 8.33 (dd, J=1.6, 8.0 Hz, 1H), 8.52 (d, J=2.0 Hz, 1H), 8.67 (dd, J=1.6, 4.4 Hz, 1H); EIMS m/z 532 (M+1).

Synthesis of 1-Benzyl-2-oxo-4-[4-(pyridine-4-carbonyl)-piperazin-1-yl]-1,2-dihydro-[1,8]-naphthyridine-3-carboxylic acid ethyl ester (53)

The compound was prepared according to General Procedure C. Yellow solid, yield 32%, mp 130-135° C. $^1$H-NMR (DMSO-d$_6$): δ 1.29 (t, J=7.2 Hz, 3H), 3.08 (b, 2H), 3.20 (b, 2H), 3.50 (b, 2H), 3.90 (b, 2H), 4.31 (q, J=7.2 Hz, 2H), 5.56 (s, 2H), 7.25 (m, 5H), 7.36 (m, 1H), 7.40 (d, J=5.6 Hz, 2H), 8.32 (d, J=7.2 Hz, 1H), 8.66 (d, J=3.2 Hz, 1H), 8.70 (d, J=5.2 Hz, 2H); EIMS m/z 498 (M+1).

Synthesis of 1-Benzyl-2-oxo-4-[4-(pyridine-2-carbonyl)-piperazin-1-yl]-1,2-dihydro-[1,8]-naphthyridine-3-carboxylic acid ethyl ester (54)

The compound was prepared according to General Procedure C. Yellow solid, yield 23%, mp 112-117° C. $^1$H-NMR (DMSO-d$_6$): δ 1.30 (t, J=7.2 Hz, 3H), 3.12 (b, 2H), 3.20 (b, 2H), 3.66 (b, 2H), 3.91 (b, 2H), 4.32 (q, J=7.2 Hz, 2H), 5.56 (s, 2H), 7.26 (m, 5H), 7.37 (m, 1H), 7.51 (m, 1H), 7.63 (d, J=8.0 Hz, 1H), 7.96 (t, J=7.6 Hz, 1H), 8.61 (d, J=4.0 Hz, 1H), 8.66 (d, J=3.6 Hz, 1H); EIMS m/z 498 (M+1).

Synthesis of 1-Benzyl-2-oxo-4-[4-(thiophene-3-carbonyl)-piperazin-1-yl]-1,2-dihydro-[1,8]-naphthyridine-3-carboxylic acid ethyl ester (55)

The compound was prepared according to general method D. White solid, yield 68%, mp 115° C. $^1$H-NMR (DMSO-d$_6$): δ 1.29 (t, J=7.2 Hz, 3H), 3.14 (b, 4H), 3.75 (b, 4H), 4.30 (q, J=7.2 Hz, 2H), 5.56 (s, 2H), 7.25 (m, 6H), 7.37 (m, 1H), 7.65 (m, 1H), 7.85 (dd, J=1.2, 2.8 Hz, 1H), 8.34 (dd, J=2.0, 8.0 Hz, 1H), 8.67 (dd, J=2.0, 4.8 Hz, 1H); EIMS m/z 503 (M+1).

Preparation of Compounds by Acylation of Piperazine Substituted at Naphthyridine Carbonitrile Moiety The compounds referred to as 56 through 64 were prepared from 1-benzyl-2-oxo-4-piperazin-1-yl-1,2-dihydro-[1,8]-naphthyridine-3-carbonitrile (9) by applying either General Procedure C or General Procedure D described above.

Synthesis of 1-Benzyl-4-(4-cyclopentanecarbonyl-piperazin-1-yl)-2-oxo-1,2-dihydro-[1,8]-naphthyridine-3-carbonitrile (56)

The compound was prepared according to General Procedure C. Brown solid, yield 64%, mp 197° C. $^1$H-NMR (DMSO-$d_6$): δ 1.7 (m, 8H), 3.07 (m, 1H), 3.70 (m, 8H), 5.55 (s, 2H), 7.23 (m, 5H), 7.37 (m, 1H), 8.31 (dd, J=1.6, 8.0 Hz, 1H), 8.69 (dd, J=1.6, 4.8 Hz, 1H); EIMS m/z 442 (M+1).

Synthesis of 4-(4-Benzoyl-piperazin-1-yl)-1-benzyl-2-oxo-1,2-dihydro-[1,8]-naphthyridine-3-carbonitrile (57)

The compound was prepared according to General Procedure C. White solid, yield 71%, mp 287° C. $^1$H-NMR (DMSO-$d_6$): δ 3.7 (m, 8H), 5.55 (s, 2H), 7.23 (m, 5H), 7.35 (m, 1H), 7.49 (m, 5H), 8.31 (dd, J=1.6, 8.4 Hz, 1H), 8.69 (dd, J=1.6, 4.8 Hz, 1H); EIMS m/z 450 (M+1).

Synthesis of 1-Benzyl-4-[4-(4-chloro-benzoyl)-piperazin-1-yl]-2-oxo-1,2-dihydro-[1,8]-naphthyridine-3-carbonitrile (58)

The compound was prepared according to General Procedure C. Yellow solid, yield 75%, mp 298° C. $^1$H-NMR (DMSO-$d_6$): δ 3.7 (m, 8H), 5.55 (s, 2H), 7.25 (m, 5H), 7.36 (m, 1H), 7.55 (m, 4H), 8.30 (dd, J=1.6, 8.0 Hz, 1H), 8.69 (dd, J=1.6, 4.4 Hz, 1H); EIMS m/z 484 (M+1).

Synthesis of 1-Benzyl-4-[4-(6-chloro-pyridine-3-carbonyl)-piperazin-1-yl]-2-oxo-1,2-dihydro-[1,8]-naphthyridine-3-carbonitrile (59)

The compound was prepared according to General Procedure C. White solid, yield 89%, mp 250° C. $^1$H-NMR (DMSO-$d_6$): δ 3.75 (m, 8H), 5.55 (s, 2H), 7.25 (m, 5H), 7.37 (m, 1H), 7.65 (d, J=8.4 Hz, 1H), 8.00 (dd, J=2.4, 8.0 Hz, 1H), 8.30 (dd, J=1.6, 8.4 Hz, 1H), 8.56 (dd, J=0.4, 2.4 Hz, 1H), 8.69 (dd, J=1.2, 4.4 Hz, 1H); EIMS m/z 485 (M+1).

Synthesis of 1-Benzyl-2-oxo-4-[4-(pyridine-4-carbonyl)-piperazin-1-yl]-1,2-dihydro-[1,8]-naphthyridine-3-carbonitrile (60)

The compound was prepared according to General Procedure C. Brown solid, yield, 93%, mp 275° C. $^1$H-NMR (DMSO-$d_6$): δ 3.55 (b, 2H), 3.65 (b, 2H), 3.76 (b, 2H), 3.92 (b, 2H), 5.55 (s, 2H), 7.25 (m, 5H), 7.36 (m, 1H), 7.48 (d, J=6.0 Hz, 2H), 8.29 (dd, J=1.6, 8.0 Hz, 1H), 8.70 (m, 3H); EIMS m/z 451 (M+1).

Synthesis of 1-Benzyl-2-oxo-4-[4-(pyridine-2-carbonyl)-piperazin-1-yl]-1,2-dihydro-[1,8]-naphthyridine-3-carbonitrile (61)

The compound was prepared according to General Procedure C. Brown solid, yield 47%, mp 256° C. $^1$H-NMR (DMSO-$d_6$): δ 3.70 (m, 6H), 3.94 (m, 2H), 5.55 (s, 2H), 7.25 (m, 5H), 7.36 (m, 1H), 7.52 (m, 1H), 7.68 (m, 1H), 7.97 (m, 1H), 8.34 (dd, J=1.6, 8.0 Hz, 1H), 8.64 (m, 1H), 8.69 (m, 1H); EIMS m/z 451 (M+1).

Synthesis of 1-Benzyl-2-oxo-4-[4-(thiophene-3-carbonyl)-piperazin-1-yl]-1,2-dihydro-[1,8]-naphthyridine-3-carbonitrile (62)

The compound was prepared according to General Procedure D. Brown solid, yield 96%, mp 257° C. $^1$H-NMR (DMSO-$d_6$): δ 3.75 (m, 8H), 5.55 (s, 2H), 7.25 (m, 6H), 7.35 (m, 1H), 7.65 (m, 1H), 7.88 (dd, J=1.2, 2.8 Hz, 1H), 8.31 (dd, J=1.6, 8.0 Hz, 1H), 8.69 (dd, J=1.6, 4.4 Hz, 1H); EIMS m/z 456 (M+1).

Synthesis of 1-Benzyl-4-[4-(5-fluoro-thiophene-2-carbonyl)-piperazin-1-yl]-2-oxo-1,2-dihydro-[1,8]-naphthyridine-3-carbonitrile (63)

The compound was prepared according to General Procedure D. White solid, yield 80%, mp 226° C. $^1$H-NMR (DMSO-$d_6$): δ 3.73 (m, 4H), 3.93 (m, 4H), 5.55 (s, 2H), 6.82 (d, J=4.4 Hz, 1H), 7.25-7.31 (m, 6H), 7.37 (dd, J=4.0, 8.0 Hz, 1H), 8.33 (d, J=8.0 Hz, 1H), 8.69 (d, J=4.4 Hz, 1H); EIMS m/z 474 (M+1). Anal. ($C_{25}H_{20}FN_5O_2S$) C, H. N.

Synthesis of 1-Benzyl-4-[4-(5-chloro-thiophene-2-carbonyl)-piperazin-1-yl]-2-oxo-1,2-dihydro-[1,8]-naphthyridine-3-carbonitrile (64)

The compound was prepared according to General Procedure D. White solid, yield 77%, mp 249° C. $^1$H-NMR (DMSO-$d_6$): δ 3.73 (m, 4H), 3.92 (m, 4H), 5.55 (s, 2H), 7.21-7.29 (m, 6H), 7.36 (dd, J=4.8, 8.0 Hz, 1H), 7.41 (d, J=4.0 Hz, 1H), 8.33 (dd, J=1.2, 8.0 Hz, 1H), 8.69 (dd, J=1.6, 4.8 Hz, 1H); EIMS m/z 490 (M+1). Anal. ($C_{25}H_{20}ClN_5O_2S$) C, H, N.

Synthesis of 2,6-Dichloro-5-fluoro-nicotinic acid ethyl ester (65)

A suspension of 2,6-dichloro-5-fluoronicotinic acid (43 g, 205 mmol) in thionyl chloride (200 mL) and toluene (200 mL) was refluxed for 3 h to yield a clear solution. The solution was cooled and the solvent was evaporated under vacuum. The residue was cooled in an ice bath and cold anhydrous ethanol was added slowly. After stirring 15 min at 0° C., the solution was refluxed for 30 min under argon. The solution was cooled and the solvent was removed under vacuum. The residue was dissolved in ethyl acetate and washed subsequently by saturated $NaHCO_3$ solution, water and brine. The organic phase was dried over $MgSO_4$ and evaporated to yield 48.5 g (99%) of 2,6-dichloro-5-fluoro-nicotinic acid ethyl ester (65) as colorless viscous oil. $^1$H-NMR (DMSO-$d_6$): δ 1.32 (t, J=7.2 Hz, 3H), 4.37 (q, J=7.2 Hz, 2H), 8.46 (d, J=8.0 Hz, 1H); EIMS m/z 238 (M).

Synthesis of 2-Chloro-6-ethylsulfanyl-5-fluoro-nicotinic acid ethyl ester (66)

Ethanethiol (15.08 mL, 204 mmol) was added slowly to a stirred suspension of NaH (60% in Mineral oil, 8.15 g, 204 mmol) in THF and stirred for 30 min at room temperature to yield a white thick suspension. This suspension was diluted by cold THF, cooled to 0° C. and transferred to an already cooled solution of 2,6-dichloro-5-fluoro-nicotinic acid ethyl ester (65) (48.5 g, 204 mmol) in THF at −20° C. under argon by maintaining the temperature below −10° C. The solution was stirred at −20° C. for 15 min and allowed to come at room temperature slowly. The solution was poured into water and extracted by ethyl acetate. The organic layer was dried over MgSO$_4$ and concentrated under reduced pressure to yield 53 g (98%) of 2-chloro-6-ethylsulfanyl-5-fluoro-nicotinic acid ethyl ester (66) as brown liquid. $^1$H-NMR (DMSO-d$_6$): δ 1.33 (m, 6H), 3.19 (q, J=7.2 Hz, 2H), 4.33 (q, J=7.2 Hz, 2H), 8.10 (d, J=9.6 Hz, 1H); EIMS m/z 264 (M+1).

Synthesis of 6-Ethylsulfanyl-5-fluoro-2-(4-methoxy-benzylamino)-nicotinic acid ethyl ester (67)

A solution of 2-chloro-6-ethylsulfanyl-5-fluoro-nicotinic acid ethyl ester (66) (53 g, 201 mmol) in anhydrous ethanol was purged with argon and added p-methoxybenzylamine (52.5 mL, 402 mmol) at room temperature. The solution was refluxed overnight under argon. The solution was cooled and the solvent was evaporated under reduced pressure. The residue was taken in dichloromethane, sonicated briefly and undissolved solids were filtered off. The filtrate washed by water, dried over MgSO$_4$ and concentrated. The crude product was purified by flash chromatography eluting with hexane:CH$_2$Cl$_2$ (1:1) to yield 47 g (64%) of 6-ethylsulfanyl-5-fluoro-2-(4-methoxy-benzylamino)-nicotinic acid ethyl ester (67) as a viscous oil which solidified to a white solids after keeping several days under vacuum at room temperature. Mp 59° C. $^1$H-NMR (DMSO-d$_6$): δ 1.18 (t, J=7.2 Hz, 3H), 1.29 (t, J=7.2 Hz, 3H), 3.08 (q, J=7.2 Hz, 2H), 3.71 (s, 3H), 4.26 (q, J=7.2 Hz, 2H), 4.62 (d, J=5.6 Hz, 2H), 6.87 (m, 2H), 7.24 (m, 2H), 7.71 (d, J=10 Hz, 1H), 8.32 (m, 1H); EIMS m/z 365 (M+1).

The sequence of reactions in the preparation of 2,6-dichloro-5-fluoro-nicotinic acid ethyl ester (65), 2-chloro-6-ethylsulfanyl-5-fluoro-nicotinic acid ethyl ester (66) and 6-ethylsulfanyl-5-fluoro-2-(4-methoxy-benzylamino)-nicotinic acid ethyl ester (67) as described above was as follows:

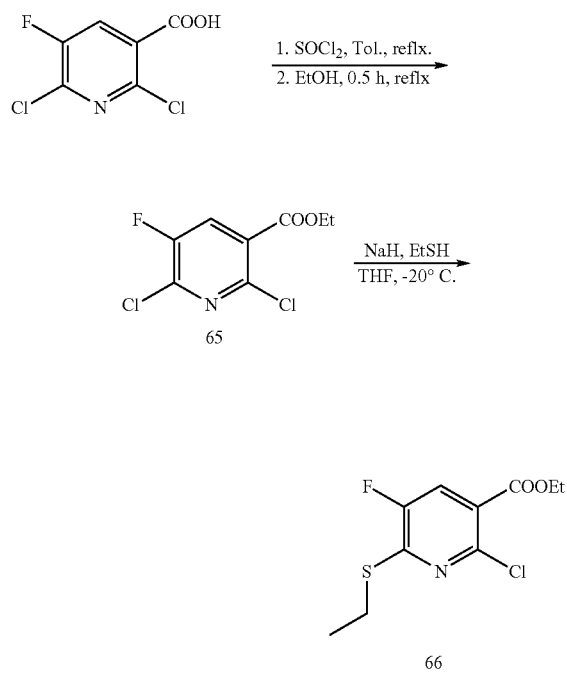

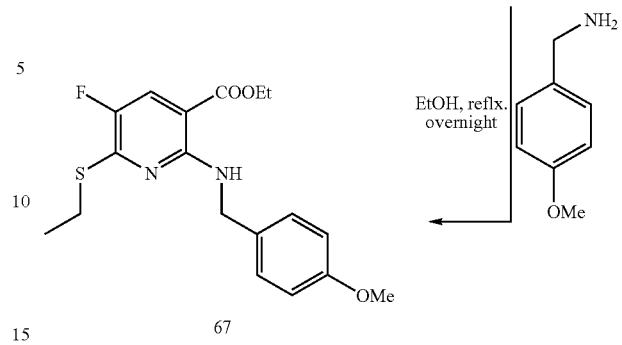

Synthesis of 5-Fluoro-2-(4-methoxy-benzylamino)-nicotinic acid ethyl ester (68)

Freshly activated raney nickel (50 g) was added to a solution of 6-ethylsulfanyl-5-fluoro-2-(4-methoxy-benzylamino)-nicotinic acid ethyl ester (67) (31 g, 85 mmol) in anhydrous ethanol and refluxed for 48 h. The solution was cooled and filtered through celite. The filtrate was evaporated under reduced pressure to yield 24 g (93%) of 5-fluoro-2-(4-methoxy-benzylamino)-nicotinic acid ethyl ester (68) as a viscous oil which solidified to a white solids after keeping several days under vacuum at room temperature. Mp 90° C. $^1$H-NMR (DMSO-d$_6$): δ 1.30 (t, J=7.2 Hz, 3H), 3.71 (s, 3H), 4.29 q, J=7.2 Hz, 2H), 4.55 (d, J=5.6 Hz, 2H), 6.87 (m, 2H), 7.26 (m, 2H), 7.96 (dd, J=3.2, 8.8 Hz, 1H), 8.12 (m, 1H), 8.35 (d, J=3.2 Hz, 1H); EIMS m/z 305 (M+1).

Synthesis of 6-Fluoro-1-(4-methoxy-benzyl)-1H-pyrido[2,3-d][1,3]oxazine-2,4-dione (69)

Trichloromethyl chloroformate (11.41 mL, 94.63 mmol) was added slowly to a solution of 5-fluoro-2-(4-methoxy-benzylamino)-nicotinic acid ethyl ester (68) (24 g, 78.86 mmol) in dioxane and refluxed for 4 h under nitrogen atmosphere. The solution was cooled and the solvent was removed under vacuum. The residue was recrystallized by ether to yield 21.5 g (90%) of 6-fluoro-1-(4-methoxy-benzyl)-1H-pyrido[2,3-d][1,3]oxazine-2,4-dione (69) as white solids. MP: 143° C.; $^1$H-NMR (DMSO-d$_6$): δ 3.71 (s, 3H), 5.27 (s, 2H), 6.85 (m, 2H), 7.35 (m, 2H), 8.40 (dd, J=2.8, 6.8 Hz, 1H), 8.82 (d, J=2.8 Hz, 1H); EIMS: 303 (M+1).

The sequence of reactions in the preparation of 5-fluoro-2-(4-methoxy-benzylamino)-nicotinic acid ethyl ester (68), 6-fluoro-1-(4-methoxy-benzyl)-1H-pyrido[2,3-d][1,3]oxazine-2,4-dione (69) as described above was as follows:

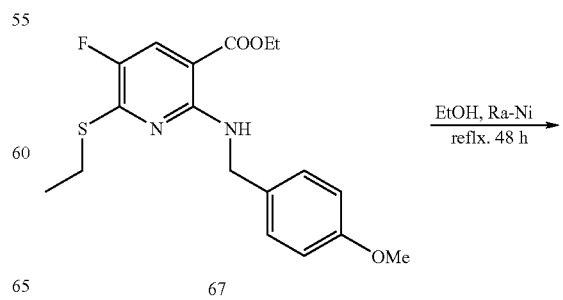

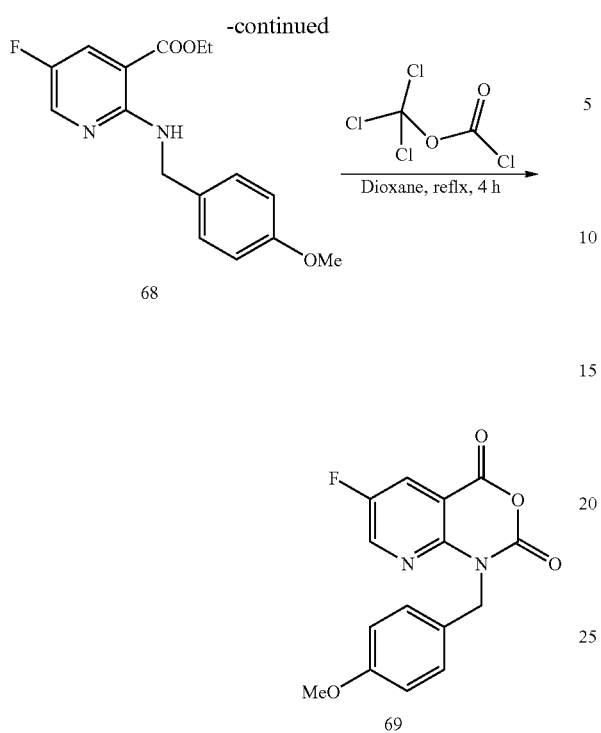

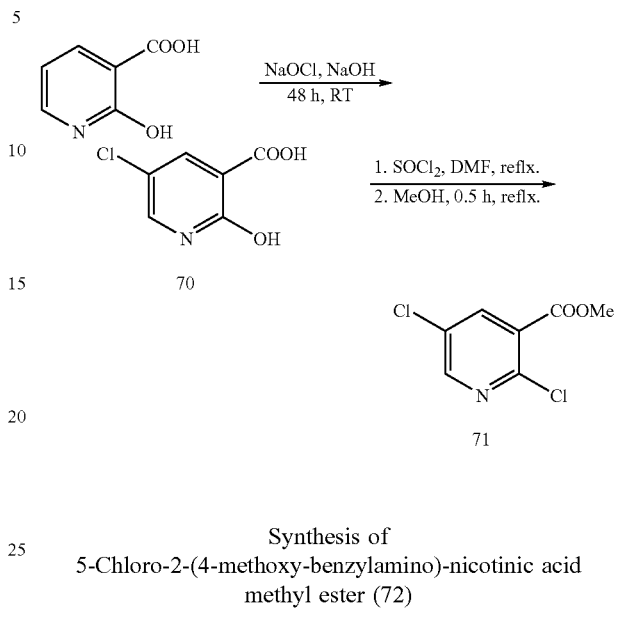

Synthesis of 5-Chloro-2-hydroxy-nicotinic acid (70)

Sodium hypochlorite (14% available chlorine, 35 mL, 82.21 mmol) solution was added to a stirred solution of 2-hydroxynicotinic acid (7 g, 50.3 mmol) in 10% aqueous NaOH solution. The solution was stirred for 48 h at room temperature. An aqueous solution of sodium sulfite (3.150 g, 25 mmol) was added and further stirred for 30 min at room temperature. The solution was diluted by cold water and pH was adjusted to 2 by cold dilute HCl. The solids formed were filtered, washed by cold water and dried to yield 6.8 g (78%) of 5-chloro-2-hydroxy-nicotinic acid (70) as white solids. MP: 276° C.; $^1$H-NMR (DMSO-d$_6$): δ 8.23 (d, J=2.8 Hz, 1H), 8.29 (d, J=2.8 Hz, 1H); EIMS: 174 (M+1).

Synthesis of 2,5-Dichloro-nicotinic acid methyl ester (71)

A suspension of 5-chloro-2-hydroxy-nicotinic acid (70) (6 g, 3.46 mmol) in thionyl chloride (200 mL) and DMF (1 mL) was refluxed for 3 h to yield a clear solution. The solution was cooled and the excess thionyl chloride was evaporated under vacuum. The residue was cooled in an ice bath and cold anhydrous methanol was added slowly. After stirring 15 min at 0° C., the solution was refluxed for 1 h under argon. The solution was cooled and the solvent was removed under vacuum. The residue was dissolved in ethyl acetate and washed subsequently by saturated NaHCO$_3$ solution, water and brine. The organic phase was dried over MgSO$_4$ and evaporated to yield 4.3 g (60%) of 2,5-dichloro-nicotinic acid methyl ester (71) as colorless viscous oil. $^1$H-NMR (DMSO-d$_6$): δ 3.88 (s, 3H), 8.39 (d, J=2.8 Hz, 1H), 8.70 (d, J=2.8 Hz, 1H); EIMS m/z 206 (M).

The sequence of reactions in the preparation of 5-chloro-2-hydroxy-nicotinic acid (70) and 2,5-dichloro-nicotinic acid methyl ester (71) as described above was as follows:

Synthesis of 5-Chloro-2-(4-methoxy-benzylamino)-nicotinic acid methyl ester (72)

A solution of 2,5-dichloro-nicotinic acid methyl ester (71) (25 g, 121 mmol) in anhydrous methanol was purged with argon and added p-methoxybenzylamine (34.5 mL, 266 mmol) at room temperature. The solution was refluxed overnight under argon. The solution was cooled and the solvent was evaporated under reduced pressure. The residue was taken in dichloromethane, sonicated briefly and undissolved solids were filtered off. The filtrate washed by water, dried over MgSO$_4$ and concentrated. The crude product was purified by flash chromatography eluting with hexane:CH$_2$Cl$_2$ (1:1) to yield 16.2 g (44%) of 5-chloro-2-(4-methoxy-benzylamino)-nicotinic acid methyl ester (72) as a white solids. Mp 94° C. $^1$H-NMR (DMSO-d$_6$): δ 3.71 (s, 3H), 3.82 (s, 3H), 4.59 (d, J=5.6 Hz, 2H), 6.87 (m, 2H), 7.24 (m, 2H), 8.06 (d, J=2.8 Hz, 1H), 8.27 (m, 1H), 8.32 (d, J=2.8 Hz, 1H); EIMS m/z 307 (M+1).

Synthesis of 6-Chloro-1-(4-methoxy-benzyl)-1H-pyrido[2,3-d][1,3]oxazine-2,4-dione (73)

Trichloromethyl chloroformate (5.40 mL, 44.82 mmol) was added slowly to a solution of 5-chloro-2-(4-methoxy-benzylamino)-nicotinic acid methyl ester (72) (12.5 g, 40.75 mmol) in dioxane and refluxed for 4 h under nitrogen atmosphere. The solution was cooled and the solvent was removed under vacuum. The residue was recrystallized by ether to yield 11.80 g (91%) of 6-chloro-1-(4-methoxy-benzyl)-1H-pyrido[2,3-d][1,3]oxazine-2,4-dione (73) as white solids. MP: 173° C.; $^1$H-NMR (DMSO-d$_6$): 3.71 (s, 3H), 5.25 (s, 2H), 6.85 (m, 2H), 7.33 (m, 2H), 8.49 (d, J=2.8 Hz, 1H), 8.82 (d, J=2.8 Hz, 1H); EIMS: 319 (M+1).

The sequence of reactions in the preparation of 5-chloro-2-(4-methoxy-benzylamino)-nicotinic acid methyl ester (72), 6-chloro-1-(4-methoxy-benzyl)-1H-pyrido[2,3-d][1,3]oxazine-2,4-dione (73) as described above was as follows:

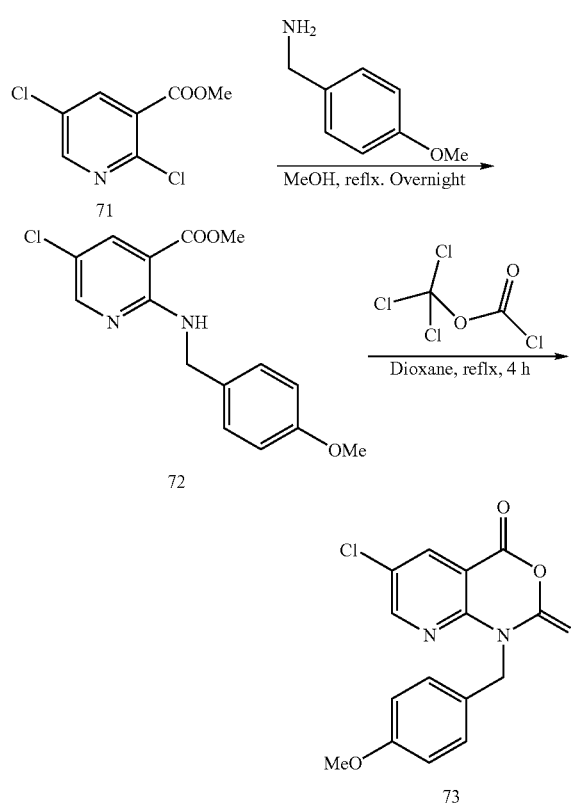

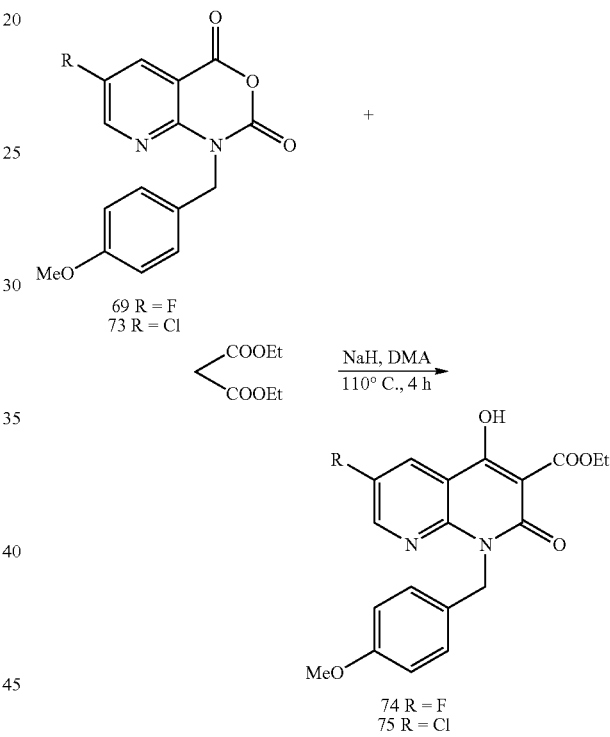

69 R = F
73 R = Cl

74 R = F
75 R = Cl

Synthesis of 6-Fluoro-4-hydroxy-1-(4-methoxy-benzyl)-2-oxo-1,2-dihydro-[1,8]-naphthyridine-3-carboxylic acid ethyl ester (74)

Diethyl malonate (10.79 mL, 71.38 mmol) was added slowly to a suspension of NaH (60% in mineral oil, 3.13 g, 78.24 mmol) in dimethylacetamide (200 mL) and stirred at room temperature for 0.5 h under inert atmosphere. 6-Fluoro-1-(4-methoxy-benzyl)-1H-pyrido-[2,3-d]-[1,3]-oxazine-2,4-dione (69) (21.5 g, 71.31 mmol) was added to the solution and heated at 110° C. for 4 h (TLC control). The solution was cooled and poured into ice water. The pH of the solution was adjusted to 3 by cold 10% HCl. The solids formed were filtered, washed by excess water, and dried in a vacuum oven to yield 26.01 g (98%) of 6-fluoro-4-hydroxy-1-(4-methoxy-benzyl)-2-oxo-1,2-dihydro-[1,8]-naphthyridine-3-carboxylic acid ethyl ester (74) as pale yellow solids. MP: 163° C.; $^1$H-NMR (DMSO-$d_6$): δ 1.27 (t, J=7.2 Hz, 3H), 3.68 (s, 3H), 4.27 (q, J=7.0 Hz, 2H), 5.43 (s, 2H), 6.81 (m, Hz, 2H), 7.19 (m, 2H), 8.26 (dd, J=2.8, 8.0 Hz, 1H), 8.74 (d, J=2.8 Hz, 1H), 13.00 (br. S, 1H); EIMS: 373 (M+1).

Synthesis of 6-Chloro-4-hydroxy-1-(4-methoxy-benzyl)-2-oxo-1,2-dihydro-[1,8]-naphthyridine-3-carboxylic acid ethyl ester (75)

Diethyl malonate (6.02 mL, 71.38 mmol) was added slowly to a suspension of NaH (60% in mineral oil, 3.13 g, 78.24 mmol) in dimethylacetamide (200 mL) and stirred at room temperature for 0.5 h under argon atmosphere. 6-Chloro-1-(4-methoxy-benzyl)-1H-pyrido-[2,3-d]-[1,3]-oxazine-2,4-dione (73) (21.5 g, 71.31 mmol) was added to the solution and heated at 110° C. for 4 h (TLC control). The solution was cooled and poured into ice water. The pH of the solution was adjusted to 3 by cold 10% HCl. The solids formed were filtered, washed by excess water, and dried in a vacuum oven to yield 14.0 g (99%) of 6-chloro-4-hydroxy-1-(4-methoxy-benzyl)-2-oxo-1,2-dihydro-[1,8]-naphthyridine-3-carboxylic acid ethyl ester (75) as white solids. MP: 198° C.; $^1$H-NMR (DMSO-$d_6$): δ 1.28 (t, J=7.2 Hz, 3H), 3.68 (s, 3H), 4.30 (q, J=7.2 Hz, 2H), 5.43 (s, 2H), 6.81 (m, Hz, 2H), 7.20 (m, 2H), 8.43 (d, J=2.8 Hz, 1H), 8.74 (d, J=2.8 Hz, 1H); EIMS: 389 (M+1).

The sequence of reactions in the preparation of 6-fluoro-4-hydroxy-1-(4-methoxy-benzyl)-2-oxo-1,2-dihydro-[1,8]-naphthyridine-3-carboxylic acid ethyl ester (74) and 6-chloro-4-hydroxy-1-(4-methoxy-benzyl)-2-oxo-1,2-dihydro-[1,8]-naphthyridine-3-carboxylic acid ethyl ester (75) as described above was as follows:

Synthesis of 4-Chloro-6-fluoro-1-(4-methoxy-benzyl)-2-oxo-1,2-dihydro-[1,8]-naphthyridine-3-carboxylic acid ethyl ester (76)

A solution of 6-fluoro-4-hydroxy-1-(4-methoxy-benzyl)-2-oxo-1,2-dihydro-[1,8]-naphthyridine-3-carboxylic acid ethyl ester (74) (7.0 g, 18.79 mmol) and triethylamine (5.2 mL, 37.58 mmol) was heated in neat POCl$_3$ at 90° C. for 3 h. The solution was cooled and the excess POCl$_3$ was distilled under vacuum. The residue was suspended in saturated NaHCO$_3$ solution, sonicated briefly and filtered. The solids were dissolved in dichloromethane, washed subsequently by saturated NaHCO$_3$ solution, water and brine. The organic phase was dried over MgSO$_4$ and evaporated to yield 6.2 g (85%) of 4-chloro-6-fluoro-1-(4-methoxy-benzyl)-2-oxo-1,2-dihydro-[1,8]-naphthyridine-3-carboxylic acid ethyl ester (76) as yellow waxy solids. $^1$H-NMR (DMSO-$d_6$): δ 1.31 (t, J=7.2 Hz, 3H), 3.70 (s, 3H), 4.37 (q, J=7.2 Hz, 2H), 5.51 (s, 2H), 6.84 (m, 2H), 7.24 (m, 2H), 8.37 (dd, J=2.8, 8.0 Hz, 1H), 8.82 (d, J=2.8 Hz, 1H); EIMS: 391 (M+1).

Synthesis of 4,6-Dichloro-1-(4-methoxy-benzyl)-2-oxo-1,2-dihydro-[1,8]-naphthyridine-3-carboxylic acid ethyl ester (77)

A solution of 6-chloro-4-hydroxy-1-(4-methoxy-benzyl)-2-oxo-1,2-dihydro-[1,8]-naphthyridine-3-carboxylic acid ethyl ester (75) (6.0 g, 15.43 mmol) and triethylamine (5.36 mL, 38.57 mmol) was heated in neat POCl3 at 90° C. for 3 h. The solution was cooled and the excess POCl3 was distilled under vacuum. The residue was suspended in saturated NaHCO3 solution, sonicated briefly and filtered. The solids were dissolved in dichloromethane, washed subsequently by saturated NaHCO3 solution, water and brine. The organic phase was dried over MgSO4 and evaporated to yield 6.2 g (85%) of 4,6-dichloro-1-(4-methoxy-benzyl)-2-oxo-1,2-dihydro-[1,8]-naphthyridine-3-carboxylic acid ethyl ester (77) as yellow waxy solids. 1H-NMR (DMSO-d6): δ 1.30 (t, J=7.2 Hz, 3H), 3.69 (s, 3H), 4.38 (q, J=7.2 Hz, 2H), 5.50 (s, 2H), 6.82 (m, 2H), 7.24 (m, 2H), 8.48 (d, J=2.4 Hz, 1H), 8.87 (d, J=2.4 Hz, 1H); EIMS: 407 (M).

Synthesis of 4-Chloro-6-fluoro-2-oxo-1,2-dihydro-[1,8]-naphthyridine-3-carboxylic acid ethyl ester (78)

A solution of 4-chloro-6-fluoro-1-(4-methoxy-benzyl)-2-oxo-1,2-dihydro-[1,8]-naphthyridine-3-carboxylic acid ethyl ester (76) (6.0 g, 15.35 mmol) in neat TFA was refluxed for 3 h. The solution was cooled and the excess TFA was distilled under vacuum. The residue was suspended in saturated NaHCO3 solution, sonicated briefly and filtered. The solids were washed by water, and dried at room temperature to yield 4.1 g (98%) of 4-chloro-6-fluoro-2-oxo-1,2-dihydro-[1,8]-naphthyridine-3-carboxylic acid ethyl ester (78) as white solids. MP: 217° C.; 1H-NM (DMSO-d6): 1.28 (t, J=7.2 Hz, 3H), 4.35 (q, J=7.2 Hz, 2H), 8.24 (dd, J=2.8, 8.0 Hz, 1H), 8.75 (d, J=2.8 Hz, 1H), 13.00 (s, 1H); EIMS: 271 (M+1).

Synthesis of 4,6-Dichloro-2-oxo-1,2-dihydro-[1,8]-naphthyridine-3-carboxylic acid ethyl ester (79)

A solution of 4,6-dichloro-1-(4-methoxy-benzyl)-2-oxo-1,2-dihydro-[1,8]-naphthyridine-3-carboxylic acid ethyl ester (77) (6.0 g, 14.73 mmol) in neat TFA was refluxed for 3 h. The solution was cooled and the excess TFA was distilled under vacuum. The residue was suspended in saturated NaHCO3 solution, sonicated briefly and filtered. The solids were washed by water, and dried at room temperature to yield 4.2 g (99%) of 4,6-dichloro-2-oxo-1,2-dihydro-[1,8]-naphthyridine-3-carboxylic acid ethyl ester (79) as white solids. MP: 228° C.; 1H-NM (DMSO-d6): δ 1.29 (t, J=7.2 Hz, 3H), 4.37 (q, J=7.2 Hz, 2H), 8.38 (d, J=2.4 Hz, 1H), 8.75 (d, J=2.4 Hz, 1H), 13.10 (s, 1H); EIMS: 287 (M).

The sequence of reactions in the preparation of 4-chloro-6-fluoro-1-(4-methoxy-benzyl)-2-oxo-1,2-dihydro-[1,8]-naphthyridine-3-carboxylic acid ethyl ester (76), 4,6-dichloro-1-(4-methoxy-benzyl)-2-oxo-1,2-dihydro-[1,8]-naphthyridine-3-carboxylic acid ethyl ester (77), 4-chloro-6-fluoro-2-oxo-1,2-dihydro-[1,8]-naphthyridine-3-carboxylic acid ethyl ester (78) and 4,6-dichloro-2-oxo-1,2-dihydro-[1,8]-naphthyridine-3-carboxylic acid ethyl ester (79) as described above was as follows:

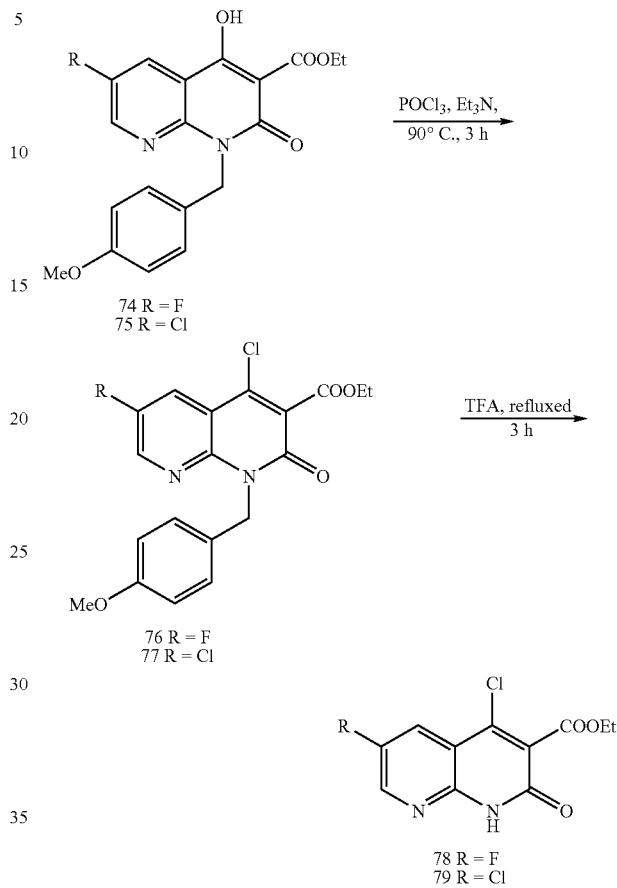

Amination of 4-chloro-naphthyridine Moiety by Substituted Piperazine Derivatives.

The compounds referred to as 80 through 82 were prepared from either 4-chloro-6-fluoro-2-oxo-1,2-dihydro-[1,8]-naphthyridine-3-carboxylic acid ethyl ester (78) or 4,6-dichloro-2-oxo-1,2-dihydro-[1,8]-naphthyridine-3-carboxylic acid ethyl ester (79) by reacting with corresponding piperazine derivative according to general procedure E.

General Procedure E

DABCO (2 mol equivalent) was added to a solution of 4-chloro-6-fluoro-2-oxo-1,2-dihydro-[1,8]-naphthyridine-3-carboxylic acid ethyl ester (78) or 4,6-dichloro-2-oxo-1,2-dihydro-[1,8]-naphthyridine-3-carboxylic acid ethyl ester (79) (1 mol. equivalent) and corresponding piperazinyl derivative (1.2 mol. equivalent) in dimethylacetamide at room temperature. The solution was heated 3 h at 110° C. The solution was cooled and poured into ice water. The solids formed were filtered, washed by water, and dried to yield corresponding product.

Synthesis of 6-Fluoro-2-oxo-4-[4-(thiophene-2-carbonyl)-piperazin-1-yl]-1,2-dihydro-[1,8]-naphthyridine-3-carboxylic acid ethyl ester (80)

This compound was prepared from 4-chloro-6-fluoro-2-oxo-1,2-dihydro-[1,8]-naphthyridine-3-carboxylic acid ethyl ester (78) and piperazine-1-yl-thiophene-2-yl-methanone according to general procedure E. Yield 3.16 g (66%), MP 124-133° C.; $^1$H-NMR (DMSO-$d_6$): δ 1.26 (t, J=7.2 Hz, 3H), 3.11 (m, 4H), 3.88 (m, 4H), 4.28 (q, J=7.2 Hz, 2H), 7.15 (dd, J=3.6, 4.8 Hz, 1H), 7.45 (dd, J=1.2, 3.6 Hz, 1H), 7.79 (dd, J=1.2, 4.8 Hz, 1H), 8.05 (dd, J=2.8, 8.0 Hz, 1H), 8.63 (d, J=2.8 Hz, 1H) 12.40 (s, 1H); EIMS: 431 (M+1).

Synthesis of 6-Fluoro-4-[4-(furan-2-carbonyl)-piperazin-1-yl]-2-oxo-1,2-dihydro-[1,8]-naphthyridine-3-carboxylic acid ethyl ester (81)

This compound was prepared from 4-chloro-6-fluoro-2-oxo-1,2-dihydro-[1,8]-naphthyridine-3-carboxylic acid ethyl ester (78) and 2-furoyl piperazine according to general procedure E. Yield 3.11 g (74%), MP 207° C.; $^1$H-NMR (DMSO-$d_6$): δ 1.27 (t, J=6.8 Hz, 3H), 3.11 (m, 4H), 3.90 (m, 4H), 4.29 (q, J=6.8 Hz, 2H), 6.65 (dd, J=2.0, 3.6, Hz, 1H), 7.04 (d, J=3.6 Hz, 1H), 7.87 (d, J=1.6 Hz, 1H), 8.06 (dd, J=2.8, 8.0 Hz, 1H), 8.63 (d, J=2.8 Hz, 1H) 12.40 (s, 1H); EIMS: 415 (M+1).

Synthesis of 6-Chloro-4-[4-(thiophene-2-carbonyl)-piperazin-1-yl]-2-oxo-1,2-dihydro-[1,8]-naphthyridine-3-carboxylic acid ethyl ester (82)

This compound was prepared from 4,6-dichloro-2-oxo-1,2-dihydro-[1,8]-naphthyridine-3-carboxylic acid ethyl ester (79) and piperazine-1-yl-thiophene-2-yl-methanone according to general procedure E. Yield 6.4 g (73%), MP 242° C.; $^1$H-NMR (DMSO-$d_6$): δ 1.28 (t, J=7.2 Hz, 3H), 3.12 (m, 4H), 3.87 (m, 4H), 4.28 (q, J=7.2 Hz, 2H), 7.15 (dd, J=3.6, 4.8 Hz, 1H), 7.46 (dd, J=1.2, 3.6 Hz, 1H), 7.80 (d, J=4.8 Hz, 1H), 8.17 (d, J=2.4 Hz, 1H), 8.61 (d, J=2.8 Hz, 1H) 12.40 (s, 1H); EIMS: 447 (M).

The sequence of reactions in the preparation of 6-fluoro-2-oxo-4-[4-(thiophene-2-carbonyl)-piperazin-1-yl]-1,2-dihydro-[1,8]-naphthyridine-3-carboxylic acid ethyl ester (80), 6-fluoro-4-[4-(furan-2-carbonyl)-piperazin-1-yl]-2-oxo-1,2-dihydro-[1,8]naphthyridine-3-carboxylic acid ethyl ester (81) and 6-chloro-4-[4-(thiophene-2-carbonyl)-piperazin-1-yl]-2-oxo-1,2-dihydro-[1,8]-naphthyridine-3-carboxylic acid ethyl ester (82) as described above was as follows:

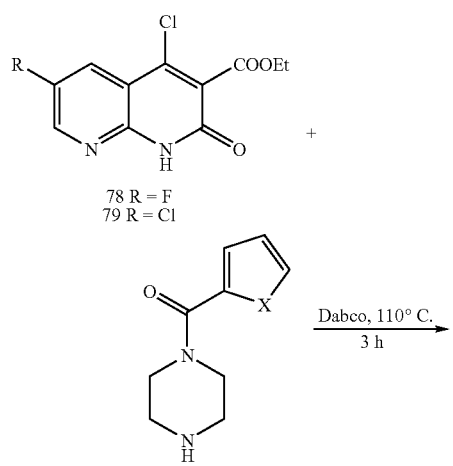

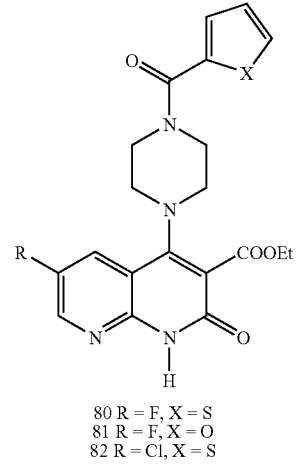

80 R = F, X = S
81 R = F, X = O
82 R = Cl, X = S

Preparation of Compounds by Alkylation at N-1 Position of 6-Substituted Naphthyridine Moiety The compounds referred to as compound 83 through 91 were prepared from either 6-fluoro-2-oxo-4-[4-(thiophene-2-carbonyl)-piperazin-1-yl]-1,2-dihydro-[1,8]-naphthyridine-3-carboxylic acid ethyl ester (80), or 6-fluoro-4-[4-(furan-2-carbonyl)-piperazin-1-yl]-2-oxo-1,2-dihydro-[1,8]-naphthyridine-3-carboxylic acid ethyl ester (81) or 6-chloro-4-[4-(thiophene-2-carbonyl)-piperazin-1-yl]-2-oxo-1,2-dihydro-[1,8]-naphthyridine-3-carboxylic acid ethyl ester (82) and corresponding alkyl halides by applying General Procedure B.

Synthesis of 1-Benzyl-6-fluoro-2-oxo-4-[4-(thiophene-2-carbonyl)-piperazin-1-yl]-1,2-dihydro-[1,8]-naphthyridine-3-carboxylic acid ethyl ester (83)

This compound was prepared from 6-fluoro-2-oxo-4-[4-(thiophene-2-carbonyl)-piperazin-1-yl]-1,2-dihydro-[1,8]-naphthyridine-3-carboxylic acid ethyl ester (80) and benzyl bromide according to General Procedure B. Yield 152 mg (21%), MP 130° C.; $^1$H-NMR (DMSO-$d_6$): δ 1.28 (t, J=7.2 Hz, 3H), 3.15 (m, 4H), 3.90 (m, 4H), 4.32 (q, J=7.2 Hz, 2H), 5.55 (s, 2H), 7.14-7.30 (m, 6H), 7.45 (d, J=3.6 Hz, 1H), 7.80 (d, J=4.8 Hz, 1H), 8.16 (dd, J=2.8, 8.8 Hz, 1H), 8.74 (d, J=2.8 Hz, 1H); EIMS: 521 (M+1). Anal. ($C_{27}H_{25}FN_4O_4S$) C, H, N.

Synthesis of 6-Fluoro-1-(3-fluorobenzyl)-2-oxo-4-[4-(thiophene-2-carbonyl)-piperazin-1-yl]-1,2-dihydro-[1,8]-naphthyridine-3-carboxylic acid ethyl ester (84)

This compound was prepared from 6-fluoro-2-oxo-4-[4-(thiophene-2-carbonyl)-piperazin-1-yl]-1,2-dihydro-[1,8]-naphthyridine-3-carboxylic acid ethyl ester (80) and 3-fluorobenzyl bromide according to General Procedure B. Yield 113 mg (8%), MP 113° C.; $^1$H-NMR (DMSO-$d_6$): δ 1.29 (t, J=7.2 Hz, 3H), 3.15 (m, 4H), 3.90 (m, 4H), 4.33 (q, J=7.2 Hz, 2H), 5.55 (s, 2H), 7.08 (m, 3H), 7.15 (dd, J=3.6, 5.2 Hz, 1H), 7.34 (m, 1H), 7.46 (dd, J=1.2, 3.6 Hz, 1H), 7.80 (dd, J=1.2, 5.2 Hz, 1H), 8.17 (dd, J=2.8, 8.8 Hz, 1H), 8.74 (d, J=2.8 Hz, 1H); EIMS: 539 (M+1). Anal. ($C_{27}H_{24}F_2N_4O_4S$) C, H, N.

Synthesis of 6-Fluoro-2-oxo-1-(2-oxo-2-phenyl-ethyl)-4-[4-(thiophene-2-carbonyl)-piperazin-1-yl]-1,2-dihydro-[1,8]-naphthyridine-3-carboxylic acid ethyl ester (85)

This compound was prepared from 6-fluoro-2-oxo-4-[4-(thiophene-2-carbonyl)-piperazin-1-yl]-1,2-dihydro-[1,8]-naphthyridine-3-carboxylic acid ethyl ester (80) and 2-bromoacetophenone according to General Procedure B. Yield 293 mg (38%), MP 262° C.; $^1$H-NMR (DMSO-d$_6$): δ 1.29 (t, J=7.2 Hz, 3H), 3.19 (m, 4H), 3.92 (m, 4H), 4.32 (q, J=7.2 Hz, 2H), 5.88 (s, 2H), 7.16 (dd, J=3.6, 4.8 Hz, 1H), 7.47 (dd, J=1.2, 3.6 Hz, 1H), 7.61 (m, 2H), 7.72 (m, 1H), 7.81 (d, J=4.8 Hz, 1H), 8.11 (m, 2H), 8.18 (dd, J=2.8, 8.8 Hz, 1H), 8.65 (d, J=2.8 Hz, 1H); EIMS: 549 (M+1). Anal. ($C_{28}H_{25}FN_4O_5S$) C, H, N.

Synthesis of 1-Benzyl-6-fluoro-4-[4-(furan-2-carbonyl)-piperazin-1-yl]-2-oxo-1,2-dihydro-[1,8]-naphthyridine-3-carboxylic acid ethyl ester (86)

This compound was prepared from 6-fluoro-4-[4-(furan-2-carbonyl)-piperazin-1-yl]-2-oxo-1,2-dihydro-[1,8]-naphthyridine-3-carboxylic acid ethyl ester (81) and benzyl bromide according to General Procedure B. Yield 391 mg (47%), MP 119° C.; $^1$H-NMR (DMSO-d$_6$): δ 1.27 (t, J=7.2 Hz, 3H), 3.15 (m, 4H), 3.92 (m, 4H), 4.29 (q, J=7.2 Hz, 2H), 5.54 (s, 2H), 6.65 (dd, J=1.6, 3.2, Hz, 1H), 7.05 (d, J=3.6 Hz, 1H), 7.20 (m, 5H), 7.87 (d, J=3.2 Hz, 1H), 8.18 (dd, J=2.8, 8.8 Hz, 1H), 8.74 (d, J=2.8 Hz, 1H); EIMS: 505 (M+1). Anal. ($C_{27}H_{25}FN_4O_5$) C, H, N.

Synthesis of 6-Fluoro-1-(3-fluorobenzyl)-4-[4-(furan-2-carbonyl)-piperazin-1-yl]-2-oxo-1,2-dihydro-[1,8]-naphthyridine-3-carboxylic acid ethyl ester (87)

This compound was prepared from 6-fluoro-4-[4-(furan-2-carbonyl)-piperazin-1-yl]-2-oxo-1,2-dihydro-[1,8]-naphthyridine-3-carboxylic acid ethyl ester (81) and 3-fluorobenzyl bromide according to General Procedure B. Yield 421 mg (49%), MP 121° C.; $^1$H-NMR (DMSO-d$_6$): δ 1.27 (t, J=7.2 Hz, 3H), 3.15 (m, 4H), 3.92 (m, 4H), 4.29 (q, J=7.2 Hz, 2H), 5.53 (s, 2H), 6.65 (dd, J=1.6, 3.2, Hz, 1H), 7.05 (m, 4H), 7.33 (m, 1H), 7.87 (d, J=1.6 Hz, 1H), 8.18 (dd, J=2.8, 8.8 Hz, 1H), 8.73 (d, J=2.8 Hz, 1H); EIMS: 523 (M+1). Anal. ($C_{27}H_{24}F_2N_4O_5$) C, H, N.

Synthesis of 6-Fluoro-4-[4-(furan-2-carbonyl)-piperazin-1-yl]-2-oxo-1-(2-oxo-2-phenyl-ethyl)-1,2-dihydro-[1,8]-naphthyridine-3-carboxylic acid ethyl ester (88)

This compound was prepared from 6-fluoro-4-[4-(furan-2-carbonyl)-piperazin-1-yl]-2-oxo-1,2-dihydro-[1,8]-naphthyridine-3-carboxylic acid ethyl ester (81) and 2-bromoacetophenone according to General Procedure B. Yield 298 mg (34%), MP 134° C.; $^1$H-NMR (DMSO-d$_6$): δ 1.27 (t, J=7.2 Hz, 3H), 3.19 (m, 4H), 3.94 (m, 4H), 4.31 (q, J=7.2 Hz, 2H), 5.88 (s, 2H), 6.66 (dd, J=1.6, 3.2, Hz, 1H), 7.07 (d, J=3.6 Hz, 1H), 7.61 (m, 2H), 7.74 (m, 1H), 7.88 (d, J=1.2 Hz, 1H), 8.11 m, 2H), 8.20 (dd, J=2.8, 8.8 Hz, 1H), 8.64 (d, J=2.8 Hz, 1H); EIMS: 533 (M+1). Anal. ($C_{28}H_{25}FN_4O_6$) C, H, N.

Synthesis of 1-Benzyl-6-chloro-2-oxo-4-[4-(thiophene-2-carbonyl)-piperazin-1-yl]-1,2-dihydro-[1,8]-naphthyridine-3-carboxylic acid ethyl ester (89)

This compound was prepared from 6-chloro-4-[4-(thiophene-2-carbonyl)-piperazin-1-yl]-2-oxo-1,2-dihydro-[1,8]-naphthyridine-3-carboxylic acid ethyl ester (82) and benzyl bromide according to General Procedure B. Yield 319 mg (59%), MP 197° C.; $^1$H-NMR (DMSO-d$_6$): δ 1.28 (t, J=7.2 Hz, 3H), 3.15 (m, 4H), 3.95 (m, 4H), 4.32 (q, J=7.2 Hz, 2H), 5.52 (s, 2H), 7.15-7.28 (m, 6H), 7.46 (d, J=3.6 Hz, 1H), 7.80 (d, J=4.8 Hz, 1H), 8.29 (d, J=2.8 Hz, 1H), 8.73 (d, J=2.8 Hz, 1H); EIMS: 537 (M+1). Anal. ($C_{27}H_{25}ClN_4O_4S$) C, H, N.

Synthesis of 6-Chloro-1-(3-fluorobenzyl)-2-oxo-4-[4-(thiophene-2-carbonyl)-piperazin-1-yl]-1,2-dihydro-[1,8]-naphthyridine-3-carboxylic acid ethyl ester (90)

This compound was prepared from 6-fluoro-6-chloro-4-[4-(thiophene-2-carbonyl)-piperazin-1-yl]-2-oxo-1,2-dihydro-[1,8]-naphthyridine-3-carboxylic acid ethyl ester (82) and 3-fluorobenzyl bromide according to General Procedure B. Yield 207 mg (37%), MP 186° C.; $^1$H-NMR (DMSO-d$_6$): δ 1.28 (t, J=7.2 Hz, 3H), 3.16 (m, 4H), 3.92 (m, 4H), 4.32 (q, J=7.2 Hz, 2H), 5.24 (s, 2H), 7.07 (m, 3H), 7.15 (dd, J=3.6, 5.2 Hz, 1H), 7.30 (m, 1H), 7.47 (dd, J=1.2, 3.6 Hz, 1H), 7.80 (d, J=4.8 Hz, 1H), 8.29 (d, J=2.8 Hz, 1H), 8.73 (d, J=2.8 Hz, 1H); EIMS: 555 (M+1). Anal. ($C_{27}H_{24}ClFN_4O_4S$) C, H, N.

Synthesis of 6-Chloro-2-oxo-1-(2-oxo-2-phenyl-ethyl)-4-[4-(thiophene-2-carbonyl)-piperazin-1-yl]-1,2-dihydro-[1,8]-naphthyridine-3-carboxylic acid ethyl ester (91)

This compound was prepared from 6-chloro-4-[4-(thiophene-2-carbonyl)-piperazin-1-yl]-2-oxo-1,2-dihydro-[1,8]-naphthyridine-3-carboxylic acid ethyl ester (82) and 2-bromoacetophenone according to General Procedure B. Yield 333 mg (59%), MP 227° C.; $^1$H-NMR (DMSO-d$_6$): δ 1.29 (t, J=7.2 Hz, 3H), 3.20 (m, 4H), 3.92 (m, 4H), 4.32 (q, J=7.2 Hz, 2H), 5.87 (s, 2H), 7.17 (dd, J=3.6, 4.8 Hz, 1H), 7.48 (dd, J=1.2, 3.6 Hz, 1H), 7.61 (m, 2H), 7.73 (m, 1H), 7.81 (dd, J=1.2, 4.8 Hz, 1H), 8.11 (m, 2H), 8.32 (d, J=2.6 Hz, 1H), 8.64 (d, J=2.8 Hz, 1H); EIMS: 565 (M+1). Anal. ($C_{28}H_{25}ClN_4O_5S$) C, H, N.

Synthesis of 6-Fluoro-4-hydroxy-1-(4-methoxybenzyl)-2-oxo-1,2-dihydro-[1,8]-naphthyridine-3-carboxylic acid cyclohexylamide (92)

Cyclohexylamine (6.14 mL, 53.65 mmol) was added to a stirred solution of 6-fluoro-4-hydroxy-1-(4-methoxy-benzyl)-2-oxo-1,2-dihydro-[1,8]-naphthyridine-3-carboxylic acid ethyl ester (74) (10 g, 26.82 mmol) in xylene and heated at 140° C. for 3 h. The solution was cooled and the solvent was evaporated under vacuum. The residue was suspended in water and extracted by dichloromethane. The combined organic phase was washed by water and brine, then dried over Na2SO4 and evaporated to yield 7.46 g (65%) of 6-fluoro-4-hydroxy-1-(4-methoxy-benzyl)-2-oxo-1,2-dihydro-[1,8]-naphthyridine-3-carboxylic acid cyclohexyl amide (92) as white solids. MP: 176° C.; $^1$H-NMR (DMSO-d6): δ 1.25-1.41 (m, 5H), 1.54 (m, 1H), 1.66 (m, 2H), 1.87 (m, 2H), 3.68 (s, 3H), 3.86 (m, 1H), 5.51 (s, 2H), 6.81 (d, J=8.8 Hz, 2H), 7.20 (d, J=8.8 Hz, 2H), 8.31 (d, J=8.0 Hz, 1H), 8.83 (s, 1H), 10.24 (s, 1H); EIMS m/z 426 (M+1).

Synthesis of 6-Chloro-4-hydroxy-1-(4-methoxybenzyl)-2-oxo-1,2-dihydro-[1,8]-naphthyridine-3-carboxylic acid cyclohexylamide (93)

Cyclohexylamine (6.15 mL, 53.70 mmol) was added to a stirred solution of 6-chloro-4-hydroxy-1-(4-methoxy-benzyl)-2-oxo-1,2-dihydro-[1,8]-naphthyridine-3-carboxylic acid ethyl ester (75) (10.44 g, 26.85 mmol) in xylene and heated at 140° C. for 3 h. The solution was cooled and the solvent was evaporated under vacuum. The residue was suspended in water and extracted by dichloromethane. The combined organic phase was washed by water and brine, then dried over Na2SO4 and evaporated to yield 10.6 g (89%) of 6-chloro-4-hydroxy-1-(4-methoxy-benzyl)-2-oxo-1,2-dihydro-[1,8]-naphthyridine-3-carboxylic acid cyclohexylamide (93) as white solids. MP: 193° C.; 1H-NMR (CDCl3): δ 1.24-1.99 (m, 10H), 3.47 (s, 3H), 3.93 (m, 1H), 5.59 (s, 2H), 6.78 (m, 2H), 7.37 (m, 2H), 8.39 (d, J=2.4 Hz, 1H), 8.60 (d, J=2.4 Hz, 1H), 10.15 (s, 1H); EIMS m/z 442 (M+1).

The sequence of reactions in the preparation of 6-fluoro-4-hydroxy-1-(4-methoxy-benzyl)-2-oxo-1,2-dihydro-[1,8]-naphthyridine-3-carboxylic acid cyclohexylamide (92) and 6-chloro-4-hydroxy-1-(4-methoxy-benzyl)-2-oxo-1,2-dihydro-[1,8]-naphthyridine-3-carboxylic acid cyclohexylamide (93) as described above was as follows:

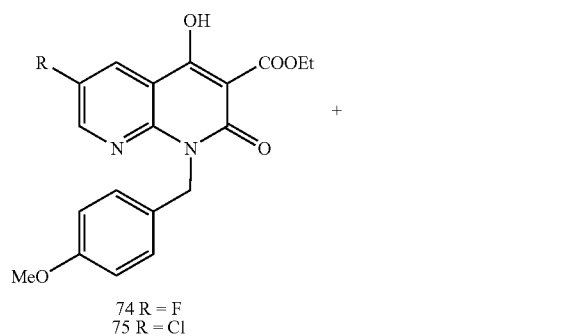

74 R = F
75 R = Cl

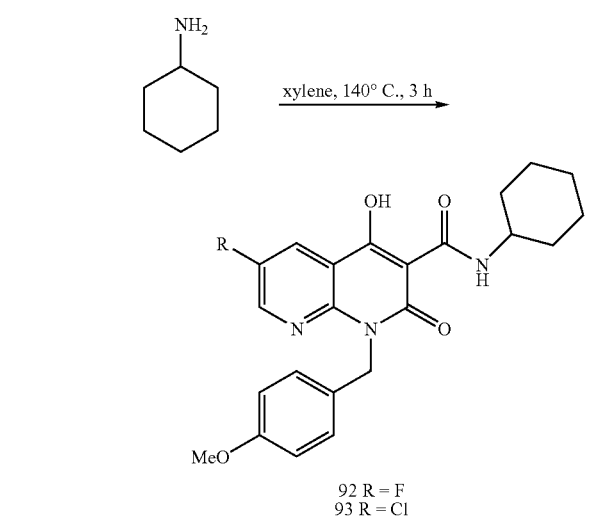

92 R = F
93 R = Cl

Synthesis of 4-Chloro-6-fluoro-1-(4-methoxybenzyl)-2-oxo-1,2-dihydro-[1,8]-naphthyridine-3-carbonitrile (94)

A solution of 6-fluoro-4-hydroxy-1-(4-methoxy-benzyl)-2-oxo-1,2-dihydro-[1,8]-naphthyridine-3-carboxylic acid cyclohexylamide (92) (7.46 g, 17.53 mmol) and triethylamine (6.1 mL, 43.83 mmol) was heated in neat POCl3 overnight at 90° C. The solution was cooled and the excess POCl3 was distilled under vacuum. The residue was suspended in saturated NaHCO3 solution, sonicated briefly and filtered. The solids were dissolved in dichloromethane, washed subsequently by saturated NaHCO3 solution, water and brine. The organic phase was dried over MgSO4 and evaporated to yield 4.2 g (69%) of 4-chloro-6-fluoro-1-(4-methoxybenzyl)-2-oxo-1,2-dihydro-1,8-naphthyridine-3-carbonitrile (94) as white solids. MP 195° C. 1H-NMR (DMSO-d6): δ 3.69 (s, 3H), 5.51 (s, 2H), 6.82 (d, J=8.8 Hz, 2H), 7.29 (d, J=8.8 Hz, 2H), 8.48 (dd, J=2.8, 8.4 Hz, 1H), 8.96 (d, J=2.8 Hz, 1H); EIMS m/z 344 (M+1).

Synthesis of 4,6-dichloro-1-(4-methoxybenzyl)-2-oxo-1,2-dihydro-[1,8]-naphthyridine-3-carbonitrile (95)

A solution of 6-chloro-4-hydroxy-1-(4-methoxy-benzyl)-2-oxo-1,2-dihydro-[1,8]-naphthyridine-3-carboxylic acid cyclohexylamide (93) (10.6 g, 24 mmol) and triethylamine (8.33 mL, 60 mmol) was heated in neat POCl3 overnight at 90° C. The solution was cooled and the excess POCl3 was distilled under vacuum. The residue was suspended in saturated NaHCO3 solution, sonicated briefly and filtered. The solids were dissolved in dichloromethane, washed subsequently by saturated NaHCO3 solution, water and brine. The organic phase was dried over MgSO4 and evaporated to yield 8.2 g (95%) of 4,6-dichloro-1-(4-methoxybenzyl)-2-oxo-1,2-dihydro-1,8-naphthyridine-3-carbonitrile (95) as white solids. MP 208° C. 1H-NMR (DMSO-d6): δ 3.69 (s, 3H), 5.50 (s, 2H), 6.82 (m, 2H), 7.87 (m, 2H), 8.59 (d, J=2.8 Hz, 1H), 8.94 (d, J=2.8 Hz, 1H); EIMS m/z 362 (M+2).

Synthesis of 4-Chloro-6-fluoro-2-oxo-1,2-dihydro-[1,8]-naphthyridine-3-carbonitrile (96)

4-Chloro-6-fluoro-1-(4-methoxybenzyl)-2-oxo-1,2-dihydro-1,8-naphthyridine-3-carbonitrile (94) (4.3 g, 12.50 mmol) in neat TFA was refluxed for 24 h. The solution was cooled and excess TFA was distilled off under reduced pressure. The residue was taken in water, basified by solid NaHCO3 and filtered. The solids were washed with excess water and dried to yield 2.6 g (96%) of 4-chloro-6-fluoro-2-oxo-1,2-dihydro-[1,8]-naphthyridine-3-carbonitrile (96) as white solids. MP: 272° C.; 1H-NMR (DMSO-d6): δ 8.26 (dd, J=2.8, 8.2 Hz, 1H), 8.81 (d, J=2.8 Hz, 1H), 13.03 (S, 1H); EIMS: 224 (M+1).

Synthesis of 4,6-dichloro-2-oxo-1,2-dihydro-[1,8]-naphthyridine-3-carbonitrile (97)

4,6-dichloro-1-(4-methoxybenzyl)-2-oxo-1,2-dihydro-1,8-naphthyridine-3-carbonitrile (95) (8.2 g, 22.70 mmol) in neat TFA was refluxed for 24 h. The solution was cooled and excess TFA was distilled off under reduced pressure. The residue was taken in water, basified by solid NaHCO3 and filtered. The solids were washed with excess water and dried to yield 5.2 g (96%) of 4,6-dichloro-2-oxo-1,2-dihydro-[1,8]-naphthyridine-3-carbonitrile (97) as yellow solids. MP:

247° C.; 1H-NMR (DMSO-d6): δ 8.45 (dd, J=2.4 Hz, 1H), 8.82 (d, J=2.4 Hz, 1H), 13.17 (S, 1H); EIMS: 240 (M).

The sequence of reactions in the preparation of 4-chloro-6-fluoro-1-(4-methoxybenzyl)-2-oxo-1,2-dihydro-1,8-naphthyridine-3-carbonitrile (94), 4,6-dichloro-1-(4-methoxybenzyl)-2-oxo-1,2-dihydro-1,8-naphthyridine-3-carbonitrile (95), 4-chloro-6-fluoro-2-oxo-1,2-dihydro-[1,8]-naphthyridine-3-carbonitrile (96) and 4,6-dichloro-2-oxo-1,2-dihydro-[1,8]-naphthyridine-3-carbonitrile (97) as described above was as follows:

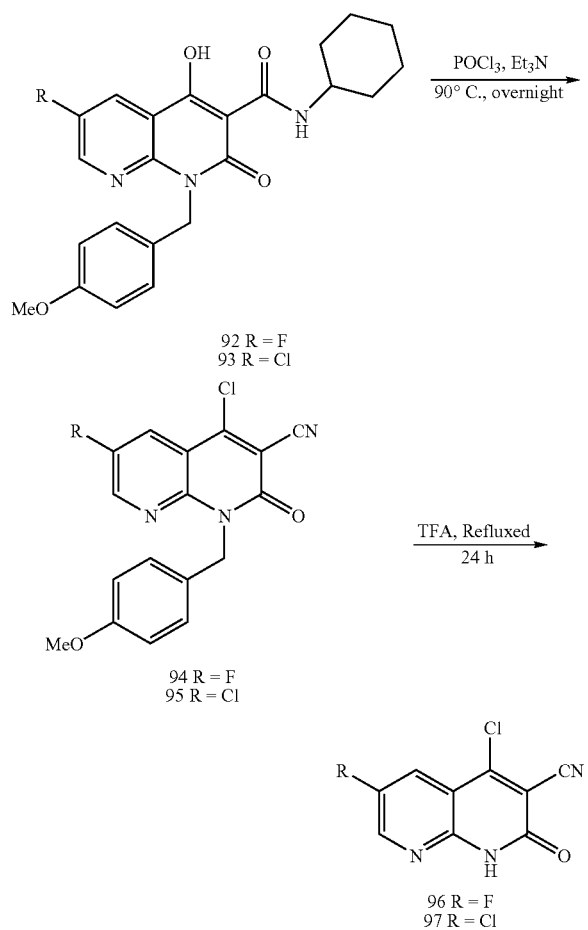

Amination of 4-chloro-naphthyridine Carbonitrile Moiety by Substituted Piperazine Derivatives The compounds referred to as 98 through 101 were prepared from either 4-chloro-6-fluoro-2-oxo-1,2-dihydro-[1,8]-naphthyridine-3-carbonitrile (96) or 4,6-dichloro-2-oxo-1,2-dihydro-[1,8]-naphthyridine-3-carbonitrile (97) by reacting with corresponding piperazine derivative according to general procedure E described above.

Synthesis of 6-Fluoro-2-oxo-4-[4-(thiophene-2-carbonyl)-piperazine-1-yl]-1,2-dihydro-[1,8]-naphthyridine-3-carbonitrile (98)

This compound was prepared from 4-chloro-6-fluoro-2-oxo-1,2-dihydro-[1,8]-naphthyridine-3-carbonitrile (96) and piperazin-1-yl-thiophene-2-yl-methanone according to general procedure E to yield 4.85 g (79%) of 6-fluoro-2-oxo-4-[4-(thiophene-2-carbonyl)-piperazine-1-yl]-1,2-dihydro-[1,8]-naphthyridine-3-carbonitrile (98) as yellow solids. MP 244° C.; $^1$H-NMR (DMSO-d$_6$): δ 3.72 (m, 4H), 3.91 (m, 4H), 7.16 (dd, J=3.6, 4.8 Hz, 1H), 7.49 (d, J=3.6 Hz, 1H), 7.80 (d, J=5.2 Hz, 1H), 8.05 (dd, J=2.8, 7.2 Hz, 1H), 8.70 (d, J=2.8 Hz, 1H); EIMS: 384 (M+1).

Synthesis of 6-Fluoro-2-oxo-4-[4-(furan-2-carbonyl)-piperazine-1-yl]-1,2-dihydro-[1,8]-naphthyridine-3-carbonitrile (99)

This compound was prepared from 4-chloro-6-fluoro-2-oxo-1,2-dihydro-[1,8]-naphthyridine-3-carbonitrile (96) and 2-furoyl piperazine according to general procedure E to yield 2.87 g (71%) of 6-fluoro-2-oxo-4-[4-(furan-2-carbonyl)-piperazine-1-yl]-1,2-dihydro-[1,8]-naphthyridine-3-carbonitrile (99) as white solids. MP 312° C.; $^1$H-NMR (DMSO-d$_6$): δ 3.69 (m, 4H), 3.93 (m, 4H), 6.66 (dd, J=1.6, 3.6 Hz, 1H), 7.08 (d, J=3.6 Hz, 1H), 7.89 (d, J=1.6 Hz, 1H), 8.07 (dd, J=2.8, 9.2 Hz, 1H), 8.69 (d, J=2.8 Hz, 1H), 12.30 (s, 1H); EIMS: 368 (M+1).

Synthesis of 6-Chloro-2-oxo-4-[4-(thiophene-2-carbonyl)-piperazine-1-yl]-1,2-dihydro-[1,8]-naphthyridine-3-carbonitrile (100)

This compound was prepared from 4,6-dichloro-2-oxo-1,2-dihydro-[1,8]-naphthyridine-3-carbonitrile (97) and piperazin-1-yl-thiophene-2-yl-methanone according to general procedure E to yield 6.8 g (74%) of 6-chloro-2-oxo-4-[4-(thiophene-2-carbonyl)-piperazine-1-yl]-1,2-dihydro-[1,8]-naphthyridine-3-carbonitrile (100) as yellow solids. MP 158° C.; $^1$H-NMR (DMSO-d$_6$): δ 3.64 (m, 4H), 3.90 (m, 4H), 7.16 (dd, J=3.6, 4.8 Hz, 1H), 7.49 (dd, J=1.2, 3.6 Hz, 1H), 7.81 (dd, J=1.2, 5.2 Hz, 1H), 8.21 (d, J=2.4 Hz, 1H), 8.66 (d, J=2.4 Hz, 1H); EIMS: 400 (M+1).

Synthesis of 6-chloro-2-oxo-4-[4-(furan-2-carbonyl)-piperazine-1-yl]-1,2-dihydro-[1,8]-naphthyridine-3-carbonitrile (101)

This compound was prepared from 4,6-dichloro-2-oxo-1,2-dihydro-[1,8]-naphthyridine-3-carbonitrile (97) and 2-furoyl piperazine according to general procedure E to yield 2.27 g (71%) of 6-chloro-2-oxo-4-[4-(furan-2-carbonyl)-piperazine-1-yl]-1,2-dihydro-[1,8]-naphthyridine-3-carbonitrile (101) as yellow solids. MP 303° C.; $^1$H-NMR (DMSO-d$_6$): δ 3.76 (m, 4H), 3.93 (m, 4H), 6.65 (dd, J=1.6, 3.6 Hz, 1H), 7.09 (d, J=3.6 Hz, 1H), 7.89 (d, J=1.6 Hz, 1H), 8.21 (d, J=2.4 Hz, 1H), 8.66 (d, J=2.4 Hz, 1H), 12.36 (s, 1H); EIMS: 384 (M+1).

The sequence of reactions in the preparation of 6-fluoro-2-oxo-4-[4-(thiophene-2-carbonyl)-piperazine-1-yl]-1,2-dihydro-[1,8]-naphthyridine-3-carbonitrile (98), 6-fluoro-2-oxo-4-[4-(furan-2-carbonyl)-piperazine-1-yl]-1,2-dihydro-[1,8]-naphthyridine-3-carbonitrile (99), 6-chloro-2-oxo-4-[4-(thiophene-2-carbonyl)-piperazine-1-yl]-1,2-dihydro-[1,8]-naphthyridine-3-carbonitrile (100) and 6-chloro-2-oxo-4-[4-(furan-2-carbonyl)-piperazine-1-yl]-1,2-dihydro-[1,8]-naphthyridine-3-carbonitrile (101) as described above was as follows:

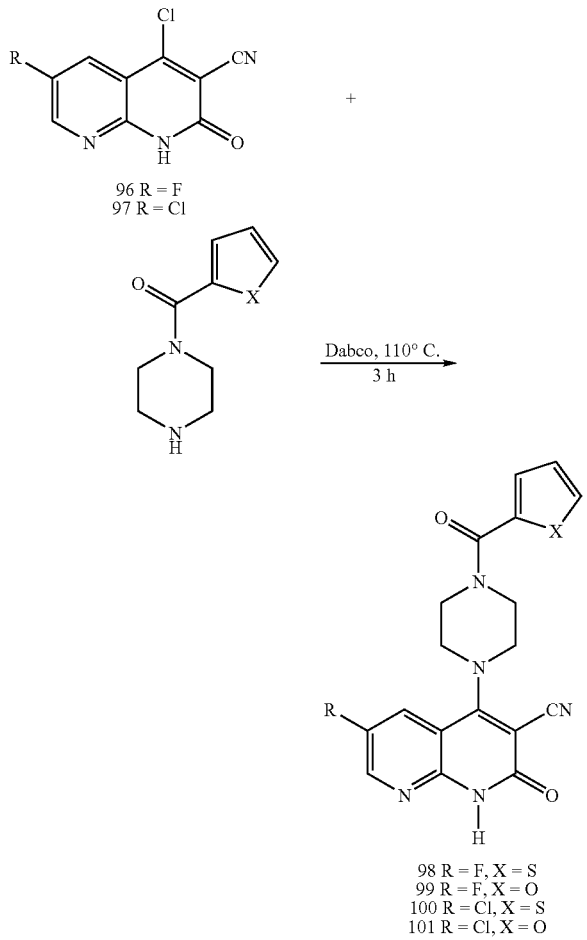

Preparation of Compounds by Alkylation at N–1 Position of 6-Substituted Naphthyridine Carbonitrile Moiety The compounds referred to as compound 102 through 113 were prepared from either 6-fluoro-2-oxo-4-[4-(thiophene-2-carbonyl)-piperazine-1-yl]-1,2-dihydro-[1,8]-naphthyridine-3-carbonitrile (98) or 6-fluoro-2-oxo-4-[4-(furan-2-carbonyl)-piperazine-1-yl]-1,2-dihydro-[1,8]-naphthyridine-3-carbonitrile (99) or 6-chloro-2-oxo-4-[4-(thiophene-2-carbonyl)-piperazine-1-yl]-1,2-dihydro-[1,8]-naphthyridine-3-carbonitrile (100) or 6-chloro-2-oxo-4-[4-(furan-2-carbonyl)-piperazine-1-yl]-1,2-dihydro-[1,8]-naphthyridine-3-carbonitrile (101) and corresponding alkyl halides by applying General Procedure B described above.

Synthesis of 1-Benzyl-6-fluoro-2-oxo-4-[4-(thiophene-2-carbonyl)-piperazin-1-yl]-1,2-dihydro-[1,8]-naphthyridine-3-carbonitrile (102)

This compound was prepared from 6-fluoro-2-oxo-4-[4-(thiophene-2-carbonyl)-piperazine-1-yl]-1,2-dihydro-[1,8]-naphthyridine-3-carbonitrile (98) and benzyl bromide according to General Procedure B. Yield 317 mg (43%), MP 173° C.; $^1$H-NMR (DMSO-$d_6$): δ 3.73 (m, 4H), 3.92 (m, 4H), 5.53 (s, 2H), 7.22-7.30 (m, 6H), 7.49 (d, J=3.6 Hz, 1H), 7.80 (dd, J=1.2, 5.2 Hz, 1H), 8.16 (dd, J=2.8, 9.2 Hz, 1H), 8.77 (d, J=2.8 Hz, 1H); EIMS: 474 (M+1). Anal. ($C_{25}H_{20}FN_5O_2S$) C, H, N.

Synthesis of 6-Fluoro-1-(3-fluorobenzyl)-2-oxo-4-[4-(thiophene-2-carbonyl)-piperazin-1-yl]-1,2-dihydro-[1,8]-naphthyridine-3-carbonitrile (103)

This compound was prepared from 6-fluoro-2-oxo-4-[4-(thiophene-2-carbonyl)-piperazine-1-yl]-1,2-dihydro-[1,8]-naphthyridine-3-carbonitrile (98) and 3-fluorobenzyl bromide according to General Procedure B. Yield 428 mg (56%), MP 137° C.; $^1$H-NMR (DMSO-$d_6$): δ 3.73 (m, 4H), 3.93 (m, 4H), 5.52 (s, 2H), 7.06-7.10 (m, 3H), 7.16 (dd, J=3.6, 4.8 Hz, 1H), 7.33 (m, 1H), 7.50 (d, J=3.6 Hz, 1H), 7.80 (dd, J=1.2, 5.2 Hz, 1H), 8.17 (dd, J=2.8, 9.2 Hz, 1H), 8.77 (d, J=2.8 Hz, 1H); EIMS: 492 (M+1). Anal ($C_{25}H_{19}F_2N_5O_2S$) C, H, N.

Synthesis of 6-Fluoro-2-oxo-1-(2-oxo-2-phenyl-ethyl)-4-[4-(thiophene-2-carbonyl)-piperazin-1-yl]-1,2-dihydro-[1,8]-naphthyridine-3-carbonitrile (104)

This compound was prepared from 6-fluoro-2-oxo-4-[4-(thiophene-2-carbonyl)-piperazine-1-yl]-1,2-dihydro-[1,8]-naphthyridine-3-carbonitrile (98) and 2-bromoacetophenone according to General Procedure B. Yield 293 mg (38%), MP 262° C.; $^1$H-NMR (DMSO-$d_6$): δ 3.79 (m, 4H), 3.95 (m, 4H), 5.87 (s, 2H), 7.16 (dd, J=3.6, 5.2 Hz, 1H), 7.51 (d, J=3.6 Hz, 1H), 7.59 (m, 2H), 7.50 (m, 1H), 7.81 (dd, J=1.2, 4.8 Hz, 1H), 8.12 (m, 2H), 8.23 (dd, J=2.8, 9.2 Hz, 1H), 8.70 (d, J=2.8 Hz, 1H); EIMS: 502 (M+1). Anal. ($C_{26}H_{20}FN_5O_3S$) C, H, N.

Synthesis of 1-Benzyl-6-fluoro-4-[4-(furan-2-carbonyl)-piperazin-1-yl]-2-oxo-1,2-dihydro-[1,8]-naphthyridine-3-carbonitrile (105)

This compound was prepared from 6-fluoro-2-oxo-4-[4-(furan-2-carbonyl)-piperazine-1-yl]-1,2-dihydro-[1,8]-naphthyridine-3-carbonitrile (99) and benzyl bromide according to General Procedure B. Yield 136 mg (18%), MP 216° C.; $^1$H-NMR (DMSO-$d_6$): δ 3.72 (m, 4H), 3.95 (m, 4H), 5.53 (s, 2H), 6.66 (dd, J=2.0, 3.6 Hz, 1H), 7.08 (d, J=3.6 Hz, 1H), 7.21-7.28 (m, 5H), 7.89 (d, J=2.0 Hz, 1H), 8.18 (dd, J=2.8, 9.2 Hz, 1H), 8.77 (d, J=2.8 Hz, 1H); EIMS: 458 (M+1). Anal. ($C_{25}H_{20}FN_5O_3$) C, H, N.

Synthesis of 6-Fluoro-1-(3-fluorobenzyl)-2-oxo-4-[4-(furan-2-carbonyl)-piperazin-1-yl]-1,2-dihydro-[1,8]-naphthyridine-3-carbonitrile (106)

This compound was prepared from 6-fluoro-2-oxo-4-[4-(furan-2-carbonyl)-piperazine-1-yl]-1,2-dihydro-[1,8]-naphthyridine-3-carbonitrile (99) and 3-fluorobenzyl bromide according to General Procedure B. Yield 297 mg (38%), MP 211° C.; $^1$H-NMR (DMSO-$d_6$): δ 3.72 (m, 4H), 3.95 (m, 4H), 5.52 (s, 2H), 6.67 (dd, J=1.6, 3.6, Hz, 1H), 7.06-7.10 (m, 4H), 7.33 (m, 1H), 7.89 (d, J=1.6 Hz, 1H), 8.18 (dd, J=2.8, 9.2 Hz, 1H), 8.78 (d, J=2.8 Hz, 1H); EIMS: 476 (M+1). Anal. ($C_{25}H_{19}F_2N_5O_3$) C, H, N.

Synthesis of 6-Fluoro-4-[4-(furan-2-carbonyl)-piperazin-1-yl]-2-oxo-1-(2-oxo-2-phenyl-ethyl)-1,2-dihydro-[1,8]-naphthyridine-3-carbonitrile (107)

This compound was prepared from 6-fluoro-2-oxo-4-[4-(furan-2-carbonyl)-piperazine-1-yl]-1,2-dihydro-[1,8]-naphthyridine-3-carbonitrile (99) and 2-bromoacetophenone according to General Procedure B. Yield 242 mg (31%), MP 293° C.; $^1$H-NMR (DMSO-$d_6$): δ 3.79 (m, 4H), 3.98 (m, 4H), 5.87 (s, 2H), 6.67 (dd, J=1.6, 3.2 Hz, 1H), 7.10 (d, J=3.6 Hz, 1H) 7.59 (m, 2H), 7.73 (m, 1H), 7.90 (d, J=1.6 Hz, 1H), 8.12 (m, 2H), 8.21 (dd, J=2.8, 9.2 Hz, 1H), 8.70 (d, J=2.8 Hz, 1H); EIMS: 486 (M+1). Anal. ($C_{26}H_{20}FN_5O_4$) C, H, N.

Synthesis of 1-Benzyl-6-chloro-2-oxo-4-[4-(thiophene-2-carbonyl)-piperazin-1-yl]-1,2-dihydro-[1,8]-naphthyridine-3-carbonitrile (108)

This compound was prepared from 6-chloro-2-oxo-4-[4-(thiophene-2-carbonyl)-piperazine-1-yl]-1,2-dihydro-[1,8]-naphthyridine-3-carbonitrile (100) and benzyl bromide according to General Procedure B. Yield 184 mg (37%), MP 221° C.; $^1$H-NMR (DMSO-$d_6$): 3.75 (m, 4H), 3.92 (m, 4H), 5.51 (s, 2H), 7.15-7.30 (m, 6H), 7.50 (d, J=3.6 Hz, 1H), 7.81(d, J=5.2 Hz, 1H), 8.32 (d, J=2.4 Hz, 1H), 8.75 (d, J=2.4 Hz, 1H); EIMS: 490 (M+1). Anal. ($C_{25}H_{20}ClN_5O_2S$) C, H, N.

Synthesis of 6-Chloro-1-(3-fluorobenzyl)-2-oxo-4-[4-(thiophene-2-carbonyl)-piperazin-1-yl]-1,2-dihydro-[1,8]-naphthyridine-3-carbonitrile (109)

This compound was prepared from 6-chloro-2-oxo-4-[4-(thiophene-2-carbonyl)-piperazine-1-yl]-1,2-dihydro-[1,8]-naphthyridine-3-carbonitrile (100) and 3-fluorobenzyl bromide according to General Procedure B. Yield 214 mg (42%), MP 204° C.; $^1$H-NMR (DMSO-$d_6$): δ 3.76 (m, 4H), 3.92 (m, 4H), 5.51 (s, 2H), 7.06 (m, 3H), 7.16 (dd, J=3.6, 4.8 Hz, 1H), 7.33 (m, 1H), 7.50 (dd, J=1.2, 3.6 Hz, 1H), 7.80 (dd, J=1.2, 5.2 Hz, 1H), 8.33 (d, J=2.4 Hz, 1H), 8.75 (d, J=2.4 Hz, 1H); EIMS: 508 (M+1). Anal. ($C_{25}H_{19}ClFN_5O_2S$) C, H, N.

Synthesis of 6-Chloro-2-oxo-1-(2-oxo-2-phenyl-ethyl)-4-[4-(thiophene-2-carbonyl)-piperazin-1-yl]-1,2-dihydro-[1,8]-naphthyridine-3-carbonitrile (110)

This compound was prepared from 6-chloro-2-oxo-4-[4-(thiophene-2-carbonyl)-piperazine-1-yl]-1,2-dihydro-[1,8]-naphthyridine-3-carbonitrile (100) and 2-bromoacetophenone according to General Procedure B. Yield 117 mg (23%), MP 316° C.; $^1$H-NMR (DMSO-$d_6$): δ 3.81 (m, 4H), 3.94 (m, 4H), 5.86 (s, 2H), 7.17 (dd, J=3.6, 5.2 Hz, 1H), 7.51 (dd, J=1.2, 3.6 Hz, 1H), 7.61 (m, 2H), 7.73 (m, 1H), 7.81 (dd, J=1.2, 5.2 Hz, 1H), 8.12 (m, 2H), 8.36 (dd, J=2.4 Hz, 1H), 8.67 (d, J=2.4 Hz, 1H); EIMS: 518 (M+1). Anal. ($C_{26}H_{20}ClN_5O_3S$) C, H, N.

Synthesis of 1-Benzyl-6-chloro-4-[4-(furan-2-carbonyl)-piperazin-1-yl]-2-oxo-1,2-dihydro-[1,8]-naphthyridine-3-carbonitrile (111)

This compound was prepared from 6-chloro-2-oxo-4-[4-(furan-2-carbonyl)-piperazine-1-yl]-1,2-dihydro-[1,8]-naphthyridine-3-carbonitrile (101) and benzyl bromide according to General Procedure B. Yield 223 mg (31%), MP 196° C.; $^1$H-NMR (DMSO-$d_6$): δ 3.75 (m, 4H), 3.94 (m, 4H), 5.51 (s, 2H), 6.66 (dd, J=1.6, 3.6 Hz, 1H), 7.09 (d, J=3.2 Hz, 1H), 7.22-7.28 (m, 5H), 7.89 (d, J=1.6 Hz, 1H), 8.32 (d, J=2.4 Hz, 1H), 8.76 (d, J=2.4 Hz, 1H); EIMS: 474 (M+1). Anal. ($C_{25}H_{20}ClN_5O_3$) C, H, N.

Synthesis of 6-Chloro-1-(3-fluorobenzyl)-2-oxo-4-[4-(furan-2-carbonyl)-piperazin-1-yl]-1,2-dihydro-[1,8]-naphthyridine-3-carbonitrile (112)

This compound was prepared from 6-chloro-2-oxo-4-[4-(furan-2-carbonyl)-piperazine-1-yl]-1,2-dihydro-[1,8]-naphthyridine-3-carbonitrile (101) and 3-fluorobenzyl bromide according to General Procedure B. Yield 113 mg (15%), MP 134° C.; $^1$H-NMR (DMSO-$d_6$): δ 3.75 (m, 4H), 3.95 (m, 4H), 5.51 (s, 2H), 6.66 (dd, J=1.6, 3.2, Hz, 1H), 7.06-7.10 (m, 4H), 7.33 (m, 1H), 7.89 (d, J=2.0 Hz, 1H), 8.33 (dd, J=2.4 Hz, 1H), 8.75 (d, J=2.4 Hz, 1H); EIMS: 492 (M+1). Anal. ($C_{25}H_{19}ClFN_5O_3$) C, H, N.

Synthesis of 6-Chloro-4-[4-(furan-2-carbonyl)-piperazin-1-yl]-2-oxo-1-(2-oxo-2-phenyl-ethyl)-1,2-dihydro-[1,8]-naphthyridine-3-carbonitrile (113)

This compound was prepared from 6-chloro-2-oxo-4-[4-(furan-2-carbonyl)-piperazine-1-yl]-1,2-dihydro-[1,8]-naphthyridine-3-carbonitrile (101) and 2-bromoacetophenone according to General Procedure B. Yield 233 mg (31%), MP 328° C.; $^1$H-NMR (DMSO-$d_6$): δ 3.81 (m, 4H), 3.97 (m, 4H), 5.86 (s, 2H), 6.66 (dd, J=1.6, 3.2 Hz, 1H), 7.10 (d, J=3.2 Hz, 1H) 7.59 (m, 2H), 7.73 (m, 1H), 7.90 (d, J=1.6 Hz, 1H), 8.14 (m, 2H), 8.37 (d, J=2.0 Hz, 1H), 8.67 (d, J=2.0 Hz, 1H); EIMS: 502 (M+1). Anal. ($C_{26}H_{20}ClN_5O_4$) C, H, N.

Synthesis of 1-Benzyl-4-hydroxy-3-(methylsulfonyl)-[1,8]-naphthyridin-2(1H)-one (114)

Ethyl methanesulfonyl acetate (1.3 mL, 9.83 mmol) was added slowly to a suspension of NaH (60% in mineral oil, 433 mg, 10.81 mmol) in dimethylacetamide (20 mL) and stirred at room temperature for 0.5 h under argon. 1-Benzyl-1H-pyrido[2,3-d][1,3]oxazine-2,4-dione (2) (2.5 g, 9.83 mmol) was added to the solution and heated at 110° C. for 4 h (TLC control). The solution was cooled and poured into ice water. The pH of the solution was adjusted to 4 by cold 10% HCl. The solids formed were filtered, washed by excess water, and dried in a vacuum oven to yield 950 mg (30%) of 1-benzyl-4-hydroxy-3-(methylsulfonyl)-[1,8]-naphthyridin-2(1H)-one (114) as white solids. MP: 155° C. $^1$H-NMR (DMSO-$d_6$): δ 3.51 (s, 3H), 5.57 (s, 2H), 7.23 (m, 1H), 7.27 (m, 4H), 7.43 (m, 1H), 8.48 (dd, J=2.0, 8.0 Hz, 1H), 8.79 (dd, J=2.0, 8.0 Hz, 1H); EIMS m/z 331 (M+1).

Synthesis of 1-Benzyl-4-chloro-3-(methylsulfonyl)-1,8-naphthyridin-2(1H)-one (115)

Triethylamine (1.2 mL, 8.6 mmol) was added to a suspension of 1-benzyl-4-hydroxy-3-(methylsulfonyl)-[1,8]-naphthyridin-2(1H)-one (114) (0.94 g, 2.9 mmol) in neat POCl$_3$ and heated at 90° C. for 3 h. The solution was cooled and the excess POCl$_3$ was distilled under vacuum. The residue was suspended in water, neutralized by solid NaHCO$_3$, and extracted by dichloromethane. The organic layer was subsequently washed by saturated NaHCO$_3$ solution, water and brine, dried over Na$_2$SO$_4$, and evaporated to yield 1-benzyl-4-chloro-3-(methylsulfonyl)-[1,8]-naphthyridin-2(1H)-one (115) as yellow solid. Yield 0.92 g (92%), mp 191° C. $^1$H-NMR (DMSO-$d_6$): δ 3.50 (s, 3H), 5.65 (s, 2H), 7.28 (m, 5H), 7.55 (m, 1H), 8.70 (dd, J=1.6, 8.4 Hz, 1H), 8.84 (dd, J=1.6, 4.4 Hz, 1H); EIMS m/z 349 (M+1).

The sequence of reactions in the preparation of 1-benzyl-4-hydroxy-3-(methylsulfonyl)-[1,8]-naphthyridin-2(1H)- one (114) and 1-benzyl-4-chloro-3-(methylsulfonyl)-[1,8]-naphthyridin-2(1H)-one (115) as described above was as follows:

The sequence of reactions in the preparation of 1-benzyl-3-methanesulfonyl-4-[4-(thiophene-2-carbonyl)-piperazin-1-yl]-1H-[1,8]-naphthyridin-2-one (116) as described above was as follows:

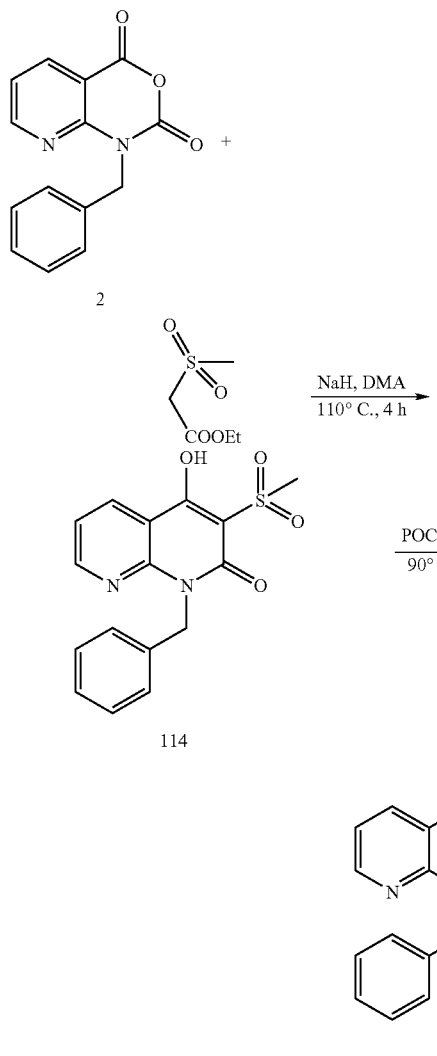

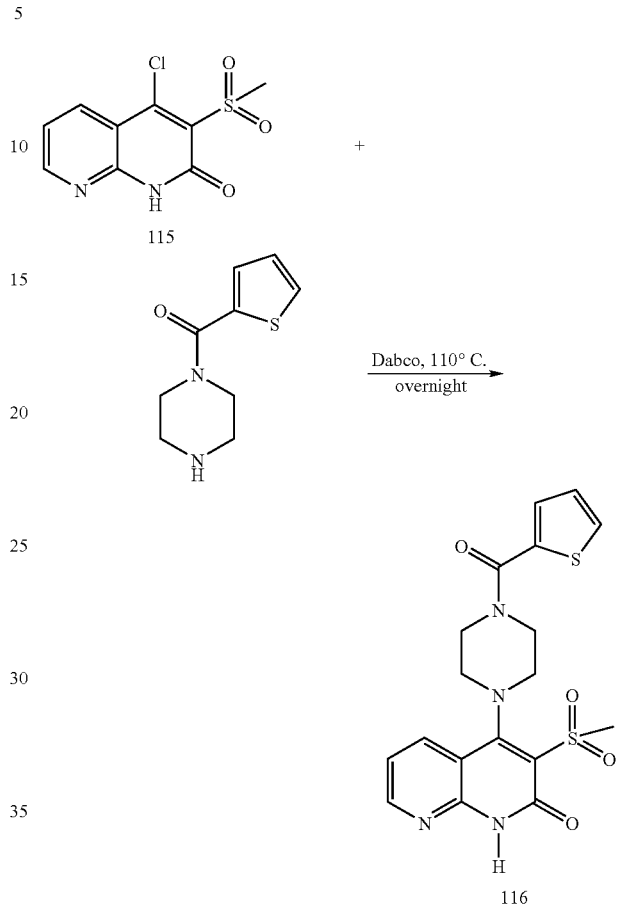

Synthesis of 1-Benzyl-3-methanesulfonyl-4-[4-(thiophene-2-carbonyl)-piperazin-1-yl]-1H-[1,8]-naphthyridin-2-one (116)

DABCO (0.57 g, 5.0 mmol) was added to a solution of 1-benzyl-4-chloro-3-(methylsulfonyl)-[1,8]-naphthyridin-2(1H)-one (115) (0.88 g, 2.5 mmol) and piperazine-1-yl-thiophene-2-yl-methanone (0.60 g, 3.08 mmol) in N-methylpyrrolidone at room temperature. The solution was heated at 110° C. for 15 min. The solution was cooled and poured into ice cold 10% ammonium chloride solution in water. The solids formed were filtered, washed by water, and dried to yield 0.95 g (74%) of 1-benzyl-3-methanesulfonyl-4-[4-(thiophene-2-carbonyl)-piperazin-1-yl]-1H-[1,8]-naphthyridin-2-one (116) as yellow solids MP: 223° C.; $^1$H-NMR (DMSO-d$_6$): δ 3.37 (s, 3H), 3.59 (m, 4H), 3.93 (b, 4H), 5.59 (s, 2H), 7.2 (m, 6H), 7.38 (m, 1H), 7.47 (dd, J=1.2, 3.6 Hz, 1H), 7.81 (dd, J=1.2, 5.2 Hz, 1H), 8.46 (dd, J=1.6, 8.0 Hz, 1H), 8.70 (dd, J=1.6, 4.4 Hz, 1H); EIMS m/z 509 (M+1).

Synthesis of Pyridine-4-yl-carbamic acid-tert-butyl ester (117)

4-Aminopyridine (25 g, 265 mmol) was added slowly by a solid addition funnel to a stirred solution of di-t-butyl-dicarbonate (63.75 g, 292 mmol) in THF at room temperature. The solution was further stirred for 1 h at room temperature. The solvent was removed under reduced pressure and the residue was recrystallised by ether to yield 43.5 g (84%) of pyridine-4-yl-carbamic acid-tert-butyl ester (117) as white solid. MP: 260° C.; 1H-NMR (DMSO-d6): δ 1.48 (s, 9H), 7.40 (dd, J=1.2, 4.8 Hz, 1H), 8.33 (dd, J=1.2, 4.8 Hz, 1H), 9.93 (s, 1H); EIMS m/z 195 (M+1).

Synthesis 4-tert-Butoxycarbonylamino-nicotinic acid (118)

n-Buli (1.6 M soln, 155 mL, 249 mmol) was added to a stirred solution of TMEDA (37.36 mL, 249 mmol) in THF at −40° C. The solution was allowed to come at room temperature over 10 min and stirred for another 10 min. The solution was cooled to −78° C. A solution of pyridine-4-yl-carbamic acid-tert-butyl ester (117) (22 g, 113.26 mmol) in THF was added slowly. The solution was allowed to come at room temperature within 3 h. After stirring at room temperature for 15 min the solution was again cooled to −78° C. and a freshly crushed dry ice was added. The solution was allowed to come at room temperature, stirred for 30 min and poured into ice cold 10% NH$_4$Cl solution. The solution was basified by 1N NaOH solution and washed by dichloromethane. The pH of aqueous phase was adjusted to 4 by cold 10% HCl solution. The solids formed were filtered, washed by water and dried under vacuum at room temperature to yield 16.3 g (30%) 4-tert-butoxycarbonylamino-nicotinic acid (118) as white solids. MP: 260° C.; $^1$H-NMR (DMSO-d$_6$): δ 1.49 (s, 9H), 8.23 (d, J=6.0 Hz, 1H), 8.55 (d, J=6.0 Hz, 1H), 8.96 (s, 1H); EIMS m/z 238 (M+1).

The sequence of reactions in the preparation of pyridine-4-yl-carbamic acid-tert-butyl ester (117), 4-tert-butoxycarbonylamino-nicotinic acid (118) as described above was as follows:

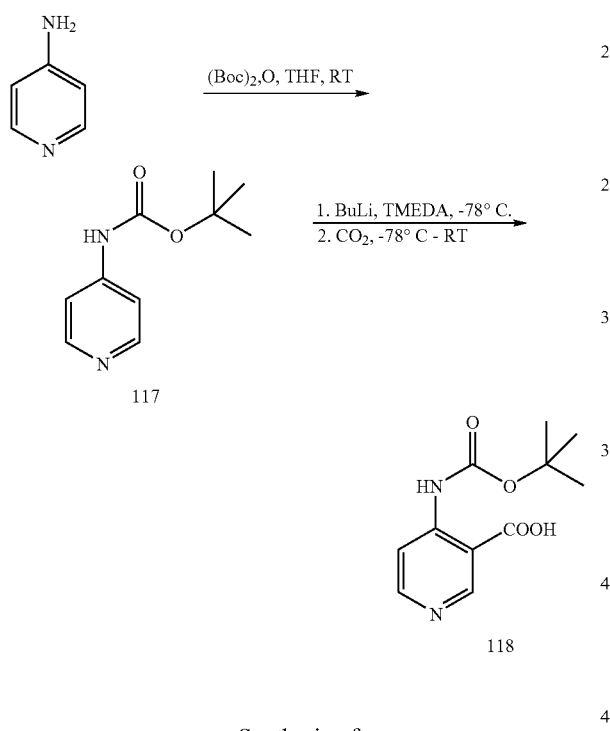

Synthesis of
1H-Pyrido[4,3-d][1,3]oxazine-2,4-dione (119)

Trichloromethyl chloroformate (9 mL, 75 mmol) was added slowly to a solution of 4-tert-butoxycarbonylamino-nicotinic acid (118) (16.2 g, 68 mmol) in dioxane and refluxed for 4 h under nitrogen atmosphere. The solution was cooled and the solvent was removed under vacuum. The residue was recrystallized by ether to yield 10.92 g (98%) of 1H-pyrido[4,3-d][1,3]oxazine-2,4-dione (119) as white solids. MP: 243° C.; $^1$H-NMR (DMSO-d$_6$): ), δ 7.32 (d, J=6.0 Hz, 1H), 8.71 (d, J=6.0 Hz, 1H), 9.11 (s, 1H); EIMS m/z 165 (M+1).

Synthesis 4-Chloro-2-oxo-1,2-dihydro-[1,6]-naphthyridine-3-carboxylic acid ethyl ester (120)

Diethyl malonate (13.77 mL, 91 mmol) was added slowly to a suspension of NaH (60% in mineral oil, 3.63 mg, 91 mmol) in dimethylacetamide and stirred at room temperature for 0.5 h under inert atmosphere. 1H-pyrido[4,3-d][1,3]oxazine-2,4-dione (119) (15 g, 91 mmol) was added to the solution and heated overnight at 110° C. The solution was cooled and poured into ice water. Basified by saturated NaHCO$_3$ solution and extracted by dichloromethane. The pH of the aqueous phase was adjusted to 3 by cold 10% HCl and extracted by n-BuOH. The residue obtained after evaporating butanol was dissolved in POCl$_3$ and heated at 90° C. for 3 h. The solution was cooled and the excess POCl$_3$ was distilled under vacuum. The residue was suspended in water, neutralized by solid NaHCO$_3$, and extracted by ethylacetate. The organic layer was subsequently washed by saturated NaHCO$_3$ solution, water and brine, dried over Na$_2$SO$_4$, and evaporated to a residue. The crude product was purified by flash chromatography to yield 0.8 g (3%) of 4-chloro-2-oxo-1,2-dihydro-[1,6]-naphthyridine-3-carboxylic acid ethyl ester (120) as white solids. MP: 219° C.; $^1$H-NMR (DMSO-d$_6$): δ 1.31 (t, J=7.2 Hz, 3H), 4.37 (q, J=7.2 Hz, 2H), 7.30 (d, J=5.6 Hz, 1H), 8.63 (d, J=5.6 Hz, 1H), 9.05 (s, 1H), 12.80 (s, 1H); EIMS: 253 (M+1).

The sequence of reactions in the preparation of 1H-pyrido[4,3-d][1,3]oxazine-2,4-dione (119), 4-chloro-2-oxo-1,2-dihydro-[1,6]-naphthyridine-3-carboxylic acid ethyl ester (120) as described above was as follows:

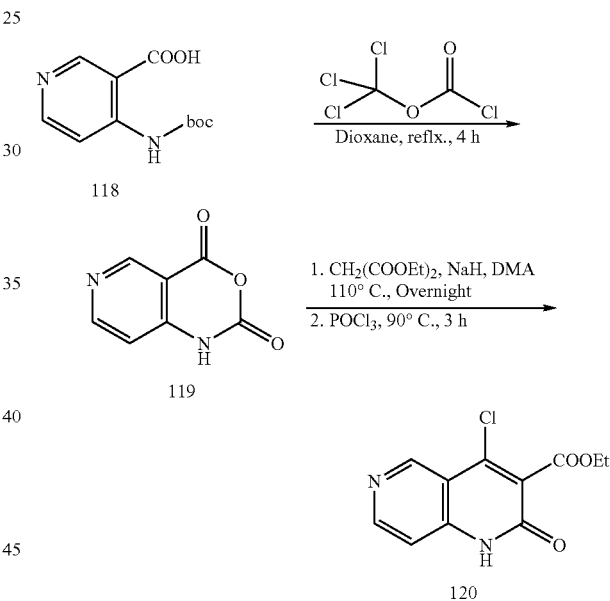

Synthesis 2-Oxo-4-[4-(thiophene-2-carbonyl)-piperazin-1-yl]-1,2-dihydro-[1,6]-naphthyridin-3-carboxylic acid ethyl ester (121)

DABCO (0.7 g, 6.3 mmol) was added to a solution of 4-chloro-2-oxo-1,2-dihydro-[1,6]-naphthyridine-3-carboxylic acid ethyl ester (120) (0.8 g, 3.16 mmol) and piperazine-1-yl-thiophene-2-yl-methanone (0.93 g, 4.74 mmol) DMA at room temperature. The solution was heated at 110° C. for 2 h. The solution was cooled and poured into ice cold 10% ammonium chloride solution in water. The solids formed were filtered, washed by water, and dried to yield 1.2 g (92%) of 2-oxo-4-[4-(thiophene-2-carbonyl)-piperazin-1-yl]-1,2-dihydro-[1,6]-naphthyridine-3-carboxylic acid ethyl ester (121) as white solids. MP: 231° C.; $^1$H-NMR (DMSO-d$_6$): δ 1.28 (t, J=7.2 Hz, 3H), 3.18 (m, 4H), 3.89 (m, 4H), 4.27 (q, J=7.2 Hz, 2H), 7.14 (dd, J=3.6, 4.8 Hz, 1H), 7.18 (d, J=6.0 Hz, 1H), 7.47 (d, J=3.6 Hz, 1H), 7.80 (d, J=4.8 Hz, 1H), 8.51 (d, J=5.6 Hz, 1H), 8.91 (s, 1H); EIMS m/z 413 (M+1).

The sequence of reaction in the preparation of 2-oxo-4-[4-(thiophene-2-carbonyl)-piperazin-1-yl]-1,2-dihydro-[1,6]-naphthyridin-3-carboxylic acid ethyl ester (121) as described above was as follows:

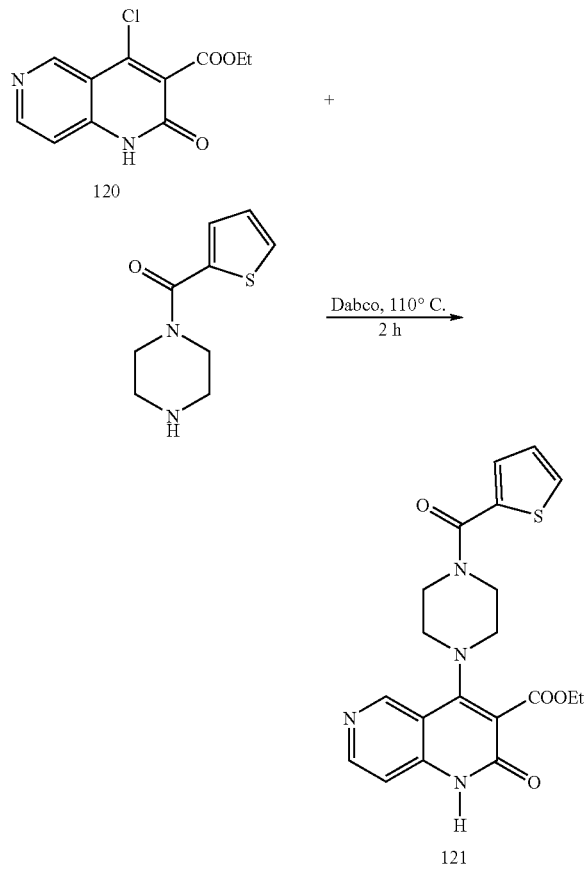

Preparation of Compounds by Alkylation at N-1 Position of 6-Substituted [1,6]naphthyridine Moiety The compounds referred to as compound 122 through 124 were prepared rom 2-oxo-4-[4-(thiophene-2-carbonyl)-piperazin-1-yl]-1,2-dihydro-[1,6]-naphthyridin-3-carboxylic acid ethyl ester (121) and corresponding alkyl halides by applying General Procedure B as described above.

Synthesis of 1-(4-fluoro-benzyl)-2-oxo-4-[4-(thiophene-2-carbonyl)-piperazin-1-yl]-1,2-dihydro-[1,6]-naphthyridine-3-carboxylic acid ethyl ester (122)

This compound was prepared from 2-oxo-4-[4-(thiophene-2-carbonyl)-piperazin-1-yl]-1,2-dihydro-[1,6]-naphthyridin-3-carboxylic acid ethyl ester (121) and 4-fluorobenzyl bromide according to General Procedure B. Yield 210 mg (55%), MP 132° C.; $^1$H-NMR (DMSO-$d_6$): δ 1.30 (t, J=7.2 Hz, 3H), 3.21 (m, 4H), 3.91 (m, 4H), 4.31 (q, J=7.2 Hz, 2H), 5.41 (s, 2H), 7.13-7.29 (m, 5H), 7.41 (d, J=6.0 Hz, 1H), 7.47 (dd, J=1.2, 3.6 Hz, 1H), 7.80 (dd, J=4.8, 1.2 Hz, 1H), 8.57 (d, J=6.0 Hz, 1H), 9.09 (s, 1H); EIMS: 521 (M+1). Anal. ($C_{27}H_{25}FN_4O_4S$) C, H, N.

Synthesis of 1-(3-Fluorobenzyl)-2-oxo-4-[4-(thiophene-2-carbonyl)-piperazin-1-yl]-1,2-dihydro-[1,6]-naphthyridine-3-carboxylic acid ethyl ester (123)

This compound was prepared from 2-oxo-4-[4-(thiophene-2-carbonyl)-piperazin-1-yl]-1,2-dihydro-[1,6]-naphthyridin-3-carboxylic acid ethyl ester (121) and 3-fluorobenzyl bromide according to General Procedure B. Yield 113 mg (22%), MP 135° C.; $^1$H-NMR (DMSO-$d_6$): δ 1.28 (t, J=7.2 Hz, 3H), 3.22 (m, 4H), 3.92 (m, 4H), 4.32 (q, J=7.2 Hz, 2H), 5.44 (s, 2H), 6.98 (d, J=7.6 Hz, 1H), 7.10 (m, 2H), 7.16 (dd, J=3.6, 4.8 Hz, 1H), 7.34 (m, 2H), 7.47 (dd, J=1.2, 3.6 Hz, 1H), 7.80 (dd, J=1.2, 4.8 Hz, 1H), 8.56 (d, J=6.0 Hz, 1H), 9.09 (s, 1H); EIMS: 521 (M+1). Anal. ($C_{27}H_{25}FN_4O_4S$) C, H, N.

Synthesis of 2-Oxo-1-(2-oxo-2-phenyl-ethyl)-4-[4-(thiophene-2-carbonyl)-piperazin-1-yl]-1,2-dihydro-[1,6]-naphthyridine-3-carboxylic acid ethyl ester (124)

This compound was prepared from 2-oxo-4-[4-(thiophene-2-carbonyl)-piperazin-1-yl]-1,2-dihydro-[1,6]-naphthyridin-3-carboxylic acid ethyl ester (121) and 2-bromoacetophenone according to General Procedure B. Yield 127 mg (24%), MP 157° C.; $^1$H-NMR (DMSO-$d_6$): δ 1.27 (t, J=6.8 Hz, 3H), 3.24 (m, 4H), 3.93 (m, 4H), 4.26 (q, J=7.2 Hz, 2H), 5.85 (s, 2H), 7.15 (dd, J=3.6, 5.2 Hz, 1H), 7.47 (m, 2H), 7.62 (m, 2H), 7.74 (m, 1H), 7.80 (d, J=5.2 Hz, 1H), 8.13 (d, J=5.2 Hz, 1H), 8.32 (d, J=7.2 Hz, 2H), 8.56 (d, J=6.0 Hz, 1H), 9.12 (s, 1H); EIMS: 531 (M+1). Anal. ($C_{28}H_{26}N_4O_5S$) C, H, N.

Synthesis of 1-Benzyl-4-hydroxy-3-nitro-1,8-naphthyridin-2(1H)-one (125)

Ethyl nitro acetate (8.7 mL, 78 mmol) was added slowly to a suspension of NaH (60% in mineral oil, 3.46 mg, 87 mmol) in dimethylacetamide and stirred at room temperature for 0.5 h under argon. 1-benzyl-1H-pyrido[2,3-d][1,3]oxazine-2,4-dione (2) (2.5 g, 9.83 mmol) was added to the solution and heated at 110° C. for 12 h (TLC control). The solution was cooled and filtered through a pad of celite. The filtrate was diluted by cold water and the pH was adjusted to 2 by cold 10% HCl. The solids formed were filtered, washed by excess water, and dried in a vacuum oven to yield white solids. Yield 9.7 g, 42%, mp ca 182° C. (not sharp). $^1$H-NMR (DMSO-$d_6$): δ 5.53 (s, 2H), 7.25 (m, 6H), 8.46 (dd, J=2.0, 7.6 Hz, 1H), 8.63 (dd, J=2.0, 4.8 Hz, 1H); EIMS m/z 298 (M+1).

Synthesis of 1-Benzyl-4-chloro-3-nitro-1,8-naphthyridin-2(1H)-one (126)

Triethylamine (12.2 mL, 88 mmol) was added to a suspension of 1-benzyl-4-hydroxy-3-nitro-1,8-naphthyridin-2(1H)-one (125) (8.7 g, 29 mmol) in neat POCl$_3$ and heated at 90° C. for 3 h. The solution was cooled and the excess POCl$_3$ was distilled under vacuum. The residue was suspended in water, neutralized by solid NaHCO$_3$, and extracted by dichloromethane. The organic layer was subsequently washed by saturated NaHCO$_3$ solution, water and brine, dried over Na$_2$SO$_4$, and evaporated to yield yellow solid. Yield 9.2 g, 98%, Mp ca 215° C. (not sharp). $^1$H-NMR (DMSO-$d_6$): δ 5.66 (s, 2H), 7.28 (m, 5H), 7.61 (m, 1H), 8.57 (dd, J=1.6, 8.4 Hz, 1H), 8.89 (dd, J=1.6, 4.8 Hz, 1H); EIMS m/z 316 (M+1).

337

The sequence of reactions in the preparation of 1-Benzyl-4-hydroxy-3-nitro-1,8-naphthyridin-2(1H)-one (125) and 1-Benzyl-4-chloro-3-nitro-1,8-naphthyridin-2(1H)-one (126) as described above was as follows:

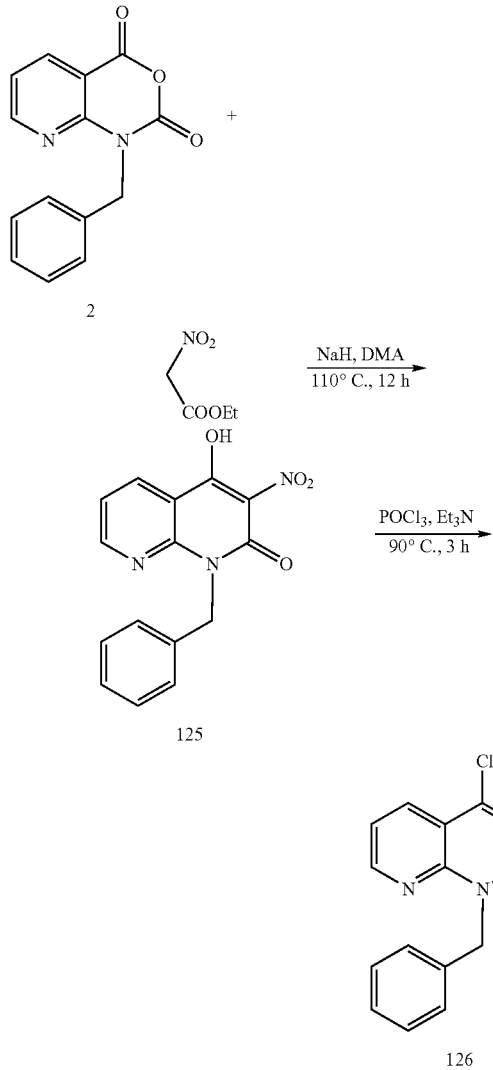

Synthesis of 1-Benzyl-3-nitro-4-[4-(thiophene-2-carbonyl)-piperazin-1-yl]-1H-[1,8]-naphthyridin-2-one (127)

DABCO (6.26 g, 55 mmol) was added to a solution of 1-benzyl-4-chloro-3-nitro-1,8-naphthyridin-2(1H)-one (126) (8.81 g, 28 mmol) and piperazine-1-yl-thiophene-2-yl-methanone (6.57 g, 33 mmol) in N-methylpyrrolidone at room temperature. The solution was heated at 110° C. for 2 h. The solution was cooled and poured into ice cold 10% ammonium chloride solution in water. The solids formed were filtered, washed by water, and dried to yield yellow solid. Yield 11 g (83%), mp 255° C. $^1$H-NMR (DMSO-d$_6$): δ 3.26 (m, 4H), 3.90 (m, 4H), 5.61 (s, 2H), 7.15 (m, 1H), 7.25 (m, 5H), 7.47 (m, 2H), 7.80 (d, J=5.2 Hz, 1H), 8.43 (d, J=7.6 Hz, 1H), 8.76 (d, J=4.4 Hz, 1H); EIMS m/z 476 (M+1).

338

Synthesis of 3-Amino-1-benzyl-4-[4-(thiophene-2-carbonyl)-piperazin-1-yl]-1H-[1,8]-naphthyridin-2-one (128)

A solution of 1-benzyl-3-nitro-4-[4-(thiophene-2-carbonyl)-piperazin-1-yl]-1H-[1,8]-naphthyridin-2-one (127) (475 mg, 1 mmol) and Pd/C (10%, 50 mg) in ethanol was stirred overnight at room temperature under hydrogen atmosphere. The solution was filtered through a pad of celite and the filtrate was concentrated to yield yellow solid, yield 75%, mp 210° C. $^1$H-NMR (DMSO-d$_6$): δ 3.05 (b, 2H), 3.35 (b, 2H), 3.70 (b, 2H), 4.00 (b, 2H), 5.54 (s, 2H), 5.68 (s, 2H), 7.2 (m, 7H), 7.47 (dd, J=1.2, 3.6 Hz, 1H), 7.77 (dd, J=1.2, 5.2 Hz, 1H), 8.24 (dd, J=2.0, 8.0 Hz, 1H), 8.31 (dd, J=1.6, 4.8 Hz, 1H); EIMS m/z 446 (M+1).

The sequence of reaction in the preparation of 1-benzyl-3-nitro-4-[4-(thiophene-2-carbonyl)-piperazin-1-yl]-1H-[1,8]-naphthyridin-2-one (127) and 3-amino-1-benzyl-4-[4-(thiophene-2-carbonyl)-piperazin-1-yl]-1H-[1,8]-naphthyridin-2-one (128) as described above was as follows:

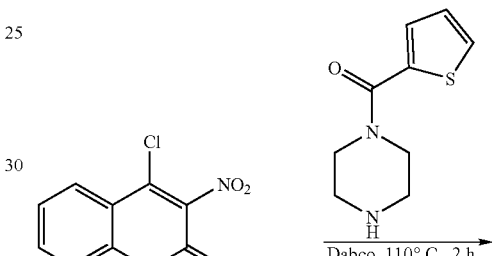

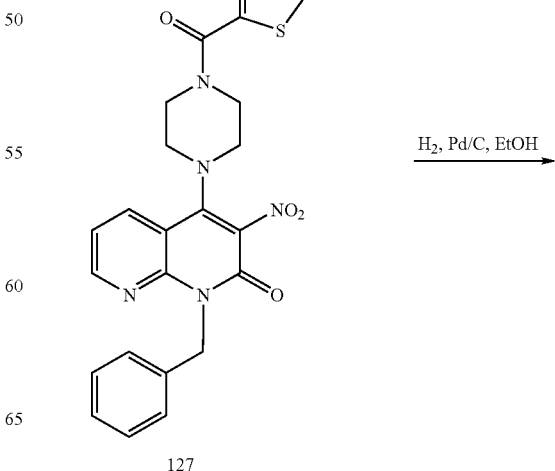

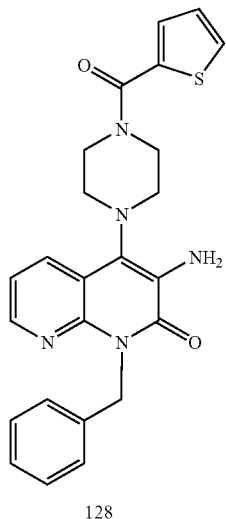

128

Synthesis of 1-Benzyl-4-[4-(furan-2-carbonyl)-piperazin-1-yl]-2-oxo-1,2-dihydro-[1,8]-naphthyridine-3-carbonitrile (129)

This compound was prepared from 2-furyl chloride and 1-benzyl-2-oxo-4-piperazin-1-yl-1,2-dihydro-[1,8]-naphthyridine-3-carbonitrile (9) according to General Procedure C. The reaction yielded 1-benzyl-4-[4-(furan-2-carbonyl)-piperazin-1-yl]-2-oxo-1,2-dihydro-[1,8]-naphthyridine-3-carbonitrile (129) as white solids. MP: 206° C.; $^1$H-NMR (DMSO-$d_6$): 3.60 (m, 4H), 3.76 (m, 4H), 5.51 (s, 2H), 6.65 (dd, J=3.5, 4.8 Hz, 1H), 7.10 (dd, J=3.5, 4.8 Hz, 1H), 7.20-7.35 (m, 5H), 7.42 (dd, J=4.8, 8.0 Hz, 1H), 7.92 (d, J=5.2 Hz, 1H), 8.39 (dd, J=1.6, 8.0 Hz, 1H), 8.73 (dd, J=1.6, 8.0 Hz, 1H); EIMS: 440 (M+1). Anal. $C_{25}H_{21}N_5O_3$ (C,H,N).

Example 2

Assays to evaluate the activity of potential MIF inhibitors are described in the following sections.

Macrophage Migration Assay

Macrophage migration is measured by using the agarose droplet assay and capillary method as described by Harrington and Stastny et al., *J. Immunol.* 110(3):752-759, 1973. Briefly, macrophage-containing samples are added to hematocrit tubes, 75 mm long with a 1.2 mm inner diameter. The tubes are heat-sealed and centrifuged at 100×G for 3 minutes, cut at the cell-fluid interface and imbedded in a drop of silicone grease in Sykes-Moore culture chambers. The culture chambers contain either a control protein (BSA) or samples. Migration areas are determined after 24 and 48 hours of incubation at 37° C. by tracing a projected image of the macrophage fans and measuring the areas of the migration by planimetry.

Alternatively, each well of a 96-well plate is pre-coated with one microliter of liquid 0.8% (w/v) Sea Plaque Agarose in water dispensed onto the middle of each well. The plate is then warmed gently on a light box until the agarose drops are just dry. Two microliters of macrophage containing cell suspensions of up to 25% (v/v) in media (with or without MIF or other controls), containing 0.2% agarose (w/v) and heated to 37° C. is added to the precoated plate wells and cooled to 4° C. for 5 min. Each well is then filled with media and incubated at 37° C. under 5% $CO_2$-95% air for 48 hr. Migration from the agarose droplets is measured at 24 and 48 hr by determining the distance from the edge of the droplet to the periphery of migration.

Migration Assay

Monocyte migration inhibitory activities of recombinant murine and human wild-type and murine mutant MIF are analyzed by use of human peripheral blood mononuclear cells or T-cell depleted mononuclear cells in a modified Boyden chamber format. Calcein AM-labeled monocytes are suspended at 2.5 to 5×10$^6$/mL in RPMI 1640 medium, with L-glutamine (without phenol red) and 0.1 mg/mL human serum albumin or bovine serum albumin. An aliquot (200 µL) of cell suspension is added to wells of a U-bottom 96-well culture plate (Costar, Cambridge, Mass.) prewarmed to 37° C. MIF in RPMI 1640 is added to the cell suspension to yield final concentrations of 1, 10, 100, and 1000 ng/mL. The culture plate is placed into the chamber of a temperature-controlled plate reader, mixed for 30 s, and incubated at 37° C. for 10-20 min. During the incubation, 28 µL of prewarmed human monocyte chemotactic protein 1 (MCP-1; Pepro Tech., Inc., Rocky Hill, N.J.) at 10 or 25 ng/mL or RPMI 1640 with 0.1 mg/mL HSA is added to the bottom well of a ChemoTX plate (Neuro Probe Inc., Gaithersburg, Md.; 3 mm well diameter, 5 µM filter pore size). The filter plate is carefully added to the base plate. Treated cell suspensions are removed from the incubator and 30 µL is added to each well of the filter plate. The assembled plate is incubated for 90 min. at 37° C. in a humidified chamber with 5% $CO_2$. Following incubation, the cell suspension is aspirated from the surface of the filter and the filter is subsequently removed from the base plate and washed three times by adding 50 µL of 1×HBSS$^-$ to each filter segment. Between washes, a squeegee (NeuroProbe) is employed to remove residual HBSS$^-$. The filter is air-dried and then read directly in the fluorescent plate reader, with excitation at 485 nm and emission at 535 nm. Chemotactic or random migration indices are defined as average filter-bound fluorescence for a given set of wells divided by average fluorescence of filters in wells containing neither MCP-1 nor MIF. Titration of fluorescently-labeled cells revealed that levels of fluorescence detected in this assay have a linear relationship to cell number (not shown).

Tautomerase Assay

The tautomerization reaction is carried out essentially as described by Rosengren et al., *Mol. Med.* 2(1):143-149, 1996. D-dopachrome conversion to 5,6-dihydroxyindole-2-carboxylic acid is assessed. 1 ml sample cuvettes containing 0.42 mM substrate and 1.4 µg of MIF in a sample solution containing 0.1 mM EDTA and 10 mM sodium phosphate buffer, pH 6.0 are prepared and the rate of decrease in iminochrome absorbance is followed at 475 nm. L-dopachrome is employed as a control. In addition, the reaction products can be followed using an HPLC, utilizing a mobile phase including 20 mM $KH_2PO_4$ buffer (pH 4.0) and 15% methanol with a flow rate of 1.2 ml/min. Fluorimetric detection is followed at 295/345 nm.

Alternatively, the tautomerization reaction utilizing phenylpyruvate or (p-hydroxyphenyl)pyruvate is carried out essentially as described by Johnson et al., *Biochem.* 38:16024-16033, 1999. In this version, ketonization of phenylpyruvate is monitored at 288 nm ($\epsilon$=17300 M$^{-1}$ cm$^{-1}$) and the ketonization of (p-hydroxyphenyl)pyruvate is monitored at 300 nm ($\epsilon$=21600 M$^{-1}$ cm$^{-1}$). The assay mixture contains 50 mM $Na_2HPO_4$ buffer (1 mL, pH 6.5) and an aliquot of a solution of MIF sufficiently dilute (0.5-1.0 µL of a 2.3 mg/mL solution, final concentration of 93-186 nM) to yield an initial liner rate. The assay is initiated by the addition of a small quantity (1-3.3 µL) of either phenylpyruvate or (p-hydroxyphenyl)pyruvate from stock solutions made up in ethanol. The crystalline forms of phenylpyruvate and (p-hydroxyphenyl)pyruvate exist exclusively as the enol isomers (Larsen et al., *Acta Chem. Scand. B* 28:92-96, 1974). The concentration of substrate can range from 10 to 150 M, with no significant inhibition of MIF activity by ethanol observed at less than 0.5% v/v.

Immunoprecipitation and Western Blot Analysis

Cell culture experiments are designed to characterize the activity of candidate compounds, MIF expression, trafficking, and export. Cell and conditioned medium fractions are prepared for immunoprecipitation essentially as described previously (Florkiewicz et al., *Growth Factors* 4:265-275, 1991; Florkiewicz et al., *Ann. N.Y. Acad. Sci.* 638:109-126) except that 400 µl of lysis buffer (1% NP-40, 0.5% deoxycholate, 20 mM Tris pH 7.5, 5 mM EDTA, 2 mM EGTA, 0.01 mM phenylmethylsulfonyl fluoride, 10 ng/ml aprotinin, 10 ng/ml leupeptin, 10 ng/ml peptstatin) is added to the medium fraction after clarification by centrifugation in a microfuge for 15 minutes. Cell or medium fractions are incubated with monoclonal or polyclonal antibodies to MIF and GammaBind™ G Sepharose® (Pharmacia LKB Biotechnology, Uppsala, Sweden) are added for an additional 30 minutes incubation. Immune complexes are sedimented by microfuge centrifugation, washed three times with lysis buffer, and four times with ice cold immunoprecipitation wash buffer (0.15M NaCl, 0.01 M Na-phosphate pH 7.2, 1% deoxycholate, 1% NP-40, 0.1% sodium dodecyl sulfate). Immune complexes are dissociated directly in SDS gel sample buffer 125 mM Tris, pH 6.8, 4% SDS, 10% glycerol, 0.004% bromophenol blue, 2 mM EGTA, and separated by 12% SDS-PAGE. The gel is processed for fluorography, dried, and exposed to X-ray film at −70° C. When neomycin phosphotransferase is immunoprecipitated, a rabbit anti-NPT antibody (5Prime-3Prime, Boulder, Colo.) is employed.

For Western blot analysis, proteins are transferred from the 12% SDS-PAGE gel to a nitrocellulose membrane (pore size 0.45 µm in cold buffer containing 25 mM 3-[dimethyl (hydroxymethyl)methylamino]-2-hydroxypropane-sulfonic acid, pH 9.5, 20% methanol for 90 minutes at 0.4 amps. For Western blotting analysis, of cell conditioned media, the media is centrifuged (10 minutes at 800 g) and the supernatants concentrated 10-fold by membrane filtration (10 kDa cut-off, Centricon-10 Amicon). Samples are then resolved on 16% SDS Tris-glycin Gel (Novex, San Diego, Calif.) under reducing condition and transferred onto nitrocellulose membrane (Novex) at 20V for 3 hours. Membrane is incubated with rabbit polyclonal anti-rat antibodies (1:1000) (Torrey Pines Biolab, San Diego, Calif.), and then with horseradish peroxidase-conjugate (1:1000)(Pierce, Rockford, Ill.). MIF is visualized by development with chloronaphthol/$H_2O_2$. Recombinant MIF (2 ng, purchased from R&D systems, Minneapolis) is electrophoresed and transferred as a standard. Membranes are blocked in 10 mM Tris, pH 7.5, 150 mM NaCl, 5 mM $NaN_3$, 0.35% polyoxyethylene-sorbitan monolaurate, and 5% nonfat dry milk (Carnation Co., Los Angeles, Calif.) for 1 hr at room temperature. Membranes are incubated with a monoclonal antibody (Catalog Number MAB289, purchased from R&D Systems, Minneapolis, Minn.) or polyclonal (goat polyclonal serum, R&D Systems cat#AF-289-PB). Following incubation, membranes are washed at room temperature with 10 changes of buffer containing 150 mM NaCl, 500 mM sodium phosphate pH 7.4, 5 mM $NaN_3$, and 0.05% polyoxyethylene-sorbitan monolaurate. When using monoclonal antibodies, membranes are then incubated in blocking buffer containing 1 µg/ml rabbit anti-mouse IgG (H+ L, affinipure, Jackson Immuno Research Laboratories, West Grove, Pa.) for 30 minutes at room temperature. For polyclonal probing, incubation employed rabbit anti-goat (Sigma, Catalog Number G5518). Membranes are subsequently washed in 1 L of buffer described above, and incubated for 1 hr in 100 ml of blocking buffer containing 15 µCi $^{125}$I-protein A (ICN Biochemicals, Costa Mesa, Calif.), and washed with 1 L of buffer. The radiosignal is visualized by autoradiography.

Extracellular Localization Assay

In order to assess in vitro activity of compounds to modulate MIF export, mouse macrophage RAW 264.7 cells (American Type Culture Collection, Manassas, Va.) are selected. Raw 264.7 macrophage ($3\times10^6$ cells per well) are plated in 12-well tissue culture plates (Costar) and are cultured in RPMI/1% heat-inactivated fetal bovine serum (FBS) (Hyclone Laboratories, Logan, Utah). After three hours of incubation at 37° C. in a humidified atmosphere with 5% $CO_2$, nonadherent cells are removed and wells are washed twice with RPMI/1% FBS. Cells are then incubated for 24 hours with LPS (0111:B4) or TSST-1 (Toxin Technology, Sarasota, Fla.), that are approximately 95% pure and are resuspended in pyrogen-free water, at a concentration ranging from 1 pg/ml to 1000 ng/ml (for the dose response experiment). For time-course experiments, conditioned media of parallel cultures are removed at 0.5, 1, 2, 4, 8 and 24 hours intervals after stimulation with 1 ng/ml TSST-1 or LPS. For the inhibition studies, RAW 264.7 cells ($3\times10^6$ cells per well) are incubated for 24 hours with 1 ng/ml of LPS (0111:B4) or 1 ng/ml of TSST-1 in the presence of 0.01 µM to 10 µM candidate compound or buffer (as control). The MIF in cell-conditioned media is concentrated on filters and the MIF remaining in the samples is analyzed by Western blotting and MIF band densities are also measured by Stratagene Eagle Eye™.

RAW cells are induced to express MIF by addition of either 1 ng/ml TSST-1 or LPS and are cultured for 24 hours. MIF in conditioned media is measured as described above. MIF inhibiting compounds reduce immunodetectable MIF levels in conditioned media in a concentration dependent manner, as compared to cells incubated with buffer only.

Cell Culture, Transfection, and Metabolic Labeling

Target cells obtained from the American Type Culture Collection (ATCC No. CRL 1650) are cultured overnight in a 48-well plate in DMEM supplemented with 10% fetal bovine serum, 2 mM L-glutamine, 1 mM sodium pyruvate, 100 nM nonessential amino acids, and 50 µg/ml gentamycin. The target cells are then transfected with 2 µg/ml of CsCl-purified plasmid DNA in transfection buffer (140 mM NaCl, 3 mM KCl, 1 mM $CaCl_2$, 0.5 mM $MgCl_2$, 0.9 mM $Na_2HPO_4$, 25 mM Tris, pH 7.4. To each well, 300 µl of the DNA in transfection buffer is added. Cells are incubated for 30 minutes at 37° C., and the buffer is aspirated. Warm medium supplemented with 100 µm chloroquine is added for 1.5 hr. This medium is removed and the cells are washed twice with complete medium. Cells are then incubated for 40-48 hr. The plasmid of interest is co-transfected with pMAMneo (Clontech, Palo Alto, Calif.), which contains the selectable marker neomycin phosphotransferase. When 2 µg of the plasmid of interest are co-transfected with 10 µg of pMAMneo, greater than 70% of transfected cells express both MIF and neo, as determined by immunofluorescence microscopy.

For immunoprecipitation assays the target cells are metabolically pulse-labeled for 15 minutes with 100 µCi of $^{35}$S-methionine and $^{35}$S-cysteine (Trans $^{35}$S-label, ICN Biomedicals, Irvine, Calif.) in 1 ml of methionine and cysteine free DMEM. Following labeling, the cell monolayers are washed once with DMEM supplemented with excess (10 mM) unlabeled methionine and cysteine for 1-2 minutes. Cells are then cultured in 2 ml of this medium for the indicated lengths of time and the cell supernatants are immunoprecipitated for the presence of leaderless protein. For the indicated cultures, chase medium is supplemented with modulator at the indicated concentrations.

Alternatively, for analysis by ELISA, the target cells are washed once with 250 µl of 0.1 M sodium carbonate, pH 11.4, for 1 to 2 minutes and immediately aspirated. A high salt solution can alternatively be preferred. The cells are washed with media containing 0.5% FBS plus 25 µg/ml heparin and then the cells are incubated in this same medium for the indicated lengths of time. For indicated cultures, chase medium is supplemented with a modulator. For cells transfected with vector encoding a protein containing a leader sequence, such as hCG-α or any other non-heparin binding protein, the carbonate wash and heparin containing medium can be omitted.

High Throughput Screening Assay for MIF Inhibitors

The high throughput screening assay for MIF inhibitors is performed in a 96-well format using MIF produced by THP-1 cells and is performed as follows. MIF assays are performed by ELISA as indicated above. THP-1 cells are resuspended to approx. $5 \times 10^6$ cells/ml in RPMI medium containing 20 µg/ml of bacterial LPS and the cells incubated for 18-20 hours. Subsequently cell supernatant is collected and incubated with putative inhibitors. Briefly, a 96-well plate (Costar Number 3590) ELISA plate is coated with a MIF monoclonal antibody (R&D Systems Catalog Number MAB289) at a concentration of 4 µg/ml for two hours at 37° C. Undiluted culture supernate is added to the ELISA plate for a two-hour incubation at room temperature. The wells are then washed, a biotinylated MIF polyclonal antibody (R&D Systems #AF-289-PB) is added followed by Streptavidin-HRP and a chromogenic substrate. The amount of MIF is calculated by interpolation from an MIF standard curve.

HPLC Analysis of Candidate Inhibitors in Serum

Prior to evaluating the effects of any small molecule in vivo it is desirable to be able to detect, in a quantitative fashion, the compound in a body fluid such as blood. An analytical method is established to first reproducibly detect test compounds, such as MIF inhibitors, and then to measure their concentrations in biological fluid.

RP-HPLC is performed with a Hewlett-Packard Model HP-1100 unit using Symmetry Shield RP-8 (4.6×75 mm id, Waters, Milford, Mass.). The mobile phase is an isocratic solution of 35% acetonitrile/water containing 0.1% trifluoroacetic acid. Absorbance is monitored at 235 nm. To measure the amount of test compound in serum, the sample serum proteins are first separated using 50% Acetonitrile (4° C. overnight) followed by centrifugation at 14000 rpm for 30 minutes. The supernatant is then analyzed by the RP-HPLC and the compound concentration is calculated based on a calibration curve of known standard. According to this procedure, reverse phase HPLC is employed to detect candidate compounds in a linear range of 1.5-800 ng using spiked test samples. When the above analytical technique is applied to blood serum from animals receiving candidate compounds (0.4 mg/20 gram mouse), circulating concentrations of candidate compounds are quantitatively measured.

With the development of the above methods to quantify candidate compounds, it is possible to evaluate the efficacy of different routes of compound administration and to characterize bioactivity. To test time dependent serum bioavailability, animals are treated with candidate compounds by intraperitoneal injection (i.p.), and orally by gavage.

In Vivo Inhibition of MIF

The purpose for in vivo experiments is to confirm initial in vitro assay results using candidate compounds to inhibit MIF. LPS-induced toxicity appears to be related to an overproduction of MIF as well as TNF-α and IL-1β, since animals can be protected from endotoxin shock by neutralizing or inhibiting these inflammation mediators. The present model is chosen because it provides reproducible and rapid lethal models of sepsis and septic shock.

Doses of lipopolysaccharide (LPS) are made fresh prior to each experiment. LPS (*Escherichia Coli* 0111:B4, Sigma) is reconstituted by adding 0.5% TEA (1 ml USP water+5 ml Triethylamine (Pierce)) to a vial of 5 mg endotoxin. Once reconstituted, the solution is incubated at 37° C. for 30 minutes. Subsequently, the solution is sonicated in a 56-60° C. bath sonicator for 30 seconds 3 times. Following sonication the mixture is vortexed for 3 minutes continuously. The stock solution of LPS is then ready for use.

Detection of IL-1β and TNF-α and MIF in Blood

Ten 10-week-old (20±2 gram) female BALB/c mice (Charles River Laboratories, Kingston, N.Y.) are housed in a group of 5 per cage with free access to food and water and are acclimatized for at least one week prior to experimentation. On the day of experiment, mice are weighed and randomly distributed into groups of 10 animals of equal mean body weight. Mice are injected i.p. with 200 µL of formulated candidate compound or buffer alone immediately before the i.p. injection of LPS (*Escherichia coli* 0111:B4, 10 mg/kg or 5 mg/kg body weight) and β-D-galactosamine (50 mg/kg body weight). Each dose of LPS (0.2 ml for 20 gram mouse) is administered intraperitoneally and is mixed with a final concentration of β-D-galactosamine of 50 mg per ml. Following collection of blood specimens taken from cardiac puncture, the animal is sacrificed. Typical collections are performed at 4 hours post LPS treatment. The serum is separated in a serum separator (Microtainer® Becton Dickinson, Minneapolis, N.J.) according to the manufacturer's protocol. Mouse serum Il-1β and TNF-α are measured by ELISA using a "mouse IL 1β immunoassay" or "mouse TNF-α immunoassay" kit (R&D System Minneapolis, Minn.) following manufacturer's direction. Serum MIF concentrations in mouse serum are quantified by a sandwich ELISA (ChemiKine MIF Kit, Chemicon, San Diego, Calif.). Samples are analyzed in duplicate, and results are averaged.

Murine LPS Model

Ten 8 to 10 week-old (20±2 gram) female BALB/c mice are housed and acclimatized as described above. On the day of the experiments, the mice are weighed and randomly distributed into groups of 5 animals of equal mean body weight. Mice are injected with 200 µl of formulated candidate compound or its Buffer (average 20 mg/kg compound)

following i.p. injection of LPS (*E. Coli* 055B5, Sigma) (40, 10, 5, 2 or 0.5 mg/kg body weight) and 50 mg/kg of β-D-galactosamine. Mice are observed every two hours during the first 18 hours and twice a day for seven days. For these studies Kaplan-Meier estimation methods are employed to assess animal survival.

For all in vivo studies, standard statistical comparisons among treatment groups are performed using the Fisher test for categorical data and the Mantel-Cox test for continuous variables. To determine if levels of serum IL-1 correlate to serum MIF, a Fisher's test is applied. The analyses are performed using Stat View 5.0 Software (Abacus Concepts, Berkeley, Calif.). All reported p values that are two-sided and of a value less than 0.05 are considered to indicate statistical significance.

An initial control experiment is conducted to determine the base line levels of endogenous MIF in the murine model system (female Balb/c mice), and further to determine the rate and extent of increase in endogenous MIF following treatment with LPS (10 mg/kg). Female Balb/c mice are treated with LPS (Sigma 0111:B1) admixed with 50 mg/kg β-D-galactosamine. The level of MIF in serum is measured by HPLC as described above at 0, 2, 5 and 6 hours following LPS/galactosamine treatment. At the initiation of this representative experiment, the baseline level of endogenous MIF is approximately 45 ng/ml. However, over the course of this six-hour experiment there is a time dependent increase in the level of MIF detected in collected serum samples. When mice are treated with candidate compound (formulated in 50% aqueous solution) and 10 mg/kg of LPS there is a significant decrease in the level of circulating MIF that can be detected. BALB/c mice are injected i.p. with 20 mg/kg body weight of candidate compound at time of LPS administration. Blood samples are collected 5.5 hours later. The results demonstrate that animals treated with the candidate compound have a decreased ability to respond to LPS and lowered MIF levels are detected. In a further study in which mice are administered with half the LPS dosage (5 mg/kg), serum MIF is determined four hours following treatment. This data reveals decrease in MIF. In a further experiment, both MIF and IL-1β are measured in mouse serum via ELISA. The experiments show a direct and highly significant correlation between MIF and IL-1β. This correlation is also observed between MIF and TNF-α. In a similar experiment, reductions in serum IL-1β level and serum TNF-α level are observed following administration of 20 mg/kg of candidate compound.

Studies of experimental toxic shock induced by LPS reveal a central role for MIF and TNF-α. The fact that LPS stimulates macrophage-like cells to produce MIF, that in turn induce TNF-α secretion by macrophage like cells suggests a potential role for MIF in the pathogenesis of LPS. To test if candidate compounds can prevent LPS shock, a model of lethal LPS mediated shock in BALB/c mice sensitized with β-D-galactosamine is employed. Treatment with candidate compound at the time of injection of a lethal dose of LPS (2, 5 and 10 mg/kg) substantially increases probability of survival. The effects are modulated by the concentration of LPS employed, demonstrating that when using a higher concentration of LPS, the effect of the candidate compound is saturable and hence specific. Candidate compounds can protect mice from LPS induced toxic shock in a concentration dependent fashion.

MIF Overcomes the Effects of Candidate Compounds

Exogenous recombinant human MIF when administered with candidate compounds can reverse the beneficial effects of the compounds, supporting the hypothesis that candidate compounds act to increase animal resistance to LPS by modulating MIF levels in mice serum. Mice are treated with the standard LPS protocol except that in addition to 1 mg/kg LPS and 20 mg/kg of the candidate compound, some animals also receive 300 μg/kg human recombinant MIF. At 12 hours, significantly more mice survive the LPS with candidate compound, but this survival is neutralized by the administration of MIF.

MIF Inhibitor in a Collagen Induced Arthritis Model

Twenty DBA/1LacJ mice, age 10-12 weeks, are immunized on day 0 at base of the tail with bovine collagen type II (CII 100 μg) emulsified in Freunds complete adjuvant (FCA; GibcoBRL). On day 7, a second dose of collagen is administrated via the same route (emulsified in Freunds incomplete adjuvant). On Day 14 mice are injected subcutaneously with 100 mg of LPS (055:B5). On day 70 mice are injected 40 μg LPS (0111:B4) intraperitoneally. Groups are divided according paw thickness, which is measured by a caliper, after randomization, to create a balanced starting group. Candidate compound in buffer is given to mice on days 71, 72, 73, and 74 (total of eight doses at 0.4 mg/dose, approximately 20 mg/kg of body weight). Mice are then examined on day 74 by two observers for paw thickness. In this experiment, subsided mice (decline of full-blown arthritis) are treated with a final i.p. injection of LPS on day 70 to stimulate cytokine production as well as acute inflammation. Candidate compound treated mice develop mildly reduced edema of the paw compared with vehicle only treated controls. In the late time point, the animals in the treated group do not reach a full-blown expression of collagen induced arthritis as compared to controls.

In another experiment, fifteen DBA/1J mice, age 10-12 weeks are immunized on day 0 at the base of the tail with bovine collagen type II (CII 100 μg), emulsified in Freunds complete adjuvant (FCA; GibcoBRL). On day 21, a second dose of collagen is administered via the same route, emulsified in Freunds incomplete adjuvant. On day 28 the mice are injected subcutaneously with 100 μg of LPS (055:B5). On day 71 the mice are injected i.p. with 40 μg LPS (0111:B4). Groups and treatment protocol are the same as described as above. On day 74 blood samples are collected and cytokines are measured. The candidate compound reduces serum MIF levels as compared to untreated CIA samples. An even more significant inhibition of serum TNF-α levels is detected.

MIF Inhibition by Selected Compounds—Tautomerase Assay

The following inhibitors of MIF were prepared by the methods of the preferred embodiments. In the following structures, "COOEt" is employed to refer to a group of formula —C(=O)OCH$_2$CH$_3$ and "Et" is employed to refer to a group of formula —CH$_2$CH$_3$. Results of tautomerase assays indicated that each of the MIF inhibitor compounds exhibited significant inhibition of MIF activity at concentrations of 100 μM or lower.

-continued
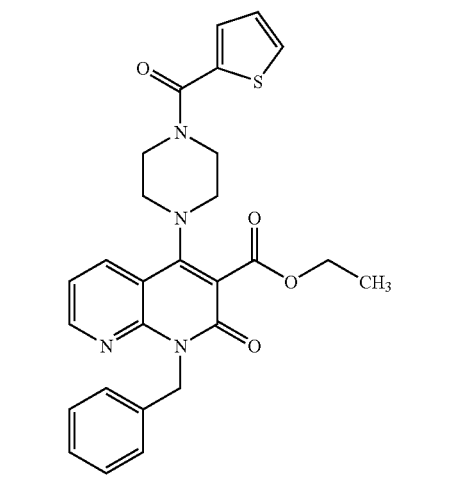
1000
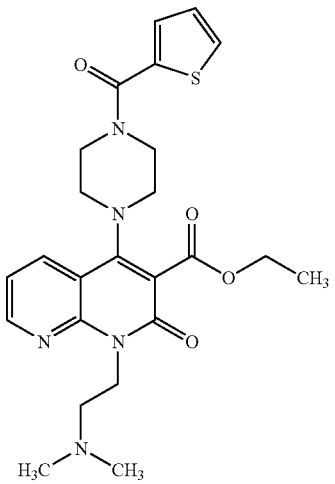
1003
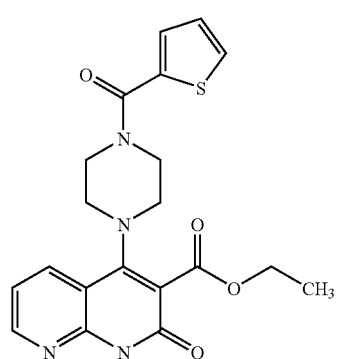
1001
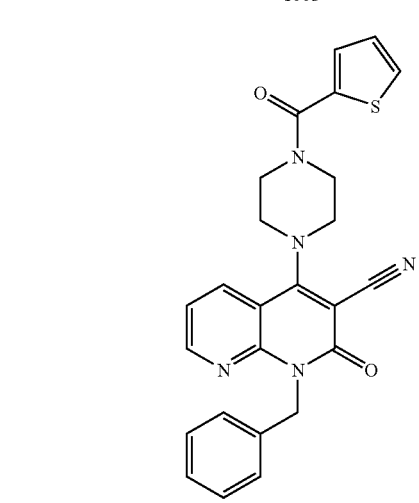
1004
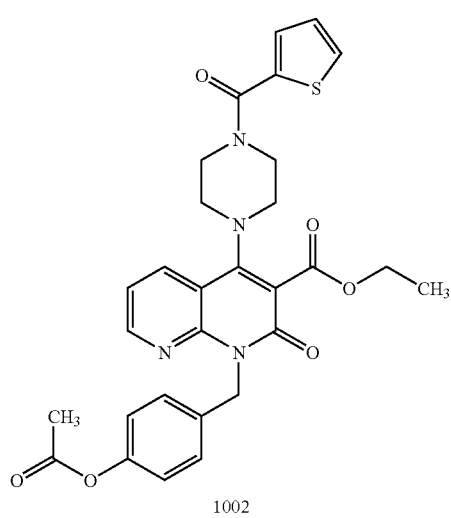
1002
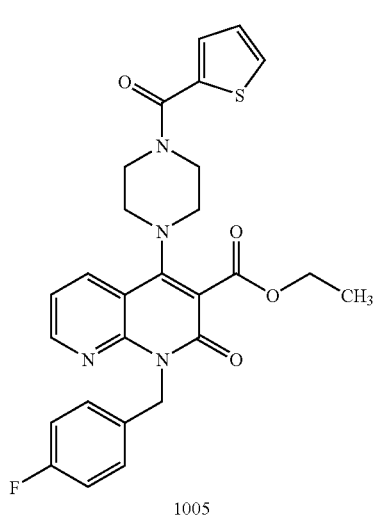
1005

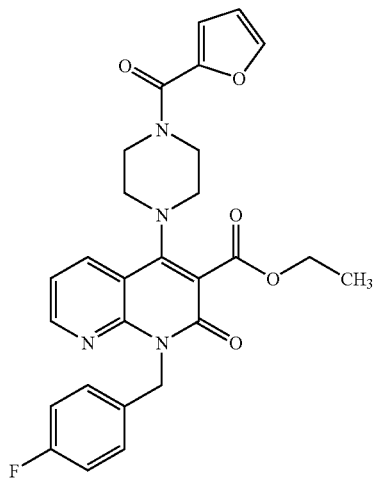
1006
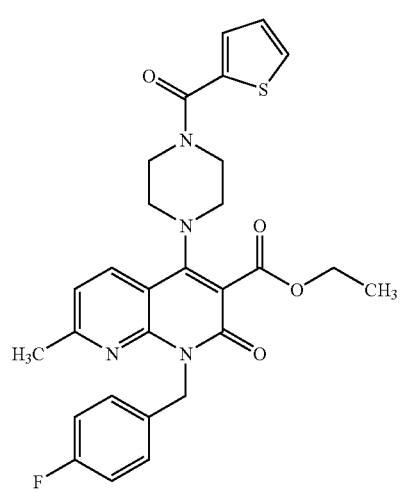
1007
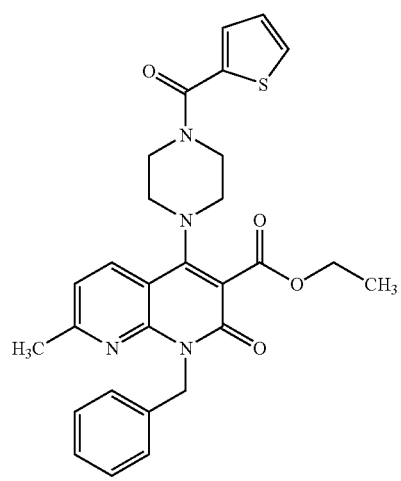
1008
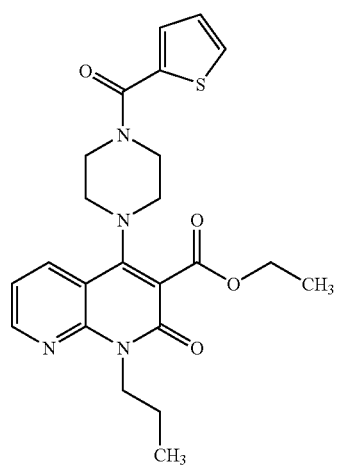
1009
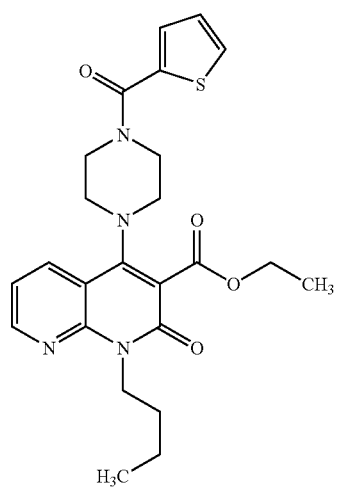
1010
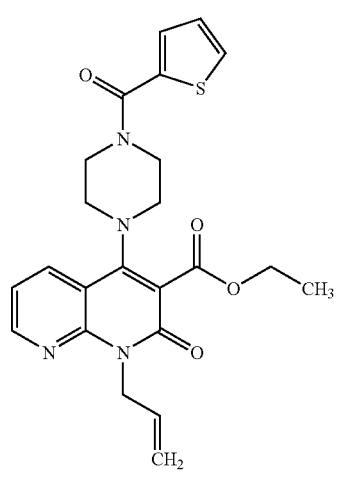
1011

-continued
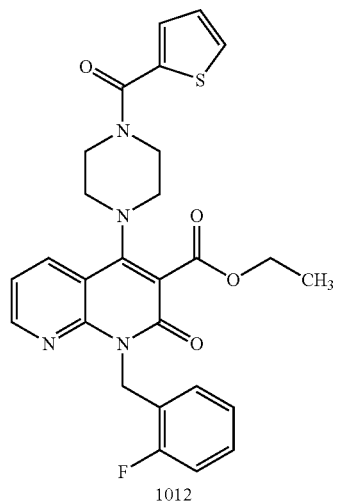
1012
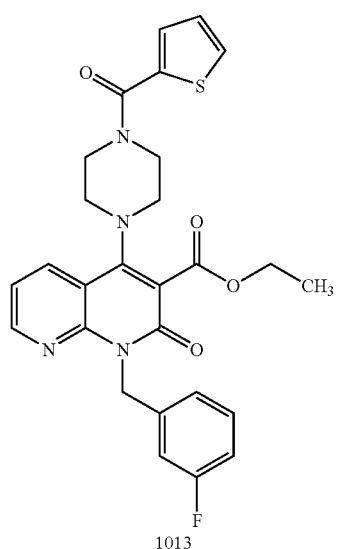
1013
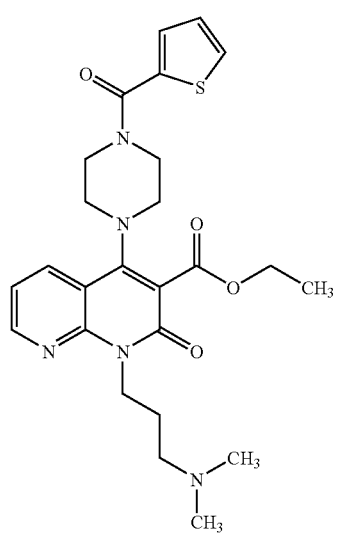
1014
-continued
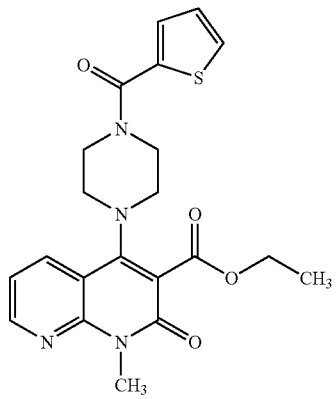
1015
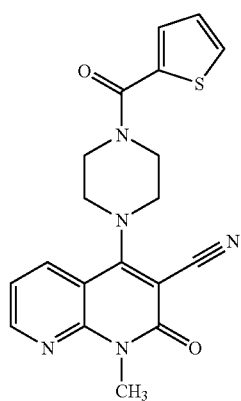
1016
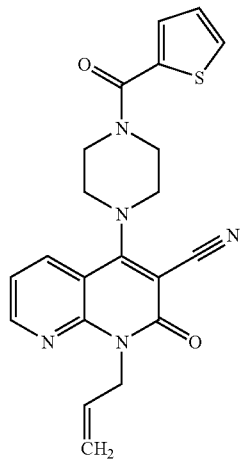
1017

-continued
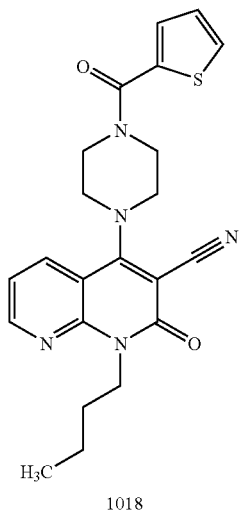
1018
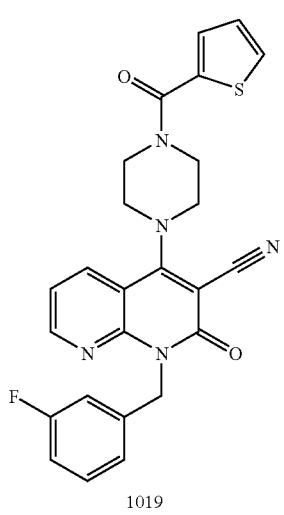
1019
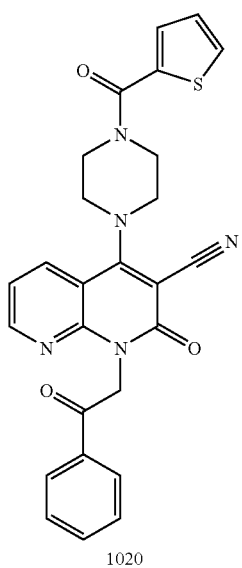
1020
-continued
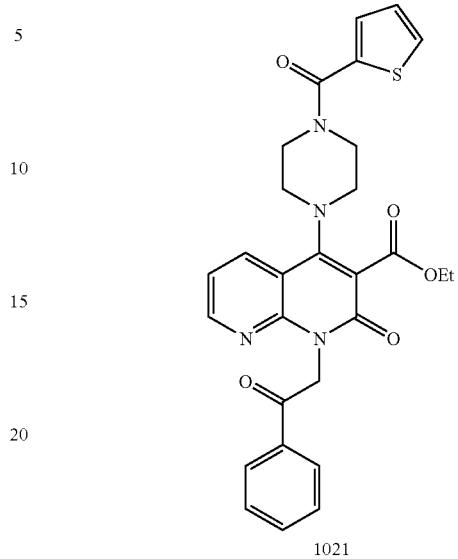
1021
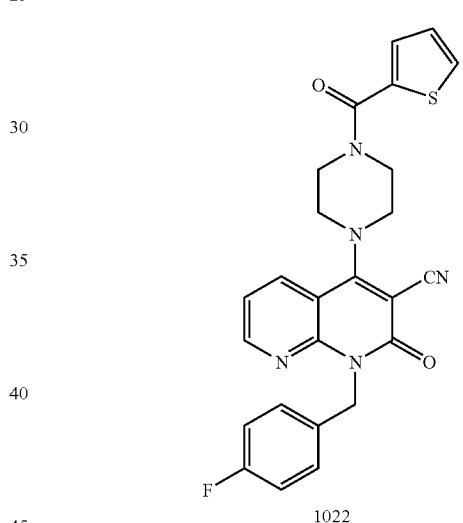
1022
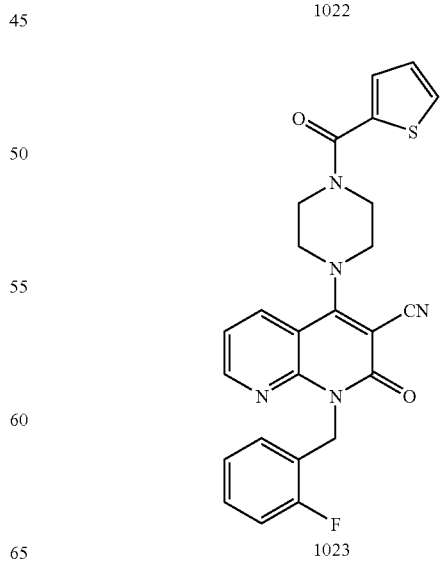
1023

-continued
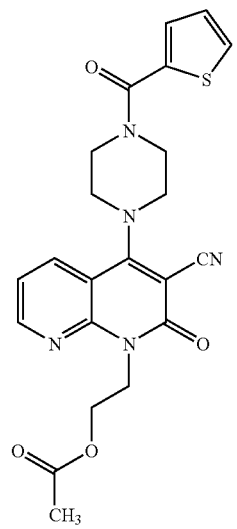
1024
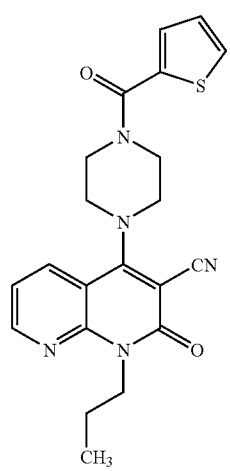
1025
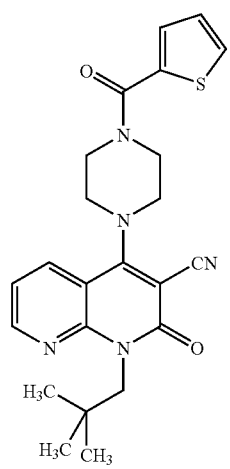
1026
-continued
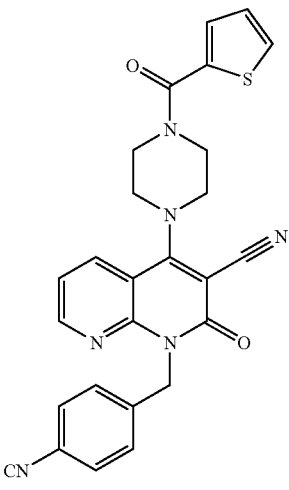
1027
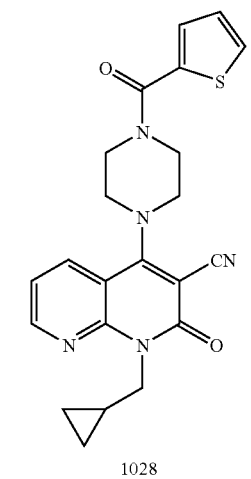
1028
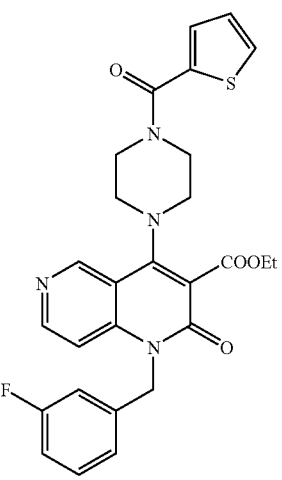
1029

-continued
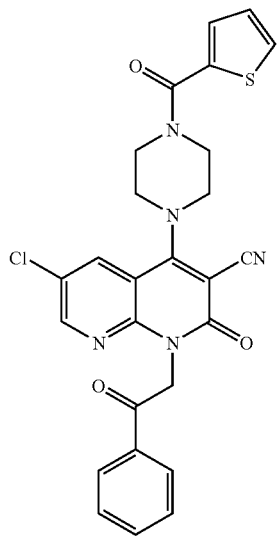
1030
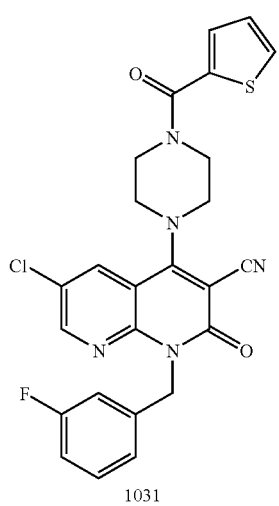
1031
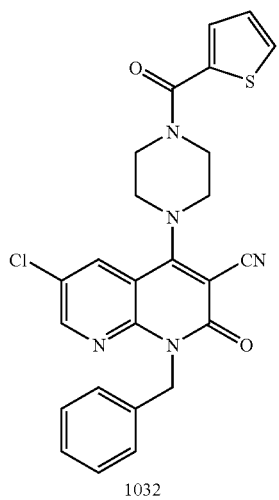
1032
-continued
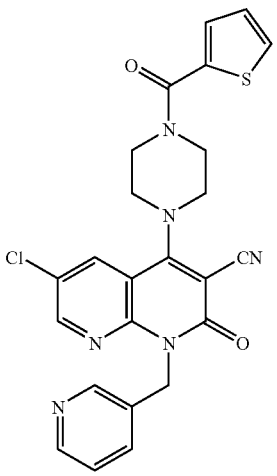
1033
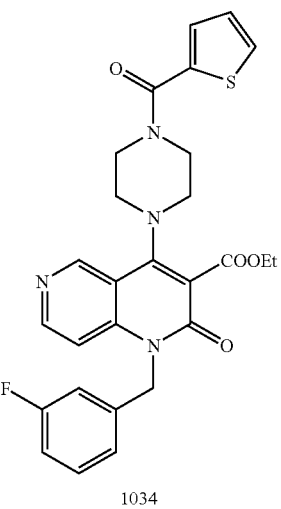
1034
MIF Inhibitor
The following compounds were prepared by the methods of the preferred embodiments, and are expected to exhibit significant inhibition of MIF activity. In the following structures, "COOEt" is employed to refer to a group of formula —C(=O)OCH$_2$CH$_3$ and "Et" is employed to refer to a group of formula —CH$_2$CH$_3$.

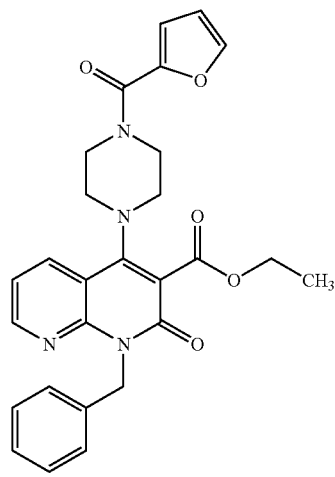
2000
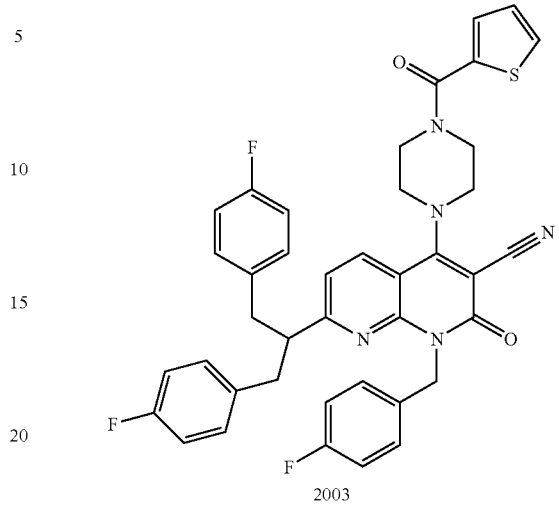
2003
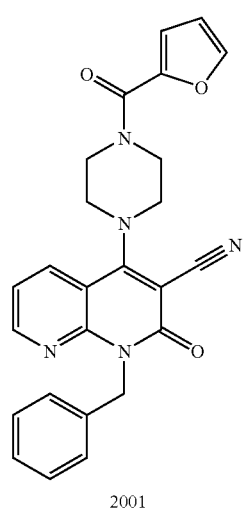
2001
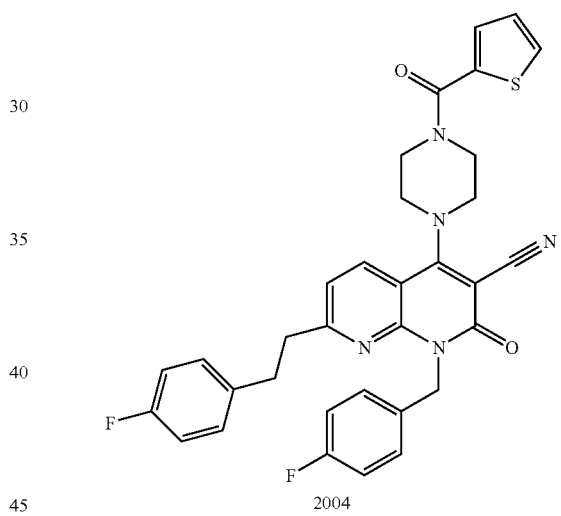
2004
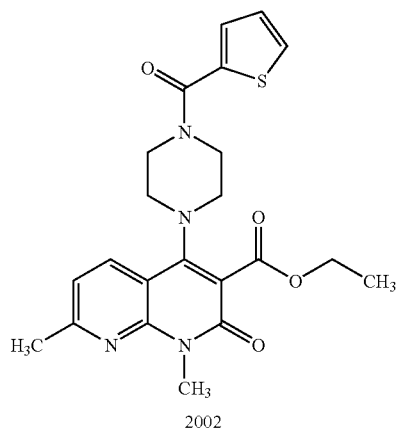
2002
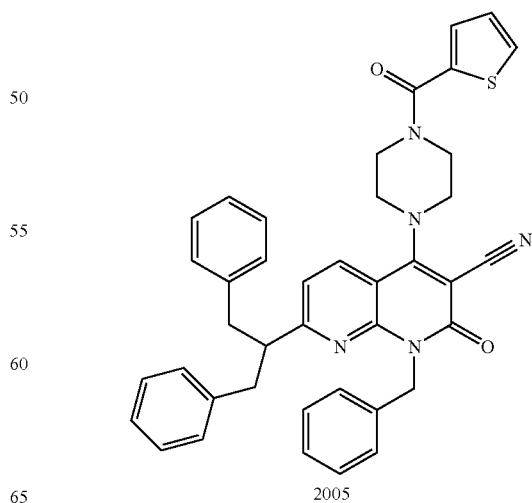
2005

| 361 | 362 |
|---|---|
| -continued | -continued |
| 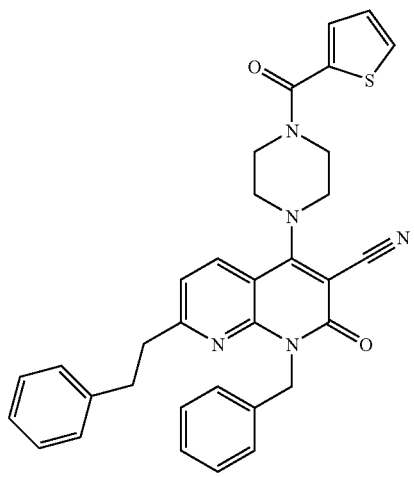
2006 | 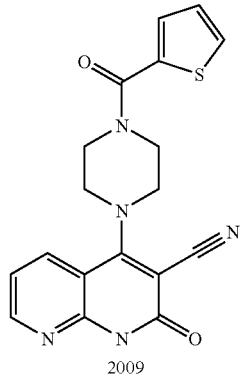
2009 |
| 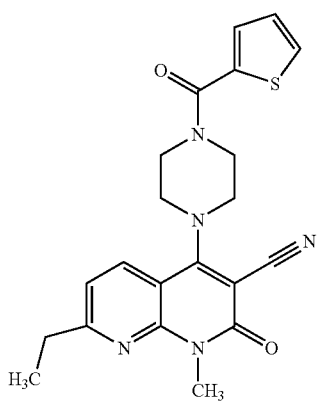
2007 | 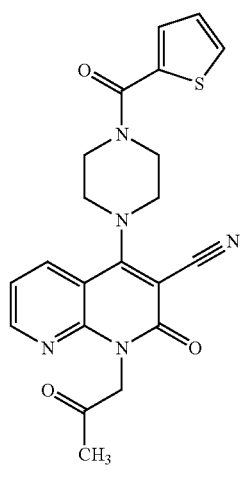
2010 |
| 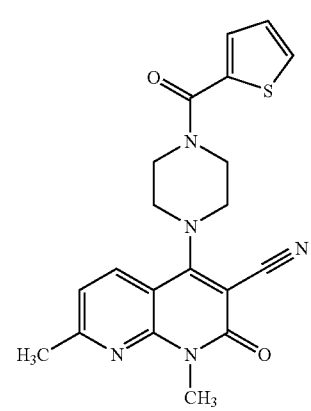
2008 | 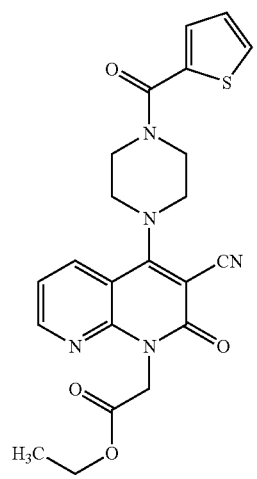
2011 |

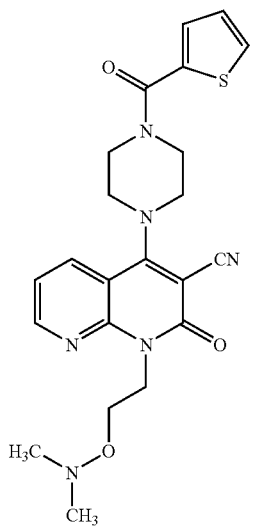
2012
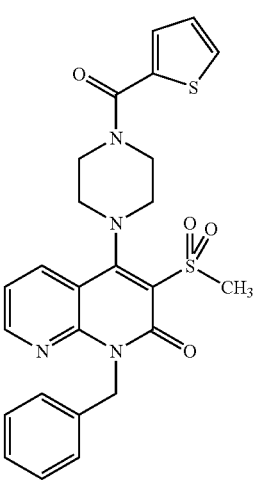
2013
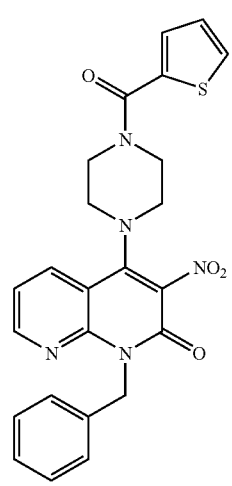
2014
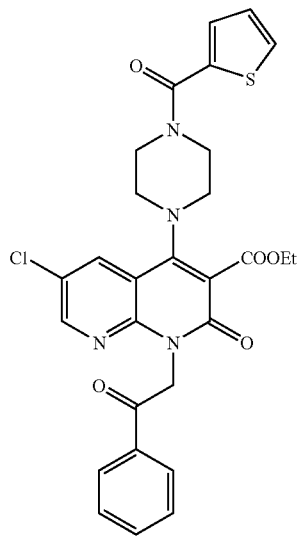
2015
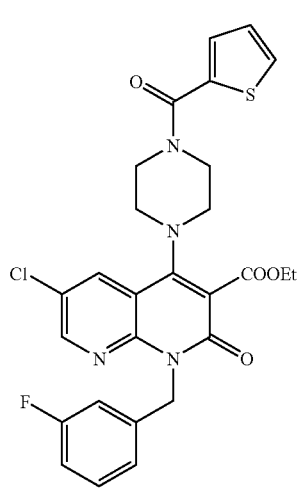
2016
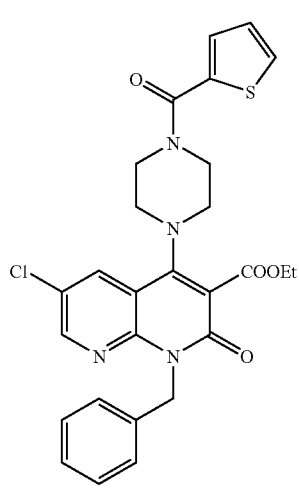
2017

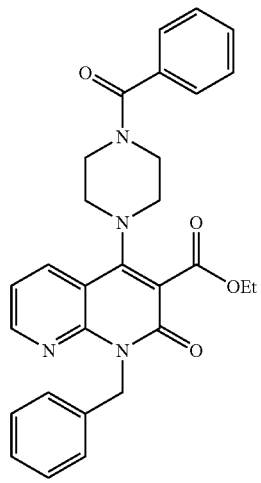
2018
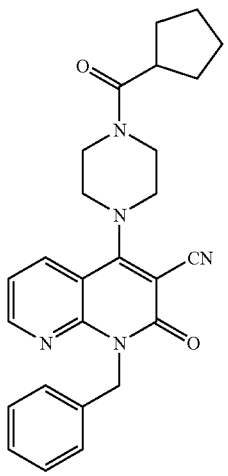
2021
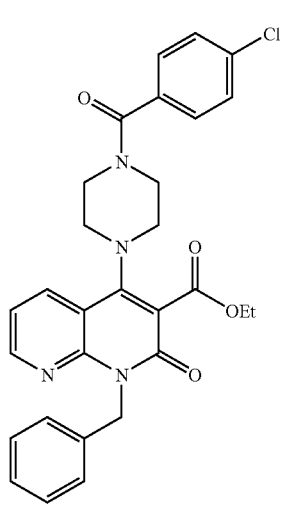
2019
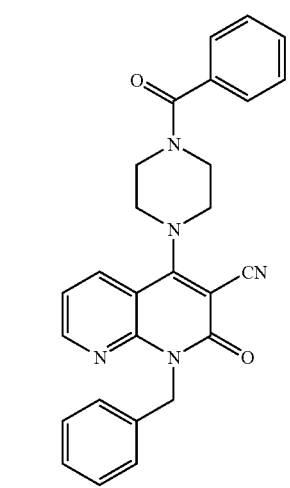
2022
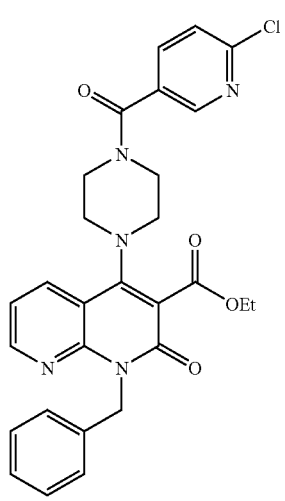
2020
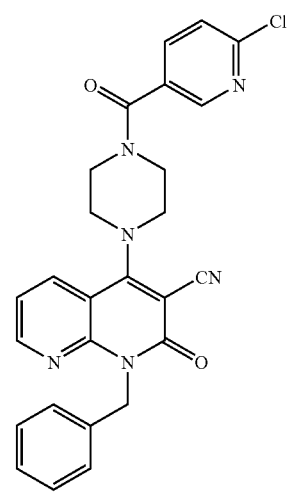
2023

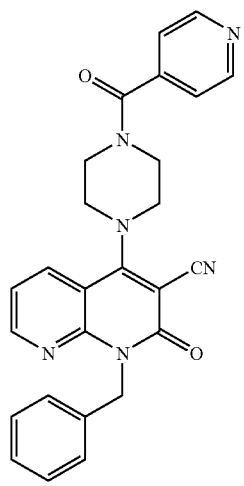
2024
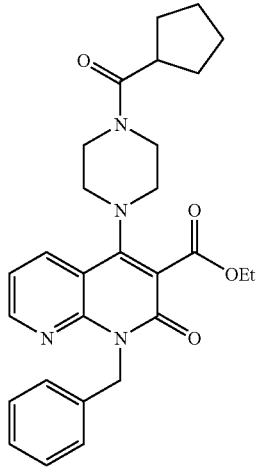
2027
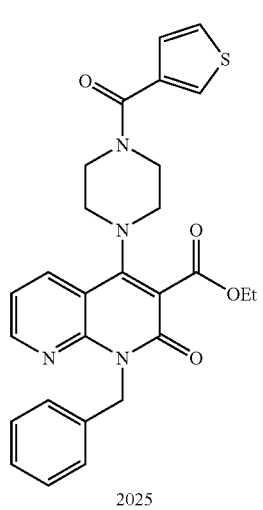
2025
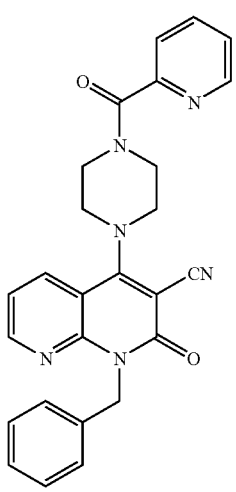
2028
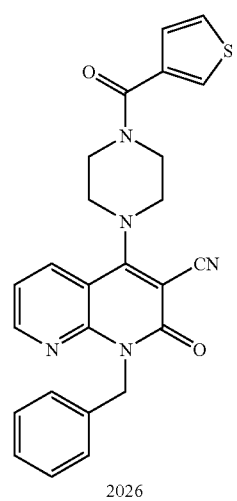
2026
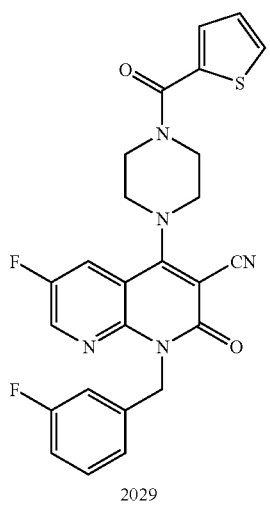
2029

-continued
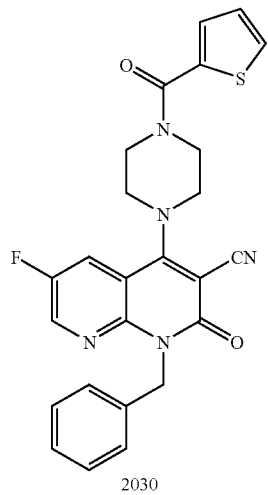
2030
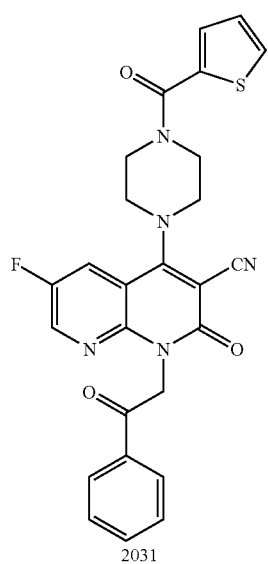
2031
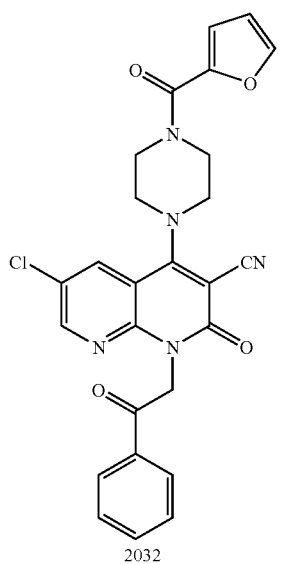
2032
-continued
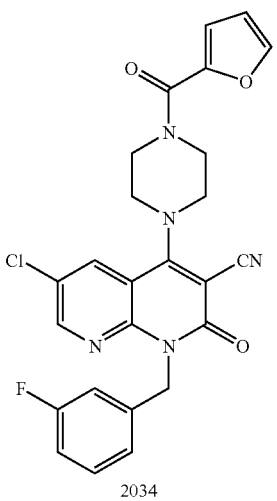
2034
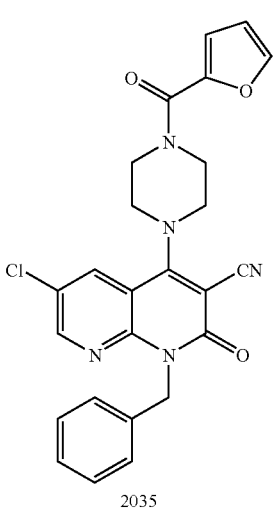
2035
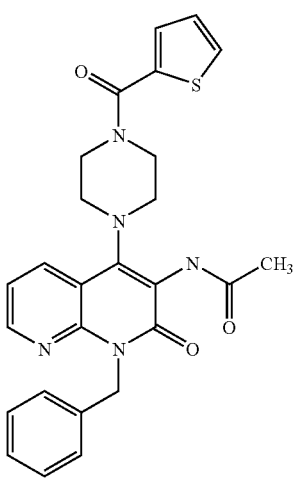
2036

-continued
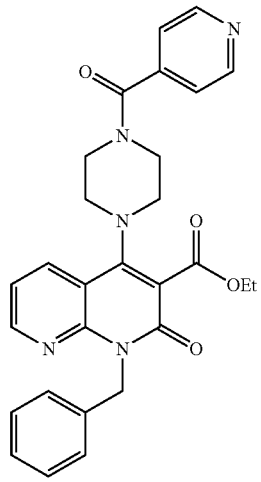
2037
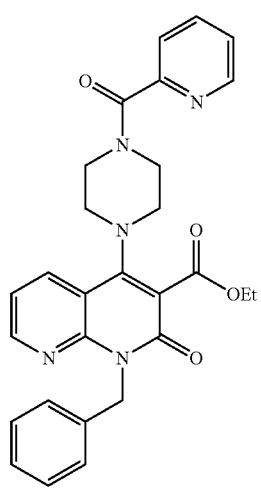
2038
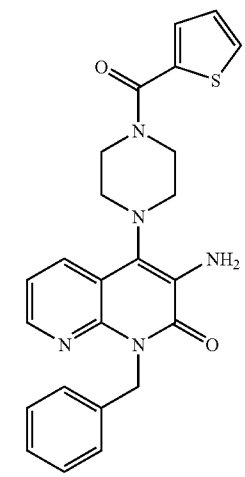
2039
-continued
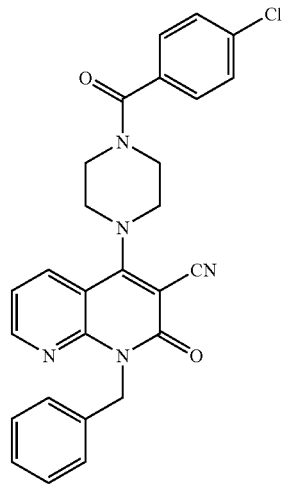
2040
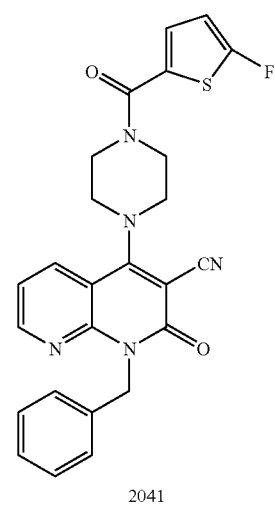
2041
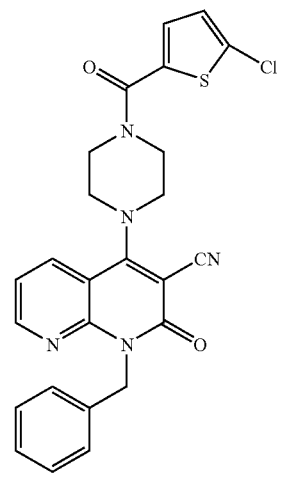
2042

-continued

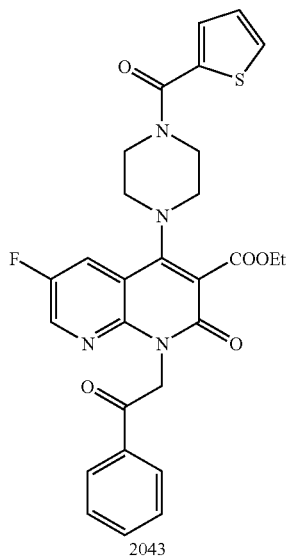

2043

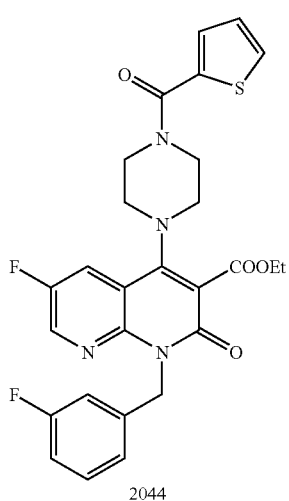

2044

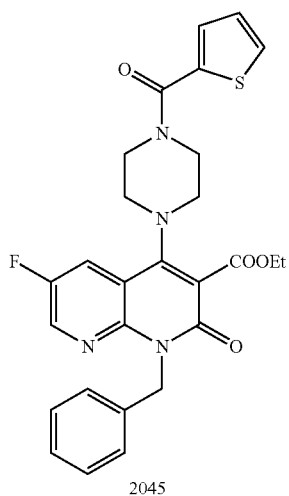

2045

All references cited herein are incorporated herein by reference in their entirety. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. A compound having a structure:

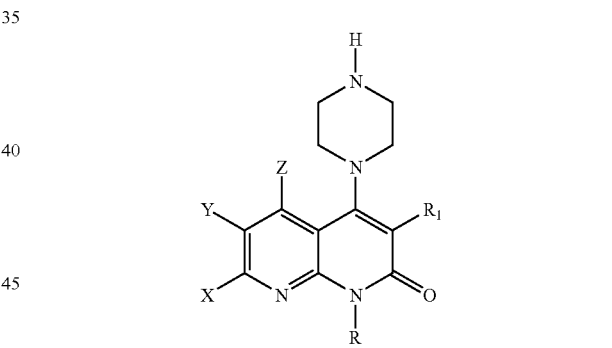

or a stereoisomer or a pharmaceutically acceptable salt thereof, wherein:

R is selected from the group consisting of $C_6$-$C_{12}$ aryl, $C_7$-$C_{12}$ arylalkyl, $C_2$-$C_{12}$ acylalkyl, —$(CH_2)_mC(\!\!=\!\!O)$Ar, and —$(CH_2)_mNR_4R_5$, wherein R is unsubstituted or substituted with at least one substituent selected from the group consisting of —F, —Cl, and —CN;

$R_1$ is selected from the group consisting of —CN, —C($=$O)O$R_3$, and —NHC($=$O)$R_3$;

$R_3$ is $C_1$-$C_{12}$ alkyl;

$R_4$ and $R_5$ are independently selected from the group consisting of hydrogen and $C_1$-$C_{12}$ alkyl;

X is selected from the group consisting of hydrogen, halogen, —F, —Cl, —CN, and $C_1$-$C_{12}$ alkyl;

Y is selected from the group consisting of hydrogen, halogen, —F, —Cl, —CN, and $C_1$-$C_{12}$ alkyl;

Z is selected from the group consisting of hydrogen, halogen, —F, —Cl, —CN, and $C_1$-$C_{12}$ alkyl;

Ar is phenyl; and m is independently 0, 1, 2, 3, or 4.

2. The compound of claim 1, wherein $R_1$ is —C(=O)OCH$_2$CH$_3$.

3. The compound of claim 1, wherein $R_1$ is —NH—C(=O)CH$_3$.

4. The compound of claim 1, wherein $R_1$ is —CN.

5. The compound of claim 1, wherein R is —(CH$_2$)$_m$C(=O)Ar.

6. The compound of claim 1, wherein R is —CH$_2$Ph.

7. The compound of claim 1, wherein X is selected from the group consisting of hydrogen, fluorine, and chlorine; wherein Y is selected from the group consisting of hydrogen, fluorine, and chlorine; and wherein Z is selected from the group consisting of hydrogen, fluorine, and chlorine.

8. A compound having a structure:

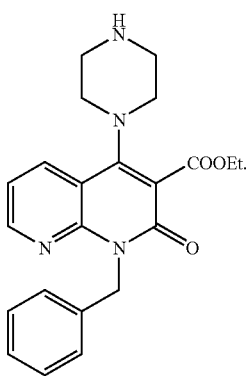

9. A compound having a structure:

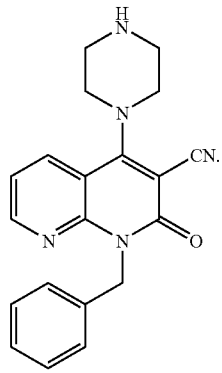

10. The compound of claim 1, wherein R is —(CH$_2$)$_m$C(=O)Ar and wherein m is 1.

11. The compound of claim 1, wherein R is —(CH$_2$)$_m$C(=O)Ar and Ar is phenyl.

12. The compound of claim 1, wherein R is C$_7$-C$_{12}$ arylalkyl.

13. The compound of claim 1, wherein R is —(CH$_2$)$_m$NR$_4$R$_5$.

14. The compound of claim 1, wherein $R_1$ is —C(=O)OR$_3$.

15. The compound of claim 1, wherein $R_1$ is —(CH$_2$)$_m$NR$_4$R$_5$.

16. The compound of claim 1, wherein $R_1$ is —(CH$_2$)$_m$NR$_4$R$_5$ and wherein R$_4$ and R$_5$ are independently C$_1$-C$_{12}$ alkyl.

17. The compound of claim 1, wherein X is hydrogen; wherein Y is halogen; and wherein Z is hydrogen.

18. The compound of claim 1, wherein X is hydrogen; wherein Y is chlorine; and wherein Z is hydrogen.

19. The compound of claim 1, wherein X is hydrogen; wherein Y is methyl; and wherein Z is hydrogen.

* * * * *